(12) United States Patent
Isfort et al.

(10) Patent No.: US 7,063,954 B2
(45) Date of Patent: *Jun. 20, 2006

(54) METHODS FOR IDENTIFYING COMPOUNDS FOR REGULATING MUSCLE MASS OR FUNCTION USING CORTICOTROPIN RELEASING FACTOR RECEPTORS

(75) Inventors: Robert Joseph Isfort, Fairfield, OH (US); Russell James Sheldon, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 271 days.

This patent is subject to a terminal disclaimer.

(21) Appl. No.: 10/649,852

(22) Filed: Aug. 27, 2003

(65) Prior Publication Data

US 2004/0101911 A1 May 27, 2004

Related U.S. Application Data

(63) Continuation-in-part of application No. 09/799,978, filed on Mar. 6, 2001, now Pat. No. 6,670,140.

(51) Int. Cl.
   *G01N 33/566* (2006.01)
(52) U.S. Cl. .................. 435/7.21; 435/6; 435/7.1; 435/7.2; 435/69.1; 435/325; 436/501
(58) Field of Classification Search .............. None
   See application file for complete search history.

(56) References Cited

U.S. PATENT DOCUMENTS

| | | | |
|---|---|---|---|
| 5,235,036 A | 8/1993 | Kornreich et al. | |
| 5,663,292 A | 9/1997 | Rivier | |
| 5,824,771 A | 10/1998 | Rivier | |
| 5,844,074 A | 12/1998 | Rivier | |
| 5,869,450 A | 2/1999 | Wei et al. | |
| 6,670,140 B1 * | 12/2003 | Isfort et al. | 435/7.21 |

FOREIGN PATENT DOCUMENTS

| | | |
|---|---|---|
| EP | 0 860 501 A2 | 8/1998 |
| WO | WO 96/37223 A1 | 11/1996 |
| WO | WO 97/00063 A2 | 1/1997 |

OTHER PUBLICATIONS

McDonnell J, et al. 1998. British Journal of Pharmacology, 125:717-726.*
Dautzenberg, et al. 1997. Journal of Neurochemistry, 69:1640-1649.*
T.M. Reyes, et al., "Urocortin II: A member of the corticotropin-releasing factor (CRF) neuropeptide family that is selectively bound by type 2 CRF receptors", *PNAS*, Feb. 27, 2001, 2843-2848, vol. 98, No. 5, USA.

(Continued)

*Primary Examiner*—Elizabeth Kemmerer
*Assistant Examiner*—Shulamith H Shafer
(74) *Attorney, Agent, or Firm*—Naishadh N. Desai

(57) ABSTRACT

Screening methods for identifying compounds that bind to or activate corticotropin releasing factor$_2$ receptors (CRF$_2$R) and regulate or potentially regulate skeletal muscle mass or function in vivo are disclosed. Also disclosed are screening methods for identifying compounds that prolong or augment the activation of CRF$_2$Rs or of CRF$_2$R signal transduction pathways, increase CRF$_2$R or increase CRF expression are provided. Pharmaceutical compositions comprising CRF$_2$R agonists, antibodies to CRF$_2$R and methods for increasing skeletal muscle mass or function or for the treatment of skeletal muscle atrophy using CRF$_2$R as the target for intervention and methods for treatment of muscular dystrophies are described.

10 Claims, 16 Drawing Sheets

OTHER PUBLICATIONS

Figure 1:
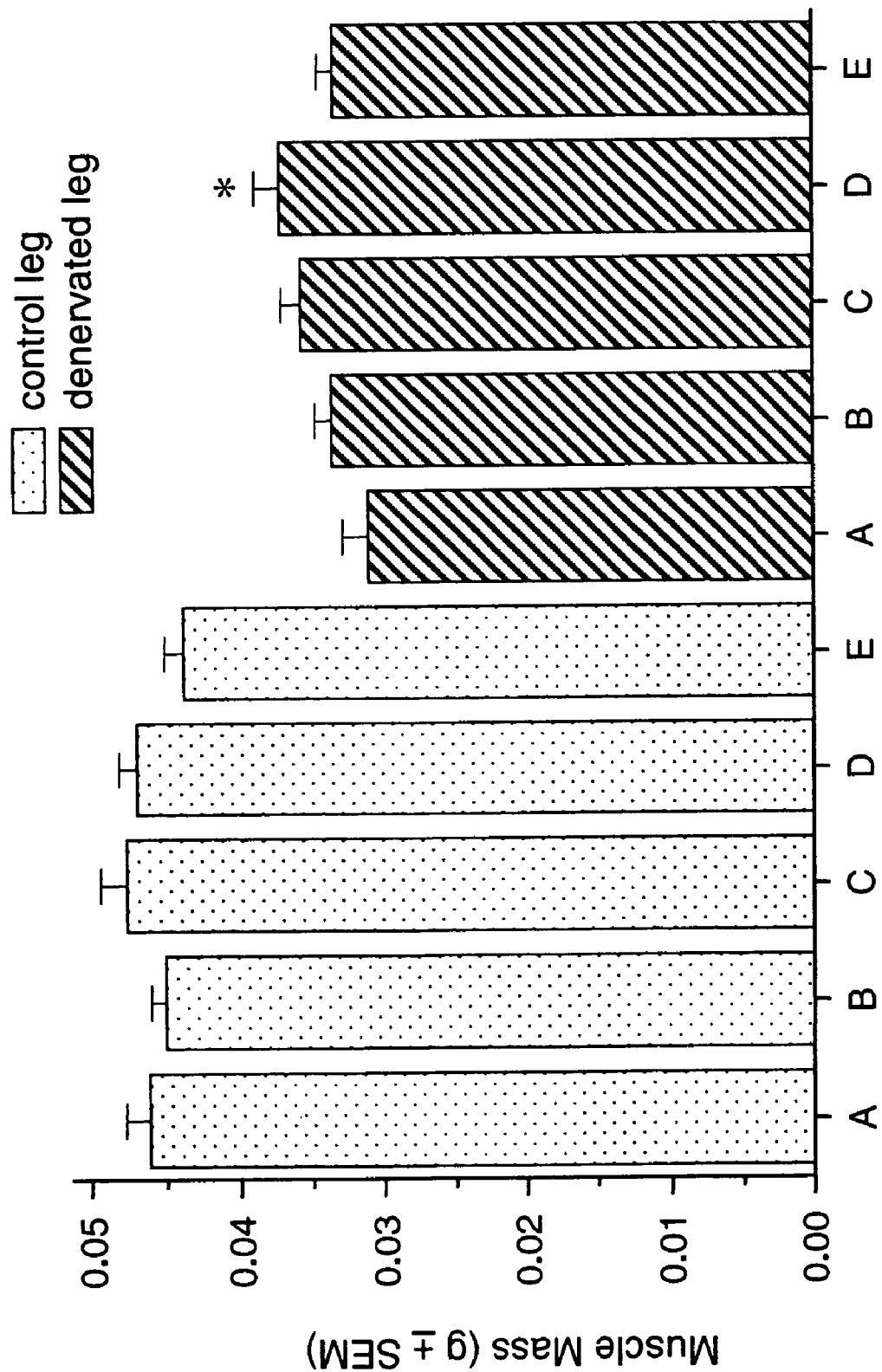

E.B De Souza, "Corticotropin-Releasing Factor Receptors: Physiology, Pharmacology, Biochemistry and Role In Central Nervous System and Immune Disorders", *Psychoneuroendocrinology*, 1995, 789-819, vol. 20, No. 8, Elsevier Science Ltd., USA.

D.T. Chalmers, et al., "Corticotropin-releasing factor receptors: from molecular biology to drug design", *TiPS*, Apr. 1996, 166-172, vol. 17, Elsevier Science Ltd., USA.

E.T. Wei, et al., "Peripheral anti-inflammatory actions of corticotropin-releasing factor", *Ciba Foundation Symposium 172*, 1993, 258-276, Wiley, Chichester.

J.R. McCarthy, et al., "Recent Advances with the $CRF_1$ Receptor: Design of Small Molecule Inhibitors, Receptor Subtypes and Clinical Indications", *Current Pharmaceutical Design*, 1999, 289-315, vol. 5, Bentham Science Publishers B.V.

G.P. Chrousos, et al., "Corticotropin Releasing Factor: Basic Studies and Clinical Applications", *Prog. Neuro-Psychopharmacol. & Biol. Psychiat.*, 1985, 349-359, vol. 9, Pergamon Press Ltd., Great Britain.

G.B. Cutler, Jr., M.D., "Corticotropin-Releasing Hormone (CRH): Clinical Studies and Use", *The Endocrinologist*, 1997, 10S-16S, vol. 7, No. 1, Suppl. 1, Williams & Wilkins.

M.J. Owens, et al., "Physiology and Pharmacology of Corticotropin-releasing Factor", *Pharmacological Reviews*, 1991, 425-473, vol. 43, No. 4, The American Society for Pharmacology and Experimental Therapeutics, USA.

L. Arborelius, et al., "The role of corticotropin-releasing factor in depression and anxiety disorders", *Journal of Endocrinology*, 1999, 1-12, vol. 160, Society for Endocrinology, Great Britain.

D.N. Orth, "Corticotropin-Releasing Hormone in Humans", *Endocrine Reviews*, 1992, 164-191, vol. 13, No. 2, The Endocrine Society, USA.

E. Emeric-Sauval, "Corticotropin-Releasing Factor (CRF)—A Review", *Psychoneuroendocrinology*, 1985, 277-294, vol. 11, No. 3, Pergamon Journals Ltd., Great Britain.

J. Spiess, et al., "Molecular Properties of the CRF Receptor", *TEM*, 1998, 140-145, vol. 9, No. 4, Elsevier Science Ltd.

K.D. Dieterich, et al., "Corticotropin-releasing factor receptors: An overview", *Exp. Clin. Endocrinol. Diabetes*, 1997, 65-82, vol. 105, Johann Ambrosius Barth.

P.J. Gilligan, et al., "Corticotropin Releasing Factor (CRF) Receptor Modulators: Progress and Opportunities for New Therapeutic Agents", *Journal of Medicinal Chemistry*, May 4, 2000, 1641-1660, vol. 43, No. 9, American Chemical Society.

C.A. Maltin, et al., "Clenbuterol, a β-adrenoceptor agonist, increases relative muscle strength in orthopaedic patients", *Clinical Science*, 1993, 651-654, vol. 84.

J.F. Signorile, et al., "Increased Muscle Strength in Paralyzed Patients after Spinal Cord Injury: Effect of Beta-2 Adrenergic Agonist", *Arch Phys Med Rehabil*, 1995, 55-58, vol. 76.

L. Martineau, et al., "Salbutamol, a $β_2$-adrenoceptor agonist, increases skeletal muscle strength in young men", *Clinical Science*, 1992, 615-621, vol. 83.

Medler, S., "Comparative trends in shortening velocity and force production in skeletal muscles", *Am. J. Physiol Regulatory Integrative Comp Physiol*, 2002, vol. 283, pp. R368-R378.

Rome, L.C., "The Design of Vertebrate Muscular Systems: Comparative and Integrative Approaches", *Clinical Orthopaedics and Related Research*, 2002, No. 403S, pp. S59-S76.

H.A. Thomas, et al., "CRF and Related Peptides as Anti-Inflammatory Agonists", *Annals New York Academy of Sciences*, 1993, vol. 697, pp. 219-228.

.R. McCarthy, et al., "Chapter 2. Recent Progress in Corticotropin-Releasing Factor Receptor Agents", *Annual Reports in Medicinal Chemistry*, 1999, vol. 34, Academic Press, pp. 11-20.

\* cited by examiner

SEQUENCE LISTING

<160> NUMBER OF SEQ ID NOS: 44

<210> SEQ ID NO 1
<211> LENGTH: 2536
<212> TYPE: DNA
<213> ORGANISM: homo sapiens
<220> FEATURE:
<221> NAME/KEY: CDS
<222> LOCATION: (227)..(1474)

<400> SEQUENCE: 1

```
ggggaaacgg cggccagact tccccgggaa ggggcgagcg agagccgggc cgggccgggc      60
cgggccgcgg ggccgggaag cgccgagccg ggcatctcct caccaggcag cgaccgagga     120
gcccggccgc ccaccccgtg ccgcccgagc ccgcagccgc ccgccggtcc ctctgggatg     180
tccgtaggac ccgggcattc aggacggtag ccgagcgagc ccgagg atg gga ggg        235
                                                 Met Gly Gly
                                                   1 cac ccg cag ctc cgt ctc gtc aag gcc ctt ctc ctt ctg ggg ctg aac       283
His Pro Gln Leu Arg Leu Val Lys Ala Leu Leu Leu Leu Gly Leu Asn
      5                  10                  15 ccc gtc tct gcc tcc ctc cag gac cag cac tgc gag agc ctg tcc ctg       331
Pro Val Ser Ala Ser Leu Gln Asp Gln His Cys Glu Ser Leu Ser Leu
 20                  25                  30                  35 gcc agc aac atc tca gga ctg cag tgc aac gca tcc gtg gac ctc att       379
Ala Ser Asn Ile Ser Gly Leu Gln Cys Asn Ala Ser Val Asp Leu Ile
                 40                  45                  50 ggc acc tgc tgg ccc cgc agc cct gcg ggg cag cta gtg gtt cgg ccc       427
Gly Thr Cys Trp Pro Arg Ser Pro Ala Gly Gln Leu Val Val Arg Pro
             55                  60                  65 tgc cct gcc ttt ttc tat ggt gtc cgc tac aat acc aca aac aat ggc       475
Cys Pro Ala Phe Phe Tyr Gly Val Arg Tyr Asn Thr Thr Asn Asn Gly
         70                  75                  80 tac cgg gag tgc ctg gcc aat ggc agc tgg gcc gcc cgc gtg aat tac       523
Tyr Arg Glu Cys Leu Ala Asn Gly Ser Trp Ala Ala Arg Val Asn Tyr
     85                  90                  95 tcc gag tgc cag gag atc ctc aat gag gag aaa aaa agc aag gtg cac       571
Ser Glu Cys Gln Glu Ile Leu Asn Glu Glu Lys Lys Ser Lys Val His
100                 105                 110                 115 tac cat gtc gca gtc atc atc aac tac ctg ggc cac tgt atc tcc ctg       619
Tyr His Val Ala Val Ile Ile Asn Tyr Leu Gly His Cys Ile Ser Leu
                 120                 125                 130 gtg gcc ctc ctg gtg gcc ttt gtc ctc ttt ctg cgg ctc agg agc atc       667
Val Ala Leu Leu Val Ala Phe Val Leu Phe Leu Arg Leu Arg Ser Ile
             135                 140                 145 cgg tgc ctg cga aac atc atc cac tgg aac ctc atc tcc gcc ttc atc       715
Arg Cys Leu Arg Asn Ile Ile His Trp Asn Leu Ile Ser Ala Phe Ile
         150                 155                 160 ctg cgc aac gcc acc tgg ttc gtg gtc cag cta acc atg agc ccc gag       763
Leu Arg Asn Ala Thr Trp Phe Val Val Gln Leu Thr Met Ser Pro Glu
     165                 170                 175 gtc cac cag agc aac gtg ggc tgg tgc agg ttg gtg aca gcc gcc tac       811
Val His Gln Ser Asn Val Gly Trp Cys Arg Leu Val Thr Ala Ala Tyr
180                 185                 190                 195 aac tac ttc cat gtg acc aac ttc ttc tgg atg ttc ggc gag ggc tgc       859
Asn Tyr Phe His Val Thr Asn Phe Phe Trp Met Phe Gly Glu Gly Cys
                 200                 205                 210 tac ctg cac aca gcc atc gtg ctc acc tac tcc act gac cgg ctg cgc       907
Tyr Leu His Thr Ala Ile Val Leu Thr Tyr Ser Thr Asp Arg Leu Arg
```

-continued

| | | |
|---|---|---|
| 215 | 220 | 225 |

| | |
|---|---|
| aaa tgg atg ttc atc tgc att ggc tgg ggt gtg ccc ttc ccc atc att<br>Lys Trp Met Phe Ile Cys Ile Gly Trp Gly Val Pro Phe Pro Ile Ile<br>230 235 240 | 955 |
| gtg gcc tgg gcc att ggg aag ctg tac tac gac aat gag aag tgc tgg<br>Val Ala Trp Ala Ile Gly Lys Leu Tyr Tyr Asp Asn Glu Lys Cys Trp<br>245 250 255 | 1003 |
| ttt ggc aaa agg cct ggg gtg tac acc gac tac atc tac cag ggc ccc<br>Phe Gly Lys Arg Pro Gly Val Tyr Thr Asp Tyr Ile Tyr Gln Gly Pro<br>260 265 270 275 | 1051 |
| atg atc ctg gtc ctg ctg atc aat ttc atc ttc ctt ttc aac atc gtc<br>Met Ile Leu Val Leu Leu Ile Asn Phe Ile Phe Leu Phe Asn Ile Val<br>280 285 290 | 1099 |
| cgc atc ctc atg acc aag ctc cgg gca tcc acg tct gag acc att<br>Arg Ile Leu Met Thr Lys Leu Arg Ala Ser Thr Thr Ser Glu Thr Ile<br>295 300 305 | 1147 |
| cag tac agg aag gct gtg aaa gcc act ctg gtg ctg ctg ccc ctc ctg<br>Gln Tyr Arg Lys Ala Val Lys Ala Thr Leu Val Leu Leu Pro Leu Leu<br>310 315 320 | 1195 |
| ggc atc acc tac atg ctg ttc ttc gtc aat ccc ggg gag gat gag gtc<br>Gly Ile Thr Tyr Met Leu Phe Phe Val Asn Pro Gly Glu Asp Glu Val<br>325 330 335 | 1243 |
| tcc cgg gtc gtc ttc atc tac ttc aac tcc ttc ctg gaa tcc ttc cag<br>Ser Arg Val Val Phe Ile Tyr Phe Asn Ser Phe Leu Glu Ser Phe Gln<br>340 345 350 355 | 1291 |
| ggc ttc ttt gtg tct gtg ttc tac tgt ttc ctc aat agt gag gtc cgt<br>Gly Phe Phe Val Ser Val Phe Tyr Cys Phe Leu Asn Ser Glu Val Arg<br>360 365 370 | 1339 |
| tct gcc atc cgg aag agg tgg cac cgg tgg cag gac aag cac tcg atc<br>Ser Ala Ile Arg Lys Arg Trp His Arg Trp Gln Asp Lys His Ser Ile<br>375 380 385 | 1387 |
| cgt gcc cga gtg gcc cgt gcc atg tcc atc ccc acc tcc cca acc cgt<br>Arg Ala Arg Val Ala Arg Ala Met Ser Ile Pro Thr Ser Pro Thr Arg<br>390 395 400 | 1435 |
| gtc agc ttt cac agc atc aag cag tcc aca gca gtc tga gctggcaggt<br>Val Ser Phe His Ser Ile Lys Gln Ser Thr Ala Val<br>405 410 415 | 1484 |
| catggagcag cccccaaaga gctgtggctg gggggatgac ggccaggctc cctgaccacc | 1544 |
| ctgcctgtgg aggtgacctg ttaggtctca tgcccactcc cccaggagca gctggcactg | 1604 |
| acagcctggg gggccgctc tcccctgca gccgtgcagg actctagctc atgagtggaa | 1664 |
| agtcacctac aggactgggc cgggcccagg gcctctggct tccctgccca atcctccctg | 1724 |
| gagaagggac atgggaatga attgaaatgg ggcgctggac acctacagca gcacgcatgt | 1784 |
| ccctccaagg ctgtcttctc ccagagcaca agaaggccag cccactgggc cctggggctg | 1844 |
| ccctcggcaa ccgtggggag gccatttgct gccctgggc atcatgggca actcgtgaca | 1904 |
| gcctctgact caccacgatg acgcctctgg acctcggtga tgccttccga caccactggg | 1964 |
| aaccaagggc cctcactcag gaaccctgga gacagaagtc aggtgtcatc atcagacttg | 2024 |
| cggccacagc actagagtca cccccccagg cctccagaac cttactggca ctgtggcact | 2084 |
| gccaccagca atgccctgcc ttgctgcctt caccctgaac atttagtacc ctgcaggcca | 2144 |
| ggccagcttc ccctcactta accaccccat accagtcacc tcctgctcct tttcctcttt | 2204 |
| tgtgagaaga tggggctgg agggggcaga gtggcctgtg agcaagagcc agggtgtcc | 2264 |
| cagtcccagc ctctggggca gagcttgtag ccctggatgg cctctgggc aggaccacta | 2324 |
| gctaagcaag ccaggagaag acccctgccc aagtggctct tgggacaacg tgctgcttac | 2384 |

```
actccaggtg tggaccggcc gcagccccca ctgacctgcc catgtccaga gggactggac   2444
agccagggca gggctttggg gggcactaga agatgagggt gtcggctgtg aggcgggtgg   2504
ctggtataaa taatatttat cttttcaacc ag                                 2536
```

<210> SEQ ID NO 2
<211> LENGTH: 415
<212> TYPE: PRT
<213> ORGANISM: homo sapiens

<400> SEQUENCE: 2

```
Met Gly Gly His Pro Gln Leu Arg Leu Val Lys Ala Leu Leu Leu Leu
 1               5                  10                  15

Gly Leu Asn Pro Val Ser Ala Ser Leu Gln Asp Gln His Cys Glu Ser
            20                  25                  30

Leu Ser Leu Ala Ser Asn Ile Ser Gly Leu Gln Cys Asn Ala Ser Val
        35                  40                  45

Asp Leu Ile Gly Thr Cys Trp Pro Arg Ser Pro Ala Gly Gln Leu Val
    50                  55                  60

Val Arg Pro Cys Pro Ala Phe Phe Tyr Gly Val Arg Tyr Asn Thr Thr
65                  70                  75                  80

Asn Asn Gly Tyr Arg Glu Cys Leu Ala Asn Gly Ser Trp Ala Ala Arg
                85                  90                  95

Val Asn Tyr Ser Glu Cys Gln Glu Ile Leu Asn Glu Glu Lys Lys Ser
           100                 105                 110

Lys Val His Tyr His Val Ala Val Ile Ile Asn Tyr Leu Gly His Cys
       115                 120                 125

Ile Ser Leu Val Ala Leu Leu Val Ala Phe Val Leu Phe Leu Arg Leu
   130                 135                 140

Arg Ser Ile Arg Cys Leu Arg Asn Ile Ile His Trp Asn Leu Ile Ser
145                 150                 155                 160

Ala Phe Ile Leu Arg Asn Ala Thr Trp Phe Val Val Gln Leu Thr Met
                165                 170                 175

Ser Pro Glu Val His Gln Ser Asn Val Gly Trp Cys Arg Leu Val Thr
           180                 185                 190

Ala Ala Tyr Asn Tyr Phe His Val Thr Asn Phe Phe Trp Met Phe Gly
       195                 200                 205

Glu Gly Cys Tyr Leu His Thr Ala Ile Val Leu Thr Tyr Ser Thr Asp
   210                 215                 220

Arg Leu Arg Lys Trp Met Phe Ile Cys Ile Gly Trp Gly Val Pro Phe
225                 230                 235                 240

Pro Ile Ile Val Ala Trp Ala Ile Gly Lys Leu Tyr Tyr Asp Asn Glu
                245                 250                 255

Lys Cys Trp Phe Gly Lys Arg Pro Gly Val Tyr Thr Asp Tyr Ile Tyr
           260                 265                 270

Gln Gly Pro Met Ile Leu Val Leu Leu Ile Asn Phe Ile Phe Leu Phe
       275                 280                 285

Asn Ile Val Arg Ile Leu Met Thr Lys Leu Arg Ala Ser Thr Thr Ser
   290                 295                 300

Glu Thr Ile Gln Tyr Arg Lys Ala Val Lys Ala Thr Leu Val Leu Leu
305                 310                 315                 320

Pro Leu Leu Gly Ile Thr Tyr Met Leu Phe Phe Val Asn Pro Gly Glu
                325                 330                 335

Asp Glu Val Ser Arg Val Val Phe Ile Tyr Phe Asn Ser Phe Leu Glu
```

-continued

```
                340                 345                 350
      Ser Phe Gln Gly Phe Val Ser Val Phe Tyr Cys Phe Leu Asn Ser
              355                 360                 365

Glu Val Arg Ser Ala Ile Arg Lys Arg Trp His Arg Trp Gln Asp Lys
          370                 375                 380

His Ser Ile Arg Ala Arg Val Ala Arg Ala Met Ser Ile Pro Thr Ser
      385                 390                 395                 400

Pro Thr Arg Val Ser Phe His Ser Ile Lys Gln Ser Thr Ala Val
                      405                 410                 415

<210> SEQ ID NO 3
<211> LENGTH: 1285
<212> TYPE: DNA
<213> ORGANISM: Homo sapiens
<220> FEATURE:
<221> NAME/KEY: CDS
<222> LOCATION: (38)..(1285)

<400> SEQUENCE: 3
cccgggcatt caggacggta gccgagcgag cccgagg atg gga ggg cac ccg cag      55
                                        Met Gly Gly His Pro Gln
                                          1               5 ctc cgt ctc gtc aag gcc ctt ctc ctt ctg ggg ctg aac ccc gtc tct     103
Leu Arg Leu Val Lys Ala Leu Leu Leu Leu Gly Leu Asn Pro Val Ser
             10                  15                  20 gcc tcc ctc cag gac cag cac tgc gag agc ctg tcc ctg gcc agc aac     151
Ala Ser Leu Gln Asp Gln His Cys Glu Ser Leu Ser Leu Ala Ser Asn
         25                  30                  35 atc tca gga ctg cag tgc aac gca tcc gtg gac ctc att ggc acc tgc     199
Ile Ser Gly Leu Gln Cys Asn Ala Ser Val Asp Leu Ile Gly Thr Cys
     40                  45                  50 tgg ccc cgc agc cct gcg ggg cag cta gtg gtt cgg ccc tgc cct gcc     247
Trp Pro Arg Ser Pro Ala Gly Gln Leu Val Val Arg Pro Cys Pro Ala
 55                  60                  65                  70 ttt ttc tat ggt gtc cgc tac aat acc aca aac aat ggc tac cgg gag     295
Phe Phe Tyr Gly Val Arg Tyr Asn Thr Thr Asn Asn Gly Tyr Arg Glu
                 75                  80                  85 tgc ctg gcc aat ggc agc tgg gcc gcc cgc gtg aat tac tcc gag tgc     343
Cys Leu Ala Asn Gly Ser Trp Ala Ala Arg Val Asn Tyr Ser Glu Cys
             90                  95                 100 cag gag atc ctc aat gag gag aaa aaa agc aag gtg cac tac cat gtc     391
Gln Glu Ile Leu Asn Glu Glu Lys Lys Ser Lys Val His Tyr His Val
         105                 110                 115 gca gtc atc atc aac tac ctg ggc cac tgt atc tcc ctg gtg gcc ctc     439
Ala Val Ile Ile Asn Tyr Leu Gly His Cys Ile Ser Leu Val Ala Leu
     120                 125                 130 ctg gtg gcc ttt gtc ctc ttt ctg cgg ctc agg agc atc cgg tgc ctg     487
Leu Val Ala Phe Val Leu Phe Leu Arg Leu Arg Ser Ile Arg Cys Leu
135                 140                 145                 150 cga aac atc atc cac tgg aac ctc atc tcc gcc ttc atc ctg cgc aac     535
Arg Asn Ile Ile His Trp Asn Leu Ile Ser Ala Phe Ile Leu Arg Asn
                155                 160                 165 gcc acc tgg ttc gtg gtc cag cta acc atg agc ccc gag gtc cac cag     583
Ala Thr Trp Phe Val Val Gln Leu Thr Met Ser Pro Glu Val His Gln
            170                 175                 180 agc aac gtg ggc tgg tgc agg ttg gtg aca gcc gcc tac aac tac ttc     631
Ser Asn Val Gly Trp Cys Arg Leu Val Thr Ala Ala Tyr Asn Tyr Phe
        185                 190                 195 cat gtg acc aac ttc ttc tgg atg ttc ggc gag ggc tgc tac ctg cac     679
His Val Thr Asn Phe Phe Trp Met Phe Gly Glu Gly Cys Tyr Leu His
```

|  |  |  |  |  |  |  |  |  |  |  |  |  |  |  |  |
|---|---|---|---|---|---|---|---|---|---|---|---|---|---|---|---|
|  | 200 |  |  |  | 205 |  |  |  |  | 210 |  |  |  |  |  |
| aca | gcc | atc | gtg | ctc | acc | tac | tcc | act | gac | cgg | ctg | cgc | aaa | tgg | atg | 727 |
| Thr | Ala | Ile | Val | Leu | Thr | Tyr | Ser | Thr | Asp | Arg | Leu | Arg | Lys | Trp | Met |  |
| 215 |  |  |  |  | 220 |  |  |  |  | 225 |  |  |  |  | 230 |  |
| ttc | atc | tgc | att | ggc | tgg | ggt | gtg | ccc | ttc | ccc | atc | att | gtg | gcc | tgg | 775 |
| Phe | Ile | Cys | Ile | Gly | Trp | Gly | Val | Pro | Phe | Pro | Ile | Ile | Val | Ala | Trp |  |
|  |  |  |  | 235 |  |  |  |  | 240 |  |  |  |  | 245 |  |  |
| gcc | att | ggg | aag | ctg | tac | tac | gac | aat | gag | aag | tgc | tgg | ttt | ggc | aaa | 823 |
| Ala | Ile | Gly | Lys | Leu | Tyr | Tyr | Asp | Asn | Glu | Lys | Cys | Trp | Phe | Gly | Lys |  |
|  |  | 250 |  |  |  |  | 255 |  |  |  |  | 260 |  |  |  |  |
| agg | cct | ggg | gtg | tac | acc | gac | tac | atc | tac | cag | ggc | ccc | atg | atc | ctg | 871 |
| Arg | Pro | Gly | Val | Tyr | Thr | Asp | Tyr | Ile | Tyr | Gln | Gly | Pro | Met | Ile | Leu |  |
|  |  |  | 265 |  |  |  |  | 270 |  |  |  |  | 275 |  |  |  |
| gtc | ctg | ctg | atc | aat | ttc | atc | ttc | ctt | ttc | aac | atc | gtc | cgc | atc | ctc | 919 |
| Val | Leu | Leu | Ile | Asn | Phe | Ile | Phe | Leu | Phe | Asn | Ile | Val | Arg | Ile | Leu |  |
|  |  |  | 280 |  |  |  |  | 285 |  |  |  |  | 290 |  |  |  |
| atg | acc | aag | ctc | cgg | gca | tcc | acc | acg | tct | gag | acc | att | cag | tac | agg | 967 |
| Met | Thr | Lys | Leu | Arg | Ala | Ser | Thr | Thr | Ser | Glu | Thr | Ile | Gln | Tyr | Arg |  |
| 295 |  |  |  |  | 300 |  |  |  |  | 305 |  |  |  |  | 310 |  |
| aag | gct | gtg | aaa | gcc | act | ctg | gtg | ctg | ctg | ccc | ctc | ctg | ggc | atc | acc | 1015 |
| Lys | Ala | Val | Lys | Ala | Thr | Leu | Val | Leu | Leu | Pro | Leu | Leu | Gly | Ile | Thr |  |
|  |  |  |  | 315 |  |  |  |  | 320 |  |  |  |  | 325 |  |  |
| tac | atg | ctg | ttc | ttc | gtc | aat | ccc | ggg | gag | gat | gag | gtc | tcc | cgg | gtc | 1063 |
| Tyr | Met | Leu | Phe | Phe | Val | Asn | Pro | Gly | Glu | Asp | Glu | Val | Ser | Arg | Val |  |
|  |  |  | 330 |  |  |  |  | 335 |  |  |  |  | 340 |  |  |  |
| gtc | ttc | atc | tac | ttc | aac | tcc | ttc | ctg | gaa | tcc | ttc | cag | ggc | ttc | ttt | 1111 |
| Val | Phe | Ile | Tyr | Phe | Asn | Ser | Phe | Leu | Glu | Ser | Phe | Gln | Gly | Phe | Phe |  |
|  |  |  |  | 345 |  |  |  |  | 350 |  |  |  |  | 355 |  |  |
| gtg | tct | gtg | ttc | tac | tgt | ttc | ctc | aat | agt | gag | gtc | cgt | tct | gcc | atc | 1159 |
| Val | Ser | Val | Phe | Tyr | Cys | Phe | Leu | Asn | Ser | Glu | Val | Arg | Ser | Ala | Ile |  |
|  |  | 360 |  |  |  |  | 365 |  |  |  |  | 370 |  |  |  |  |
| cgg | aag | agg | tgg | cac | cgg | tgg | cag | gac | aag | cac | tcg | atc | cgt | gcc | cga | 1207 |
| Arg | Lys | Arg | Trp | His | Arg | Trp | Gln | Asp | Lys | His | Ser | Ile | Arg | Ala | Arg |  |
| 375 |  |  |  |  | 380 |  |  |  |  | 385 |  |  |  |  | 390 |  |
| gtg | gcc | cgt | gcc | atg | tcc | atc | ccc | acc | tcc | cca | acc | cgt | gtc | agc | ttt | 1255 |
| Val | Ala | Arg | Ala | Met | Ser | Ile | Pro | Thr | Ser | Pro | Thr | Arg | Val | Ser | Phe |  |
|  |  |  |  | 395 |  |  |  |  | 400 |  |  |  |  | 405 |  |  |
| cac | agc | atc | aag | cag | tcc | aca | gca | gtc | tga |  |  |  |  |  |  | 1285 |
| His | Ser | Ile | Lys | Gln | Ser | Thr | Ala | Val |  |  |  |  |  |  |  |  |
|  |  | 410 |  |  |  |  | 415 |  |  |  |  |  |  |  |  |  |

<210> SEQ ID NO 4
<211> LENGTH: 415
<212> TYPE: PRT
<213> ORGANISM: Homo sapiens

<400> SEQUENCE: 4

Met Gly Gly His Pro Gln Leu Arg Leu Val Lys Ala Leu Leu Leu Leu
1               5                   10                  15

Gly Leu Asn Pro Val Ser Ala Ser Leu Gln Asp Gln His Cys Glu Ser
                20                  25                  30

Leu Ser Leu Ala Ser Asn Ile Ser Gly Leu Gln Cys Asn Ala Ser Val
            35                  40                  45

Asp Leu Ile Gly Thr Cys Trp Pro Arg Ser Pro Ala Gly Gln Leu Val
        50                  55                  60

Val Arg Pro Cys Pro Ala Phe Phe Tyr Gly Val Arg Tyr Asn Thr Thr
65                  70                  75                  80

Asn Asn Gly Tyr Arg Glu Cys Leu Ala Asn Gly Ser Trp Ala Ala Arg
                85                  90                  95

-continued

```
Val Asn Tyr Ser Glu Cys Gln Glu Ile Leu Asn Glu Lys Lys Ser
            100                 105                 110

Lys Val His Tyr His Val Ala Val Ile Ile Asn Tyr Leu Gly His Cys
        115                 120                 125

Ile Ser Leu Val Ala Leu Leu Val Ala Phe Val Leu Phe Leu Arg Leu
    130                 135                 140

Arg Ser Ile Arg Cys Leu Arg Asn Ile Ile His Trp Asn Leu Ile Ser
145                 150                 155                 160

Ala Phe Ile Leu Arg Asn Ala Thr Trp Phe Val Val Gln Leu Thr Met
                165                 170                 175

Ser Pro Glu Val His Gln Ser Asn Val Gly Trp Cys Arg Leu Val Thr
            180                 185                 190

Ala Ala Tyr Asn Tyr Phe His Val Thr Asn Phe Phe Trp Met Phe Gly
        195                 200                 205

Glu Gly Cys Tyr Leu His Thr Ala Ile Val Leu Thr Tyr Ser Thr Asp
    210                 215                 220

Arg Leu Arg Lys Trp Met Phe Ile Cys Ile Gly Trp Gly Val Pro Phe
225                 230                 235                 240

Pro Ile Ile Val Ala Trp Ala Ile Gly Lys Leu Tyr Tyr Asp Asn Glu
                245                 250                 255

Lys Cys Trp Phe Gly Lys Arg Pro Gly Val Tyr Thr Asp Tyr Ile Tyr
            260                 265                 270

Gln Gly Pro Met Ile Leu Val Leu Leu Ile Asn Phe Ile Phe Leu Phe
        275                 280                 285

Asn Ile Val Arg Ile Leu Met Thr Lys Leu Arg Ala Ser Thr Thr Ser
    290                 295                 300

Glu Thr Ile Gln Tyr Arg Lys Ala Val Lys Ala Thr Leu Val Leu Leu
305                 310                 315                 320

Pro Leu Leu Gly Ile Thr Tyr Met Leu Phe Phe Val Asn Pro Gly Glu
                325                 330                 335

Asp Glu Val Ser Arg Val Val Phe Ile Tyr Phe Asn Ser Phe Leu Glu
            340                 345                 350

Ser Phe Gln Gly Phe Phe Val Ser Val Phe Tyr Cys Phe Leu Asn Ser
        355                 360                 365

Glu Val Arg Ser Ala Ile Arg Lys Arg Trp His Arg Trp Gln Asp Lys
    370                 375                 380

His Ser Ile Arg Ala Arg Val Ala Arg Ala Met Ser Ile Pro Thr Ser
385                 390                 395                 400

Pro Thr Arg Val Ser Phe His Ser Ile Lys Gln Ser Thr Ala Val
                405                 410                 415
```

<210> SEQ ID NO 5
<211> LENGTH: 1146
<212> TYPE: DNA
<213> ORGANISM: Homo sapiens
<220> FEATURE:
<221> NAME/KEY: CDS
<222> LOCATION: (19)..(1146)

<400> SEQUENCE: 5

```
agccgagcga gcccgagg atg gga ggg cac ccg cag ctc cgt ctc gtc aag      51
                    Met Gly Gly His Pro Gln Leu Arg Leu Val Lys
                     1               5                  10 gcc ctt ctc ctt ctg ggg ctg aac ccc gtc tct gcc tcc ctc cag gac      99
Ala Leu Leu Leu Leu Gly Leu Asn Pro Val Ser Ala Ser Leu Gln Asp
            15                  20                  25
```

-continued

| | |
|---|---|
| cag cac tgc gag agc ctg tcc ctg gcc agc aac atc tca gac aat ggc<br>Gln His Cys Glu Ser Leu Ser Leu Ala Ser Asn Ile Ser Asp Asn Gly<br>30             35              40 | 147 |
| tac cgg gag tgc ctg gcc aat ggc agc tgg gcc gcc cgc gtg aat tac<br>Tyr Arg Glu Cys Leu Ala Asn Gly Ser Trp Ala Ala Arg Val Asn Tyr<br>45              50              55 | 195 |
| tcc gag tgc cag gag atc ctc aat gag gag aaa aaa agc aag gtg cac<br>Ser Glu Cys Gln Glu Ile Leu Asn Glu Glu Lys Lys Ser Lys Val His<br>60              65              70              75 | 243 |
| tac cat gtc gca gtc atc atc aac tac ctg ggc cac tgt atc tcc ctg<br>Tyr His Val Ala Val Ile Ile Asn Tyr Leu Gly His Cys Ile Ser Leu<br>80              85              90 | 291 |
| gtg gcc ctc ctg gtg gcc ttt gtc ctc ttt ctg cgg ctc agg agc atc<br>Val Ala Leu Leu Val Ala Phe Val Leu Phe Leu Arg Leu Arg Ser Ile<br>95              100             105 | 339 |
| cgg tgc ctg cga aac atc atc cac tgg aac ctc atc tcc gcc ttc atc<br>Arg Cys Leu Arg Asn Ile Ile His Trp Asn Leu Ile Ser Ala Phe Ile<br>110             115             120 | 387 |
| ctg cgc aac gcc acc tgg ttc gtg gtc cag cta acc atg agc ccc gag<br>Leu Arg Asn Ala Thr Trp Phe Val Val Gln Leu Thr Met Ser Pro Glu<br>125             130             135 | 435 |
| gtc cac cag agc aac gtg ggc tgg tgc agg ttg gtg aca gcc gcc tac<br>Val His Gln Ser Asn Val Gly Trp Cys Arg Leu Val Thr Ala Ala Tyr<br>140             145             150             155 | 483 |
| aac tac ttc cat gtg acc aac ttc ttc tgg atg ttc ggc gag ggc tgc<br>Asn Tyr Phe His Val Thr Asn Phe Phe Trp Met Phe Gly Glu Gly Cys<br>160             165             170 | 531 |
| tac ctg cac aca gcc atc gtg ctc acc tac tcc act gac cgg ctg cgc<br>Tyr Leu His Thr Ala Ile Val Leu Thr Tyr Ser Thr Asp Arg Leu Arg<br>175             180             185 | 579 |
| aaa tgg atg ttc atc tgc att ggc tgg ggt gtg ccc ttc ccc atc att<br>Lys Trp Met Phe Ile Cys Ile Gly Trp Gly Val Pro Phe Pro Ile Ile<br>190             195             200 | 627 |
| gtg gcc tgg gcc att ggg aag ctg tac tac gac aat gag aag tgc tgg<br>Val Ala Trp Ala Ile Gly Lys Leu Tyr Tyr Asp Asn Glu Lys Cys Trp<br>205             210             215 | 675 |
| ttt ggc aaa agg cct ggg gtg tac acc gac tac atc tac cag ggc ccc<br>Phe Gly Lys Arg Pro Gly Val Tyr Thr Asp Tyr Ile Tyr Gln Gly Pro<br>220             225             230             235 | 723 |
| atg atc ctg gtc ctg ctg atc aat ttc atc ttc ctt ttc aac atc gtc<br>Met Ile Leu Val Leu Leu Ile Asn Phe Ile Phe Leu Phe Asn Ile Val<br>240             245             250 | 771 |
| cgc atc ctc atg acc aag ctc cgg gca tcc acc acg tct gag acc att<br>Arg Ile Leu Met Thr Lys Leu Arg Ala Ser Thr Thr Ser Glu Thr Ile<br>255             260             265 | 819 |
| cag tac agg aag gct gtg aaa gcc act ctg gtg ctg ctg ccc ctc ctg<br>Gln Tyr Arg Lys Ala Val Lys Ala Thr Leu Val Leu Leu Pro Leu Leu<br>270             275             280 | 867 |
| ggc atc acc tac atg ctg ttc ttc gtc aat ccc ggg gag gat gag gtc<br>Gly Ile Thr Tyr Met Leu Phe Phe Val Asn Pro Gly Glu Asp Glu Val<br>285             290             295 | 915 |
| tcc cgg gtc gtc ttc atc tac ttc aac tcc ttc ctg gaa tcc ttc cag<br>Ser Arg Val Val Phe Ile Tyr Phe Asn Ser Phe Leu Glu Ser Phe Gln<br>300             305             310             315 | 963 |
| ggc ttc ttt gtg tct gtg ttc tac tgt ttc ctc aat agt gag gtc cgt<br>Gly Phe Phe Val Ser Val Phe Tyr Cys Phe Leu Asn Ser Glu Val Arg<br>320             325             330 | 1011 |
| tct gcc atc cgg aag agg tgg cac cgg tgg cag gac aag cac tcg atc<br>Ser Ala Ile Arg Lys Arg Trp His Arg Trp Gln Asp Lys His Ser Ile | 1059 |

```
                335                 340                 345
cgt gcc cga gtg gcc cgt gcc atg tcc atc ccc acc tcc cca acc cgt    1107
Arg Ala Arg Val Ala Arg Ala Met Ser Ile Pro Thr Ser Pro Thr Arg
        350                 355                 360 gtc agc ttt cac agc atc aag cag tcc aca gca gtc tga                1146
Val Ser Phe His Ser Ile Lys Gln Ser Thr Ala Val
    365                 370                 375

<210> SEQ ID NO 6
<211> LENGTH: 375
<212> TYPE: PRT
<213> ORGANISM: Homo sapiens

<400> SEQUENCE: 6

Met Gly Gly His Pro Gln Leu Arg Leu Val Lys Ala Leu Leu Leu Leu
1               5                   10                  15

Gly Leu Asn Pro Val Ser Ala Ser Leu Gln Asp Gln His Cys Glu Ser
            20                  25                  30

Leu Ser Leu Ala Ser Asn Ile Ser Asp Asn Gly Tyr Arg Glu Cys Leu
        35                  40                  45

Ala Asn Gly Ser Trp Ala Ala Arg Val Asn Tyr Ser Glu Cys Gln Glu
    50                  55                  60

Ile Leu Asn Glu Glu Lys Lys Ser Lys Val His Tyr His Val Ala Val
65                  70                  75                  80

Ile Ile Asn Tyr Leu Gly His Cys Ile Ser Leu Val Ala Leu Leu Val
                85                  90                  95

Ala Phe Val Leu Phe Leu Arg Leu Arg Ser Ile Arg Cys Leu Arg Asn
            100                 105                 110

Ile Ile His Trp Asn Leu Ile Ser Ala Phe Ile Leu Arg Asn Ala Thr
        115                 120                 125

Trp Phe Val Val Gln Leu Thr Met Ser Pro Glu Val His Gln Ser Asn
    130                 135                 140

Val Gly Trp Cys Arg Leu Val Thr Ala Ala Tyr Asn Tyr Phe His Val
145                 150                 155                 160

Thr Asn Phe Phe Trp Met Phe Gly Glu Gly Cys Tyr Leu His Thr Ala
                165                 170                 175

Ile Val Leu Thr Tyr Ser Thr Asp Arg Leu Arg Lys Trp Met Phe Ile
            180                 185                 190

Cys Ile Gly Trp Gly Val Pro Phe Pro Ile Ile Val Ala Trp Ala Ile
        195                 200                 205

Gly Lys Leu Tyr Tyr Asp Asn Glu Lys Cys Trp Phe Gly Lys Arg Pro
    210                 215                 220

Gly Val Tyr Thr Asp Tyr Ile Tyr Gln Gly Pro Met Ile Leu Val Leu
225                 230                 235                 240

Leu Ile Asn Phe Ile Phe Leu Phe Asn Ile Val Arg Ile Leu Met Thr
                245                 250                 255

Lys Leu Arg Ala Ser Thr Thr Ser Glu Thr Ile Gln Tyr Arg Lys Ala
            260                 265                 270

Val Lys Ala Thr Leu Val Leu Leu Pro Leu Leu Gly Ile Thr Tyr Met
        275                 280                 285

Leu Phe Phe Val Asn Pro Gly Glu Asp Glu Val Ser Arg Val Val Phe
    290                 295                 300

Ile Tyr Phe Asn Ser Phe Leu Glu Ser Phe Gln Gly Phe Phe Val Ser
305                 310                 315                 320

Val Phe Tyr Cys Phe Leu Asn Ser Glu Val Arg Ser Ala Ile Arg Lys
```

```
                        325                 330                 335
Arg Trp His Arg Trp Gln Asp Lys His Ser Ile Arg Ala Arg Val Ala
                340                 345                 350
Arg Ala Met Ser Ile Pro Thr Ser Pro Thr Arg Val Ser Phe His Ser
            355                 360                 365
Ile Lys Gln Ser Thr Ala Val
        370                 375

<210> SEQ ID NO 7
<211> LENGTH: 1206
<212> TYPE: DNA
<213> ORGANISM: Homo sapiens
<220> FEATURE:
<221> NAME/KEY: CDS
<222> LOCATION: (1)..(1206)

<400> SEQUENCE: 7 atg gga ggg cac ccg cag ctc cgt ctc gtc aag gcc ctt ctc ctt ctg      48
Met Gly Gly His Pro Gln Leu Arg Leu Val Lys Ala Leu Leu Leu Leu
  1               5                  10                  15 ggg ctg aac ccc gtc tct gcc tcc ctc cag gac cag cac tgc gag agc      96
Gly Leu Asn Pro Val Ser Ala Ser Leu Gln Asp Gln His Cys Glu Ser
             20                  25                  30 ctg tcc ctg gcc agc aac atc tca gga ctg cag tgc aac gca tcc gtg     144
Leu Ser Leu Ala Ser Asn Ile Ser Gly Leu Gln Cys Asn Ala Ser Val
         35                  40                  45 gac ctc att ggc acc tgc tgg ccc cgc agc cct gcg ggg cag cta gtg     192
Asp Leu Ile Gly Thr Cys Trp Pro Arg Ser Pro Ala Gly Gln Leu Val
     50                  55                  60 gtt cgg ccc tgc cct gcc ttt ttc tat ggt gtc cgc tac aat acc aca     240
Val Arg Pro Cys Pro Ala Phe Phe Tyr Gly Val Arg Tyr Asn Thr Thr
 65                  70                  75                  80 aac aat ggc tac cgg gag tgc ctg gcc aat ggc agc tgg gcc gcc cgc     288
Asn Asn Gly Tyr Arg Glu Cys Leu Ala Asn Gly Ser Trp Ala Ala Arg
                 85                  90                  95 gtg aat tac tcc gag tgc cag gag atc ctc aat gag gag aaa aaa agc     336
Val Asn Tyr Ser Glu Cys Gln Glu Ile Leu Asn Glu Glu Lys Lys Ser
            100                 105                 110 aag gtg cac tac cat gtc gca gtc atc atc aac tac ctg ggc cac tgt     384
Lys Val His Tyr His Val Ala Val Ile Ile Asn Tyr Leu Gly His Cys
        115                 120                 125 atc tcc ctg gtg gcc ctc ctg gtg gcc ttt gtc ctc ttt ctg cgg ctc     432
Ile Ser Leu Val Ala Leu Leu Val Ala Phe Val Leu Phe Leu Arg Leu
    130                 135                 140 agg agc atc cgg tgc ctg cga aac atc atc cac tgg aac ctc atc tcc     480
Arg Ser Ile Arg Cys Leu Arg Asn Ile Ile His Trp Asn Leu Ile Ser
145                 150                 155                 160 gcc ttc atc ctg cgc aac gcc acc tgg ttc gtg gtc cag cta acc atg     528
Ala Phe Ile Leu Arg Asn Ala Thr Trp Phe Val Val Gln Leu Thr Met
                165                 170                 175 agc ccc gag gtc cac cag agc aac gtg ggc tgg tgc agg ttg gtg aca     576
Ser Pro Glu Val His Gln Ser Asn Val Gly Trp Cys Arg Leu Val Thr
            180                 185                 190 gcc gcc tac aac tac ttc cat gtg acc aac ttc ttc tgg atg ttc ggc     624
Ala Ala Tyr Asn Tyr Phe His Val Thr Asn Phe Phe Trp Met Phe Gly
        195                 200                 205 gag ggc tgc tac ctg cac aca gcc atc gtg ctc acc tac tcc act gac     672
Glu Gly Cys Tyr Leu His Thr Ala Ile Val Leu Thr Tyr Ser Thr Asp
    210                 215                 220 cgg ctg cgc aaa tgg atg ttc atc tgc att ggc tgg ggt gtg ccc ttc     720
```

```
Arg Leu Arg Lys Trp Met Phe Ile Cys Ile Gly Trp Gly Val Pro Phe
225                 230                 235                 240 ccc atc att gtg gcc tgg gcc att ggg aag ctg tac tac gac aat gag      768
Pro Ile Ile Val Ala Trp Ala Ile Gly Lys Leu Tyr Tyr Asp Asn Glu
                    245                 250                 255 aag tgc tgg ttt ggc aaa agg cct ggg gtg tac acc gac tac atc tac      816
Lys Cys Trp Phe Gly Lys Arg Pro Gly Val Tyr Thr Asp Tyr Ile Tyr
            260                 265                 270 cag ggc ccc atg atc ctg gtc ctg ctg atc aat ttc atc ttc ctt ttc      864
Gln Gly Pro Met Ile Leu Val Leu Leu Ile Asn Phe Ile Phe Leu Phe
        275                 280                 285 aac atc gtc cgc atc ctc atg acc aag ctc cgg gca tcc acc acg tct      912
Asn Ile Val Arg Ile Leu Met Thr Lys Leu Arg Ala Ser Thr Thr Ser
290                 295                 300 gag acc att cag tac agg aag gct gtg aaa gcc act ctg gtg ctg ctg      960
Glu Thr Ile Gln Tyr Arg Lys Ala Val Lys Ala Thr Leu Val Leu Leu
305                 310                 315                 320 ccc ctc ctg ggc atc acc tac atg ctg ttc ttc gtc aat ccc ggg gag      1008
Pro Leu Leu Gly Ile Thr Tyr Met Leu Phe Phe Val Asn Pro Gly Glu
                    325                 330                 335 gat gag gtc tcc cgg gtc gtc ttc atc tac ttc aac tcc ttc ctg gaa      1056
Asp Glu Val Ser Arg Val Val Phe Ile Tyr Phe Asn Ser Phe Leu Glu
            340                 345                 350 tcc ttc cag gtc cgt tct gcc atc cgg aag agg tgg cac cgg tgg cag      1104
Ser Phe Gln Val Arg Ser Ala Ile Arg Lys Arg Trp His Arg Trp Gln
        355                 360                 365 gac aag cac tcg atc cgt gcc cga gtg gcc cgt gcc atg tcc atc ccc      1152
Asp Lys His Ser Ile Arg Ala Arg Val Ala Arg Ala Met Ser Ile Pro
370                 375                 380 acc tcc cca acc cgt gtc agc ttt cac agc atc aag cag tcc aca gca      1200
Thr Ser Pro Thr Arg Val Ser Phe His Ser Ile Lys Gln Ser Thr Ala
385                 390                 395                 400 gtc tga                                                               1206
Val

<210> SEQ ID NO 8
<211> LENGTH: 401
<212> TYPE: PRT
<213> ORGANISM: Homo sapiens

<400> SEQUENCE: 8

Met Gly Gly His Pro Gln Leu Arg Leu Val Lys Ala Leu Leu Leu Leu
1               5                   10                  15

Gly Leu Asn Pro Val Ser Ala Ser Leu Gln Asp Gln His Cys Glu Ser
                20                  25                  30

Leu Ser Leu Ala Ser Asn Ile Ser Gly Leu Gln Cys Asn Ala Ser Val
            35                  40                  45

Asp Leu Ile Gly Thr Cys Trp Pro Arg Ser Pro Ala Gly Gln Leu Val
50                  55                  60

Val Arg Pro Cys Pro Ala Phe Phe Tyr Gly Val Arg Tyr Asn Thr Thr
65                  70                  75                  80

Asn Asn Gly Tyr Arg Glu Cys Leu Ala Asn Gly Ser Trp Ala Ala Arg
                85                  90                  95

Val Asn Tyr Ser Glu Cys Gln Glu Ile Leu Asn Glu Glu Lys Lys Ser
            100                 105                 110

Lys Val His Tyr His Val Ala Val Ile Ile Asn Tyr Leu Gly His Cys
        115                 120                 125

Ile Ser Leu Val Ala Leu Leu Val Ala Phe Val Leu Phe Leu Arg Leu
```

```
              130                 135                 140
Arg Ser Ile Arg Cys Leu Arg Asn Ile Ile His Trp Asn Leu Ile Ser
145                 150                 155                 160

Ala Phe Ile Leu Arg Asn Ala Thr Trp Phe Val Val Gln Leu Thr Met
                165                 170                 175

Ser Pro Glu Val His Gln Ser Asn Val Gly Trp Cys Arg Leu Val Thr
                180                 185                 190

Ala Ala Tyr Asn Tyr Phe His Val Thr Asn Phe Phe Trp Met Phe Gly
                195                 200                 205

Glu Gly Cys Tyr Leu His Thr Ala Ile Val Leu Thr Tyr Ser Thr Asp
210                 215                 220

Arg Leu Arg Lys Trp Met Phe Ile Cys Ile Gly Trp Gly Val Pro Phe
225                 230                 235                 240

Pro Ile Ile Val Ala Trp Ala Ile Gly Lys Leu Tyr Tyr Asp Asn Glu
                245                 250                 255

Lys Cys Trp Phe Gly Lys Arg Pro Gly Val Tyr Thr Asp Tyr Ile Tyr
                260                 265                 270

Gln Gly Pro Met Ile Leu Val Leu Leu Ile Asn Phe Ile Phe Leu Phe
                275                 280                 285

Asn Ile Val Arg Ile Leu Met Thr Lys Leu Arg Ala Ser Thr Thr Ser
290                 295                 300

Glu Thr Ile Gln Tyr Arg Lys Ala Val Lys Ala Thr Leu Val Leu Leu
305                 310                 315                 320

Pro Leu Leu Gly Ile Thr Tyr Met Leu Phe Phe Val Asn Pro Gly Glu
                325                 330                 335

Asp Glu Val Ser Arg Val Val Phe Ile Tyr Phe Asn Ser Phe Leu Glu
                340                 345                 350

Ser Phe Gln Val Arg Ser Ala Ile Arg Lys Arg Trp His Arg Trp Gln
                355                 360                 365

Asp Lys His Ser Ile Arg Ala Arg Val Ala Arg Ala Met Ser Ile Pro
                370                 375                 380

Thr Ser Pro Thr Arg Val Ser Phe His Ser Ile Lys Gln Ser Thr Ala
385                 390                 395                 400

Val

<210> SEQ ID NO 9
<211> LENGTH: 2110
<212> TYPE: DNA
<213> ORGANISM: Homo sapiens
<220> FEATURE:
<221> NAME/KEY: CDS
<222> LOCATION: (1)..(1236)

<400> SEQUENCE: 9 atg gac gcg gca ctg ctc cac agc ctg ctg gag gcc aac tgc agc ctg      48
Met Asp Ala Ala Leu Leu His Ser Leu Leu Glu Ala Asn Cys Ser Leu
1               5                   10                  15 gcg ctg gct gaa gag ctg ctc ttg gac ggc tgg ggg cca ccc ctg gac      96
Ala Leu Ala Glu Glu Leu Leu Leu Asp Gly Trp Gly Pro Pro Leu Asp
            20                  25                  30 ccc gag ggt ccc tac tcc tac tgc aac acg acc ttg gac cag atc gga     144
Pro Glu Gly Pro Tyr Ser Tyr Cys Asn Thr Thr Leu Asp Gln Ile Gly
        35                  40                  45 acg tgc tgg ccc cgc agc gct gcc gga gcc ctc gtg gag agg ccg tgc     192
Thr Cys Trp Pro Arg Ser Ala Ala Gly Ala Leu Val Glu Arg Pro Cys
    50                  55                  60
```

-continued

| | |
|---|---|
| ccc gag tac ttc aac ggc gtc aag tac aac acg acc cgg aat gcc tat<br>Pro Glu Tyr Phe Asn Gly Val Lys Tyr Asn Thr Thr Arg Asn Ala Tyr<br>65                    70                    75                    80 | 240 |
| cga gaa tgc ttg gag aat ggg acg tgg gcc tca aag atc aac tac tca<br>Arg Glu Cys Leu Glu Asn Gly Thr Trp Ala Ser Lys Ile Asn Tyr Ser<br>                    85                    90                    95 | 288 |
| cag tgt gag ccc att ttg gat gac aag cag agg aag tat gac ctg cac<br>Gln Cys Glu Pro Ile Leu Asp Asp Lys Gln Arg Lys Tyr Asp Leu His<br>          100                    105                    110 | 336 |
| tac cgc atc gcc ctt gtc gtc aac tac ctg ggc cac tgc gta tct gtg<br>Tyr Arg Ile Ala Leu Val Val Asn Tyr Leu Gly His Cys Val Ser Val<br>               115                    120                    125 | 384 |
| gca gcc ctg gtg gcc gcc ttc ctg ctt ttc ctg gcc ctg cgg agc att<br>Ala Ala Leu Val Ala Ala Phe Leu Leu Phe Leu Ala Leu Arg Ser Ile<br>130                      135                    140 | 432 |
| cgc tgt ctg cgg aat gtg att cac tgg aac ctc atc acc acc ttt atc<br>Arg Cys Leu Arg Asn Val Ile His Trp Asn Leu Ile Thr Thr Phe Ile<br>145                    150                    155                    160 | 480 |
| ctg cga aat gtc atg tgg ttc ctg ctg cag ctc gtt gac cat gaa gtg<br>Leu Arg Asn Val Met Trp Phe Leu Leu Gln Leu Val Asp His Glu Val<br>               165                    170                    175 | 528 |
| cac gag agc aat gag gtc tgg tgc cac tgc atc acc acc atc ttc aac<br>His Glu Ser Asn Glu Val Trp Cys His Cys Ile Thr Thr Ile Phe Asn<br>                    180                    185                    190 | 576 |
| tac ttc gtg gtg acc aac ttc ttc tgg atg ttt gtg gaa ggc tgc tac<br>Tyr Phe Val Val Thr Asn Phe Phe Trp Met Phe Val Glu Gly Cys Tyr<br>               195                    200                    205 | 624 |
| ctg cac acg gcc att gtc atg acc tac tcc act gag cgc ctg cgc aag<br>Leu His Thr Ala Ile Val Met Thr Tyr Ser Thr Glu Arg Leu Arg Lys<br>          210                    215                    220 | 672 |
| tgc ctc ttc ctc ttc atc gga tgg tgc atc ccc ttc ccc atc atc gtc<br>Cys Leu Phe Leu Phe Ile Gly Trp Cys Ile Pro Phe Pro Ile Ile Val<br>225                      230                    235                    240 | 720 |
| gcc tgg gcc atc ggc aag ctc tac tat gag aat gaa cag tgc tgg ttt<br>Ala Trp Ala Ile Gly Lys Leu Tyr Tyr Glu Asn Glu Gln Cys Trp Phe<br>                    245                    250                    255 | 768 |
| ggc aag gag cct ggc gac ctg gtg gac tac atc tac caa ggc ccc atc<br>Gly Lys Glu Pro Gly Asp Leu Val Asp Tyr Ile Tyr Gln Gly Pro Ile<br>          260                    265                    270 | 816 |
| att ctc gtg ctc ctg atc aat ttc gta ttt ctg ttc aac atc gtc agg<br>Ile Leu Val Leu Leu Ile Asn Phe Val Phe Leu Phe Asn Ile Val Arg<br>               275                    280                    285 | 864 |
| atc cta atg aca aag tta cgc gcg tcc acc aca tcc gag aca atc cag<br>Ile Leu Met Thr Lys Leu Arg Ala Ser Thr Thr Ser Glu Thr Ile Gln<br>          290                    295                    300 | 912 |
| tac agg aag gca gtg aag gcc acc ctg gtg ctc ctg ccc ctc ctg ggc<br>Tyr Arg Lys Ala Val Lys Ala Thr Leu Val Leu Leu Pro Leu Leu Gly<br>305                      310                    315                    320 | 960 |
| atc acc tac atg ctc ttc ttc gtc aat ccc ggg gag gac gac ctg tca<br>Ile Thr Tyr Met Leu Phe Phe Val Asn Pro Gly Glu Asp Asp Leu Ser<br>               325                    330                    335 | 1008 |
| cag atc atg ttc atc tat ttc aac tcc ttc ctg cag tcg ttc cag ggt<br>Gln Ile Met Phe Ile Tyr Phe Asn Ser Phe Leu Gln Ser Phe Gln Gly<br>          340                    345                    350 | 1056 |
| ttc ttc gtg tct gtc ttc tac tgc ttc ttc aat gga gag gtg cgc tca<br>Phe Phe Val Ser Val Phe Tyr Cys Phe Phe Asn Gly Glu Val Arg Ser<br>               355                    360                    365 | 1104 |
| gcc gtg agg aag agg tgg cac cgc tgg cag gac cat cac tcc ctt cga<br>Ala Val Arg Lys Arg Trp His Arg Trp Gln Asp His His Ser Leu Arg<br>          370                    375                    380 | 1152 |

```
gtc ccc atg gcc cgg gcc atg tcc atc cct aca tca ccc aca cgg atc    1200
Val Pro Met Ala Arg Ala Met Ser Ile Pro Thr Ser Pro Thr Arg Ile
385                 390                 395                 400 agc ttc cac agc atc aag cag acg gcc gct gtg tga cccctcggtc         1246
Ser Phe His Ser Ile Lys Gln Thr Ala Ala Val
                405                 410 gcccacctgc acagtcccc tgtcctcctc caccttcttc ctctgggttc tctgtgctgg   1306
gcaggctctc gtggggcagg agatgggagg ggagagacca gctctccagc ctggcaggaa  1366 agaggggtg cggcagccaa ggggactgc aagggacagg gatgagtggg ggccaccagg    1426
ctcagcgcaa gaggaagcag agggaattca caggaccccc tgagaagagc cagtcagatg  1486
tctgcaggca tttgcccatc ccagcctctc tggccaggc cttactgggc ccagagcaga   1546
gaaggacctg tccaacacac acagctattt atagtagcag acacagggct cccctgccct  1606
actcatggag ccagcagcca ggcaatggtg tggccctgca ctggcccttg gactccacac  1666
tcagtggtgc cctgcagttg ggtgggttaa cgccaagcaa aggatcagtt tggctgcctt  1726
atcccagggc tgtcacctag agaggctcac ttgtacccca ccctgttcct gtgtcccctc  1786
cccagccatc ctccccgcct tgggggctcc atgaaggatg caggcttcca ggcctggctt  1846
cctctcttgg gagacccctt ctctgcctag tccacagatt aggcaatcaa ggaagacgcc  1906
atcagggaag ccacatcctt agtcaaccag ttgcatcgtg cggggcaaaa tgaggagcag  1966
aggcatggag gagggaggcg tgggatggga atagcagaac caccatgtct tcagtgattg  2026
aaactcatac cccattgccc tttgccctcc agtctcccct tcagaaacat ctctgctctc  2086
tgtgaaataa accatgcctc ttgg                                         2110
```

<210> SEQ ID NO 10
<211> LENGTH: 411
<212> TYPE: PRT
<213> ORGANISM: Homo sapiens

<400> SEQUENCE: 10

```
Met Asp Ala Ala Leu Leu His Ser Leu Leu Glu Ala Asn Cys Ser Leu
1               5                   10                  15

Ala Leu Ala Glu Glu Leu Leu Leu Asp Gly Trp Gly Pro Pro Leu Asp
                20                  25                  30

Pro Glu Gly Pro Tyr Ser Tyr Cys Asn Thr Thr Leu Asp Gln Ile Gly
            35                  40                  45

Thr Cys Trp Pro Arg Ser Ala Gly Ala Leu Val Glu Arg Pro Cys
        50                  55                  60

Pro Glu Tyr Phe Asn Gly Val Lys Tyr Asn Thr Thr Arg Asn Ala Tyr
65                  70                  75                  80

Arg Glu Cys Leu Glu Asn Gly Thr Trp Ala Ser Lys Ile Asn Tyr Ser
                85                  90                  95

Gln Cys Glu Pro Ile Leu Asp Asp Lys Gln Arg Lys Tyr Asp Leu His
            100                 105                 110

Tyr Arg Ile Ala Leu Val Val Asn Tyr Leu Gly His Cys Val Ser Val
        115                 120                 125

Ala Ala Leu Val Ala Ala Phe Leu Leu Phe Leu Ala Leu Arg Ser Ile
    130                 135                 140

Arg Cys Leu Arg Asn Val Ile His Trp Asn Leu Ile Thr Thr Phe Ile
145                 150                 155                 160

Leu Arg Asn Val Met Trp Phe Leu Leu Gln Leu Val Asp His Glu Val
                165                 170                 175
```

```
His Glu Ser Asn Glu Val Trp Cys His Cys Ile Thr Thr Ile Phe Asn
            180                 185                 190
Tyr Phe Val Val Thr Asn Phe Phe Trp Met Phe Val Glu Gly Cys Tyr
        195                 200                 205
Leu His Thr Ala Ile Val Met Thr Tyr Ser Thr Glu Arg Leu Arg Lys
        210                 215                 220
Cys Leu Phe Leu Phe Ile Gly Trp Cys Ile Pro Phe Pro Ile Ile Val
225                 230                 235                 240
Ala Trp Ala Ile Gly Lys Leu Tyr Tyr Glu Asn Glu Gln Cys Trp Phe
                245                 250                 255
Gly Lys Glu Pro Gly Asp Leu Val Asp Tyr Ile Tyr Gln Gly Pro Ile
            260                 265                 270
Ile Leu Val Leu Leu Ile Asn Phe Val Phe Leu Phe Asn Ile Val Arg
        275                 280                 285
Ile Leu Met Thr Lys Leu Arg Ala Ser Thr Thr Ser Glu Thr Ile Gln
        290                 295                 300
Tyr Arg Lys Ala Val Lys Ala Thr Leu Val Leu Leu Pro Leu Leu Gly
305                 310                 315                 320
Ile Thr Tyr Met Leu Phe Phe Val Asn Pro Gly Glu Asp Asp Leu Ser
                325                 330                 335
Gln Ile Met Phe Ile Tyr Phe Asn Ser Phe Leu Gln Ser Phe Gln Gly
            340                 345                 350
Phe Phe Val Ser Val Phe Tyr Cys Phe Phe Asn Gly Glu Val Arg Ser
        355                 360                 365
Ala Val Arg Lys Arg Trp His Arg Trp Gln Asp His His Ser Leu Arg
        370                 375                 380
Val Pro Met Ala Arg Ala Met Ser Ile Pro Thr Ser Pro Thr Arg Ile
385                 390                 395                 400
Ser Phe His Ser Ile Lys Gln Thr Ala Ala Val
                405                 410

<210> SEQ ID NO 11
<211> LENGTH: 1600
<212> TYPE: DNA
<213> ORGANISM: Homo sapiens
<220> FEATURE:
<221> NAME/KEY: CDS
<222> LOCATION: (71)..(1387)

<400> SEQUENCE: 11
ggggctggcc agggtgtgac caccgtgctg gcagcaggc tccagtccct aaccccccagc      60 cactactggc atg agg ggt ccc tca ggg ccc cca ggc ctc ctc tac gtc        109
            Met Arg Gly Pro Ser Gly Pro Pro Gly Leu Leu Tyr Val
              1               5                   10 cca cac ctc ctc ctc tgc ctg ctc tgc ctc ctc cca ccg ccg ctc caa      157
Pro His Leu Leu Leu Cys Leu Leu Cys Leu Leu Pro Pro Pro Leu Gln
        15                  20                  25 tac gca gcc ggg cag agc cag atg ccc aaa gac cag ccc ctg tgg gca      205
Tyr Ala Ala Gly Gln Ser Gln Met Pro Lys Asp Gln Pro Leu Trp Ala
30                  35                  40                  45 ctt ctg gag cag tac tgc cac acc atc atg acc ctc acc aac ctc tca      253
Leu Leu Glu Gln Tyr Cys His Thr Ile Met Thr Leu Thr Asn Leu Ser
                50                  55                  60 ggt ccc tac tcc tac tgc aac acg acc ttg gac cag atc gga acg tgc      301
Gly Pro Tyr Ser Tyr Cys Asn Thr Thr Leu Asp Gln Ile Gly Thr Cys
            65                  70                  75
```

-continued

| | |
|---|---|
| tgg ccc cgc agc gct gcc gga gcc ctc gtg gag agg ccg tgc ccc gag<br>Trp Pro Arg Ser Ala Ala Gly Ala Leu Val Glu Arg Pro Cys Pro Glu<br>        80                      85                      90 | 349 |
| tac ttc aac ggc gtc aag tac aac acg acc cgg aat gcc tat cga gaa<br>Tyr Phe Asn Gly Val Lys Tyr Asn Thr Thr Arg Asn Ala Tyr Arg Glu<br>        95                      100                      105 | 397 |
| tgc ttg gag aat ggg acg tgg gcc tca aag atc aac tac tca cag tgt<br>Cys Leu Glu Asn Gly Thr Trp Ala Ser Lys Ile Asn Tyr Ser Gln Cys<br>110                      115                      120                      125 | 445 |
| gag ccc att ttg gat gac aag cag agg aag tat gac ctg cac tac cgc<br>Glu Pro Ile Leu Asp Asp Lys Gln Arg Lys Tyr Asp Leu His Tyr Arg<br>                      130                      135                      140 | 493 |
| atc gcc ctt gtc gtc aac tac ctg ggc cac tgc gta tct gtg gca gcc<br>Ile Ala Leu Val Val Asn Tyr Leu Gly His Cys Val Ser Val Ala Ala<br>                  145                      150                      155 | 541 |
| ctg gtg gcc gcc ttc ctg ctt ttc ctg gcc ctg cgg agc att cgc tgt<br>Leu Val Ala Ala Phe Leu Leu Phe Leu Ala Leu Arg Ser Ile Arg Cys<br>                160                      165                      170 | 589 |
| ctg cgg aat gtg att cac tgg aac ctc atc acc acc ttt atc ctg cga<br>Leu Arg Asn Val Ile His Trp Asn Leu Ile Thr Thr Phe Ile Leu Arg<br>175                      180                      185 | 637 |
| aat gtc atg tgg ttc ctg ctg cag ctc gtt gac cat gaa gtg cac gag<br>Asn Val Met Trp Phe Leu Leu Gln Leu Val Asp His Glu Val His Glu<br>190                      195                      200                      205 | 685 |
| agc aat gag gtc tgg tgc cgc tgc atc acc acc atc ttc aac tac ttc<br>Ser Asn Glu Val Trp Cys Arg Cys Ile Thr Thr Ile Phe Asn Tyr Phe<br>                  210                      215                      220 | 733 |
| gtg gtg acc aac ttc ttc tgg atg ttt gtg gaa ggc tgc tac ctg cac<br>Val Val Thr Asn Phe Phe Trp Met Phe Val Glu Gly Cys Tyr Leu His<br>                  225                      230                      235 | 781 |
| acg gcc att gtc atg acc tac tcc act gag cgc ctg cgc aag tgc ctc<br>Thr Ala Ile Val Met Thr Tyr Ser Thr Glu Arg Leu Arg Lys Cys Leu<br>                240                      245                      250 | 829 |
| ttc ctc ttc atc gga tgg tgc atc ccc ttc ccc atc atc gtc gcc tgg<br>Phe Leu Phe Ile Gly Trp Cys Ile Pro Phe Pro Ile Ile Val Ala Trp<br>255                      260                      265 | 877 |
| gcc atc ggc aag ctc tac tat gag aat gaa cag tgc tgg ttt ggc aag<br>Ala Ile Gly Lys Leu Tyr Tyr Glu Asn Glu Gln Cys Trp Phe Gly Lys<br>270                      275                      280                      285 | 925 |
| gag cct ggc gac ctg gtg gac tac atc tac caa ggc ccc atc att ctc<br>Glu Pro Gly Asp Leu Val Asp Tyr Ile Tyr Gln Gly Pro Ile Ile Leu<br>                  290                      295                      300 | 973 |
| gtg ctc ctg atc aat ttc gta ttt ctg ttc aac atc gtc agg atc cta<br>Val Leu Leu Ile Asn Phe Val Phe Leu Phe Asn Ile Val Arg Ile Leu<br>                305                      310                      315 | 1021 |
| atg aca aag tta cgc gcg tcc acc aca tcc gag aca atc cag tac agg<br>Met Thr Lys Leu Arg Ala Ser Thr Thr Ser Glu Thr Ile Gln Tyr Arg<br>                320                      325                      330 | 1069 |
| aag gca gtg aag gcc acc ctg gtg ctc ctg ccc ctc ctg ggc atc acc<br>Lys Ala Val Lys Ala Thr Leu Val Leu Leu Pro Leu Leu Gly Ile Thr<br>335                      340                      345 | 1117 |
| tac atg ctc ttc ttc gtc aat ccc ggg gag gac gac ctg tca cag atc<br>Tyr Met Leu Phe Phe Val Asn Pro Gly Glu Asp Asp Leu Ser Gln Ile<br>350                      355                      360                      365 | 1165 |
| atg ttc atc tat ttc aac tcc ttc ctg cag tcg ttc cag ggt ttc ttc<br>Met Phe Ile Tyr Phe Asn Ser Phe Leu Gln Ser Phe Gln Gly Phe Phe<br>                  370                      375                      380 | 1213 |
| gtg tct gtc ttc tac tgc ttc ttc aat gga gag gtg cgc tca gcc gtg<br>Val Ser Val Phe Tyr Cys Phe Phe Asn Gly Glu Val Arg Ser Ala Val<br>385                      390                      395 | 1261 |

```
agg aag agg tgg cac cgc tgg cag gac cat cac tcc ctt cga gtc ccc    1309
Arg Lys Arg Trp His Arg Trp Gln Asp His His Ser Leu Arg Val Pro
        400                 405                 410 atg gcc cgg gcc atg tcc atc cct aca tca ccc aca cgg atc agc ttc    1357
Met Ala Arg Ala Met Ser Ile Pro Thr Ser Pro Thr Arg Ile Ser Phe
    415                 420                 425 cac agc atc aag cag acg gcc gct gtg tga cccctcggtc gcccacctgc      1407
His Ser Ile Lys Gln Thr Ala Ala Val
430                 435 acagctcccc tgtcctcctc caccttcttc ctctgggttc tctgtgctgg gcaggctctc  1467
gtggggcagg agatgggagg ggagagacca gctctccagc ctggcaggaa agaggggtg   1527 cggcagccaa gggggactgc aagggacagg gatgagtggg ggccaccagg ctcagcgcaa  1587
gaggaagcag agg                                                    1600

<210> SEQ ID NO 12
<211> LENGTH: 438
<212> TYPE: PRT
<213> ORGANISM: Homo sapiens

<400> SEQUENCE: 12
```

Met Arg Gly Pro Ser Gly Pro Pro Gly Leu Leu Tyr Val Pro His Leu
1               5                   10                  15

Leu Leu Cys Leu Leu Cys Leu Leu Pro Pro Leu Gln Tyr Ala Ala
            20                  25                  30

Gly Gln Ser Gln Met Pro Lys Asp Gln Pro Leu Trp Ala Leu Leu Glu
        35                  40                  45

Gln Tyr Cys His Thr Ile Met Thr Leu Thr Asn Leu Ser Gly Pro Tyr
    50                  55                  60

Ser Tyr Cys Asn Thr Thr Leu Asp Gln Ile Gly Thr Cys Trp Pro Arg
65                  70                  75                  80

Ser Ala Ala Gly Ala Leu Val Glu Arg Pro Cys Pro Glu Tyr Phe Asn
                85                  90                  95

Gly Val Lys Tyr Asn Thr Thr Arg Asn Ala Tyr Arg Glu Cys Leu Glu
            100                 105                 110

Asn Gly Thr Trp Ala Ser Lys Ile Asn Tyr Ser Gln Cys Glu Pro Ile
        115                 120                 125

Leu Asp Asp Lys Gln Arg Lys Tyr Asp Leu His Tyr Arg Ile Ala Leu
    130                 135                 140

Val Val Asn Tyr Leu Gly His Cys Val Ser Val Ala Ala Leu Val Ala
145                 150                 155                 160

Ala Phe Leu Leu Phe Leu Ala Leu Arg Ser Ile Arg Cys Leu Arg Asn
                165                 170                 175

Val Ile His Trp Asn Leu Ile Thr Thr Phe Ile Leu Arg Asn Val Met
            180                 185                 190

Trp Phe Leu Leu Gln Leu Val Asp His Glu Val His Glu Ser Asn Glu
        195                 200                 205

Val Trp Cys Arg Cys Ile Thr Thr Ile Phe Asn Tyr Phe Val Val Thr
    210                 215                 220

Asn Phe Phe Trp Met Phe Val Glu Gly Cys Tyr Leu His Thr Ala Ile
225                 230                 235                 240

Val Met Thr Tyr Ser Thr Glu Arg Leu Arg Lys Cys Leu Phe Leu Phe
                245                 250                 255

Ile Gly Trp Cys Ile Pro Phe Pro Ile Ile Val Ala Trp Ala Ile Gly
            260                 265                 270

```
Lys Leu Tyr Tyr Glu Asn Glu Gln Cys Trp Phe Gly Lys Glu Pro Gly
            275                 280                 285

Asp Leu Val Asp Tyr Ile Tyr Gln Gly Pro Ile Ile Leu Val Leu Leu
        290                 295                 300

Ile Asn Phe Val Phe Leu Phe Asn Ile Val Arg Ile Leu Met Thr Lys
305                 310                 315                 320

Leu Arg Ala Ser Thr Thr Ser Glu Thr Ile Gln Tyr Arg Lys Ala Val
                325                 330                 335

Lys Ala Thr Leu Val Leu Leu Pro Leu Leu Gly Ile Thr Tyr Met Leu
            340                 345                 350

Phe Phe Val Asn Pro Gly Glu Asp Asp Leu Ser Gln Ile Met Phe Ile
        355                 360                 365

Tyr Phe Asn Ser Phe Leu Gln Ser Phe Gln Gly Phe Phe Val Ser Val
    370                 375                 380

Phe Tyr Cys Phe Phe Asn Gly Glu Val Arg Ser Ala Val Arg Lys Arg
385                 390                 395                 400

Trp His Arg Trp Gln Asp His His Ser Leu Arg Val Pro Met Ala Arg
                405                 410                 415

Ala Met Ser Ile Pro Thr Ser Pro Thr Arg Ile Ser Phe His Ser Ile
            420                 425                 430

Lys Gln Thr Ala Ala Val
            435

<210> SEQ ID NO 13
<211> LENGTH: 1558
<212> TYPE: DNA
<213> ORGANISM: Homo sapiens
<220> FEATURE:
<221> NAME/KEY: CDS
<222> LOCATION: (152)..(1345)

<400> SEQUENCE: 13
ctgtgctcaa gcaatctgcc taccttggct tccccaagtg ctgagattat gggtgtgagc      60
cactgcacct ggccaagaat ccgaatggat tcaaagatac cttgaaataa ttcctcaatg     120
caacacacac acatatgcca gggttggtca a atg gga aga gag cct tgg cct        172
                                   Met Gly Arg Glu Pro Trp Pro
                                     1               5 gaa gac agg gac ctg ggc ttt cct cag ctc ttc tgc caa ggt ccc tac        220
Glu Asp Arg Asp Leu Gly Phe Pro Gln Leu Phe Cys Gln Gly Pro Tyr
         10                  15                  20 tcc tac tgc aac acg acc ttg gac cag atc gga acg tgc tgg ccc cgc        268
Ser Tyr Cys Asn Thr Thr Leu Asp Gln Ile Gly Thr Cys Trp Pro Arg
 25                  30                  35 agc gct gcc gga gcc ctc gtg gag agg ccg tgc ccc gag tac ttc aac        316
Ser Ala Ala Gly Ala Leu Val Glu Arg Pro Cys Pro Glu Tyr Phe Asn
 40                  45                  50                  55 ggc gtc aag tac aac acg acc cgg aat gcc tat cga gaa tgc ttg gag        364
Gly Val Lys Tyr Asn Thr Thr Arg Asn Ala Tyr Arg Glu Cys Leu Glu
                 60                  65                  70 aat ggg acg tgg gcc tca aag atc aac tac tca cag tgt gag ccc att        412
Asn Gly Thr Trp Ala Ser Lys Ile Asn Tyr Ser Gln Cys Glu Pro Ile
             75                  80                  85 ttg gat gac aag cag agg aag tat gac ctg cac tac cgc atc gcc ctt        460
Leu Asp Asp Lys Gln Arg Lys Tyr Asp Leu His Tyr Arg Ile Ala Leu
         90                  95                 100 gtc gtc aac tac ctg ggc cac tgc gta tct gtg gca gcc ctg gtg gcc        508
Val Val Asn Tyr Leu Gly His Cys Val Ser Val Ala Ala Leu Val Ala
```

-continued

```
              105                 110                 115
gcc ttc ctg ctt ttc ctg gcc ctg cgg agc att cgc tgt ctg cgg aat       556
Ala Phe Leu Leu Phe Leu Ala Leu Arg Ser Ile Arg Cys Leu Arg Asn
120                 125                 130                 135 gtg att cac tgg aac ctc atc acc acc ttt atc ctg cga aat gtc atg       604
Val Ile His Trp Asn Leu Ile Thr Thr Phe Ile Leu Arg Asn Val Met
                140                 145                 150 tgg ttc ctg ctg cag ctc gtt gac cat gaa gtg cac gag agc aat gag       652
Trp Phe Leu Leu Gln Leu Val Asp His Glu Val His Glu Ser Asn Glu
            155                 160                 165 gtc tgg tgc cgc tgc atc acc acc atc ttc aac tac ttc gtg gtg acc       700
Val Trp Cys Arg Cys Ile Thr Thr Ile Phe Asn Tyr Phe Val Val Thr
        170                 175                 180 aac ttc ttc tgg atg ttt gtg gaa ggc tgc tac ctg cac acg gcc att       748
Asn Phe Phe Trp Met Phe Val Glu Gly Cys Tyr Leu His Thr Ala Ile
    185                 190                 195 gtc atg acc tac tcc act gag cgc ctg cgc aag tgc ctc ttc ctc ttc       796
Val Met Thr Tyr Ser Thr Glu Arg Leu Arg Lys Cys Leu Phe Leu Phe
200                 205                 210                 215 atc gga tgg tgc atc ccc ttc ccc atc atc gtc gcc tgg gcc atc ggc       844
Ile Gly Trp Cys Ile Pro Phe Pro Ile Ile Val Ala Trp Ala Ile Gly
                220                 225                 230 aag ctc tac tat gag aat gaa cag tgc tgg ttt ggc aag gag cct ggc       892
Lys Leu Tyr Tyr Glu Asn Glu Gln Cys Trp Phe Gly Lys Glu Pro Gly
            235                 240                 245 gac ctg gtg gac tac atc tac caa ggc ccc atc att ctc gtg ctc ctg       940
Asp Leu Val Asp Tyr Ile Tyr Gln Gly Pro Ile Ile Leu Val Leu Leu
        250                 255                 260 atc aat ttc gta ttt ctg ttc aac atc gtc agg atc cta atg aca aag       988
Ile Asn Phe Val Phe Leu Phe Asn Ile Val Arg Ile Leu Met Thr Lys
    265                 270                 275 tta cgc gcg tcc acc aca tcc gag aca atc cag tac agg aag gca gtg      1036
Leu Arg Ala Ser Thr Thr Ser Glu Thr Ile Gln Tyr Arg Lys Ala Val
280                 285                 290                 295 aag gcc acc ctg gtg ctc ctg ccc ctc ctg ggc atc acc tac atg ctc      1084
Lys Ala Thr Leu Val Leu Leu Pro Leu Leu Gly Ile Thr Tyr Met Leu
                300                 305                 310 ttc ttc gtc aat ccc ggg gag gac gac ctg tca cag atc atg ttc atc      1132
Phe Phe Val Asn Pro Gly Glu Asp Asp Leu Ser Gln Ile Met Phe Ile
            315                 320                 325 tat ttc aac tcc ttc ctg cag tcg ttc cag ggt ttc ttc gtg tct gtc      1180
Tyr Phe Asn Ser Phe Leu Gln Ser Phe Gln Gly Phe Phe Val Ser Val
        330                 335                 340 ttc tac tgc ttc ttc aat gga gag gtg cgc tca gcc gtg agg aag agg      1228
Phe Tyr Cys Phe Phe Asn Gly Glu Val Arg Ser Ala Val Arg Lys Arg
    345                 350                 355 tgg cac cgc tgg cag gac cat cac tcc ctt cga gtc ccc atg gcc cgg      1276
Trp His Arg Trp Gln Asp His His Ser Leu Arg Val Pro Met Ala Arg
360                 365                 370                 375 gcc atg tcc atc cct aca tca ccc aca cgg atc agc ttc cac agc atc      1324
Ala Met Ser Ile Pro Thr Ser Pro Thr Arg Ile Ser Phe His Ser Ile
                380                 385                 390 aag cag acg gcc gct gtg tga cccctcggtc gcccacctgc acagctcccc        1375
Lys Gln Thr Ala Ala Val
            395 tgtcctcctc caccttcttc ctctgggttc tctgtgctgg gcaggctctc gtggggcagg   1435 agatgggagg ggagagacca gctctccagc ctggcaggaa agaggggtg cggcagccaa   1495 gggggactgc aagggacagg gatgagtggg ggccaccagg ctcagcgcaa gaggaagcag   1555
``` agg                                                                1558

<210> SEQ ID NO 14
<211> LENGTH: 397
<212> TYPE: PRT
<213> ORGANISM: Homo sapiens

<400> SEQUENCE: 14

Met Gly Arg Glu Pro Trp Pro Glu Asp Arg Asp Leu Gly Phe Pro Gln
1               5                   10                  15

Leu Phe Cys Gln Gly Pro Tyr Ser Tyr Cys Asn Thr Thr Leu Asp Gln
            20                  25                  30

Ile Gly Thr Cys Trp Pro Arg Ser Ala Ala Gly Ala Leu Val Glu Arg
        35                  40                  45

Pro Cys Pro Glu Tyr Phe Asn Gly Val Lys Tyr Asn Thr Thr Arg Asn
    50                  55                  60

Ala Tyr Arg Glu Cys Leu Glu Asn Gly Thr Trp Ala Ser Lys Ile Asn
65                  70                  75                  80

Tyr Ser Gln Cys Glu Pro Ile Leu Asp Asp Lys Gln Arg Lys Tyr Asp
            85                  90                  95

Leu His Tyr Arg Ile Ala Leu Val Val Asn Tyr Leu Gly His Cys Val
            100                 105                 110

Ser Val Ala Ala Leu Val Ala Ala Phe Leu Leu Phe Leu Ala Leu Arg
        115                 120                 125

Ser Ile Arg Cys Leu Arg Asn Val Ile His Trp Asn Leu Ile Thr Thr
    130                 135                 140

Phe Ile Leu Arg Asn Val Met Trp Phe Leu Leu Gln Leu Val Asp His
145                 150                 155                 160

Glu Val His Glu Ser Asn Glu Val Trp Cys Arg Cys Ile Thr Thr Ile
            165                 170                 175

Phe Asn Tyr Phe Val Val Thr Asn Phe Phe Trp Met Phe Val Glu Gly
            180                 185                 190

Cys Tyr Leu His Thr Ala Ile Val Met Thr Tyr Ser Thr Glu Arg Leu
        195                 200                 205

Arg Lys Cys Leu Phe Leu Phe Ile Gly Trp Cys Ile Pro Phe Pro Ile
    210                 215                 220

Ile Val Ala Trp Ala Ile Gly Lys Leu Tyr Tyr Glu Asn Glu Gln Cys
225                 230                 235                 240

Trp Phe Gly Lys Glu Pro Gly Asp Leu Val Asp Tyr Ile Tyr Gln Gly
            245                 250                 255

Pro Ile Ile Leu Val Leu Leu Ile Asn Phe Val Phe Leu Phe Asn Ile
            260                 265                 270

Val Arg Ile Leu Met Thr Lys Leu Arg Ala Ser Thr Thr Ser Glu Thr
        275                 280                 285

Ile Gln Tyr Arg Lys Ala Val Lys Ala Thr Leu Val Leu Leu Pro Leu
    290                 295                 300

Leu Gly Ile Thr Tyr Met Leu Phe Phe Val Asn Pro Gly Glu Asp Asp
305                 310                 315                 320

Leu Ser Gln Ile Met Phe Ile Tyr Phe Asn Ser Phe Leu Gln Ser Phe
            325                 330                 335

Gln Gly Phe Phe Val Ser Val Phe Tyr Cys Phe Phe Asn Gly Glu Val
            340                 345                 350

Arg Ser Ala Val Arg Lys Arg Trp His Arg Trp Gln Asp His His Ser
        355                 360                 365

```
Leu Arg Val Pro Met Ala Arg Ala Met Ser Ile Pro Thr Ser Pro Thr
    370                 375                 380

Arg Ile Ser Phe His Ser Ile Lys Gln Thr Ala Ala Val
385                 390                 395

<210> SEQ ID NO 15
<211> LENGTH: 1411
<212> TYPE: DNA
<213> ORGANISM: Rattus norvegicus
<220> FEATURE:
<221> NAME/KEY: CDS
<222> LOCATION: (80)..(1327)

<400> SEQUENCE: 15
agaccgcagc cgcccgccct ccgtctgggg atgtcggagc gatccaggca tccaggacgc    60
tgacggagcg agcccgagg atg gga cgg cgc ccg cag ctc cgg ctc gtg aag   112
                     Met Gly Arg Arg Pro Gln Leu Arg Leu Val Lys
                       1               5                  10 gcc ctt ctc ctt ctg ggg ctg aac cct gtg tcc acc tcc ctt cag gat    160
Ala Leu Leu Leu Leu Gly Leu Asn Pro Val Ser Thr Ser Leu Gln Asp
             15                  20                  25 cag cgc tgt gag aac ctg tcc ctg acc agc aat gtt tct ggc ctg cag    208
Gln Arg Cys Glu Asn Leu Ser Leu Thr Ser Asn Val Ser Gly Leu Gln
         30                  35                  40 tgc aat gca tcc gtg gac ctc att ggc acc tgc tgg ccc cgg agc cct    256
Cys Asn Ala Ser Val Asp Leu Ile Gly Thr Cys Trp Pro Arg Ser Pro
     45                  50                  55 gcg ggc cag ttg gtg gtc cga ccc tgc cct gcc ttt ttc tac ggt gtc    304
Ala Gly Gln Leu Val Val Arg Pro Cys Pro Ala Phe Phe Tyr Gly Val
 60                  65                  70                  75 cgc tac aac acg aca aac aat ggc tac cgg gag tgc ctg gcc aac ggc    352
Arg Tyr Asn Thr Thr Asn Asn Gly Tyr Arg Glu Cys Leu Ala Asn Gly
                 80                  85                  90 agc tgg gca gcc cgt gtg aat tat tct gag tgc cag gag att ctc aac    400
Ser Trp Ala Ala Arg Val Asn Tyr Ser Glu Cys Gln Glu Ile Leu Asn
             95                 100                 105 gaa gag aag aag agc aaa gta cac tac cat gtt gca gtc atc atc aac    448
Glu Glu Lys Lys Ser Lys Val His Tyr His Val Ala Val Ile Ile Asn
        110                 115                 120 tac ctg ggt cac tgc atc tcc ctg gta gcc ctc ctg gtg gcc ttt gtc    496
Tyr Leu Gly His Cys Ile Ser Leu Val Ala Leu Leu Val Ala Phe Val
    125                 130                 135 ctc ttc ttg cgg ctc agg agc atc cgg tgc ctg aga aac atc atc cac    544
Leu Phe Leu Arg Leu Arg Ser Ile Arg Cys Leu Arg Asn Ile Ile His
140                 145                 150                 155 tgg aac ctc atc tcg gct ttc atc cta cgc aac gcc acg tgg ttt gtg    592
Trp Asn Leu Ile Ser Ala Phe Ile Leu Arg Asn Ala Thr Trp Phe Val
                160                 165                 170 gtc cag ctc acc gtg agc ccc gag gtg cac cag agc aat gtg gcc tgg    640
Val Gln Leu Thr Val Ser Pro Glu Val His Gln Ser Asn Val Ala Trp
            175                 180                 185 tgt agg ttg gtg aca gcc gcc tac aat tac ttc cat gta acc aac ttc    688
Cys Arg Leu Val Thr Ala Ala Tyr Asn Tyr Phe His Val Thr Asn Phe
        190                 195                 200 ttc tgg atg ttc ggt gag ggc tgc tac ctg cac aca gcc att gtg ctc    736
Phe Trp Met Phe Gly Glu Gly Cys Tyr Leu His Thr Ala Ile Val Leu
    205                 210                 215 acg tac tcc acc gac cgt ctg cgc aag tgg atg ttc gtc tgc att ggc    784
Thr Tyr Ser Thr Asp Arg Leu Arg Lys Trp Met Phe Val Cys Ile Gly
220                 225                 230                 235
```

-continued

| | | | | | | | | | | | | | | | | |
|---|---|---|---|---|---|---|---|---|---|---|---|---|---|---|---|---|
| tgg | ggt | gta | cct | ttc | ccc | atc | att | gtg | gct | tgg | gcc | att | ggg | aag | ctg | 832 |
| Trp | Gly | Val | Pro | Phe | Pro | Ile | Ile | Val | Ala | Trp | Ala | Ile | Gly | Lys | Leu | |
| | | | 240 | | | | 245 | | | | 250 | | | | | |
| cac | tac | gac | aat | gaa | aag | tgc | tgg | ttt | ggc | aaa | cgt | cct | ggg | gta | tac | 880 |
| His | Tyr | Asp | Asn | Glu | Lys | Cys | Trp | Phe | Gly | Lys | Arg | Pro | Gly | Val | Tyr | |
| | | | 255 | | | | 260 | | | | 265 | | | | | |
| act | gac | tac | atc | tac | cag | ggc | ccc | atg | atc | ctg | gtc | ctg | ctg | atc | aac | 928 |
| Thr | Asp | Tyr | Ile | Tyr | Gln | Gly | Pro | Met | Ile | Leu | Val | Leu | Leu | Ile | Asn | |
| | | | 270 | | | | 275 | | | | 280 | | | | | |
| ttt | atc | ttt | ctc | ttc | aac | att | gtc | cgc | atc | ctc | atg | acc | aaa | ctc | cgg | 976 |
| Phe | Ile | Phe | Leu | Phe | Asn | Ile | Val | Arg | Ile | Leu | Met | Thr | Lys | Leu | Arg | |
| | | | 285 | | | | 290 | | | | 295 | | | | | |
| gca | tcc | act | aca | tct | gag | acc | att | cag | tac | agg | aag | gct | gtg | aag | gcc | 1024 |
| Ala | Ser | Thr | Thr | Ser | Glu | Thr | Ile | Gln | Tyr | Arg | Lys | Ala | Val | Lys | Ala | |
| 300 | | | | 305 | | | | 310 | | | | 315 | | | | |
| act | ctg | gtg | ctc | ctg | ccc | ctt | ctg | ggc | atc | acc | tac | atg | ttg | ttc | ttc | 1072 |
| Thr | Leu | Val | Leu | Leu | Pro | Leu | Leu | Gly | Ile | Thr | Tyr | Met | Leu | Phe | Phe | |
| | | | 320 | | | | 325 | | | | 330 | | | | | |
| gtc | aac | cct | gga | gag | gac | gag | gtc | tcc | agg | gtc | gtc | ttc | atc | tac | ttc | 1120 |
| Val | Asn | Pro | Gly | Glu | Asp | Glu | Val | Ser | Arg | Val | Val | Phe | Ile | Tyr | Phe | |
| | | | 335 | | | | 340 | | | | 345 | | | | | |
| aac | tct | ttt | ctg | gag | tcc | ttt | cag | ggc | ttc | ttt | gtg | tct | gtg | ttc | tac | 1168 |
| Asn | Ser | Phe | Leu | Glu | Ser | Phe | Gln | Gly | Phe | Phe | Val | Ser | Val | Phe | Tyr | |
| | | | 350 | | | | 355 | | | | 360 | | | | | |
| tgt | ttt | ctg | aac | agt | gag | gtc | cgc | tcc | gct | atc | cgg | aag | agg | tgg | cgt | 1216 |
| Cys | Phe | Leu | Asn | Ser | Glu | Val | Arg | Ser | Ala | Ile | Arg | Lys | Arg | Trp | Arg | |
| | | | 365 | | | | 370 | | | | 375 | | | | | |
| cgg | tgg | cag | gac | aag | cac | tcc | atc | aga | gcc | cga | gtg | gcc | cga | gct | atg | 1264 |
| Arg | Trp | Gln | Asp | Lys | His | Ser | Ile | Arg | Ala | Arg | Val | Ala | Arg | Ala | Met | |
| 380 | | | | 385 | | | | 390 | | | | 395 | | | | |
| tcc | atc | ccc | acc | tcc | ccg | acc | aga | gtc | agc | ttt | cac | agc | atc | aag | cag | 1312 |
| Ser | Ile | Pro | Thr | Ser | Pro | Thr | Arg | Val | Ser | Phe | His | Ser | Ile | Lys | Gln | |
| | | | 400 | | | | 405 | | | | 410 | | | | | |
| tcc | aca | gca | gtg | tga | gctccaggcc | | acagagcagc | | | ccccaagacc | | | tgaggccggg | | | 1367 |
| Ser | Thr | Ala | Val | | | | | | | | | | | | | |
| | | | 415 | | | | | | | | | | | | | | gagatgatgc aagctcactg acgagccagt ctgcagacgc aagc 1411

<210> SEQ ID NO 16
<211> LENGTH: 415
<212> TYPE: PRT
<213> ORGANISM: Rattus norvegicus

<400> SEQUENCE: 16

Met Gly Arg Arg Pro Gln Leu Arg Leu Val Lys Ala Leu Leu Leu Leu
1               5                   10                  15

Gly Leu Asn Pro Val Ser Thr Ser Leu Gln Asp Gln Arg Cys Glu Asn
            20                  25                  30

Leu Ser Leu Thr Ser Asn Val Ser Gly Leu Gln Cys Asn Ala Ser Val
        35                  40                  45

Asp Leu Ile Gly Thr Cys Trp Pro Arg Ser Pro Ala Gly Gln Leu Val
    50                  55                  60

Val Arg Pro Cys Pro Ala Phe Phe Tyr Gly Val Arg Tyr Asn Thr Thr
65                  70                  75                  80

Asn Asn Gly Tyr Arg Glu Cys Leu Ala Asn Gly Ser Trp Ala Ala Arg
                85                  90                  95

Val Asn Tyr Ser Glu Cys Gln Glu Ile Leu Asn Glu Glu Lys Lys Ser
            100                 105                 110

```
Lys Val His Tyr His Val Ala Val Ile Ile Asn Tyr Leu Gly His Cys
            115                 120                 125
Ile Ser Leu Val Ala Leu Leu Val Ala Phe Val Leu Phe Leu Arg Leu
        130                 135                 140
Arg Ser Ile Arg Cys Leu Arg Asn Ile Ile His Trp Asn Leu Ile Ser
145                 150                 155                 160
Ala Phe Ile Leu Arg Asn Ala Thr Trp Phe Val Gln Leu Thr Val
                165                 170                 175
Ser Pro Glu Val His Gln Ser Asn Val Ala Trp Cys Arg Leu Val Thr
            180                 185                 190
Ala Ala Tyr Asn Tyr Phe His Val Thr Asn Phe Phe Trp Met Phe Gly
            195                 200                 205
Glu Gly Cys Tyr Leu His Thr Ala Ile Val Leu Thr Tyr Ser Thr Asp
    210                 215                 220
Arg Leu Arg Lys Trp Met Phe Val Cys Ile Gly Trp Gly Val Pro Phe
225                 230                 235                 240
Pro Ile Ile Val Ala Trp Ala Ile Gly Lys Leu His Tyr Asp Asn Glu
                245                 250                 255
Lys Cys Trp Phe Gly Lys Arg Pro Gly Val Tyr Thr Asp Tyr Ile Tyr
            260                 265                 270
Gln Gly Pro Met Ile Leu Val Leu Leu Ile Asn Phe Ile Phe Leu Phe
        275                 280                 285
Asn Ile Val Arg Ile Leu Met Thr Lys Leu Arg Ala Ser Thr Thr Ser
        290                 295                 300
Glu Thr Ile Gln Tyr Arg Lys Ala Val Lys Ala Thr Leu Val Leu Leu
305                 310                 315                 320
Pro Leu Leu Gly Ile Thr Tyr Met Leu Phe Phe Val Asn Pro Gly Glu
                325                 330                 335
Asp Glu Val Ser Arg Val Val Phe Ile Tyr Phe Asn Ser Phe Leu Glu
            340                 345                 350
Ser Phe Gln Gly Phe Phe Val Ser Val Phe Tyr Cys Phe Leu Asn Ser
        355                 360                 365
Glu Val Arg Ser Ala Ile Arg Lys Arg Trp Arg Arg Trp Gln Asp Lys
        370                 375                 380
His Ser Ile Arg Ala Arg Val Ala Arg Ala Met Ser Ile Pro Thr Ser
385                 390                 395                 400
Pro Thr Arg Val Ser Phe His Ser Ile Lys Gln Ser Thr Ala Val
                405                 410                 415
```

<210> SEQ ID NO 17
<211> LENGTH: 1626
<212> TYPE: DNA
<213> ORGANISM: Rattus norvegicus
<220> FEATURE:
<221> NAME/KEY: CDS
<222> LOCATION: (216)..(1451)

<400> SEQUENCE: 17

```
gcggcccctc atctccgtga gccccgaggc ttctcttggc caaggtccta ggagtgatcc      60
gattgagagc ggcgccccaa agctgccggg ctggccgggg tgggcgggga ggcacctgga     120
cgctgcactc tctggtggct ccgcgtcgcg ccaggtccct cgcagccacg cggggcgcgc     180
actcccactc ccaacgcgcg cggctccgga gcgca atg gac gcg gcg ctg ctc       233
                                        Met Asp Ala Ala Leu Leu
                                         1               5
```

```
                                                               -continued ctc agc ctg ctg gag gcc aac tgc agc ctg gca ctg gcc gaa gag ctg       281
Leu Ser Leu Leu Glu Ala Asn Cys Ser Leu Ala Leu Ala Glu Glu Leu
        10                  15                  20 ctt ttg gac ggc tgg gga gag ccc ccg gac ccc gaa ggt ccc tac tcc       329
Leu Leu Asp Gly Trp Gly Glu Pro Pro Asp Pro Glu Gly Pro Tyr Ser
            25                  30                  35 tac tgc aac acg acc ttg gac cag atc ggg acc tgc tgg ccc cag agc       377
Tyr Cys Asn Thr Thr Leu Asp Gln Ile Gly Thr Cys Trp Pro Gln Ser
    40                  45                  50 gcg cct gga gcc cta gtg gag aga cca tgc ccc gaa tac ttc aac ggc       425
Ala Pro Gly Ala Leu Val Glu Arg Pro Cys Pro Glu Tyr Phe Asn Gly
55                  60                  65                  70 atc aag tac aac acg acc cgg aat gcc tac aga gaa tgc ctg gag aat       473
Ile Lys Tyr Asn Thr Thr Arg Asn Ala Tyr Arg Glu Cys Leu Glu Asn
                75                  80                  85 ggg acc tgg gcc tca agg atc aac tac tca cac tgt gaa ccc att ttg       521
Gly Thr Trp Ala Ser Arg Ile Asn Tyr Ser His Cys Glu Pro Ile Leu
        90                  95                 100 gat gac aag cag agg aag tat gac ctg cat tac cga atc gcc ctc atc       569
Asp Asp Lys Gln Arg Lys Tyr Asp Leu His Tyr Arg Ile Ala Leu Ile
            105                 110                 115 atc aac tac ctg ggc cac tgt gtt tcc gtg gtg gcc ctg gtg gct gct       617
Ile Asn Tyr Leu Gly His Cys Val Ser Val Val Ala Leu Val Ala Ala
    120                 125                 130 ttc ctg ctt ttc cta gtg ctg cgg agt atc cgc tgc ctg cgg aat gtg       665
Phe Leu Leu Phe Leu Val Leu Arg Ser Ile Arg Cys Leu Arg Asn Val
135                 140                 145                 150 atc cac tgg aac ctc atc acc acc ttc atc ctg aga aac atc acg tgg       713
Ile His Trp Asn Leu Ile Thr Thr Phe Ile Leu Arg Asn Ile Thr Trp
                155                 160                 165 ttc ctg ctg caa ctc atc gac cac gaa gtg cat gag ggc aat gag gtc       761
Phe Leu Leu Gln Leu Ile Asp His Glu Val His Glu Gly Asn Glu Val
        170                 175                 180 tgg tgc cgc tgc gtc acc acc ata ttc aac tac ttt gtg gtc acc aac       809
Trp Cys Arg Cys Val Thr Thr Ile Phe Asn Tyr Phe Val Val Thr Asn
            185                 190                 195 ttc ttc tgg atg ttt gtg gaa ggc tgc tac ctg cac acg gcc atc gtc       857
Phe Phe Trp Met Phe Val Glu Gly Cys Tyr Leu His Thr Ala Ile Val
    200                 205                 210 atg acg tac tcc acg gag cat ctg cgc aag tgg ctc ttc ctc ttc att       905
Met Thr Tyr Ser Thr Glu His Leu Arg Lys Trp Leu Phe Leu Phe Ile
215                 220                 225                 230 gga tgg tgc ata ccc tgc cct atc att gtc gcc tgg gca gtt ggc aaa       953
Gly Trp Cys Ile Pro Cys Pro Ile Ile Val Ala Trp Ala Val Gly Lys
                235                 240                 245 ctc tac tat gag aat gag cag tgc tgg ttt ggc aag gaa cct ggt gac      1001
Leu Tyr Tyr Glu Asn Glu Gln Cys Trp Phe Gly Lys Glu Pro Gly Asp
        250                 255                 260 tta gtg gac tac atc tac cag ggc ccc atc atc ctc gtg ctc ctc atc      1049
Leu Val Asp Tyr Ile Tyr Gln Gly Pro Ile Ile Leu Val Leu Leu Ile
            265                 270                 275 aat ttt gtg ttt ctg ttc aac atc gtc agg atc ctg atg aca aaa ctg      1097
Asn Phe Val Phe Leu Phe Asn Ile Val Arg Ile Leu Met Thr Lys Leu
    280                 285                 290 cga gcc tcc acc aca tcc gag acc atc cag tac agg aag gca gtg aag      1145
Arg Ala Ser Thr Thr Ser Glu Thr Ile Gln Tyr Arg Lys Ala Val Lys
295                 300                 305                 310 gcc acc ctg gtc ctc ctc ccc ctg ttg ggc atc acc tac atg ctc ttc      1193
Ala Thr Leu Val Leu Leu Pro Leu Leu Gly Ile Thr Tyr Met Leu Phe
                315                 320                 325
```

```
ttt gtc aat cct gga gag gac gac ctg tca cag att gtg ttc atc tac    1241
Phe Val Asn Pro Gly Glu Asp Asp Leu Ser Gln Ile Val Phe Ile Tyr
            330                 335                 340 ttc aac tct ttc ctg cag tcc ttt cag ggt ttc ttt gtg tcc gtt ttc    1289
Phe Asn Ser Phe Leu Gln Ser Phe Gln Gly Phe Phe Val Ser Val Phe
        345                 350                 355 tac tgc ttc ttc aat gga gag gtg cgc tcc gcc ctg aga aag cgg tgg    1337
Tyr Cys Phe Phe Asn Gly Glu Val Arg Ser Ala Leu Arg Lys Arg Trp
    360                 365                 370 cac cgt tgg cag gac cac cac gcc ctc cga gtg cct gtg gcc cgg gcc    1385
His Arg Trp Gln Asp His His Ala Leu Arg Val Pro Val Ala Arg Ala
375                 380                 385                 390 atg tcc att ccc aca tcg ccc acc agg atc agc ttc cac agc atc aag    1433
Met Ser Ile Pro Thr Ser Pro Thr Arg Ile Ser Phe His Ser Ile Lys
                395                 400                 405 cag aca gct gcc gtg tga tcccctgtca cccatctgcc cagcactcca           1481
Gln Thr Ala Ala Val
            410 ccaccgaggc ggcttcctca ttcttcacag ccttccctgg gtcctccttg ctacactgac  1541 ccttgggtgc aggagaaggg ggggtggatg aactctcctg ccggaagaaa ggaaaactat  1601 gaaatggagg ctctgaaaga ccagg                                       1626

<210> SEQ ID NO 18
<211> LENGTH: 411
<212> TYPE: PRT
<213> ORGANISM: Rattus norvegicus

<400> SEQUENCE: 18

Met Asp Ala Ala Leu Leu Ser Leu Leu Glu Ala Asn Cys Ser Leu
1               5                   10                  15

Ala Leu Ala Glu Glu Leu Leu Asp Gly Trp Gly Glu Pro Pro Asp
            20                  25                  30

Pro Glu Gly Pro Tyr Ser Tyr Cys Asn Thr Thr Leu Asp Gln Ile Gly
        35                  40                  45

Thr Cys Trp Pro Gln Ser Ala Pro Gly Ala Leu Val Glu Arg Pro Cys
    50                  55                  60

Pro Glu Tyr Phe Asn Gly Ile Lys Tyr Asn Thr Thr Arg Asn Ala Tyr
65                  70                  75                  80

Arg Glu Cys Leu Glu Asn Gly Thr Trp Ala Ser Arg Ile Asn Tyr Ser
                85                  90                  95

His Cys Glu Pro Ile Leu Asp Asp Lys Gln Arg Lys Tyr Asp Leu His
            100                 105                 110

Tyr Arg Ile Ala Leu Ile Ile Asn Tyr Leu Gly His Cys Val Ser Val
        115                 120                 125

Val Ala Leu Val Ala Ala Phe Leu Leu Phe Leu Val Leu Arg Ser Ile
    130                 135                 140

Arg Cys Leu Arg Asn Val Ile His Trp Asn Leu Ile Thr Thr Phe Ile
145                 150                 155                 160

Leu Arg Asn Ile Thr Trp Phe Leu Leu Gln Leu Ile Asp His Glu Val
                165                 170                 175

His Glu Gly Asn Glu Val Trp Cys Arg Cys Val Thr Thr Ile Phe Asn
            180                 185                 190

Tyr Phe Val Val Thr Asn Phe Phe Trp Met Phe Val Glu Gly Cys Tyr
        195                 200                 205

Leu His Thr Ala Ile Val Met Thr Tyr Ser Thr Glu His Leu Arg Lys
```

```
                210              215                  220
Trp Leu Phe Leu Phe Ile Gly Trp Cys Ile Pro Cys Pro Ile Ile Val
225                 230                 235                 240

Ala Trp Ala Val Gly Lys Leu Tyr Tyr Glu Asn Glu Gln Cys Trp Phe
                245                 250                 255

Gly Lys Glu Pro Gly Asp Leu Val Asp Tyr Ile Tyr Gln Gly Pro Ile
                260                 265                 270

Ile Leu Val Leu Leu Ile Asn Phe Val Phe Leu Phe Asn Ile Val Arg
            275                 280                 285

Ile Leu Met Thr Lys Leu Arg Ala Ser Thr Thr Ser Glu Thr Ile Gln
290                 295                 300

Tyr Arg Lys Ala Val Lys Ala Thr Leu Val Leu Leu Pro Leu Leu Gly
305                 310                 315                 320

Ile Thr Tyr Met Leu Phe Phe Val Asn Pro Gly Glu Asp Asp Leu Ser
                325                 330                 335

Gln Ile Val Phe Ile Tyr Phe Asn Ser Phe Leu Gln Ser Phe Gln Gly
                340                 345                 350

Phe Phe Val Ser Val Phe Tyr Cys Phe Phe Asn Gly Glu Val Arg Ser
                355                 360                 365

Ala Leu Arg Lys Arg Trp His Arg Trp Gln Asp His His Ala Leu Arg
370                 375                 380

Val Pro Val Ala Arg Ala Met Ser Ile Pro Thr Ser Pro Thr Arg Ile
385                 390                 395                 400

Ser Phe His Ser Ile Lys Gln Thr Ala Ala Val
                405                 410

<210> SEQ ID NO 19
<211> LENGTH: 1514
<212> TYPE: DNA
<213> ORGANISM: Rattus norvegicus
<220> FEATURE:
<221> NAME/KEY: CDS
<222> LOCATION: (44)..(1339)

<400> SEQUENCE: 19
gatccctatc cctgagcaag cgagtggcag gatctggtgt ccc atg ggg cac cca      55
                                             Met Gly His Pro
                                              1 ggc tct ctt ccc agt gca caa ctc ctc ctc tgc cta tac tct ctg ctc    103
Gly Ser Leu Pro Ser Ala Gln Leu Leu Leu Cys Leu Tyr Ser Leu Leu
 5                  10                  15                  20 cca ctg ctc cag gtg gcc caa cca ggc agg cca ctc cag gac cag ccc    151
Pro Leu Leu Gln Val Ala Gln Pro Gly Arg Pro Leu Gln Asp Gln Pro
                25                  30                  35 ctg tgg aca ctt ttg gag cag tac tgc cat agg acc aca act cgg aat    199
Leu Trp Thr Leu Leu Glu Gln Tyr Cys His Arg Thr Thr Thr Arg Asn
            40                  45                  50 ttt tca ggt ccc tac tcc tac tgc tac acg acc ttg gac cag atc ggg    247
Phe Ser Gly Pro Tyr Ser Tyr Cys Tyr Thr Thr Leu Asp Gln Ile Gly
        55                  60                  65 acc tgc tgg ccc cag agc gcg cct gga gcc cta gtg gag aga cca tgc    295
Thr Cys Trp Pro Gln Ser Ala Pro Gly Ala Leu Val Glu Arg Pro Cys
    70                  75                  80 ccc gaa tac ttc aac ggc atc aag tac aac acg acc cgg aat gcc tac    343
Pro Glu Tyr Phe Asn Gly Ile Lys Tyr Asn Thr Thr Arg Asn Ala Tyr
85                  90                  95                 100 aga gaa tgc ctg gag aat ggg acc tgg gcc tca agg atc aac tac tca    391
Arg Glu Cys Leu Glu Asn Gly Thr Trp Ala Ser Arg Ile Asn Tyr Ser
```

-continued

```
            105                 110                 115
cac tgt gaa ccc att ttg gat gac aag cag agg aag tat gac ctg cat      439
His Cys Glu Pro Ile Leu Asp Asp Lys Gln Arg Lys Tyr Asp Leu His
            120                 125                 130 tac cga atc gcc ctc atc atc aac tac ctg ggc cac tgt gtt tcc gtg      487
Tyr Arg Ile Ala Leu Ile Ile Asn Tyr Leu Gly His Cys Val Ser Val
            135                 140                 145 gtg gcc ctg gtg gct gct ttc ctg ctt ttc cta gtg ctg cgg agt atc      535
Val Ala Leu Val Ala Ala Phe Leu Leu Phe Leu Val Leu Arg Ser Ile
    150                 155                 160 cgc tgc ctg cgg aat gtg atc cac tgg aac ctc atc acc acc ttc atc      583
Arg Cys Leu Arg Asn Val Ile His Trp Asn Leu Ile Thr Thr Phe Ile
165                 170                 175                 180 ctg aga aac atc acg tgg ttc ctg ctg caa ctc atc gac cac gaa gtg      631
Leu Arg Asn Ile Thr Trp Phe Leu Leu Gln Leu Ile Asp His Glu Val
                185                 190                 195 cat gag ggc aat gag gtc tgg tgc cgc tgc gtc acc acc ata ttc aac      679
His Glu Gly Asn Glu Val Trp Cys Arg Cys Val Thr Thr Ile Phe Asn
            200                 205                 210 tac ttt gtg gtc acc aac ttc ttc tgg atg ttt gtg gaa ggc tgc tac      727
Tyr Phe Val Val Thr Asn Phe Phe Trp Met Phe Val Glu Gly Cys Tyr
            215                 220                 225 ctg cac acg gcc atc gtc atg acg tac tcc acg gag cat ctg cgc aag      775
Leu His Thr Ala Ile Val Met Thr Tyr Ser Thr Glu His Leu Arg Lys
            230                 235                 240 tgg ctc ttc ctc ttc att gga tgg tgc ata ccc tgc cct atc att gtc      823
Trp Leu Phe Leu Phe Ile Gly Trp Cys Ile Pro Cys Pro Ile Ile Val
245                 250                 255                 260 gcc tgg gca gtt ggc aaa ctc tac tat gag aat gag cag tgc tgg ttt      871
Ala Trp Ala Val Gly Lys Leu Tyr Tyr Glu Asn Glu Gln Cys Trp Phe
                265                 270                 275 ggc aag gaa cct ggt gac tta gtg gac tac atc tac cag ggc ccc atc      919
Gly Lys Glu Pro Gly Asp Leu Val Asp Tyr Ile Tyr Gln Gly Pro Ile
            280                 285                 290 atc ctc gtg ctc ctc atc aat ttt gtg ttt ctg ttc aac atc gtc agg      967
Ile Leu Val Leu Leu Ile Asn Phe Val Phe Leu Phe Asn Ile Val Arg
            295                 300                 305 atc ctg atg aca aaa ctg cga gcc tcc acc aca tcc gag acc atc cag     1015
Ile Leu Met Thr Lys Leu Arg Ala Ser Thr Thr Ser Glu Thr Ile Gln
            310                 315                 320 tac agg aag gca gtg aag gcc aac ctg gtc ctc ctc ccc ctg ttg ggc     1063
Tyr Arg Lys Ala Val Lys Ala Asn Leu Val Leu Leu Pro Leu Leu Gly
325                 330                 335                 340 atc acc tac atg ctc ttc ttt gtc aat cct gga gag gac gac ctg tca     1111
Ile Thr Tyr Met Leu Phe Phe Val Asn Pro Gly Glu Asp Asp Leu Ser
                345                 350                 355 cag att gtg ttc atc tac ttc aac tct ttc ctg cag tcc ttt cag ggt     1159
Gln Ile Val Phe Ile Tyr Phe Asn Ser Phe Leu Gln Ser Phe Gln Gly
            360                 365                 370 ttc ttt gtg tcc gtt ttc tac tgc ttc ttc aat gga gag gtg cgc tcc     1207
Phe Phe Val Ser Val Phe Tyr Cys Phe Phe Asn Gly Glu Val Arg Ser
            375                 380                 385 gcc ctg aga aag cgg tgg cac cgt tgg cag gac cac cac gcc ctc cga     1255
Ala Leu Arg Lys Arg Trp His Arg Trp Gln Asp His His Ala Leu Arg
            390                 395                 400 gtg cct gtg gcc cgg gcc atg tcc att ccc aca tcg ccc acc agg atc     1303
Val Pro Val Ala Arg Ala Met Ser Ile Pro Thr Ser Pro Thr Arg Ile
405                 410                 415                 420 agc ttc cac agc atc aag cag aca gct gcc gtg tga tcccctgtca         1349
Ser Phe His Ser Ile Lys Gln Thr Ala Ala Val
```

-continued

Ser Phe His Ser Ile Lys Gln Thr Ala Ala Val
                425                 430 cccatctgcc cagcactcca ccaccgaggc ggcttcctca ttcttcacag ccttccctgg    1409
gtcctccttg ctacactgac ccttgggtgc aggagaaggg ggggtggatg aactctcctg    1469
ccggaagaaa ggaaaactat gaatggagg ctctgaaaga ccagg    1514

<210> SEQ ID NO 20
<211> LENGTH: 431
<212> TYPE: PRT
<213> ORGANISM: Rattus norvegicus

<400> SEQUENCE: 20

Met Gly His Pro Gly Ser Leu Pro Ser Ala Gln Leu Leu Cys Leu
1               5                   10                  15

Tyr Ser Leu Leu Pro Leu Leu Gln Val Ala Gln Pro Gly Arg Pro Leu
                20                  25                  30

Gln Asp Gln Pro Leu Trp Thr Leu Leu Glu Gln Tyr Cys His Arg Thr
            35                  40                  45

Thr Thr Arg Asn Phe Ser Gly Pro Tyr Ser Tyr Cys Tyr Thr Thr Leu
        50                  55                  60

Asp Gln Ile Gly Thr Cys Trp Pro Gln Ser Ala Pro Gly Ala Leu Val
65                  70                  75                  80

Glu Arg Pro Cys Pro Glu Tyr Phe Asn Gly Ile Lys Tyr Asn Thr Thr
                85                  90                  95

Arg Asn Ala Tyr Arg Glu Cys Leu Glu Asn Gly Thr Trp Ala Ser Arg
            100                 105                 110

Ile Asn Tyr Ser His Cys Glu Pro Ile Leu Asp Asp Lys Gln Arg Lys
        115                 120                 125

Tyr Asp Leu His Tyr Arg Ile Ala Leu Ile Ile Asn Tyr Leu Gly His
130                 135                 140

Cys Val Ser Val Val Ala Leu Val Ala Ala Phe Leu Leu Phe Leu Val
145                 150                 155                 160

Leu Arg Ser Ile Arg Cys Leu Arg Asn Val Ile His Trp Asn Leu Ile
                165                 170                 175

Thr Thr Phe Ile Leu Arg Asn Ile Thr Trp Phe Leu Leu Gln Leu Ile
            180                 185                 190

Asp His Glu Val His Glu Gly Asn Glu Val Trp Cys Arg Cys Val Thr
        195                 200                 205

Thr Ile Phe Asn Tyr Phe Val Val Thr Asn Phe Phe Trp Met Phe Val
210                 215                 220

Glu Gly Cys Tyr Leu His Thr Ala Ile Val Met Thr Tyr Ser Thr Glu
225                 230                 235                 240

His Leu Arg Lys Trp Leu Phe Leu Phe Ile Gly Trp Cys Ile Pro Cys
                245                 250                 255

Pro Ile Ile Val Ala Trp Ala Val Gly Lys Leu Tyr Tyr Glu Asn Glu
            260                 265                 270

Gln Cys Trp Phe Gly Lys Glu Pro Gly Asp Leu Val Asp Tyr Ile Tyr
        275                 280                 285

Gln Gly Pro Ile Ile Leu Val Leu Leu Ile Asn Phe Val Phe Leu Phe
    290                 295                 300

Asn Ile Val Arg Ile Leu Met Thr Lys Leu Arg Ala Ser Thr Thr Ser
305                 310                 315                 320

Glu Thr Ile Gln Tyr Arg Lys Ala Val Lys Ala Asn Leu Val Leu Leu
                325                 330                 335

```
Pro Leu Leu Gly Ile Thr Tyr Met Leu Phe Phe Val Asn Pro Gly Glu
            340                 345                 350

Asp Asp Leu Ser Gln Ile Val Phe Ile Tyr Phe Asn Ser Phe Leu Gln
            355                 360                 365

Ser Phe Gln Gly Phe Phe Val Ser Val Phe Tyr Cys Phe Phe Asn Gly
            370                 375                 380

Glu Val Arg Ser Ala Leu Arg Lys Arg Trp His Arg Trp Gln Asp His
385                 390                 395                 400

His Ala Leu Arg Val Pro Val Ala Arg Ala Met Ser Ile Pro Thr Ser
            405                 410                 415

Pro Thr Arg Ile Ser Phe His Ser Ile Lys Gln Thr Ala Ala Val
            420                 425                 430

<210> SEQ ID NO 21
<211> LENGTH: 2273
<212> TYPE: DNA
<213> ORGANISM: Mus musculus
<220> FEATURE:
<221> NAME/KEY: CDS
<222> LOCATION: (32)..(1279)

<400> SEQUENCE: 21
```

| | | |
|---|---|---|
| tatccaggac gctgacagag cgagcccgag g atg gga cag cgc ccg cag ctc<br>                                  Met Gly Gln Arg Pro Gln Leu<br>                                    1               5 | | 52 |
| cgg ctc gtg aag gcc ctt ctc ctt ctg ggg ctg aac ccc gtc tcc acc<br>Arg Leu Val Lys Ala Leu Leu Leu Leu Gly Leu Asn Pro Val Ser Thr<br>        10                  15                  20 | | 100 |
| tcc ctc cag gat cag cag tgt gag agc ctg tcc ctg gcc agc aat gtc<br>Ser Leu Gln Asp Gln Gln Cys Glu Ser Leu Ser Leu Ala Ser Asn Val<br>    25                  30                  35 | | 148 |
| tct ggc ctg cag tgc aat gcc tcc gtg gac ctc att ggc acc tgc tgg<br>Ser Gly Leu Gln Cys Asn Ala Ser Val Asp Leu Ile Gly Thr Cys Trp<br>40                  45                  50                  55 | | 196 |
| ccc agg agc cct gca ggg cag ttg gtg gtt cgg ccc tgc cct gcc ttt<br>Pro Arg Ser Pro Ala Gly Gln Leu Val Val Arg Pro Cys Pro Ala Phe<br>                60                  65                  70 | | 244 |
| ttc tac ggt gtc cgc tac aac acc aca aac aat ggc tac cgg gaa tgc<br>Phe Tyr Gly Val Arg Tyr Asn Thr Thr Asn Asn Gly Tyr Arg Glu Cys<br>            75                  80                  85 | | 292 |
| ctg gcc aac ggc agc tgg gca gcc cgt gtg aat tat tct gag tgc cag<br>Leu Ala Asn Gly Ser Trp Ala Ala Arg Val Asn Tyr Ser Glu Cys Gln<br>            90                  95                  100 | | 340 |
| gag att ctc aac gaa gag aag aag agc aaa gtg cac tac cac att gcc<br>Glu Ile Leu Asn Glu Glu Lys Lys Ser Lys Val His Tyr His Ile Ala<br>    105                 110                 115 | | 388 |
| gtc atc atc aac tac ctg ggc cac tgc atc tcc ctg gtg gcc ctc ctg<br>Val Ile Ile Asn Tyr Leu Gly His Cys Ile Ser Leu Val Ala Leu Leu<br>120                 125                 130                 135 | | 436 |
| gtg gcc ttt gtc ctc ttc ctg cgg ctc agg agc atc cgg tgc ctg agg<br>Val Ala Phe Val Leu Phe Leu Arg Leu Arg Ser Ile Arg Cys Leu Arg<br>                140                 145                 150 | | 484 |
| aac atc atc cac tgg aac ctc atc tcg gct ttc atc ctg cgc aac gcc<br>Asn Ile Ile His Trp Asn Leu Ile Ser Ala Phe Ile Leu Arg Asn Ala<br>            155                 160                 165 | | 532 |
| acg tgg ttt gtg gtc cag ctc acc gtg agc ccc gag gtc cac cag agc<br>Thr Trp Phe Val Val Gln Leu Thr Val Ser Pro Glu Val His Gln Ser<br>        170                 175                 180 | | 580 |
| aac gtg gcc tgg tgc agg ctg gtg aca gcc gcc tac aac tac ttc cac | | 628 |

-continued

```
                  Asn Val Ala Trp Cys Arg Leu Val Thr Ala Ala Tyr Asn Tyr Phe His
                      185                 190                 195 gta acc aac ttc ttc tgg atg ttc ggt gag ggc tgc tac ctg cac aca              676
Val Thr Asn Phe Phe Trp Met Phe Gly Glu Gly Cys Tyr Leu His Thr
200                 205                 210                 215 gcc atc gta ctc acg tac tcc acc gac cgt ctg cgc aag tgg atg ttc              724
Ala Ile Val Leu Thr Tyr Ser Thr Asp Arg Leu Arg Lys Trp Met Phe
                220                 225                 230 gtc tgc atc ggc tgg ggt gtg cct ttc ccc atc att gtg gct tgg gcc              772
Val Cys Ile Gly Trp Gly Val Pro Phe Pro Ile Ile Val Ala Trp Ala
                    235                 240                 245 att ggg aaa ctt tac tac gac aat gaa aag tgc tgg ttt ggc aaa cgt              820
Ile Gly Lys Leu Tyr Tyr Asp Asn Glu Lys Cys Trp Phe Gly Lys Arg
                250                 255                 260 cct gga gta tat act gac tac atc tac cag ggc ccc atg atc ctg gtc              868
Pro Gly Val Tyr Thr Asp Tyr Ile Tyr Gln Gly Pro Met Ile Leu Val
        265                 270                 275 ctg ctg atc aac ttt atc ttt ctc ttc aac att gtc cgc atc ctc atg              916
Leu Leu Ile Asn Phe Ile Phe Leu Phe Asn Ile Val Arg Ile Leu Met
280                 285                 290                 295 acc aaa ctc cga gca tcc acc aca tct gag act att cag tac agg aag              964
Thr Lys Leu Arg Ala Ser Thr Thr Ser Glu Thr Ile Gln Tyr Arg Lys
                300                 305                 310 gct gtg aag gcc act ctg gtg ctc ttg ccc ctc ctg ggc atc acc tac             1012
Ala Val Lys Ala Thr Leu Val Leu Leu Pro Leu Leu Gly Ile Thr Tyr
                315                 320                 325 atg ttg ttc ttc gtc aac cct ggg gag gac gag gtc tcc agg gtt gtc             1060
Met Leu Phe Phe Val Asn Pro Gly Glu Asp Glu Val Ser Arg Val Val
                330                 335                 340 ttc atc tac ttc aac tct ttc ctg gag tcc ttt cag ggc ttc ttc gtg             1108
Phe Ile Tyr Phe Asn Ser Phe Leu Glu Ser Phe Gln Gly Phe Phe Val
        345                 350                 355 tct gtg ttc tat tgt ttt ctg aac agt gag gtc cgc tct gcc atc cgg             1156
Ser Val Phe Tyr Cys Phe Leu Asn Ser Glu Val Arg Ser Ala Ile Arg
360                 365                 370                 375 aag agg tgg cgg cga tgg cag gac aag cac tcc atc aga gcc cga gtg             1204
Lys Arg Trp Arg Arg Trp Gln Asp Lys His Ser Ile Arg Ala Arg Val
                380                 385                 390 gcc cgc gcc atg tcc atc ccc acc tcc ccc acc aga gtc agc ttc cac             1252
Ala Arg Ala Met Ser Ile Pro Thr Ser Pro Thr Arg Val Ser Phe His
                395                 400                 405 agc atc aag cag tcc aca gca gtg tga acctcaggcc acagagcagc                   1299
Ser Ile Lys Gln Ser Thr Ala Val
                410                 415 ccccaagacc cgaggctggg gaaatgatgc aagctcacta gcgagcctgt ctgcagaggc           1359
aggcagcctt cccatccctg cccctgggat gcagacctgt aagcctgccc agccgtggac           1419
aaagcccata gcactggggt gggccttgg catctagctc cctgctgccc attctccctg            1479
ggaagttgaa atgggcattg ggggctggaa accctgcagc agtttgatgg gcctgtgagc           1539
gctgtcttct cccagagcag cttactgaag atctgtcgtc tccaggagct gttggggagg           1599
ccaactgtta ccctggggca tcatggaaaa ctcccttctg agactgtaaa gtctctgagt           1659
gttagcgatg ccttgggatg ctaccgagga ccaacatggt ccagtcagga gaccgggaga          1719
tagcggtaga aatctgggaa cgtcatcaga tggcactcca cctccctaca agtcactcct          1779
gagccaccag gatttcatca gcactgtggc actgccactg gaaagccctg ccttgctgct          1839
ttgctgccct gcacctttag acatttacta ttctgcaggc caagccagct ttctgtcact          1899
```

-continued

```
tatccactga cagcaacggt cccctcgccc ccaaatcctc ccacctctgg gtatcttcta    1959
acctgtgaga agatgggggt cgggaagggg acttgagttg ccaggaacca gagtgggccc    2019
agtctatgag gaaggagtgg cccctgggta cccaggccac tggcttcagt ggctggcctc    2079
ttgaacacag tcacaagctg ggggaaggat ctattcaagt gccctgacca gcgacaggtg    2139
gctcctggga caactaacta actaagccct tgctcccagg cttggaatgg cccagtcctc    2199
agtgggtagg agagctgagg agccgcagca ggactgaggt ggggtgata taaataatat     2259 ttatcttttc aact                                                      2273
```

<210> SEQ ID NO 22
<211> LENGTH: 415
<212> TYPE: PRT
<213> ORGANISM: Mus musculus

<400> SEQUENCE: 22

```
Met Gly Gln Arg Pro Gln Leu Arg Leu Val Lys Ala Leu Leu Leu Leu
  1               5                  10                  15

Gly Leu Asn Pro Val Ser Thr Ser Leu Gln Asp Gln Gln Cys Glu Ser
             20                  25                  30

Leu Ser Leu Ala Ser Asn Val Ser Gly Leu Gln Cys Asn Ala Ser Val
         35                  40                  45

Asp Leu Ile Gly Thr Cys Trp Pro Arg Ser Pro Ala Gly Gln Leu Val
     50                  55                  60

Val Arg Pro Cys Pro Ala Phe Phe Tyr Gly Val Arg Tyr Asn Thr Thr
 65                  70                  75                  80

Asn Asn Gly Tyr Arg Glu Cys Leu Ala Asn Gly Ser Trp Ala Ala Arg
                 85                  90                  95

Val Asn Tyr Ser Glu Cys Gln Glu Ile Leu Asn Glu Glu Lys Lys Ser
            100                 105                 110

Lys Val His Tyr His Ile Ala Val Ile Ile Asn Tyr Leu Gly His Cys
        115                 120                 125

Ile Ser Leu Val Ala Leu Leu Val Ala Phe Val Leu Phe Leu Arg Leu
    130                 135                 140

Arg Ser Ile Arg Cys Leu Arg Asn Ile Ile His Trp Asn Leu Ile Ser
145                 150                 155                 160

Ala Phe Ile Leu Arg Asn Ala Thr Trp Phe Val Val Gln Leu Thr Val
                165                 170                 175

Ser Pro Glu Val His Gln Ser Asn Val Ala Trp Cys Arg Leu Val Thr
            180                 185                 190

Ala Ala Tyr Asn Tyr Phe His Val Thr Asn Phe Phe Trp Met Phe Gly
        195                 200                 205

Glu Gly Cys Tyr Leu His Thr Ala Ile Val Leu Thr Tyr Ser Thr Asp
    210                 215                 220

Arg Leu Arg Lys Trp Met Phe Val Cys Ile Gly Trp Gly Val Pro Phe
225                 230                 235                 240

Pro Ile Ile Val Ala Trp Ala Ile Gly Lys Leu Tyr Tyr Asp Asn Glu
                245                 250                 255

Lys Cys Trp Phe Gly Lys Arg Pro Gly Val Tyr Thr Asp Tyr Ile Tyr
            260                 265                 270

Gln Gly Pro Met Ile Leu Val Leu Leu Ile Asn Phe Ile Phe Leu Phe
        275                 280                 285

Asn Ile Val Arg Ile Leu Met Thr Lys Leu Arg Ala Ser Thr Thr Ser
    290                 295                 300
```

| | | | | | | | | | | | | |
|---|---|---|---|---|---|---|---|---|---|---|---|---|
|Glu|Thr|Ile|Gln|Tyr|Arg|Lys|Ala|Val|Lys|Ala|Thr|Leu|Val|Leu|Leu|
|305| | | | |310| | | | |315| | | | |320|

Pro Leu Leu Gly Ile Thr Tyr Met Leu Phe Val Asn Pro Gly Glu
           325                 330                 335

Asp Glu Val Ser Arg Val Val Phe Ile Tyr Phe Asn Ser Phe Leu Glu
           340                 345                 350

Ser Phe Gln Gly Phe Phe Val Ser Val Phe Tyr Cys Phe Leu Asn Ser
           355                 360                 365

Glu Val Arg Ser Ala Ile Arg Lys Arg Trp Arg Arg Trp Gln Asp Lys
           370                 375                 380

His Ser Ile Arg Ala Arg Val Ala Arg Ala Met Ser Ile Pro Thr Ser
385                 390                 395                 400

Pro Thr Arg Val Ser Phe His Ser Ile Lys Gln Ser Thr Ala Val
           405                 410                 415

<210> SEQ ID NO 23
<211> LENGTH: 1374
<212> TYPE: DNA
<213> ORGANISM: Mus musculus
<220> FEATURE:
<221> NAME/KEY: CDS
<222> LOCATION: (79)..(1374)

<400> SEQUENCE: 23

```
gccggacaga cctcctttgg aagcagccac ttctggtccc catccctgga gcgatcgagc      60
ggcaggatct gctgtccc atg ggg acc cca ggc tct ctt ccc agt gca cag       111
                    Met Gly Thr Pro Gly Ser Leu Pro Ser Ala Gln
                      1               5                  10 ctt ctc ctc tgc ctg ttt tcc ctg ctt cca gtg ctc cag gtg gcc caa      159
Leu Leu Leu Cys Leu Phe Ser Leu Leu Pro Val Leu Gln Val Ala Gln
             15                  20                  25 cca ggc cag gca ccc cag gac cag ccc ctg tgg aca ctt ttg gag cag      207
Pro Gly Gln Ala Pro Gln Asp Gln Pro Leu Trp Thr Leu Leu Glu Gln
         30                  35                  40 tac tgc cac agg acc aca att ggg aat ttt tca ggt ccc tac acc tac      255
Tyr Cys His Arg Thr Thr Ile Gly Asn Phe Ser Gly Pro Tyr Thr Tyr
     45                  50                  55 tgc aac acg acc ttg gac cag atc ggg acc tgc tgg cca cag agc gca      303
Cys Asn Thr Thr Leu Asp Gln Ile Gly Thr Cys Trp Pro Gln Ser Ala
 60                  65                  70                  75 ccc gga gcc cta gta gag aga ccg tgc ccc gag tac ttc aat ggc atc      351
Pro Gly Ala Leu Val Glu Arg Pro Cys Pro Glu Tyr Phe Asn Gly Ile
                 80                  85                  90 aag tac aac acg acc cgg aat gcc tac aga gag tgc ctg gag aac ggg      399
Lys Tyr Asn Thr Thr Arg Asn Ala Tyr Arg Glu Cys Leu Glu Asn Gly
             95                 100                 105 acc tgg gcc tca agg gtc aac tac tca cac tgc gaa ccc att ttg gat      447
Thr Trp Ala Ser Arg Val Asn Tyr Ser His Cys Glu Pro Ile Leu Asp
         110                 115                 120 gac aag cag aga aag tat gac ctg cat tac cga atc gcc ctc att gtc      495
Asp Lys Gln Arg Lys Tyr Asp Leu His Tyr Arg Ile Ala Leu Ile Val
     125                 130                 135 aac tac ctg ggt cac tgt gtt tcc gtg gtg gcc ctg gtg gcc gct ttc      543
Asn Tyr Leu Gly His Cys Val Ser Val Val Ala Leu Val Ala Ala Phe
140                 145                 150                 155 ctg ctt ttc cta gtg ctg cgg agt atc cgc tgc ctg agg aat gtg atc      591
Leu Leu Phe Leu Val Leu Arg Ser Ile Arg Cys Leu Arg Asn Val Ile
                 160                 165                 170 cac tgg aac ctc atc acc acc ttc att ctg aga aac atc gcg tgg ttc      639
```

| | | | | | | | | | | | | | | | | |
|---|---|---|---|---|---|---|---|---|---|---|---|---|---|---|---|---|
|His|Trp|Asn|Leu|Ile|Thr|Thr|Phe|Ile|Leu|Arg|Asn|Ile|Ala|Trp|Phe| |
| | |175| | | |180| | | |185| | | | | | |

```
ctg ctg caa ctc atc gac cac gaa gtg cac gag ggc aat gag gtc tgg    687
Leu Leu Gln Leu Ile Asp His Glu Val His Glu Gly Asn Glu Val Trp
        190             195             200 tgc cgc tgc atc acc acc atc ttc aac tat ttt gtg gtc acc aac ttc    735
Cys Arg Cys Ile Thr Thr Ile Phe Asn Tyr Phe Val Val Thr Asn Phe
205             210             215 ttc tgg atg ttt gtg gag ggc tgc tac ctg cac acg gcc att gtc atg    783
Phe Trp Met Phe Val Glu Gly Cys Tyr Leu His Thr Ala Ile Val Met
220             225             230             235 acg tac tcc aca gag cac ctg cgc aag tgg ctt ttc ctc ttc att gga    831
Thr Tyr Ser Thr Glu His Leu Arg Lys Trp Leu Phe Leu Phe Ile Gly
        240             245             250 tgg tgc att ccc tgc cct atc atc atc gcc tgg gca gtt ggc aaa ctc    879
Trp Cys Ile Pro Cys Pro Ile Ile Ile Ala Trp Ala Val Gly Lys Leu
        255             260             265 tac tat gag aat gag cag tgc tgg ttt ggc aag gaa gct ggt gat ttg    927
Tyr Tyr Glu Asn Glu Gln Cys Trp Phe Gly Lys Glu Ala Gly Asp Leu
        270             275             280 gtg gac tac atc tac cag ggc ccc gtc atg ctt gtg ctg ttg atc aat    975
Val Asp Tyr Ile Tyr Gln Gly Pro Val Met Leu Val Leu Leu Ile Asn
285             290             295 ttt gta ttt ctg ttt aac atc gtc agg atc ctg atg acg aag tta cga   1023
Phe Val Phe Leu Phe Asn Ile Val Arg Ile Leu Met Thr Lys Leu Arg
300             305             310             315 gca tcc acc acg tcc gag aca atc caa tac agg aag gca gtg aag gcc   1071
Ala Ser Thr Thr Ser Glu Thr Ile Gln Tyr Arg Lys Ala Val Lys Ala
        320             325             330 acg ctg gtc ctc ctc ccc ctg ttg ggc atc acc tac atg ctc ttc ttt   1119
Thr Leu Val Leu Leu Pro Leu Leu Gly Ile Thr Tyr Met Leu Phe Phe
        335             340             345 gtc aat cct ggc gag gac gac ctg tcc cag att gtg ttc atc tac ttc   1167
Val Asn Pro Gly Glu Asp Asp Leu Ser Gln Ile Val Phe Ile Tyr Phe
        350             355             360 aac tct ttc ctg cag tcc ttc cag ggt ttc ttt gtg tcc gtt ttc tac   1215
Asn Ser Phe Leu Gln Ser Phe Gln Gly Phe Phe Val Ser Val Phe Tyr
365             370             375 tgc ttc ttc aat gga gag gtg cgc gcg gcc ctg aga aag cgg tgg cac   1263
Cys Phe Phe Asn Gly Glu Val Arg Ala Ala Leu Arg Lys Arg Trp His
380             385             390             395 cgc tgg cag gac cac cac gcc ctc cgg gtg cct gtg gcc cgg gcc atg   1311
Arg Trp Gln Asp His His Ala Leu Arg Val Pro Val Ala Arg Ala Met
                400             405             410 tcc atc cct acg tcg ccc acc agg atc agc ttc cac agc atc aag cag   1359
Ser Ile Pro Thr Ser Pro Thr Arg Ile Ser Phe His Ser Ile Lys Gln
        415             420             425 aca gct gct gtg tga                                                1374
Thr Ala Ala Val
        430

<210> SEQ ID NO 24
<211> LENGTH: 431
<212> TYPE: PRT
<213> ORGANISM: Mus musculus

<400> SEQUENCE: 24

Met Gly Thr Pro Gly Ser Leu Pro Ser Ala Gln Leu Leu Leu Cys Leu
1               5                   10                  15

Phe Ser Leu Leu Pro Val Leu Gln Val Ala Gln Pro Gly Gln Ala Pro
```

```
                20                  25                  30
Gln Asp Gln Pro Leu Trp Thr Leu Leu Glu Gln Tyr Cys His Arg Thr
             35                  40                  45
Thr Ile Gly Asn Phe Ser Gly Pro Tyr Thr Tyr Cys Asn Thr Thr Leu
             50                  55                  60
Asp Gln Ile Gly Thr Cys Trp Pro Gln Ser Ala Pro Gly Ala Leu Val
 65                  70                  75                  80
Glu Arg Pro Cys Pro Glu Tyr Phe Asn Gly Ile Lys Tyr Asn Thr Thr
                 85                  90                  95
Arg Asn Ala Tyr Arg Glu Cys Leu Glu Asn Gly Thr Trp Ala Ser Arg
            100                 105                 110
Val Asn Tyr Ser His Cys Glu Pro Ile Leu Asp Asp Lys Gln Arg Lys
            115                 120                 125
Tyr Asp Leu His Tyr Arg Ile Ala Leu Ile Val Asn Tyr Leu Gly His
            130                 135                 140
Cys Val Ser Val Val Ala Leu Val Ala Ala Phe Leu Leu Phe Leu Val
145                 150                 155                 160
Leu Arg Ser Ile Arg Cys Leu Arg Asn Val Ile His Trp Asn Leu Ile
                165                 170                 175
Thr Thr Phe Ile Leu Arg Asn Ile Ala Trp Phe Leu Leu Gln Leu Ile
            180                 185                 190
Asp His Glu Val His Glu Gly Asn Glu Val Trp Cys Arg Cys Ile Thr
            195                 200                 205
Thr Ile Phe Asn Tyr Phe Val Val Thr Asn Phe Phe Trp Met Phe Val
210                 215                 220
Glu Gly Cys Tyr Leu His Thr Ala Ile Val Met Thr Tyr Ser Thr Glu
225                 230                 235                 240
His Leu Arg Lys Trp Leu Phe Leu Phe Ile Gly Trp Cys Ile Pro Cys
                245                 250                 255
Pro Ile Ile Ile Ala Trp Ala Val Gly Lys Leu Tyr Tyr Glu Asn Glu
            260                 265                 270
Gln Cys Trp Phe Gly Lys Glu Ala Gly Asp Leu Val Asp Tyr Ile Tyr
            275                 280                 285
Gln Gly Pro Val Met Leu Val Leu Leu Ile Asn Phe Val Phe Leu Phe
            290                 295                 300
Asn Ile Val Arg Ile Leu Met Thr Lys Leu Arg Ala Ser Thr Thr Ser
305                 310                 315                 320
Glu Thr Ile Gln Tyr Arg Lys Ala Val Lys Ala Thr Leu Val Leu Leu
                325                 330                 335
Pro Leu Leu Gly Ile Thr Tyr Met Leu Phe Phe Val Asn Pro Gly Glu
            340                 345                 350
Asp Asp Leu Ser Gln Ile Val Phe Ile Tyr Phe Asn Ser Phe Leu Gln
            355                 360                 365
Ser Phe Gln Gly Phe Phe Val Ser Val Phe Tyr Cys Phe Phe Asn Gly
            370                 375                 380
Glu Val Arg Ala Ala Leu Arg Lys Arg Trp His Arg Trp Gln Asp His
385                 390                 395                 400
His Ala Leu Arg Val Pro Val Ala Arg Ala Met Ser Ile Pro Thr Ser
                405                 410                 415
Pro Thr Arg Ile Ser Phe His Ser Ile Lys Gln Thr Ala Ala Val
            420                 425                 430

<210> SEQ ID NO 25
```

```
<211> LENGTH: 2617
<212> TYPE: DNA
<213> ORGANISM: Mus musculus
<220> FEATURE:
<221> NAME/KEY: CDS
<222> LOCATION: (132)..(1424)

<400> SEQUENCE: 25
gggcattacc ttggtgggta ggtcgggcag ggtaggacag gcctaagaga gaggccggac      60
agacctcctt tggaagcagc cacttctggt ccccatccct ggagcgatcg agcggcagga     120
tctgctgtcc c atg ggg acc cca ggc tct ctt ccc agt gca cag ctt ctc     170
            Met Gly Thr Pro Gly Ser Leu Pro Ser Ala Gln Leu Leu
             1               5                  10 ctc tgc ctg ttt tcc ctg ctt cca gtg ctc cag gtg gcc caa cca ggc       218
Leu Cys Leu Phe Ser Leu Leu Pro Val Leu Gln Val Ala Gln Pro Gly
     15                  20                  25 cag gca ccc cag gac cag ccc ctg tgg aca ctt ttg gag cag tac tgc       266
Gln Ala Pro Gln Asp Gln Pro Leu Trp Thr Leu Leu Glu Gln Tyr Cys
 30                  35                  40                  45 cac agg acc aca att ggg aat ttt tca ggt ccc tac acc tac tgc aac       314
His Arg Thr Thr Ile Gly Asn Phe Ser Gly Pro Tyr Thr Tyr Cys Asn
                 50                  55                  60 acg acc ttg gac cag atc ggg acc tgc tgg cca cag agc gca ccc gga       362
Thr Thr Leu Asp Gln Ile Gly Thr Cys Trp Pro Gln Ser Ala Pro Gly
             65                  70                  75 gcc cta gta gag aga ccg tgc ccc gag tac ttc aat ggc atc aag tac       410
Ala Leu Val Glu Arg Pro Cys Pro Glu Tyr Phe Asn Gly Ile Lys Tyr
         80                  85                  90 aac acg acc cgg aat gcc tac aga gag tgc ctg gag aac ggg acc tgg       458
Asn Thr Thr Arg Asn Ala Tyr Arg Glu Cys Leu Glu Asn Gly Thr Trp
     95                 100                 105 gcc tca agg gtc aac tac tca cac tgc gaa ccc att ttg gat gac aag       506
Ala Ser Arg Val Asn Tyr Ser His Cys Glu Pro Ile Leu Asp Asp Lys
110                 115                 120                 125 aga aag tat gac ctg cat tac cga atc gcc ctc att gtc aac tac ctg       554
Arg Lys Tyr Asp Leu His Tyr Arg Ile Ala Leu Ile Val Asn Tyr Leu
                 130                 135                 140 ggt cac tgt gtt tcc gtg gtg gcc ctg gtg gcc gct ttc ctg ctt ttc       602
Gly His Cys Val Ser Val Val Ala Leu Val Ala Ala Phe Leu Leu Phe
             145                 150                 155 cta gtg ctg cgg agt atc cgc tgc ctg agg aat gtg atc cac tgg aac       650
Leu Val Leu Arg Ser Ile Arg Cys Leu Arg Asn Val Ile His Trp Asn
         160                 165                 170 ctc atc acc acc ttc att ctg aga aac atc gcg tgg ttc ctg ctg caa       698
Leu Ile Thr Thr Phe Ile Leu Arg Asn Ile Ala Trp Phe Leu Leu Gln
     175                 180                 185 ctc atc gac cac gaa gtg cac gag ggc aat gag gtc tgg tgc cgc tgc       746
Leu Ile Asp His Glu Val His Glu Gly Asn Glu Val Trp Cys Arg Cys
190                 195                 200                 205 atc acc acc atc ttc aac tat ttt gtg gtc acc aac ttc ttc tgg atg       794
Ile Thr Thr Ile Phe Asn Tyr Phe Val Val Thr Asn Phe Phe Trp Met
                 210                 215                 220 ttt gtg gag ggc tgc tac ctg cac acg gcc att gtc atg acg tac tcc       842
Phe Val Glu Gly Cys Tyr Leu His Thr Ala Ile Val Met Thr Tyr Ser
             225                 230                 235 aca gag cac ctg cgc aag tgg ctt ttc ctc ttc att gga tgg tgc att       890
Thr Glu His Leu Arg Lys Trp Leu Phe Leu Phe Ile Gly Trp Cys Ile
         240                 245                 250 ccc tgc cct atc atc atc gcc tgg gca gtt ggc aaa ctc tac tat gag       938
Pro Cys Pro Ile Ile Ile Ala Trp Ala Val Gly Lys Leu Tyr Tyr Glu
```

-continued

|  |  |  |  |
|---|---|---|---|
| 255 | 260 | 265 | |
| aat gag cag tgc tgg ttt ggc aag gaa gct ggt gat ttg gtg gac tac<br>Asn Glu Gln Cys Trp Phe Gly Lys Glu Ala Gly Asp Leu Val Asp Tyr<br>270                       275                    280                     285 | | | 986 |
| atc tac cag ggc ccc gtc atg ctt gtg ctg ttg atc aat ttt gta ttt<br>Ile Tyr Gln Gly Pro Val Met Leu Val Leu Leu Ile Asn Phe Val Phe<br>                  290                       295                    300 | | | 1034 |
| ctg ttt aac atc gtc agg atc ctg atg acg aag tta cga gca tcc acc<br>Leu Phe Asn Ile Val Arg Ile Leu Met Thr Lys Leu Arg Ala Ser Thr<br>            305                      310                    315 | | | 1082 |
| acg tcc gag aca atc caa tac agg aag gca gtg aag gcc acg ctg gtc<br>Thr Ser Glu Thr Ile Gln Tyr Arg Lys Ala Val Lys Ala Thr Leu Val<br>          320                       325                    330 | | | 1130 |
| ctc ctc ccc ctg ttg ggc atc acc tac atg ctc ttc ttt gtc aat cct<br>Leu Leu Pro Leu Leu Gly Ile Thr Tyr Met Leu Phe Phe Val Asn Pro<br>     335                     340                    345 | | | 1178 |
| ggc gag gac gac ctg tcc cag att gtg ttc atc tac ttc aac tct ttc<br>Gly Glu Asp Asp Leu Ser Gln Ile Val Phe Ile Tyr Phe Asn Ser Phe<br>350                       355                    360                    365 | | | 1226 |
| ctg cag tcc ttc cag ggt ttc ttt gtg tcc gtt ttc tac tgc ttc ttc<br>Leu Gln Ser Phe Gln Gly Phe Phe Val Ser Val Phe Tyr Cys Phe Phe<br>                  370                       375                    380 | | | 1274 |
| aat gga gag gtg cgc gcg gcc ctg aga aac ggg tgg cac cgc tgg cag<br>Asn Gly Glu Val Arg Ala Ala Leu Arg Asn Gly Trp His Arg Trp Gln<br>            385                      390                    395 | | | 1322 |
| gac cac cac gcc ctc cgg gtg cct gtg gcc cgg gcc atg tcc atc cct<br>Asp His His Ala Leu Arg Val Pro Val Ala Arg Ala Met Ser Ile Pro<br>          400                      405                    410 | | | 1370 |
| acg tcg ccc acc agg atc agc ttc cac agc atc aag cag aca gct gct<br>Thr Ser Pro Thr Arg Ile Ser Phe His Ser Ile Lys Gln Thr Ala Ala<br>     415                     420                    425 | | | 1418 |
| gtg tga ccctctgtca ccgtctgccc ggcagtccac cactgaggca gcttctccat<br>Val<br>430 | | | 1474 |
| cctttacagc cttcccctgg gtcctccttg ctaccctgac ccacagggta caaggtacag | | | 1534 |
| gagaagggag gagaacgaac actcccgcct ggaaggaaag gaaagctatg acatgggggg | | | 1594 |
| gctctgaagg accagggccc agtgcagcca gccacacatc tccaagcacg aaggagcagg | | | 1654 |
| aggacatcac aggaccctca gaagggatgc atctcacacc atcaagcctc tgtgcaccca | | | 1714 |
| gcctcttttg tggggtcctc actgcagcac catttacatc tgaagaaact gaggctcaga | | | 1774 |
| gcaggcaggg acctggccaa gtcacatagc tacttgcccc acccacagca cccacagttg | | | 1834 |
| gctctgctcc ttgctttcca tctccacacg tgagggcgcc ctctaaaggt gagggagaca | | | 1894 |
| agaatgacct tatctggctt catcccagaa gctgtcgagc agagatgacc agccctttac | | | 1954 |
| caaggtagcc ttcttcttcc ccagtctgtt tccatgtgt ctccaggaga atgctggctt | | | 2014 |
| tcagtcggcc atccctcctg ggagtcccca attcagtctg ggctcagtct ggggacctag | | | 2074 |
| accacgggaa gtgagttaga tggaaagtca cactctccac agtgccagac agaagggaga | | | 2134 |
| acagaagcgc ctggggaaga aggtgagga tcccccaaat cagagtatgc ctgggagtga | | | 2194 |
| ttgaaacaag ggccccagga tctcagtgac atcagccagg catctgtgga gttggccaca | | | 2254 |
| attcaagcaa cgagatgttg gagagatatt gtgagccagt aataaggca gaatgtctgc | | | 2314 |
| aggacatatc catgcccctc ttcttactgg ctaggcccaa gcaggccttc ctgtggagtc | | | 2374 |
| tttaggttca aagggcccga atcattcctg tcacccaaa gggtggcatc tgcaccaccc | | | 2434 |
| ccagcgtaga ccccacctgt gccagggact aatattctgg aattggaggg agaggaggc | | | 2494 |

```
aaggcccttc aggctccgaa agcaagaaga cacagtttga tttcaggctt ctcttccatt    2554
cctctgtccc tggagcagaa gagggtgtt ggggcaagcc aacagacttg aaaaggcccc     2614
cgg                                                                  2617
```

<210> SEQ ID NO 26
<211> LENGTH: 430
<212> TYPE: PRT
<213> ORGANISM: Mus musculus

<400> SEQUENCE: 26

```
Met Gly Thr Pro Gly Ser Leu Pro Ser Ala Gln Leu Leu Cys Leu
1               5                   10                  15

Phe Ser Leu Leu Pro Val Leu Gln Val Ala Gln Pro Gly Gln Ala Pro
            20                  25                  30

Gln Asp Gln Pro Leu Trp Thr Leu Leu Glu Gln Tyr Cys His Arg Thr
        35                  40                  45

Thr Ile Gly Asn Phe Ser Gly Pro Tyr Thr Tyr Cys Asn Thr Thr Leu
    50                  55                  60

Asp Gln Ile Gly Thr Cys Trp Pro Gln Ser Ala Pro Gly Ala Leu Val
65                  70                  75                  80

Glu Arg Pro Cys Pro Glu Tyr Phe Asn Gly Ile Lys Tyr Asn Thr Thr
                85                  90                  95

Arg Asn Ala Tyr Arg Glu Cys Leu Glu Asn Gly Thr Trp Ala Ser Arg
            100                 105                 110

Val Asn Tyr Ser His Cys Glu Pro Ile Leu Asp Asp Lys Arg Lys Tyr
        115                 120                 125

Asp Leu His Tyr Arg Ile Ala Leu Ile Val Asn Tyr Leu Gly His Cys
130                 135                 140

Val Ser Val Val Ala Leu Val Ala Ala Phe Leu Leu Phe Leu Val Leu
145                 150                 155                 160

Arg Ser Ile Arg Cys Leu Arg Asn Val Ile His Trp Asn Leu Ile Thr
                165                 170                 175

Thr Phe Ile Leu Arg Asn Ile Ala Trp Phe Leu Leu Gln Leu Ile Asp
            180                 185                 190

His Glu Val His Glu Gly Asn Glu Val Trp Cys Arg Cys Ile Thr Thr
        195                 200                 205

Ile Phe Asn Tyr Phe Val Val Thr Asn Phe Phe Trp Met Phe Val Glu
    210                 215                 220

Gly Cys Tyr Leu His Thr Ala Ile Val Met Thr Tyr Ser Thr Glu His
225                 230                 235                 240

Leu Arg Lys Trp Leu Phe Leu Phe Ile Gly Trp Cys Ile Pro Cys Pro
                245                 250                 255

Ile Ile Ile Ala Trp Ala Val Gly Lys Leu Tyr Tyr Glu Asn Glu Gln
            260                 265                 270

Cys Trp Phe Gly Lys Glu Ala Gly Asp Leu Val Asp Tyr Ile Tyr Gln
        275                 280                 285

Gly Pro Val Met Leu Val Leu Leu Ile Asn Phe Val Phe Leu Phe Asn
    290                 295                 300

Ile Val Arg Ile Leu Met Thr Lys Leu Arg Ala Ser Thr Thr Ser Glu
305                 310                 315                 320

Thr Ile Gln Tyr Arg Lys Ala Val Lys Ala Thr Leu Val Leu Leu Pro
                325                 330                 335

Leu Leu Gly Ile Thr Tyr Met Leu Phe Phe Val Asn Pro Gly Glu Asp
```

```
                    340                 345                 350
Asp Leu Ser Gln Ile Val Phe Ile Tyr Phe Asn Ser Phe Leu Gln Ser
            355                 360                 365

Phe Gln Gly Phe Phe Val Ser Val Phe Tyr Cys Phe Phe Asn Gly Glu
    370                 375                 380

Val Arg Ala Ala Leu Arg Asn Gly Trp His Arg Trp Gln Asp His His
385                 390                 395                 400

Ala Leu Arg Val Pro Val Ala Arg Ala Met Ser Ile Pro Thr Ser Pro
                405                 410                 415

Thr Arg Ile Ser Phe His Ser Ile Lys Gln Thr Ala Ala Val
            420                 425                 430

<210> SEQ ID NO 27
<211> LENGTH: 1248
<212> TYPE: DNA
<213> ORGANISM: Ovis aries
<220> FEATURE:
<221> NAME/KEY: CDS
<222> LOCATION: (1)..(1248)

<400> SEQUENCE: 27 atg gga cgg cgc ccg cag ctc cgg ctt gtc aag gcc ctt ctc ctc ctg      48
Met Gly Arg Arg Pro Gln Leu Arg Leu Val Lys Ala Leu Leu Leu Leu
1               5                   10                  15 ggg ctg aac tcc atc tcc gcc tcc ctc cag gac cag cat tgc gag agc      96
Gly Leu Asn Ser Ile Ser Ala Ser Leu Gln Asp Gln His Cys Glu Ser
                20                  25                  30 ttg tcc ctg gcc agc aac gtc tct gga ctg cag tgc aac gct tcc gtg     144
Leu Ser Leu Ala Ser Asn Val Ser Gly Leu Gln Cys Asn Ala Ser Val
            35                  40                  45 gac ctt aat ggc acc tgc tgg ccc cag agt cct gca ggg cag ttg gtg     192
Asp Leu Asn Gly Thr Cys Trp Pro Gln Ser Pro Ala Gly Gln Leu Val
        50                  55                  60 gtt cga ccc tgc ctc gta ttt ttc tat ggt gtc cgc tac aat acc aca     240
Val Arg Pro Cys Leu Val Phe Phe Tyr Gly Val Arg Tyr Asn Thr Thr
65                  70                  75                  80 agc aat ggc tac cgg gtg tgc ctg gcc aat ggc acg tgg gca gcc cgc     288
Ser Asn Gly Tyr Arg Val Cys Leu Ala Asn Gly Thr Trp Ala Ala Arg
                85                  90                  95 gtg aat cac tcc gag tgc caa gag atc ctc agc gaa gga gag aag agc     336
Val Asn His Ser Glu Cys Gln Glu Ile Leu Ser Glu Gly Glu Lys Ser
                100                 105                 110 aag gcg cac tac cac atc gcc gtc atc atc aac tac ctg ggc cac tgc     384
Lys Ala His Tyr His Ile Ala Val Ile Ile Asn Tyr Leu Gly His Cys
            115                 120                 125 atc tcc ctg gcg gcc ctc ctg gtg gcc ttt gtc ctc ttt ctg cgg ctc     432
Ile Ser Leu Ala Ala Leu Leu Val Ala Phe Val Leu Phe Leu Arg Leu
        130                 135                 140 agg agc atc cgg tgc gtg aga aac atc atc cac tgg aac ctc atc tca     480
Arg Ser Ile Arg Cys Val Arg Asn Ile Ile His Trp Asn Leu Ile Ser
145                 150                 155                 160 gcc ttc atc ctg cgc aat gcc acg tgg ttc gtg gtc cag ctc acc atg     528
Ala Phe Ile Leu Arg Asn Ala Thr Trp Phe Val Val Gln Leu Thr Met
                165                 170                 175 agc ccc gaa gtc cat cag agc aac gtg ggc tgg tgc agg ctg gtg aca     576
Ser Pro Glu Val His Gln Ser Asn Val Gly Trp Cys Arg Leu Val Thr
            180                 185                 190 gcc gcc tac aac tac ttc cac gtg acc aac ttc ttc tgg atg ttc ggc     624
Ala Ala Tyr Asn Tyr Phe His Val Thr Asn Phe Phe Trp Met Phe Gly
        195                 200                 205
```

-continued

```
gag ggc tgc tac ctg cac acg gct gtc gtg ctc aca tac tcc acg gac        672
Glu Gly Cys Tyr Leu His Thr Ala Val Val Leu Thr Tyr Ser Thr Asp
    210                 215                 220 cgg ctg cgc aaa tgg atg ttt atc tgc atc ggc tgg ggt gtg ccc ttc        720
Arg Leu Arg Lys Trp Met Phe Ile Cys Ile Gly Trp Gly Val Pro Phe
225                 230                 235                 240 ccc atc att gtg gcc tgg gcc att gga aag ttg tac tac gac aat gag        768
Pro Ile Ile Val Ala Trp Ala Ile Gly Lys Leu Tyr Tyr Asp Asn Glu
                245                 250                 255 aag tgc tgg ttt ggc aaa agg cct ggg gtg tac act gat tac atc tac        816
Lys Cys Trp Phe Gly Lys Arg Pro Gly Val Tyr Thr Asp Tyr Ile Tyr
            260                 265                 270 cag ggc ccg atg atc ttg gtc ctg ctg atc aat ttc atc ttc ctt ttc        864
Gln Gly Pro Met Ile Leu Val Leu Leu Ile Asn Phe Ile Phe Leu Phe
        275                 280                 285 aac atc gtt cgc atc ctc atg acc aaa ctc cgg gca tcc acc acc tct        912
Asn Ile Val Arg Ile Leu Met Thr Lys Leu Arg Ala Ser Thr Thr Ser
    290                 295                 300 gag acc att cag tac agg aag gct gtg aag gcc act ctg gtg ctg ctc        960
Glu Thr Ile Gln Tyr Arg Lys Ala Val Lys Ala Thr Leu Val Leu Leu
305                 310                 315                 320 ccc ctc ctg ggc atc acg tac atg ctg ttc ttc gtg aac ccc ggg gag       1008
Pro Leu Leu Gly Ile Thr Tyr Met Leu Phe Phe Val Asn Pro Gly Glu
                325                 330                 335 gac gag gtc tcc cgg gtc gtc ttc atc tac ttc aac tcc ttc ctg gaa       1056
Asp Glu Val Ser Arg Val Val Phe Ile Tyr Phe Asn Ser Phe Leu Glu
            340                 345                 350 tct ttc cag ggc ttc ttc gtg tct gtg ttc tac tgc ttc ctc aac agc       1104
Ser Phe Gln Gly Phe Phe Val Ser Val Phe Tyr Cys Phe Leu Asn Ser
        355                 360                 365 gag gtc cgc tct gcc atc cgg aag agg tgg cac cgc tgg cag gac aag       1152
Glu Val Arg Ser Ala Ile Arg Lys Arg Trp His Arg Trp Gln Asp Lys
    370                 375                 380 cac tca atc cgt gcc cgt gtg gct cgc gcc atg tcc atc ccc acc tcc       1200
His Ser Ile Arg Ala Arg Val Ala Arg Ala Met Ser Ile Pro Thr Ser
385                 390                 395                 400 ccc acc cgt gtc agc ttt cac agc atc aag cag tcc aca gca gtg tga       1248
Pro Thr Arg Val Ser Phe His Ser Ile Lys Gln Ser Thr Ala Val
                405                 410                 415

<210> SEQ ID NO 28
<211> LENGTH: 415
<212> TYPE: PRT
<213> ORGANISM: Ovis aries

<400> SEQUENCE: 28

Met Gly Arg Arg Pro Gln Leu Arg Leu Val Lys Ala Leu Leu Leu Leu
1               5                   10                  15

Gly Leu Asn Ser Ile Ser Ala Ser Leu Gln Asp Gln His Cys Glu Ser
                20                  25                  30

Leu Ser Leu Ala Ser Asn Val Ser Gly Leu Gln Cys Asn Ala Ser Val
            35                  40                  45

Asp Leu Asn Gly Thr Cys Trp Pro Gln Ser Pro Ala Gly Gln Leu Val
        50                  55                  60

Val Arg Pro Cys Leu Val Phe Phe Tyr Gly Val Arg Tyr Asn Thr Thr
65                  70                  75                  80

Ser Asn Gly Tyr Arg Val Cys Leu Ala Asn Gly Thr Trp Ala Ala Arg
                85                  90                  95
```

```
Val Asn His Ser Glu Cys Gln Glu Ile Leu Ser Glu Gly Glu Lys Ser
            100                 105                 110

Lys Ala His Tyr His Ile Ala Val Ile Ile Asn Tyr Leu Gly His Cys
        115                 120                 125

Ile Ser Leu Ala Ala Leu Leu Val Ala Phe Val Leu Phe Leu Arg Leu
        130                 135                 140

Arg Ser Ile Arg Cys Val Arg Asn Ile Ile His Trp Asn Leu Ile Ser
145                 150                 155                 160

Ala Phe Ile Leu Arg Asn Ala Thr Trp Phe Val Val Gln Leu Thr Met
                165                 170                 175

Ser Pro Glu Val His Gln Ser Asn Val Gly Trp Cys Arg Leu Val Thr
            180                 185                 190

Ala Ala Tyr Asn Tyr Phe His Val Thr Asn Phe Phe Trp Met Phe Gly
        195                 200                 205

Glu Gly Cys Tyr Leu His Thr Ala Val Val Leu Thr Tyr Ser Thr Asp
    210                 215                 220

Arg Leu Arg Lys Trp Met Phe Ile Cys Ile Gly Trp Gly Val Pro Phe
225                 230                 235                 240

Pro Ile Ile Val Ala Trp Ala Ile Gly Lys Leu Tyr Tyr Asp Asn Glu
                245                 250                 255

Lys Cys Trp Phe Gly Lys Arg Pro Gly Val Tyr Thr Asp Tyr Ile Tyr
            260                 265                 270

Gln Gly Pro Met Ile Leu Val Leu Leu Ile Asn Phe Ile Phe Leu Phe
        275                 280                 285

Asn Ile Val Arg Ile Leu Met Thr Lys Leu Arg Ala Ser Thr Thr Ser
    290                 295                 300

Glu Thr Ile Gln Tyr Arg Lys Ala Val Lys Ala Thr Leu Val Leu Leu
305                 310                 315                 320

Pro Leu Leu Gly Ile Thr Tyr Met Leu Phe Phe Val Asn Pro Gly Glu
                325                 330                 335

Asp Glu Val Ser Arg Val Val Phe Ile Tyr Phe Asn Ser Phe Leu Glu
            340                 345                 350

Ser Phe Gln Gly Phe Phe Val Ser Val Phe Tyr Cys Phe Leu Asn Ser
        355                 360                 365

Glu Val Arg Ser Ala Ile Arg Lys Arg Trp His Arg Trp Gln Asp Lys
    370                 375                 380

His Ser Ile Arg Ala Arg Val Ala Arg Ala Met Ser Ile Pro Thr Ser
385                 390                 395                 400

Pro Thr Arg Val Ser Phe His Ser Ile Lys Gln Ser Thr Ala Val
                405                 410                 415

<210> SEQ ID NO 29
<211> LENGTH: 1248
<212> TYPE: DNA
<213> ORGANISM: Xenopus laevis
<220> FEATURE:
<221> NAME/KEY: CDS
<222> LOCATION: (1)..(1248)

<400> SEQUENCE: 29 atg ctg ttg gcc aaa act cca tgt cta cta ctg gtg cag gtg atc gct     48
Met Leu Leu Ala Lys Thr Pro Cys Leu Leu Leu Val Gln Val Ile Ala
1               5                   10                  15 gct gga atc agt ttt gcc ctc acc tct ctc cag gac caa tgt gaa acc     96
Ala Gly Ile Ser Phe Ala Leu Thr Ser Leu Gln Asp Gln Cys Glu Thr
            20                  25                  30
```

-continued

| | |
|---|---|
| ctg cag cac aat tct aac ttc aca ggt ctt gcc tgc aac gct tcc att<br>Leu Gln His Asn Ser Asn Phe Thr Gly Leu Ala Cys Asn Ala Ser Ile<br>35                        40                        45 | 144 |
| gat atg atc ggc act tgc tgg ccc agt act gca gct gga cag atg gtg<br>Asp Met Ile Gly Thr Cys Trp Pro Ser Thr Ala Ala Gly Gln Met Val<br>50                        55                        60 | 192 |
| gcc aga ccc tgc ccc gag tac ttc cat ggg gtg caa tac aac aca aca<br>Ala Arg Pro Cys Pro Glu Tyr Phe His Gly Val Gln Tyr Asn Thr Thr<br>65                        70                        75                        80 | 240 |
| ggg aat gtg tac aga gaa tgt cac ctg aac ggc agc tgg gct ggg aga<br>Gly Asn Val Tyr Arg Glu Cys His Leu Asn Gly Ser Trp Ala Gly Arg<br>                        85                        90                        95 | 288 |
| gga gac tac gct caa tgc cag gag att cta aag caa gag aag aaa acc<br>Gly Asp Tyr Ala Gln Cys Gln Glu Ile Leu Lys Gln Glu Lys Lys Thr<br>                        100                      105                      110 | 336 |
| aaa gtt cat tat cac ata gcc atc gtg att aac ttc ctg ggt cac tcc<br>Lys Val His Tyr His Ile Ala Ile Val Ile Asn Phe Leu Gly His Ser<br>                        115                      120                      125 | 384 |
| att tcc ctt tgt gct ctc ctg gtg gct ttt atc ctg ttc ttg agg ttg<br>Ile Ser Leu Cys Ala Leu Leu Val Ala Phe Ile Leu Phe Leu Arg Leu<br>130                        135                      140 | 432 |
| agg agc atc cgg tgc cta cgt aat atc atc cac tgg aac ctg atc acg<br>Arg Ser Ile Arg Cys Leu Arg Asn Ile Ile His Trp Asn Leu Ile Thr<br>145                        150                      155                      160 | 480 |
| gct ttt att ctg cgt aat gta acc tgg ttt gtg atg cag ctc act ctc<br>Ala Phe Ile Leu Arg Asn Val Thr Trp Phe Val Met Gln Leu Thr Leu<br>                        165                      170                      175 | 528 |
| agc cat gaa gcc cac gac agc aat gtg gtt tgg tgc cgc ctg gtc acc<br>Ser His Glu Ala His Asp Ser Asn Val Val Trp Cys Arg Leu Val Thr<br>                        180                      185                      190 | 576 |
| atc gct cac aat tat ttt tat gtt acc aac ttc ttc tgg atg ttt ggg<br>Ile Ala His Asn Tyr Phe Tyr Val Thr Asn Phe Phe Trp Met Phe Gly<br>                        195                      200                      205 | 624 |
| gag ggc tgt tac ctg cac acg gcc att gtt cta acc tac tca act gac<br>Glu Gly Cys Tyr Leu His Thr Ala Ile Val Leu Thr Tyr Ser Thr Asp<br>                        210                      215                      220 | 672 |
| aaa ctg cgc aaa tgg atg ttc atc tgt att ggc tgg tgt atc ccc ttt<br>Lys Leu Arg Lys Trp Met Phe Ile Cys Ile Gly Trp Cys Ile Pro Phe<br>225                        230                      235                      240 | 720 |
| ccc atc att gtg gct tgg gcc att ggc aaa ctt tac tac gac aat gaa<br>Pro Ile Ile Val Ala Trp Ala Ile Gly Lys Leu Tyr Tyr Asp Asn Glu<br>                        245                      250                      255 | 768 |
| aag tgc tgg ttt ggg aag aaa gcg gga gtc tac aca gat ttt atc tac<br>Lys Cys Trp Phe Gly Lys Lys Ala Gly Val Tyr Thr Asp Phe Ile Tyr<br>                        260                      265                      270 | 816 |
| caa gga cct gtc atc ctt gtg ctg ctg atc aac ttc ata ttt tta ttc<br>Gln Gly Pro Val Ile Leu Val Leu Leu Ile Asn Phe Ile Phe Leu Phe<br>                        275                      280                      285 | 864 |
| aac att gta cgg att ctg atg aca aag ctc aga gct tcc acc act tca<br>Asn Ile Val Arg Ile Leu Met Thr Lys Leu Arg Ala Ser Thr Thr Ser<br>                        290                      295                      300 | 912 |
| gag acc ata cag tac agg aaa gct gtt aaa gcc acc ctg gtg ctc ctg<br>Glu Thr Ile Gln Tyr Arg Lys Ala Val Lys Ala Thr Leu Val Leu Leu<br>305                        310                      315                      320 | 960 |
| cct ttg ctt ggg atc acc tac atg ctt ttc ttt gtg acg ccc ggg gag<br>Pro Leu Leu Gly Ile Thr Tyr Met Leu Phe Phe Val Thr Pro Gly Glu<br>                        325                      330                      335 | 1008 |
| gat gaa atc tca cgt atc gtc ttt atc tat ttc aac tct ttc ctg cag<br>Asp Glu Ile Ser Arg Ile Val Phe Ile Tyr Phe Asn Ser Phe Leu Gln<br>                        340                      345                      350 | 1056 |

```
tcc ttt cag ggt ttc ttt gtt tca gtt ttc tac tgc ttc ctt aat agt    1104
Ser Phe Gln Gly Phe Phe Val Ser Val Phe Tyr Cys Phe Leu Asn Ser
    355                 360                 365 gag gtg cgc tca gca gtc cgg aag cga tgg cac cga tgg cag gac aag    1152
Glu Val Arg Ser Ala Val Arg Lys Arg Trp His Arg Trp Gln Asp Lys
370                 375                 380 cat tca atc cgt gct cgc gtg gcc cgt gcc atg tcc att ccc aca tca    1200
His Ser Ile Arg Ala Arg Val Ala Arg Ala Met Ser Ile Pro Thr Ser
385                 390                 395                 400 ccc act cgg att agt ttc cac agc atc aag caa tct tct gcc att tga    1248
Pro Thr Arg Ile Ser Phe His Ser Ile Lys Gln Ser Ser Ala Ile
                405                 410                 415

<210> SEQ ID NO 30
<211> LENGTH: 415
<212> TYPE: PRT
<213> ORGANISM: Xenopus laevis

<400> SEQUENCE: 30

Met Leu Leu Ala Lys Thr Pro Cys Leu Leu Val Gln Val Ile Ala
1               5                   10                  15

Ala Gly Ile Ser Phe Ala Leu Thr Ser Leu Gln Asp Gln Cys Glu Thr
                20                  25                  30

Leu Gln His Asn Ser Asn Phe Thr Gly Leu Ala Cys Asn Ala Ser Ile
            35                  40                  45

Asp Met Ile Gly Thr Cys Trp Pro Ser Thr Ala Ala Gly Gln Met Val
    50                  55                  60

Ala Arg Pro Cys Pro Glu Tyr Phe His Gly Val Gln Tyr Asn Thr Thr
65                  70                  75                  80

Gly Asn Val Tyr Arg Glu Cys His Leu Asn Gly Ser Trp Ala Gly Arg
                85                  90                  95

Gly Asp Tyr Ala Gln Cys Gln Glu Ile Leu Lys Gln Glu Lys Lys Thr
            100                 105                 110

Lys Val His Tyr His Ile Ala Ile Val Ile Asn Phe Leu Gly His Ser
        115                 120                 125

Ile Ser Leu Cys Ala Leu Leu Val Ala Phe Ile Leu Phe Leu Arg Leu
    130                 135                 140

Arg Ser Ile Arg Cys Leu Arg Asn Ile Ile His Trp Asn Leu Ile Thr
145                 150                 155                 160

Ala Phe Ile Leu Arg Asn Val Thr Trp Phe Val Met Gln Leu Thr Leu
                165                 170                 175

Ser His Glu Ala His Asp Ser Asn Val Val Trp Cys Arg Leu Val Thr
            180                 185                 190

Ile Ala His Asn Tyr Phe Tyr Val Thr Asn Phe Phe Trp Met Phe Gly
        195                 200                 205

Glu Gly Cys Tyr Leu His Thr Ala Ile Val Leu Thr Tyr Ser Thr Asp
    210                 215                 220

Lys Leu Arg Lys Trp Met Phe Ile Cys Ile Gly Trp Cys Ile Pro Phe
225                 230                 235                 240

Pro Ile Ile Val Ala Trp Ala Ile Gly Lys Leu Tyr Tyr Asp Asn Glu
                245                 250                 255

Lys Cys Trp Phe Gly Lys Lys Ala Gly Val Tyr Thr Asp Phe Ile Tyr
            260                 265                 270

Gln Gly Pro Val Ile Leu Val Leu Leu Ile Asn Phe Ile Phe Leu Phe
        275                 280                 285
```

```
Asn Ile Val Arg Ile Leu Met Thr Lys Leu Arg Ala Ser Thr Thr Ser
290                 295                 300

Glu Thr Ile Gln Tyr Arg Lys Ala Val Lys Ala Thr Leu Val Leu Leu
305                 310                 315                 320

Pro Leu Leu Gly Ile Thr Tyr Met Leu Phe Phe Val Thr Pro Gly Glu
                325                 330                 335

Asp Glu Ile Ser Arg Ile Val Phe Ile Tyr Phe Asn Ser Phe Leu Gln
                340                 345                 350

Ser Phe Gln Gly Phe Phe Val Ser Val Phe Tyr Cys Phe Leu Asn Ser
                355                 360                 365

Glu Val Arg Ser Ala Val Arg Lys Arg Trp His Arg Trp Gln Asp Lys
370                 375                 380

His Ser Ile Arg Ala Arg Val Ala Arg Ala Met Ser Ile Pro Thr Ser
385                 390                 395                 400

Pro Thr Arg Ile Ser Phe His Ser Ile Lys Gln Ser Ser Ala Ile
                405                 410                 415

<210> SEQ ID NO 31
<211> LENGTH: 1242
<212> TYPE: DNA
<213> ORGANISM: Xenopus laevis
<220> FEATURE:
<221> NAME/KEY: CDS
<222> LOCATION: (1)..(1242)

<400> SEQUENCE: 31 atg gac agc acc atc ttt gag att atc att gat gaa ttt gat gcc aac      48
Met Asp Ser Thr Ile Phe Glu Ile Ile Ile Asp Glu Phe Asp Ala Asn
1               5                   10                  15 tgc agc ctt ttg gat gct ttt cag gac agt ttt ttg cac tct gag tcc      96
Cys Ser Leu Leu Asp Ala Phe Gln Asp Ser Phe Leu His Ser Glu Ser
            20                  25                  30 tcc tct ttc ttt ggc ttt gaa ggt ccc tat tgt agc gct acc att gac     144
Ser Ser Phe Phe Gly Phe Glu Gly Pro Tyr Cys Ser Ala Thr Ile Asp
        35                  40                  45 cag att ggc acg tgc tgg ccc agg agc cta gcc ggg gaa ctt gtg gaa     192
Gln Ile Gly Thr Cys Trp Pro Arg Ser Leu Ala Gly Glu Leu Val Glu
    50                  55                  60 aga ccc tgc ccg gat tcc ttc aat ggg atc aga tac aac aca act aga     240
Arg Pro Cys Pro Asp Ser Phe Asn Gly Ile Arg Tyr Asn Thr Thr Arg
65                  70                  75                  80 aac gtc tac aga gaa tgc ttt gag aat gga acc tgg gcg tcc tgg atg     288
Asn Val Tyr Arg Glu Cys Phe Glu Asn Gly Thr Trp Ala Ser Trp Met
                85                  90                  95 aat tac tct cag tgt gtg ccc att ctg gat aat aag agg aag tac gcc     336
Asn Tyr Ser Gln Cys Val Pro Ile Leu Asp Asn Lys Arg Lys Tyr Ala
            100                 105                 110 ctt cat tac aag att gct ctc atc ata aac tac ctg ggg cac tgc atc     384
Leu His Tyr Lys Ile Ala Leu Ile Ile Asn Tyr Leu Gly His Cys Ile
        115                 120                 125 tcc atc ttg gct ctc gtt atc gct ttc ttg ctc ttt ctg tgt ttg agg     432
Ser Ile Leu Ala Leu Val Ile Ala Phe Leu Leu Phe Leu Cys Leu Arg
    130                 135                 140 agt ata aga tgc ctt cgg aac att atc cac tgg aat tta atc act act     480
Ser Ile Arg Cys Leu Arg Asn Ile Ile His Trp Asn Leu Ile Thr Thr
145                 150                 155                 160 ttc atc ctg agg aac atc atg tgg ttc ctg ctg cag atg att gac cat     528
Phe Ile Leu Arg Asn Ile Met Trp Phe Leu Leu Gln Met Ile Asp His
                165                 170                 175
```

```
aac att cat gaa agc aac gag gtc tgg tgt cgg tgt atc aca act att        576
Asn Ile His Glu Ser Asn Glu Val Trp Cys Arg Cys Ile Thr Thr Ile
            180                 185                 190 tac aat tac ttt gtg gtg acc aac ttc ttc tgg atg ttt gtg gaa gga        624
Tyr Asn Tyr Phe Val Val Thr Asn Phe Phe Trp Met Phe Val Glu Gly
        195                 200                 205 tgt tac cta cac aca gct ata gtg atg aca tac tca acg gac aaa ctt        672
Cys Tyr Leu His Thr Ala Ile Val Met Thr Tyr Ser Thr Asp Lys Leu
    210                 215                 220 agg aaa tgg gtg ttc ctc ttc ata gga tgg tgt att cca tct ccg atc        720
Arg Lys Trp Val Phe Leu Phe Ile Gly Trp Cys Ile Pro Ser Pro Ile
225                 230                 235                 240 att gtc acc tgg gcc atc tgc aag ctt ttc tat gaa aat gaa cag tgt        768
Ile Val Thr Trp Ala Ile Cys Lys Leu Phe Tyr Glu Asn Glu Gln Cys
                245                 250                 255 tgg att ggg aag gag ccc ggg aaa tac att gat tac att tac cag ggc        816
Trp Ile Gly Lys Glu Pro Gly Lys Tyr Ile Asp Tyr Ile Tyr Gln Gly
            260                 265                 270 cgg gtg att ctc gta ctt ctg ata aat ttt gtg ttc tta ttc aac att        864
Arg Val Ile Leu Val Leu Leu Ile Asn Phe Val Phe Leu Phe Asn Ile
        275                 280                 285 gta aga att ttg atg aca aaa ctg aga gct tca act aca tct gaa acg        912
Val Arg Ile Leu Met Thr Lys Leu Arg Ala Ser Thr Thr Ser Glu Thr
    290                 295                 300 ata cag tac agg aag gct gtg aag gca acg tta gtc ctt ctc cct ctt        960
Ile Gln Tyr Arg Lys Ala Val Lys Ala Thr Leu Val Leu Leu Pro Leu
305                 310                 315                 320 ctg gga atc acc tac atg ctc ttc ttc gtc aac cct gga gag gat gac       1008
Leu Gly Ile Thr Tyr Met Leu Phe Phe Val Asn Pro Gly Glu Asp Asp
                325                 330                 335 gtt tct cag atc gtt ttt att tac ttc aac tcg ttt ctt cag tcc ttt       1056
Val Ser Gln Ile Val Phe Ile Tyr Phe Asn Ser Phe Leu Gln Ser Phe
            340                 345                 350 cag ggt ttc ttt gtg tca gta ttt tac tgc ttc ctt aat ggg gag gtc       1104
Gln Gly Phe Phe Val Ser Val Phe Tyr Cys Phe Leu Asn Gly Glu Val
        355                 360                 365 cgg tcg gct gca agg aaa aga tgg cac cgc tgg caa gac cac cat tct       1152
Arg Ser Ala Ala Arg Lys Arg Trp His Arg Trp Gln Asp His His Ser
    370                 375                 380 ctg cgg gtt cgg gta gcc aga gcc atg tcc ata cca aca tca ccg acc       1200
Leu Arg Val Arg Val Ala Arg Ala Met Ser Ile Pro Thr Ser Pro Thr
385                 390                 395                 400 aga atc agc ttt cac agt ata aag caa acg gca gcc gtc tga              1242
Arg Ile Ser Phe His Ser Ile Lys Gln Thr Ala Ala Val
                405                 410

<210> SEQ ID NO 32
<211> LENGTH: 413
<212> TYPE: PRT
<213> ORGANISM: Xenopus laevis

<400> SEQUENCE: 32

Met Asp Ser Thr Ile Phe Glu Ile Ile Asp Glu Phe Asp Ala Asn
1               5                   10                  15

Cys Ser Leu Leu Asp Ala Phe Gln Asp Ser Phe Leu His Ser Glu Ser
                20                  25                  30

Ser Ser Phe Phe Gly Phe Glu Gly Pro Tyr Cys Ser Ala Thr Ile Asp
            35                  40                  45

Gln Ile Gly Thr Cys Trp Pro Arg Ser Leu Ala Gly Glu Leu Val Glu
        50                  55                  60
```

```
Arg Pro Cys Pro Asp Ser Phe Asn Gly Ile Arg Tyr Asn Thr Thr Arg
 65                  70                  75                  80

Asn Val Tyr Arg Glu Cys Phe Glu Asn Gly Thr Trp Ala Ser Trp Met
             85                  90                  95

Asn Tyr Ser Gln Cys Val Pro Ile Leu Asp Asn Lys Arg Lys Tyr Ala
            100                 105                 110

Leu His Tyr Lys Ile Ala Leu Ile Ile Asn Tyr Leu Gly His Cys Ile
        115                 120                 125

Ser Ile Leu Ala Leu Val Ile Ala Phe Leu Leu Phe Leu Cys Leu Arg
130                 135                 140

Ser Ile Arg Cys Leu Arg Asn Ile Ile His Trp Asn Leu Ile Thr Thr
145                 150                 155                 160

Phe Ile Leu Arg Asn Ile Met Trp Phe Leu Gln Met Ile Asp His
                165                 170                 175

Asn Ile His Glu Ser Asn Glu Val Trp Cys Arg Cys Ile Thr Thr Ile
            180                 185                 190

Tyr Asn Tyr Phe Val Val Thr Asn Phe Phe Trp Met Phe Val Glu Gly
            195                 200                 205

Cys Tyr Leu His Thr Ala Ile Val Met Thr Tyr Ser Thr Asp Lys Leu
            210                 215                 220

Arg Lys Trp Val Phe Leu Phe Ile Gly Trp Cys Ile Pro Ser Pro Ile
225                 230                 235                 240

Ile Val Thr Trp Ala Ile Cys Lys Leu Phe Tyr Glu Asn Glu Gln Cys
                245                 250                 255

Trp Ile Gly Lys Glu Pro Gly Lys Tyr Ile Asp Tyr Ile Tyr Gln Gly
            260                 265                 270

Arg Val Ile Leu Val Leu Leu Ile Asn Phe Val Phe Leu Phe Asn Ile
            275                 280                 285

Val Arg Ile Leu Met Thr Lys Leu Arg Ala Ser Thr Thr Ser Glu Thr
            290                 295                 300

Ile Gln Tyr Arg Lys Ala Val Lys Ala Thr Leu Val Leu Leu Pro Leu
305                 310                 315                 320

Leu Gly Ile Thr Tyr Met Leu Phe Phe Val Asn Pro Gly Glu Asp Asp
                325                 330                 335

Val Ser Gln Ile Val Phe Ile Tyr Phe Asn Ser Phe Leu Gln Ser Phe
            340                 345                 350

Gln Gly Phe Phe Val Ser Val Phe Tyr Cys Phe Leu Asn Gly Glu Val
            355                 360                 365

Arg Ser Ala Ala Arg Lys Arg Trp His Arg Trp Gln Asp His His Ser
370                 375                 380

Leu Arg Val Arg Val Ala Arg Ala Met Ser Ile Pro Thr Ser Pro Thr
385                 390                 395                 400

Arg Ile Ser Phe His Ser Ile Lys Gln Thr Ala Ala Val
                405                 410
```

<210> SEQ ID NO 33
<211> LENGTH: 1338
<212> TYPE: DNA
<213> ORGANISM: Ameiurus nebulosus
<220> FEATURE:
<221> NAME/KEY: CDS
<222> LOCATION: (1)..(1338)

<400> SEQUENCE: 33 atg cat ttc ctt cta cgt cct cag gtg ttt tct atc tgg atc aca cta          48

```
                                                                  -continued Met His Phe Leu Leu Arg Pro Gln Val Phe Ser Ile Trp Ile Thr Leu
1               5                  10                 15 ttc tct ggg gcc aca gct gag ctc aca tgc gac act ctg ctc ctg ctc      96
Phe Ser Gly Ala Thr Ala Glu Leu Thr Cys Asp Thr Leu Leu Leu Leu
                20                  25                  30 tcc acc aac cgc aca gct cgc aca tta ata cta tgg aac cag acg tcg     144
Ser Thr Asn Arg Thr Ala Arg Thr Leu Ile Leu Trp Asn Gln Thr Ser
            35                  40                  45 agc tca agt aat gcc aca ggt aca agc tca agt aat gcc aca ggt aca     192
Ser Ser Ser Asn Ala Thr Gly Thr Ser Ser Ser Asn Ala Thr Gly Thr
        50                  55                  60 agc tca agc aat gcc aca ggt ttg ttc tgt aat ata tct ata gat ggc     240
Ser Ser Ser Asn Ala Thr Gly Leu Phe Cys Asn Ile Ser Ile Asp Gly
65                  70                  75                  80 atc ggg acg tgt tgg ccc agg agc aac gca ggg gaa ata gta tca cgt     288
Ile Gly Thr Cys Trp Pro Arg Ser Asn Ala Gly Glu Ile Val Ser Arg
                85                  90                  95 cca tgt cct gag acc ttc ttg ggt gtc cgc tac aac acc acc aat aac     336
Pro Cys Pro Glu Thr Phe Leu Gly Val Arg Tyr Asn Thr Thr Asn Asn
            100                 105                 110 gtc tac aga gaa tgc ctc gcc aat gga acg tgg gcg aag aag ggg aat     384
Val Tyr Arg Glu Cys Leu Ala Asn Gly Thr Trp Ala Lys Lys Gly Asn
        115                 120                 125 tat tct cag tgt cag gaa att ctc aat gaa gag aaa aag agc aag ctg     432
Tyr Ser Gln Cys Gln Glu Ile Leu Asn Glu Glu Lys Lys Ser Lys Leu
    130                 135                 140 cac tac cac att gca gtg att ata aac tac ctg ggc cac tgc atc tct     480
His Tyr His Ile Ala Val Ile Ile Asn Tyr Leu Gly His Cys Ile Ser
145                 150                 155                 160 ctc gga gcc ctg ctg gtt gcc ttc att ctc ttt atg agg ctg agg atg     528
Leu Gly Ala Leu Leu Val Ala Phe Ile Leu Phe Met Arg Leu Arg Met
                165                 170                 175 atc cgc tgc ctc agg aac atc att cac tgg aat ctg att atg gct ttc     576
Ile Arg Cys Leu Arg Asn Ile Ile His Trp Asn Leu Ile Met Ala Phe
            180                 185                 190 atc ctg cgc aat gct aca tgg ttc gta gtg cag ctg acc atg aac cca     624
Ile Leu Arg Asn Ala Thr Trp Phe Val Val Gln Leu Thr Met Asn Pro
        195                 200                 205 gag gtg cat gag agc aat gtg atc tgg tgc agg ctg gtt aca gca gcg     672
Glu Val His Glu Ser Asn Val Ile Trp Cys Arg Leu Val Thr Ala Ala
    210                 215                 220 tat aat tac ttt cat gtg acc aac ttc ttc tgg atg ttt ggt gag ggc     720
Tyr Asn Tyr Phe His Val Thr Asn Phe Phe Trp Met Phe Gly Glu Gly
225                 230                 235                 240 tgc tat ctg cac acg gcc atc gtg ctg act tac tcc act gat aag ctc     768
Cys Tyr Leu His Thr Ala Ile Val Leu Thr Tyr Ser Thr Asp Lys Leu
                245                 250                 255 agg aag tgg ctg ttc atc tgt atc ggc tgg tgt att ccc ttt cct atc     816
Arg Lys Trp Leu Phe Ile Cys Ile Gly Trp Cys Ile Pro Phe Pro Ile
            260                 265                 270 atc gtt gca tgg gcc att ggt aag ctg tat tac gac aat gaa aag tgc     864
Ile Val Ala Trp Ala Ile Gly Lys Leu Tyr Tyr Asp Asn Glu Lys Cys
        275                 280                 285 tgg ttt gga aaa cga gct ggt gtt tat act gac tac atc tat cag ggc     912
Trp Phe Gly Lys Arg Ala Gly Val Tyr Thr Asp Tyr Ile Tyr Gln Gly
    290                 295                 300 ccc atg atc ctt gtt ctt ctg atc aac ttt att ttc ctt ttc aac atc     960
Pro Met Ile Leu Val Leu Leu Ile Asn Phe Ile Phe Leu Phe Asn Ile
305                 310                 315                 320
```

-continued

```
gtg agg atc ctg atg aca aag cta aga gcc tcc acc aca tca gag acg    1008
Val Arg Ile Leu Met Thr Lys Leu Arg Ala Ser Thr Thr Ser Glu Thr
            325                 330                 335 att cag tac agg aaa gct gtg aag gcc act ctg gtc ctg ctg cct ctc    1056
Ile Gln Tyr Arg Lys Ala Val Lys Ala Thr Leu Val Leu Leu Pro Leu
    340                 345                 350 ctc ggg atc acc tac atg ctt ttc ttt gtt aac cct gga gag gac gag    1104
Leu Gly Ile Thr Tyr Met Leu Phe Phe Val Asn Pro Gly Glu Asp Glu
355                 360                 365 atc tcc caa atc gtc ttc atc tat ttc aat tct ttc ctc gag tcc ttt    1152
Ile Ser Gln Ile Val Phe Ile Tyr Phe Asn Ser Phe Leu Glu Ser Phe
    370                 375                 380 caa ggt ttc ttc gtg tct gtg ttt tat tgc ttc ctg aac agt gaa gtc    1200
Gln Gly Phe Phe Val Ser Val Phe Tyr Cys Phe Leu Asn Ser Glu Val
385                 390                 395                 400 cgt tcg gct gtt cgg aag cgc tgg cac cgc cgg cag gac aag cac tca    1248
Arg Ser Ala Val Arg Lys Arg Trp His Arg Arg Gln Asp Lys His Ser
                405                 410                 415 atc cgg gca cgg gtg gca cgg gcc atg tcc att ccc acc tcg cct act    1296
Ile Arg Ala Arg Val Ala Arg Ala Met Ser Ile Pro Thr Ser Pro Thr
            420                 425                 430 cgg gtc agc ttc cac agc atc aag caa tcc tca gca gtg tga            1338
Arg Val Ser Phe His Ser Ile Lys Gln Ser Ser Ala Val
        435                 440                 445
```

<210> SEQ ID NO 34
<211> LENGTH: 445
<212> TYPE: PRT
<213> ORGANISM: Ameiurus nebulosus

<400> SEQUENCE: 34

```
Met His Phe Leu Leu Arg Pro Gln Val Phe Ser Ile Trp Ile Thr Leu
1               5                   10                  15

Phe Ser Gly Ala Thr Ala Glu Leu Thr Cys Asp Thr Leu Leu Leu Leu
            20                  25                  30

Ser Thr Asn Arg Thr Ala Arg Thr Leu Ile Leu Trp Asn Gln Thr Ser
        35                  40                  45

Ser Ser Ser Asn Ala Thr Gly Thr Ser Ser Asn Ala Thr Gly Thr
    50                  55                  60

Ser Ser Ser Asn Ala Thr Gly Leu Phe Cys Asn Ile Ser Ile Asp Gly
65                  70                  75                  80

Ile Gly Thr Cys Trp Pro Arg Ser Asn Ala Gly Glu Ile Val Ser Arg
                85                  90                  95

Pro Cys Pro Glu Thr Phe Leu Gly Val Arg Tyr Asn Thr Thr Asn Asn
            100                 105                 110

Val Tyr Arg Glu Cys Leu Ala Asn Gly Thr Trp Ala Lys Lys Gly Asn
        115                 120                 125

Tyr Ser Gln Cys Gln Glu Ile Leu Asn Glu Lys Lys Ser Lys Leu
    130                 135                 140

His Tyr His Ile Ala Val Ile Asn Tyr Leu Gly His Cys Ile Ser
145                 150                 155                 160

Leu Gly Ala Leu Leu Val Ala Phe Ile Leu Phe Met Arg Leu Arg Met
                165                 170                 175

Ile Arg Cys Leu Arg Asn Ile Ile His Trp Asn Leu Ile Met Ala Phe
            180                 185                 190

Ile Leu Arg Asn Ala Thr Trp Phe Val Val Gln Leu Thr Met Asn Pro
        195                 200                 205
```

-continued

```
Glu Val His Glu Ser Asn Val Ile Trp Cys Arg Leu Val Thr Ala Ala
    210                 215                 220
Tyr Asn Tyr Phe His Val Thr Asn Phe Phe Trp Met Phe Gly Glu Gly
225                 230                 235                 240
Cys Tyr Leu His Thr Ala Ile Val Leu Thr Tyr Ser Thr Asp Lys Leu
                245                 250                 255
Arg Lys Trp Leu Phe Ile Cys Ile Gly Trp Cys Ile Pro Phe Pro Ile
            260                 265                 270
Ile Val Ala Trp Ala Ile Gly Lys Leu Tyr Tyr Asp Asn Glu Lys Cys
        275                 280                 285
Trp Phe Gly Lys Arg Ala Gly Val Tyr Thr Asp Tyr Ile Tyr Gln Gly
290                 295                 300
Pro Met Ile Leu Val Leu Leu Ile Asn Phe Ile Phe Leu Phe Asn Ile
305                 310                 315                 320
Val Arg Ile Leu Met Thr Lys Leu Arg Ala Ser Thr Thr Ser Glu Thr
                325                 330                 335
Ile Gln Tyr Arg Lys Ala Val Lys Ala Thr Leu Val Leu Leu Pro Leu
                340                 345                 350
Leu Gly Ile Thr Tyr Met Leu Phe Phe Val Asn Pro Gly Glu Asp Glu
            355                 360                 365
Ile Ser Gln Ile Val Phe Ile Tyr Phe Asn Ser Phe Leu Glu Ser Phe
        370                 375                 380
Gln Gly Phe Phe Val Ser Val Phe Tyr Cys Phe Leu Asn Ser Glu Val
385                 390                 395                 400
Arg Ser Ala Val Arg Lys Arg Trp His Arg Arg Gln Asp Lys His Ser
                405                 410                 415
Ile Arg Ala Arg Val Ala Arg Ala Met Ser Ile Pro Thr Ser Pro Thr
            420                 425                 430
Arg Val Ser Phe His Ser Ile Lys Gln Ser Ser Ala Val
        435                 440                 445

<210> SEQ ID NO 35
<211> LENGTH: 1442
<212> TYPE: DNA
<213> ORGANISM: Ameiurus nebulosus
<220> FEATURE:
<221> NAME/KEY: CDS
<222> LOCATION: (102)..(1388)

<400> SEQUENCE: 35
cagaaatatg gagatggaga ctgctttaca gtcactcggg tcaaacagga tgttaagctg          60
aactgattaa taatcctgcc agctgatcaa ctggaaaggg a atg tgg atc tgc cta        116
                                             Met Trp Ile Cys Leu
                                               1               5 atg cta aag gtc ttg tct atc ttg tct ttt gtg gtt gtg aag gtg tca          164
Met Leu Lys Val Leu Ser Ile Leu Ser Phe Val Val Val Lys Val Ser
             10                  15                  20 gct gat ctt acc tgc gat gcc gtg cta atg ctg gct tct gga aac cac          212
Ala Asp Leu Thr Cys Asp Ala Val Leu Met Leu Ala Ser Gly Asn His
         25                  30                  35 aca ttg tac cat ctg gat gcc gct aat cac tct gac act aat aac tcg          260
Thr Leu Tyr His Leu Asp Ala Ala Asn His Ser Asp Thr Asn Asn Ser
     40                  45                  50 ggt gtg ttt tgc agc aca gtt atc gat ggc atc ggc acc tgc tgg ccg          308
Gly Val Phe Cys Ser Thr Val Ile Asp Gly Ile Gly Thr Cys Trp Pro
 55                  60                  65 cgc agc gtg gcc ggg gag atg gtg tcg cgt ccg tgt ccg gaa ttc ctc          356
```

-continued

```
Arg Ser Val Ala Gly Glu Met Val Ser Arg Pro Cys Pro Glu Phe Leu
70              75                  80                  85 tac gga gtc cga tac aac acc acc aat aaa atc ttc cgg aaa tgt ctt    404
Tyr Gly Val Arg Tyr Asn Thr Thr Asn Lys Ile Phe Arg Lys Cys Leu
            90                  95                 100 gct aat gga acc tgg gcg ccc aaa agc aac tac tct cag tgc aag gct    452
Ala Asn Gly Thr Trp Ala Pro Lys Ser Asn Tyr Ser Gln Cys Lys Ala
                105                 110                115 att ctc aat gta cag agg aag agc aag ctg cat tat cga atc gct gtc    500
Ile Leu Asn Val Gln Arg Lys Ser Lys Leu His Tyr Arg Ile Ala Val
        120                 125                 130 atc att aac tac ctg ggt cac tgc ttg tca ctg ttc act ctt ctt atc    548
Ile Ile Asn Tyr Leu Gly His Cys Leu Ser Leu Phe Thr Leu Leu Ile
    135                 140                 145 gcc ttc ata atc ttc tta cga ctc agg agt att cgc tgt tta agg aac    596
Ala Phe Ile Ile Phe Leu Arg Leu Arg Ser Ile Arg Cys Leu Arg Asn
150                 155                 160                 165 atc atc cac tgg aat cta acc tct gcc ttc atc ctg aga aat gcg acg    644
Ile Ile His Trp Asn Leu Thr Ser Ala Phe Ile Leu Arg Asn Ala Thr
            170                 175                 180 tgg ttc atc gtt cag ctc acc atg aac cct gat gta cac gag agc aac    692
Trp Phe Ile Val Gln Leu Thr Met Asn Pro Asp Val His Glu Ser Asn
                185                 190                195 gtg cca tgg tgc cgt tta gtg acg acg gca tat aac tac ttc cac atg    740
Val Pro Trp Cys Arg Leu Val Thr Thr Ala Tyr Asn Tyr Phe His Met
        200                 205                 210 gcc aat ttt ttc tgg atg ttc ggc gaa ggc tgt tat ctt cac aca gcc    788
Ala Asn Phe Phe Trp Met Phe Gly Glu Gly Cys Tyr Leu His Thr Ala
    215                 220                 225 atc gtg ctc acc tac tcc act gac aaa ctc aag aaa tgg atg ttc atc    836
Ile Val Leu Thr Tyr Ser Thr Asp Lys Leu Lys Lys Trp Met Phe Ile
230                 235                 240                 245 tgc atc gga tgg tgt att cct tcg cct att atc gtc gcc tgg gcc atc    884
Cys Ile Gly Trp Cys Ile Pro Ser Pro Ile Ile Val Ala Trp Ala Ile
            250                 255                 260 gga aag ctg tac tac gac aac gag aag tgt tgg ttt ggg aag aga gca    932
Gly Lys Leu Tyr Tyr Asp Asn Glu Lys Cys Trp Phe Gly Lys Arg Ala
                265                 270                275 ggc ata tac aca gac tac atc tac cag ggc ccc atg atc ctg gta ctt    980
Gly Ile Tyr Thr Asp Tyr Ile Tyr Gln Gly Pro Met Ile Leu Val Leu
        280                 285                 290 atg atc aat ttc gtg ttc ctc ttc aac ata gta agg atc ctc atg acc   1028
Met Ile Asn Phe Val Phe Leu Phe Asn Ile Val Arg Ile Leu Met Thr
    295                 300                 305 aaa ctc cgg gcc tcc acc aca tcc gaa acc atc cag tac agg aag gcg   1076
Lys Leu Arg Ala Ser Thr Thr Ser Glu Thr Ile Gln Tyr Arg Lys Ala
310                 315                 320                 325 gtg aag gcc acg ctc gtg tta ctg cct ctg ctc ggg atc acg tac atg   1124
Val Lys Ala Thr Leu Val Leu Leu Pro Leu Leu Gly Ile Thr Tyr Met
            330                 335                 340 ctg ttc ttc gta aac cca gga gag gac gaa atc tcg cag atc gtc ttc   1172
Leu Phe Phe Val Asn Pro Gly Glu Asp Glu Ile Ser Gln Ile Val Phe
                345                 350                355 atc tac ttc aat tcc ttt ctg cag tcc ttt cag ggc ttc ttt gtg tcc   1220
Ile Tyr Phe Asn Ser Phe Leu Gln Ser Phe Gln Gly Phe Phe Val Ser
        360                 365                 370 gtg ttc tac tgt ttt cta aac agc gag gtc cgc tcg gct gtt cgg aag   1268
Val Phe Tyr Cys Phe Leu Asn Ser Glu Val Arg Ser Ala Val Arg Lys
    375                 380                 385
```

-continued

```
cac tgg cac cgc tgg cag gac cac cat tcc atc cgc gca cga gtt gcg      1316
His Trp His Arg Trp Gln Asp His His Ser Ile Arg Ala Arg Val Ala
390                 395                 400                 405 aga gcg atg tcc att ccc acc tca cct tcg cgc ctc agc ttc cac agc      1364
Arg Ala Met Ser Ile Pro Thr Ser Pro Ser Arg Leu Ser Phe His Ser
            410                 415                 420 atc aaa cag tcc acc tct gtc tga tacagggacg cataacattg aaaaagaaag    1418
Ile Lys Gln Ser Thr Ser Val
                425 aggcaggcac tctatcagtg agga                                          1442
```

<210> SEQ ID NO 36
<211> LENGTH: 428
<212> TYPE: PRT
<213> ORGANISM: Ameiurus nebulosus

<400> SEQUENCE: 36

```
Met Trp Ile Cys Leu Met Leu Lys Val Leu Ser Ile Leu Ser Phe Val
1               5                   10                  15

Val Val Lys Val Ser Ala Asp Leu Thr Cys Asp Ala Val Leu Met Leu
            20                  25                  30

Ala Ser Gly Asn His Thr Leu Tyr His Leu Asp Ala Ala Asn His Ser
        35                  40                  45

Asp Thr Asn Asn Ser Gly Val Phe Cys Ser Thr Val Ile Asp Gly Ile
    50                  55                  60

Gly Thr Cys Trp Pro Arg Ser Val Ala Gly Glu Met Val Ser Arg Pro
65                  70                  75                  80

Cys Pro Glu Phe Leu Tyr Gly Val Arg Tyr Asn Thr Thr Asn Lys Ile
                85                  90                  95

Phe Arg Lys Cys Leu Ala Asn Gly Thr Trp Ala Pro Lys Ser Asn Tyr
            100                 105                 110

Ser Gln Cys Lys Ala Ile Leu Asn Val Gln Arg Lys Ser Lys Leu His
        115                 120                 125

Tyr Arg Ile Ala Val Ile Ile Asn Tyr Leu Gly His Cys Leu Ser Leu
    130                 135                 140

Phe Thr Leu Leu Ile Ala Phe Ile Ile Phe Leu Arg Leu Arg Ser Ile
145                 150                 155                 160

Arg Cys Leu Arg Asn Ile Ile His Trp Asn Leu Thr Ser Ala Phe Ile
                165                 170                 175

Leu Arg Asn Ala Thr Trp Phe Ile Val Gln Leu Thr Met Asn Pro Asp
            180                 185                 190

Val His Glu Ser Asn Val Pro Trp Cys Arg Leu Val Thr Thr Ala Tyr
        195                 200                 205

Asn Tyr Phe His Met Ala Asn Phe Phe Trp Met Phe Gly Glu Gly Cys
    210                 215                 220

Tyr Leu His Thr Ala Ile Val Leu Thr Tyr Ser Thr Asp Lys Leu Lys
225                 230                 235                 240

Lys Trp Met Phe Ile Cys Ile Gly Trp Cys Ile Pro Ser Pro Ile Ile
                245                 250                 255

Val Ala Trp Ala Ile Gly Lys Leu Tyr Tyr Asp Asn Glu Lys Cys Trp
            260                 265                 270

Phe Gly Lys Arg Ala Gly Ile Tyr Thr Asp Tyr Ile Tyr Gln Gly Pro
        275                 280                 285

Met Ile Leu Val Leu Met Ile Asn Phe Val Phe Leu Phe Asn Ile Val
    290                 295                 300
```

```
Arg Ile Leu Met Thr Lys Leu Arg Ala Ser Thr Thr Ser Glu Thr Ile
305                 310                 315                 320

Gln Tyr Arg Lys Ala Val Lys Ala Thr Leu Val Leu Pro Leu Leu
            325                 330                 335

Gly Ile Thr Tyr Met Leu Phe Phe Val Asn Pro Gly Glu Asp Glu Ile
            340                 345                 350

Ser Gln Ile Val Phe Ile Tyr Phe Asn Ser Phe Leu Gln Ser Phe Gln
            355                 360                 365

Gly Phe Phe Val Ser Val Phe Tyr Cys Phe Leu Asn Ser Glu Val Arg
370                 375                 380

Ser Ala Val Arg Lys His Trp His Arg Trp Gln Asp His His Ser Ile
385                 390                 395                 400

Arg Ala Arg Val Ala Arg Ala Met Ser Ile Pro Thr Ser Pro Ser Arg
            405                 410                 415

Leu Ser Phe His Ser Ile Lys Gln Ser Thr Ser Val
            420                 425

<210> SEQ ID NO 37
<211> LENGTH: 1218
<212> TYPE: DNA
<213> ORGANISM: Ameiurus nebulosus
<220> FEATURE:
<221> NAME/KEY: CDS
<222> LOCATION: (1)..(1218)

<400> SEQUENCE: 37 atg gag gtc agt ctg ctg gag ctg ctc agt gtg gag gtg aac tgc agc        48
Met Glu Val Ser Leu Leu Glu Leu Leu Ser Val Glu Val Asn Cys Ser
1               5                   10                  15 ctc gcg gac gcg ttt gga gac cct gcg tac gga aac gca tca gac gct        96
Leu Ala Asp Ala Phe Gly Asp Pro Ala Tyr Gly Asn Ala Ser Asp Ala
                20                  25                  30 ctg tac tgc aac gcc acg gcg gat gag atc ggc acg tgc tgg ccg agg       144
Leu Tyr Cys Asn Ala Thr Ala Asp Glu Ile Gly Thr Cys Trp Pro Arg
            35                  40                  45 agc ggc gcg ggg aga gtg gtg gcg cgg ccg tgc ccc gac ttc atc aac       192
Ser Gly Ala Gly Arg Val Val Ala Arg Pro Cys Pro Asp Phe Ile Asn
        50                  55                  60 ggg gtc aag tac aac agc acc agg agc gcg tat aga gaa tgc ctg gag       240
Gly Val Lys Tyr Asn Ser Thr Arg Ser Ala Tyr Arg Glu Cys Leu Glu
65                  70                  75                  80 aac ggc aca tgg gct ttc aag atc aac tac tcc agc tgc gag ccc att       288
Asn Gly Thr Trp Ala Phe Lys Ile Asn Tyr Ser Ser Cys Glu Pro Ile
                85                  90                  95 tta gag gaa aag agg aag tac ccg gtc cac tac aag atc gct ctc atc       336
Leu Glu Glu Lys Arg Lys Tyr Pro Val His Tyr Lys Ile Ala Leu Ile
                100                 105                 110 atc aac tat ttg gga cac tgc ata tct gta ggt gct ctc gtc atc gcc       384
Ile Asn Tyr Leu Gly His Cys Ile Ser Val Gly Ala Leu Val Ile Ala
            115                 120                 125 ttc gtt ctc ttc ctg tgc ttg aga agc atc cgg tgt ttg cgg aat gta       432
Phe Val Leu Phe Leu Cys Leu Arg Ser Ile Arg Cys Leu Arg Asn Val
130                 135                 140 att cac tgg aat tta ata acc acc ttc atc ctg agg aac atc atg tgg       480
Ile His Trp Asn Leu Ile Thr Thr Phe Ile Leu Arg Asn Ile Met Trp
145                 150                 155                 160 ctt ctg ctg cag ctc atc gac cac aac atc cat gaa agg aac gag ccg       528
Leu Leu Leu Gln Leu Ile Asp His Asn Ile His Glu Arg Asn Glu Pro
                165                 170                 175
```

```
tgg tgc cgc ctc ata acc acc gtc tat aac tat ttt gtg gtg acg aat      576
Trp Cys Arg Leu Ile Thr Thr Val Tyr Asn Tyr Phe Val Val Thr Asn
            180                 185                 190 ttt ttc tgg atg ttc gtg gag ggc tgt tat ctt cac aca gcc atc gtt      624
Phe Phe Trp Met Phe Val Glu Gly Cys Tyr Leu His Thr Ala Ile Val
        195                 200                 205 atg acc tac tcc acc gac aag ctc cgg aag tgg gtc ttc ctc ttc atc      672
Met Thr Tyr Ser Thr Asp Lys Leu Arg Lys Trp Val Phe Leu Phe Ile
    210                 215                 220 ggg tgg tgt att ccg tgt ccg gtc atc att gcg tgg gcc gtc ggg aag      720
Gly Trp Cys Ile Pro Cys Pro Val Ile Ile Ala Trp Ala Val Gly Lys
225                 230                 235                 240 ctg tac aac gaa aac gaa cag tgc tgg ttt gga aaa gaa ccc gga aaa      768
Leu Tyr Asn Glu Asn Glu Gln Cys Trp Phe Gly Lys Glu Pro Gly Lys
                245                 250                 255 tac gtg gac tac att tat cag ggt cct gtg att gtt gtt ctg ctg ata      816
Tyr Val Asp Tyr Ile Tyr Gln Gly Pro Val Ile Val Val Leu Leu Ile
            260                 265                 270 aac ttc gtg ttc ctg ttc aac atc gta cgt att ctc atg acg aag ctg      864
Asn Phe Val Phe Leu Phe Asn Ile Val Arg Ile Leu Met Thr Lys Leu
        275                 280                 285 cga gcc tcc acc acg tca gag acc ata cag tac agg aaa gcg gtg aag      912
Arg Ala Ser Thr Thr Ser Glu Thr Ile Gln Tyr Arg Lys Ala Val Lys
    290                 295                 300 gcg acg tta gtg ctg ctt cct ctg ctc ggc atc aca tac atg ctg ttc      960
Ala Thr Leu Val Leu Leu Pro Leu Leu Gly Ile Thr Tyr Met Leu Phe
305                 310                 315                 320 ttc gtg aat ccg ggg gat gat gac atc tca cag att gtc ttt att tat     1008
Phe Val Asn Pro Gly Asp Asp Asp Ile Ser Gln Ile Val Phe Ile Tyr
                325                 330                 335 ttc aat tcc ttc ctg cag tcc ttt cag ggt ttc ttc gtc tca gtg ttt     1056
Phe Asn Ser Phe Leu Gln Ser Phe Gln Gly Phe Phe Val Ser Val Phe
            340                 345                 350 tac tgc ttc ctc aac ggt gag gta cgg tca gca gta agg aaa cgt tgg     1104
Tyr Cys Phe Leu Asn Gly Glu Val Arg Ser Ala Val Arg Lys Arg Trp
        355                 360                 365 cac aga tgg cag gat aac cac gct ctc cgt gtt cgg gtt gcc agg gcg     1152
His Arg Trp Gln Asp Asn His Ala Leu Arg Val Arg Val Ala Arg Ala
    370                 375                 380 atg tcc atc cca aca tca cct act cgc atc agc ttc cac agc att aaa     1200
Met Ser Ile Pro Thr Ser Pro Thr Arg Ile Ser Phe His Ser Ile Lys
385                 390                 395                 400 cac acc acc gct gtg tga                                              1218
His Thr Thr Ala Val
            405

<210> SEQ ID NO 38
<211> LENGTH: 405
<212> TYPE: PRT
<213> ORGANISM: Ameiurus nebulosus

<400> SEQUENCE: 38

Met Glu Val Ser Leu Leu Glu Leu Leu Ser Val Glu Val Asn Cys Ser
1               5                   10                  15

Leu Ala Asp Ala Phe Gly Asp Pro Ala Tyr Gly Asn Ala Ser Asp Ala
            20                  25                  30

Leu Tyr Cys Asn Ala Thr Ala Asp Glu Ile Gly Thr Cys Trp Pro Arg
        35                  40                  45

Ser Gly Ala Gly Arg Val Val Ala Arg Pro Cys Pro Asp Phe Ile Asn
    50                  55                  60
```

```
Gly Val Lys Tyr Asn Ser Thr Arg Ser Ala Tyr Arg Glu Cys Leu Glu
 65                  70                  75                  80

Asn Gly Thr Trp Ala Phe Lys Ile Asn Tyr Ser Ser Cys Glu Pro Ile
                 85                  90                  95

Leu Glu Glu Lys Arg Lys Tyr Pro Val His Tyr Lys Ile Ala Leu Ile
            100                 105                 110

Ile Asn Tyr Leu Gly His Cys Ile Ser Val Gly Ala Leu Val Ile Ala
        115                 120                 125

Phe Val Leu Phe Leu Cys Leu Arg Ser Ile Arg Cys Leu Arg Asn Val
    130                 135                 140

Ile His Trp Asn Leu Ile Thr Thr Phe Ile Leu Arg Asn Ile Met Trp
145                 150                 155                 160

Leu Leu Leu Gln Leu Ile Asp His Asn Ile His Glu Arg Asn Glu Pro
                165                 170                 175

Trp Cys Arg Leu Ile Thr Thr Val Tyr Asn Tyr Phe Val Val Thr Asn
            180                 185                 190

Phe Phe Trp Met Phe Val Glu Gly Cys Tyr Leu His Thr Ala Ile Val
        195                 200                 205

Met Thr Tyr Ser Thr Asp Lys Leu Arg Lys Trp Val Phe Leu Phe Ile
210                 215                 220

Gly Trp Cys Ile Pro Cys Pro Val Ile Ile Ala Trp Ala Val Gly Lys
225                 230                 235                 240

Leu Tyr Asn Glu Asn Glu Gln Cys Trp Phe Gly Lys Glu Pro Gly Lys
                245                 250                 255

Tyr Val Asp Tyr Ile Tyr Gln Gly Pro Val Ile Val Leu Leu Ile
            260                 265                 270

Asn Phe Val Phe Leu Phe Asn Ile Val Arg Ile Leu Met Thr Lys Leu
        275                 280                 285

Arg Ala Ser Thr Thr Ser Glu Thr Ile Gln Tyr Arg Lys Ala Val Lys
    290                 295                 300

Ala Thr Leu Val Leu Leu Pro Leu Leu Gly Ile Thr Tyr Met Leu Phe
305                 310                 315                 320

Phe Val Asn Pro Gly Asp Asp Ile Ser Gln Ile Val Phe Ile Tyr
                325                 330                 335

Phe Asn Ser Phe Leu Gln Ser Phe Gln Gly Phe Phe Val Ser Val Phe
            340                 345                 350

Tyr Cys Phe Leu Asn Gly Glu Val Arg Ser Ala Val Arg Lys Arg Trp
        355                 360                 365

His Arg Trp Gln Asp Asn His Ala Leu Arg Val Arg Val Ala Arg Ala
    370                 375                 380

Met Ser Ile Pro Thr Ser Pro Thr Arg Ile Ser Phe His Ser Ile Lys
385                 390                 395                 400

His Thr Thr Ala Val
                405

<210> SEQ ID NO 39
<211> LENGTH: 1248
<212> TYPE: DNA
<213> ORGANISM: Bos taurus
<220> FEATURE:
<221> NAME/KEY: CDS
<222> LOCATION: (1)..(1248)

<400> SEQUENCE: 39 atg gga cgg cgc ccg cag ctc cgg ctt gtc aag gcc ctt ctc ctc ctg      48
```

```
                                                                  -continued Met Gly Arg Arg Pro Gln Leu Arg Leu Val Lys Ala Leu Leu Leu Leu
 1               5                  10                  15 ggg ctg aac tcc atc tct gcc tcc ctc cag gac cag cat tgc gag agc     96
Gly Leu Asn Ser Ile Ser Ala Ser Leu Gln Asp Gln His Cys Glu Ser
                20                  25                  30 ttg tcc gtg gcc agc aac gtc tct gga ctg cag tgc aat gct tcc gtg    144
Leu Ser Val Ala Ser Asn Val Ser Gly Leu Gln Cys Asn Ala Ser Val
            35                  40                  45 gac ctt att ggt acc tgc tgg ccc cag agt cct gca ggg cag ttg gtg    192
Asp Leu Ile Gly Thr Cys Trp Pro Gln Ser Pro Ala Gly Gln Leu Val
    50                  55                  60 gtt cga ccc tgc ctc gta ttt ttc tat ggt gtc cgc tac aat acc aca    240
Val Arg Pro Cys Leu Val Phe Phe Tyr Gly Val Arg Tyr Asn Thr Thr
65                  70                  75                  80 aac aac ggc tac cgg gag tgc ctg gcc aat ggc acg tgg gcc gcc cgc    288
Asn Asn Gly Tyr Arg Glu Cys Leu Ala Asn Gly Thr Trp Ala Ala Arg
                85                  90                  95 gtg aac tac tcc gag tgc caa gag atc ctc agc gag gag aag aag agc    336
Val Asn Tyr Ser Glu Cys Gln Glu Ile Leu Ser Glu Glu Lys Lys Ser
                100                 105                 110 aag gtg cac tac cac atc gct gtc atc atc aac tac cta ggc cac tgc    384
Lys Val His Tyr His Ile Ala Val Ile Ile Asn Tyr Leu Gly His Cys
            115                 120                 125 atc tcc ctg gcg gcc ctc ctg gtg gcc ttt gtc ctc ttt ctg cgg ctc    432
Ile Ser Leu Ala Ala Leu Leu Val Ala Phe Val Leu Phe Leu Arg Leu
    130                 135                 140 agg agc atc cgg tgc ctg aga aac atc atc cac tgg aac ctc atc tca    480
Arg Ser Ile Arg Cys Leu Arg Asn Ile Ile His Trp Asn Leu Ile Ser
145                 150                 155                 160 gcc ttc atc ctg cgc aat gcc acg tgg ttc gtg gtc cag ctc acc atg    528
Ala Phe Ile Leu Arg Asn Ala Thr Trp Phe Val Val Gln Leu Thr Met
                165                 170                 175 agc ccc gaa gtc cat cag agc aac gtg ggc tgg tgc agg ctg gtg aca    576
Ser Pro Glu Val His Gln Ser Asn Val Gly Trp Cys Arg Leu Val Thr
                180                 185                 190 gcc gcc tac aac tac ttc cac gtg acc aac ttc ttc tgg atg ttc ggt    624
Ala Ala Tyr Asn Tyr Phe His Val Thr Asn Phe Phe Trp Met Phe Gly
            195                 200                 205 gag ggc tgc tac ctg cac acg gcc atc gtg ctc acg tac tcc aca gac    672
Glu Gly Cys Tyr Leu His Thr Ala Ile Val Leu Thr Tyr Ser Thr Asp
    210                 215                 220 cgg ctg cga aag tgg atg ttt atc tgc atc ggc tgg ggt gtg cct ttc    720
Arg Leu Arg Lys Trp Met Phe Ile Cys Ile Gly Trp Gly Val Pro Phe
225                 230                 235                 240 ccc atc att gtg gcc tgg gcc att ggg aag ctg tac tac gac aat gag    768
Pro Ile Ile Val Ala Trp Ala Ile Gly Lys Leu Tyr Tyr Asp Asn Glu
                245                 250                 255 aag tgc tgg ttt ggc aaa agg cct ggg gtg tac act gac tac atc tac    816
Lys Cys Trp Phe Gly Lys Arg Pro Gly Val Tyr Thr Asp Tyr Ile Tyr
                260                 265                 270 cag ggc ccg atg atc ttg gtc ctg ctg atc aat ttc atc ttc ctt ttc    864
Gln Gly Pro Met Ile Leu Val Leu Leu Ile Asn Phe Ile Phe Leu Phe
            275                 280                 285 aac atc gtc cgc atc ctc atg acc aaa ctc cgg gca tcc acc acc tct    912
Asn Ile Val Arg Ile Leu Met Thr Lys Leu Arg Ala Ser Thr Thr Ser
    290                 295                 300 gag acc att cag tac agg aag gct gtg aag gcc act ctg gtg ctg ctc    960
Glu Thr Ile Gln Tyr Arg Lys Ala Val Lys Ala Thr Leu Val Leu Leu
305                 310                 315                 320
```

```
ccc ctc ctg ggc atc acg tac atg ctg ttc ttc gtg aac cct ggg gag      1008
Pro Leu Leu Gly Ile Thr Tyr Met Leu Phe Phe Val Asn Pro Gly Glu
            325                 330                 335 gac gag gtc tcc agg gtc gtc ttc atc tac ttc aac tcc ttc ctg gaa      1056
Asp Glu Val Ser Arg Val Val Phe Ile Tyr Phe Asn Ser Phe Leu Glu
        340                 345                 350 tct ttc cag ggc ttc ttc gtg tct gtg ttc tac tgc ttc ctc aac agc      1104
Ser Phe Gln Gly Phe Phe Val Ser Val Phe Tyr Cys Phe Leu Asn Ser
    355                 360                 365 gag gtc cgc tct gcc atc cgg aag agg tgg cac cgc tgg cag gac aag      1152
Glu Val Arg Ser Ala Ile Arg Lys Arg Trp His Arg Trp Gln Asp Lys
370                 375                 380 cac tca atc cgt gcc cgc gtg gct cgc gcc atg tcc atc ccc acc tcc      1200
His Ser Ile Arg Ala Arg Val Ala Arg Ala Met Ser Ile Pro Thr Ser
385                 390                 395                 400 ccc acc cgt gtc agc ttt cac agc atc aag cag tcc aca gca gtg tga      1248
Pro Thr Arg Val Ser Phe His Ser Ile Lys Gln Ser Thr Ala Val
            405                 410                 415

<210> SEQ ID NO 40
<211> LENGTH: 415
<212> TYPE: PRT
<213> ORGANISM: Bos taurus

<400> SEQUENCE: 40

Met Gly Arg Arg Pro Gln Leu Arg Leu Val Lys Ala Leu Leu Leu Leu
1               5                   10                  15

Gly Leu Asn Ser Ile Ser Ala Ser Leu Gln Asp Gln His Cys Glu Ser
            20                  25                  30

Leu Ser Val Ala Ser Asn Val Ser Gly Leu Gln Cys Asn Ala Ser Val
        35                  40                  45

Asp Leu Ile Gly Thr Cys Trp Pro Gln Ser Pro Ala Gly Gln Leu Val
    50                  55                  60

Val Arg Pro Cys Leu Val Phe Phe Tyr Gly Val Arg Tyr Asn Thr Thr
65                  70                  75                  80

Asn Asn Gly Tyr Arg Glu Cys Leu Ala Asn Gly Thr Trp Ala Ala Arg
                85                  90                  95

Val Asn Tyr Ser Glu Cys Gln Glu Ile Leu Ser Glu Glu Lys Lys Ser
            100                 105                 110

Lys Val His Tyr His Ile Ala Val Ile Ile Asn Tyr Leu Gly His Cys
        115                 120                 125

Ile Ser Leu Ala Ala Leu Leu Val Ala Phe Val Leu Phe Leu Arg Leu
    130                 135                 140

Arg Ser Ile Arg Cys Leu Arg Asn Ile Ile His Trp Asn Leu Ile Ser
145                 150                 155                 160

Ala Phe Ile Leu Arg Asn Ala Thr Trp Phe Val Val Gln Leu Thr Met
                165                 170                 175

Ser Pro Glu Val His Gln Ser Asn Val Gly Trp Cys Arg Leu Val Thr
            180                 185                 190

Ala Ala Tyr Asn Tyr Phe His Val Thr Asn Phe Phe Trp Met Phe Gly
        195                 200                 205

Glu Gly Cys Tyr Leu His Thr Ala Ile Val Leu Thr Tyr Ser Thr Asp
    210                 215                 220

Arg Leu Arg Lys Trp Met Phe Ile Cys Ile Gly Trp Gly Val Pro Phe
225                 230                 235                 240

Pro Ile Ile Val Ala Trp Ala Ile Gly Lys Leu Tyr Tyr Asp Asn Glu
                245                 250                 255
```

-continued

```
Lys Cys Trp Phe Gly Lys Arg Pro Gly Val Tyr Thr Asp Tyr Ile Tyr
            260                 265                 270

Gln Gly Pro Met Ile Leu Val Leu Leu Ile Asn Phe Ile Phe Leu Phe
        275                 280                 285

Asn Ile Val Arg Ile Leu Met Thr Lys Leu Arg Ala Ser Thr Thr Ser
    290                 295                 300

Glu Thr Ile Gln Tyr Arg Lys Ala Val Lys Ala Thr Leu Val Leu Leu
305                 310                 315                 320

Pro Leu Leu Gly Ile Thr Tyr Met Leu Phe Phe Val Asn Pro Gly Glu
                325                 330                 335

Asp Glu Val Ser Arg Val Val Phe Ile Tyr Phe Asn Ser Phe Leu Glu
            340                 345                 350

Ser Phe Gln Gly Phe Phe Val Ser Val Phe Tyr Cys Phe Leu Asn Ser
        355                 360                 365

Glu Val Arg Ser Ala Ile Arg Lys Arg Trp His Arg Trp Gln Asp Lys
    370                 375                 380

His Ser Ile Arg Ala Arg Val Ala Arg Ala Met Ser Ile Pro Thr Ser
385                 390                 395                 400

Pro Thr Arg Val Ser Phe His Ser Ile Lys Gln Ser Thr Ala Val
                405                 410                 415

<210> SEQ ID NO 41
<211> LENGTH: 1422
<212> TYPE: DNA
<213> ORGANISM: Gallus gallus
<220> FEATURE:
<221> NAME/KEY: CDS
<222> LOCATION: (138)..(1400)

<400> SEQUENCE: 41
tcacagggag gttataaaag gcagtgagtg gggagcgggg cacgcggagc cacctgagca     60
cgaggatttg gagccccgac ggcagcggga gcggagccgg ccatgccccg ggtcgttggg    120
tgcggaggga gctaagg atg gtg ccc ggc ccg cgt cct gcc ctc ctc ctc       170
                Met Val Pro Gly Pro Arg Pro Ala Leu Leu Leu
                  1               5                  10 ctc ctc ttt ctc ctg cag gcg ttt ctc ctc tgg gat agt ccc gtt gca      218
Leu Leu Phe Leu Leu Gln Ala Phe Leu Leu Trp Asp Ser Pro Val Ala
            15                  20                  25 gcc tcc atc caa gag cag tac tgt gag agc ctg ctg ccc acc acc aac      266
Ala Ser Ile Gln Glu Gln Tyr Cys Glu Ser Leu Leu Pro Thr Thr Asn
        30                  35                  40 cac aca gga cct cag tgc aac gcc tcg gtg gac ctg att ggc acg tgc      314
His Thr Gly Pro Gln Cys Asn Ala Ser Val Asp Leu Ile Gly Thr Cys
    45                  50                  55 tgg ccc cgc agt gca gtg gga caa ctg gtg gct cgg ccc tgc ccc gag      362
Trp Pro Arg Ser Ala Val Gly Gln Leu Val Ala Arg Pro Cys Pro Glu
60                  65                  70                  75 tat ttc tac ggc gtg cgg tac aac acc aca aac aat ggc tac agg gaa      410
Tyr Phe Tyr Gly Val Arg Tyr Asn Thr Thr Asn Asn Gly Tyr Arg Glu
                80                  85                  90 tgc ctc gct aac ggg agc tgg gca gca cgg gtc aac tac tcc cag tgc      458
Cys Leu Ala Asn Gly Ser Trp Ala Ala Arg Val Asn Tyr Ser Gln Cys
            95                 100                 105 cag gag atc ctc agt gag gag aag agg agc aag ctg cac tac cac atc      506
Gln Glu Ile Leu Ser Glu Glu Lys Arg Ser Lys Leu His Tyr His Ile
        110                 115                 120 gct gtc atc atc aac tac ctg ggg cac tgc gtc tcg ctg ggg acc ctc      554
```

```
                Ala Val Ile Ile Asn Tyr Leu Gly His Cys Val Ser Leu Gly Thr Leu
                    125                 130                 135 ctt gtg gcc ttc gtc ctc ttc atg cgc ctg cgg agc atc cgg tgc ttg             602
Leu Val Ala Phe Val Leu Phe Met Arg Leu Arg Ser Ile Arg Cys Leu
140                 145                 150                 155 agg aac atc atc cac tgg aac ctg atc aca gcc ttc atc cta cgc aat             650
Arg Asn Ile Ile His Trp Asn Leu Ile Thr Ala Phe Ile Leu Arg Asn
                    160                 165                 170 gcc acg tgg ttt gtg gtg cag ctc acg atg aac cca gag gtg cac gag             698
Ala Thr Trp Phe Val Val Gln Leu Thr Met Asn Pro Glu Val His Glu
                175                 180                 185 agc aac gtg gtc tgg tgc cgc ttg gtc act gct gcc tac aat tac ttc             746
Ser Asn Val Val Trp Cys Arg Leu Val Thr Ala Ala Tyr Asn Tyr Phe
            190                 195                 200 cat gtc acc aac ttc ttc tgg atg ttt ggc gag ggc tgc tac ctg cac             794
His Val Thr Asn Phe Phe Trp Met Phe Gly Glu Gly Cys Tyr Leu His
        205                 210                 215 aca gcc atc gtc ctc acc tat tcc acc gac aag ctc cgc aag tgg atg             842
Thr Ala Ile Val Leu Thr Tyr Ser Thr Asp Lys Leu Arg Lys Trp Met
220                 225                 230                 235 ttc atc tgc att ggc tgg tgt atc ccc ttt ccc atc att gtc gcc tgg             890
Phe Ile Cys Ile Gly Trp Cys Ile Pro Phe Pro Ile Ile Val Ala Trp
                    240                 245                 250 gcc atc ggg aag ctg tac tac gac aac gag aag tgc tgg ttt ggg aag             938
Ala Ile Gly Lys Leu Tyr Tyr Asp Asn Glu Lys Cys Trp Phe Gly Lys
                255                 260                 265 cga gca gga gtt tat act gac tac atc tat caa ggt ccc atg atc ctg             986
Arg Ala Gly Val Tyr Thr Asp Tyr Ile Tyr Gln Gly Pro Met Ile Leu
            270                 275                 280 gtg ctt ctg atc aac ttc atc ttt ctg ttc aac att gtt cgg att ctc            1034
Val Leu Leu Ile Asn Phe Ile Phe Leu Phe Asn Ile Val Arg Ile Leu
        285                 290                 295 atg acc aag ctc cga gca tca acc acg tca gag aca atc cag tac aga            1082
Met Thr Lys Leu Arg Ala Ser Thr Thr Ser Glu Thr Ile Gln Tyr Arg
300                 305                 310                 315 aaa gca gtc aag gct acg ctg gtg ctg ctg tcc ttg ctg gga atc acc            1130
Lys Ala Val Lys Ala Thr Leu Val Leu Leu Ser Leu Leu Gly Ile Thr
                    320                 325                 330 tac atg ctg ttc ttt gtc aat ccg ggg gag gat gag atc tcc agg atc            1178
Tyr Met Leu Phe Phe Val Asn Pro Gly Glu Asp Glu Ile Ser Arg Ile
                335                 340                 345 gtc ttc atc tac ttc aac tcc ttc ctg gag tcc ttc cag ggc ttc ttt            1226
Val Phe Ile Tyr Phe Asn Ser Phe Leu Glu Ser Phe Gln Gly Phe Phe
            350                 355                 360 gtc tct gtc ttc tac tgc ttc ctg aac agc gag gtg cgt tcg gct gtg            1274
Val Ser Val Phe Tyr Cys Phe Leu Asn Ser Glu Val Arg Ser Ala Val
        365                 370                 375 cgg aag cgg tgg cac cga tgg cag gac aag cac tcc atc cgc gct cgg            1322
Arg Lys Arg Trp His Arg Trp Gln Asp Lys His Ser Ile Arg Ala Arg
380                 385                 390                 395 gtg gct cgg gcc atg tcc atc ccc acc tcc cca acc cgg gtc agc ttc            1370
Val Ala Arg Ala Met Ser Ile Pro Thr Ser Pro Thr Arg Val Ser Phe
                    400                 405                 410 cac agc atc aag cag tcc tca gca gtg tga ggcaggagga ggcagctgcc ga           1422
His Ser Ile Lys Gln Ser Ser Ala Val
                415                 420

<210> SEQ ID NO 42
<211> LENGTH: 420
<212> TYPE: PRT
```

<213> ORGANISM: Gallus gallus

<400> SEQUENCE: 42

```
Met Val Pro Gly Pro Arg Pro Ala Leu Leu Leu Leu Phe Leu Leu
1               5                   10                  15

Gln Ala Phe Leu Leu Trp Asp Ser Pro Val Ala Ala Ser Ile Gln Glu
            20                  25                  30

Gln Tyr Cys Glu Ser Leu Leu Pro Thr Thr Asn His Thr Gly Pro Gln
        35                  40                  45

Cys Asn Ala Ser Val Asp Leu Ile Gly Thr Cys Trp Pro Arg Ser Ala
    50                  55                  60

Val Gly Gln Leu Val Ala Arg Pro Cys Pro Glu Tyr Phe Tyr Gly Val
65                  70                  75                  80

Arg Tyr Asn Thr Thr Asn Asn Gly Tyr Arg Glu Cys Leu Ala Asn Gly
                85                  90                  95

Ser Trp Ala Ala Arg Val Asn Tyr Ser Gln Cys Gln Glu Ile Leu Ser
            100                 105                 110

Glu Glu Lys Arg Ser Lys Leu His Tyr His Ile Ala Val Ile Ile Asn
        115                 120                 125

Tyr Leu Gly His Cys Val Ser Leu Gly Thr Leu Leu Val Ala Phe Val
    130                 135                 140

Leu Phe Met Arg Leu Arg Ser Ile Arg Cys Leu Arg Asn Ile Ile His
145                 150                 155                 160

Trp Asn Leu Ile Thr Ala Phe Ile Leu Arg Asn Ala Thr Trp Phe Val
                165                 170                 175

Val Gln Leu Thr Met Asn Pro Glu Val His Glu Ser Asn Val Val Trp
            180                 185                 190

Cys Arg Leu Val Thr Ala Ala Tyr Asn Tyr Phe His Val Thr Asn Phe
        195                 200                 205

Phe Trp Met Phe Gly Glu Gly Cys Tyr Leu His Thr Ala Ile Val Leu
    210                 215                 220

Thr Tyr Ser Thr Asp Lys Leu Arg Lys Trp Met Phe Ile Cys Ile Gly
225                 230                 235                 240

Trp Cys Ile Pro Phe Pro Ile Ile Val Ala Trp Ala Ile Gly Lys Leu
                245                 250                 255

Tyr Tyr Asp Asn Glu Lys Cys Trp Phe Gly Lys Arg Ala Gly Val Tyr
            260                 265                 270

Thr Asp Tyr Ile Tyr Gln Gly Pro Met Ile Leu Val Leu Leu Ile Asn
        275                 280                 285

Phe Ile Phe Leu Phe Asn Ile Val Arg Ile Leu Met Thr Lys Leu Arg
    290                 295                 300

Ala Ser Thr Thr Ser Glu Thr Ile Gln Tyr Arg Lys Ala Val Lys Ala
305                 310                 315                 320

Thr Leu Val Leu Leu Ser Leu Leu Gly Ile Thr Tyr Met Leu Phe Phe
                325                 330                 335

Val Asn Pro Gly Glu Asp Glu Ile Ser Arg Ile Val Phe Ile Tyr Phe
            340                 345                 350

Asn Ser Phe Leu Glu Ser Phe Gln Gly Phe Phe Val Ser Val Phe Tyr
        355                 360                 365

Cys Phe Leu Asn Ser Glu Val Arg Ser Ala Val Arg Lys Arg Trp His
    370                 375                 380

Arg Trp Gln Asp Lys His Ser Ile Arg Ala Arg Val Ala Arg Ala Met
385                 390                 395                 400
```

```
-continued

Ser Ile Pro Thr Ser Pro Thr Arg Val Ser Phe His Ser Ile Lys Gln
                405             410             415

Ser Ser Ala Val
            420

<210> SEQ ID NO 43
<211> LENGTH: 38
<212> TYPE: PRT
<213> ORGANISM: Mus musculus

<400> SEQUENCE: 43

Val Ile Leu Ser Leu Asp Val Pro Ile Gly Leu Leu Arg Ile Leu Leu
1               5                   10                  15

Glu Gln Ala Arg Tyr Lys Ala Ala Arg Asn Gln Ala Ala Thr Asn Ala
            20                  25                  30

Gln Ile Leu Ala His Val
            35

<210> SEQ ID NO 44
<211> LENGTH: 38
<212> TYPE: PRT
<213> ORGANISM: Homo sapiens

<400> SEQUENCE: 44

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val
            35
```

METHODS FOR IDENTIFYING COMPOUNDS FOR REGULATING MUSCLE MASS OR FUNCTION USING CORTICOTROPIN RELEASING FACTOR RECEPTORS

CROSS REFERENCE TO RELATED APPLICATION

This application is a continuation-in-part of application Ser. No. 09/799,978 filed Mar. 6, 2001, now U.S. Pat. No. 6,670,140 which is herein incorporated by reference in its entirety.

TECHNICAL FIELD

The present invention relates to methods of identifying candidate compounds for regulating skeletal muscle mass or function or regulating the activity or expression of a corticotropin releasing factor-2 receptor ($CRF_2R$). The invention also relates to methods for the treatment of skeletal muscle atrophy or methods for inducing skeletal muscle hypertrophy using $CRF_2R$ as the target for intervention and to methods of treating muscular dystrophies using $CRF_2R$ and corticotropin releasing factor-1 receptor ($CRF_1R$) as targets.

BACKGROUND

CRFR and Ligands

There are two corticotropin releasing factor receptors, identified to date ($CRF_1R$ and $CRF_2R$) which belong to G-protein coupled receptor (GPCR) class. Agonist activation of $CRF_1R$ or $CRF_2R$ leads to $G_{\alpha s}$ activation of adenylate cyclase. Adenylate cyclase catalyzes the formation of cAMP, which in turn has multiple effects including the activation of protein kinase A, intracellular calcium release and activation of mitogen-activated protein kinase (MAP kinase). In other studies, the enhancement of intracellular inositol triphosphate synthesis, after agonist activation of CRF receptors, suggests that CRFRs also couple to $G_{\alpha q}$.

$CRF_1R$ and $CRF_2R$ have been cloned from human, rat, mouse, chicken, cow, catfish, frog and sheep. $CRF_1R$ and $CRF_2R$ each have a unique distribution patterns. In humans three isoforms, alpha, beta and gamma, of the $CRF_2R$ receptor have been cloned. Homologs for alpha and beta $CRF_2R$ have been identified in rat.

Several ligands/agonists of the CRFRs are known. Corticotropin releasing factor (or hormone, CRF or CRH) binds to and activates $CRF_1R$ and $CRF_2R$. CRF is a major modulator of the body's responses to stress. This 41-amino acid peptide presides over a panoply of neuronal, endocrine, and immune processes as the primary regulator of the hypothalamus-pituitary-adrenal hormonal axis (HPA axis). In addition, there is substantial sequence homology between CRF and the amphibian peptide sauvagine as well as the telostian peptide urotensin, both of which act as agonists of $CRF_1R$ and $CRF_2R$. These three peptides have similar biological properties as hypotensive agents and ACTH secretogogues. In addition, a mammalian congener of urotensin, urocortin, has been characterized.

The CRF receptors can be distinguished, from non-CRFRs, pharmacologically through the use of receptor selective agonists and antagonists. These selective agonists and antagonist, along with the CRFR knockout mice, have been useful in determining which CRF receptor mediates specific biological responses.

The role of $CRF_1R$ has been fairly well established. Mice in which the $CRF_1R$ gene has been ablated ($CRF_1R$ knockout) demonstrate an impaired stress response and reduced anxiety-like behavior. $CRF_1R$ is a major mediator of the HPA axis. Specifically, corticotropin releasing factor, which is released from the hypothalamus and transported to the anterior pituitary via the hypothalamic-hypophysial portal system, interacts with the $CRF_1R$ present on cells located in the anterior pituitary. Agonist activation of the $CRF_1R$ results in release of ACTH from the cells of the anterior pituitary into the systemic circulation. The released ACTH binds the ACTH receptor present on cells located in the adrenal cortex, resulting in the release of adrenal hormones including corticosteroids. Corticosteroids mediate many effects including, but not limited to, immune system suppression via a mechanism which involves thymic and splenic atrophy. Thus activation of the $CRF_1R$ indirectly results in the down-regulation of the immune system via activation of the HPA axis.

The role of $CRF_2R$ is less well developed. Mice in which the $CRF_2R$ gene has been ablated ($CRF_2R$ knockout) demonstrate an impaired food intake reduction following stimulation with urocortin, lack of vasodilation, but a normal stress response. Experiments with $CRF_2R$ demonstrated that $CRF_2R$ is responsible for the hypotensive/vasodilatory effects of CRFR agonists and for the reduction in food intake observed following treatment of mice with CRFR agonists.

Skeletal Muscle Atrophy and Hypertrophy

Skeletal muscle is a plastic tissue which readily adapts to changes in either physiological demand for work or metabolic need. Hypertrophy refers to an increase in skeletal muscle mass while skeletal muscle atrophy refers to a decrease in skeletal muscle mass. Acute skeletal muscle atrophy is traceable to a variety of causes including, but not limited to: disuse due to surgery, bed rest, or broken bones; denervation/nerve damage due to spinal cord injury, autoimmune disease, or infectious disease; glucocorticoid use for unrelated conditions; sepsis due to infection or other causes; nutrient limitation due to illness or starvation; and space travel. Skeletal muscle atrophy occurs through normal biological processes, however, in certain medical situations this normal biological process results in a debilitating level of muscle atrophy. For example, acute skeletal muscle atrophy presents a significant limitation in the rehabilitation of patients from immobilizations, including, but not limited to, those accompanying an orthopedic procedure. In such cases, the rehabilitation period required to reverse the skeletal muscle atrophy is often far longer than the period of time required to repair the original injury. Such acute disuse atrophy is a particular problem in the elderly, who may already suffer from substantial age-related deficits in muscle function and mass, because such atrophy can lead to permanent disability and premature mortality.

Skeletal muscle atrophy can also result from chronic conditions such as cancer cachexia, chronic inflammation, AIDS cachexia, chronic obstructive pulmonary disease (COPD), congestive heart failure, genetic disorders, e.g., muscular dystrophies, neurodegenerative diseases and sarcopenia (age associated muscle loss). In these chronic conditions, skeletal muscle atrophy can lead to premature loss of mobility, thereby adding to the disease-related morbidity.

Little is known regarding the molecular processes which control atrophy or hypertrophy of skeletal muscle. While the initiating trigger of the skeletal muscle atrophy is different for the various atrophy initiating events, several common biochemical changes occur in the affected skeletal muscle fiber, including a decrease in protein synthesis and an increase in protein degradation and changes in both contractile and metabolic enzyme protein isozymes characteristic of a slow (highly oxidative metabolism/slow contractile protein isoforms) to fast (highly glycolytic metabolism/fast contractile protein isoforms) fiber switch. Additional changes in skeletal muscle which occur include the loss of vasculature and remodeling of the extracellular matrix. Both fast and slow twitch muscle demonstrate atrophy under the appropriate conditions, with the relative muscle loss depending on the specific atrophy stimuli or condition. Importantly, all these changes are coordinately regulated and are switched on or off depending on changes in physiological and metabolic need.

The processes by which atrophy and hypertrophy occur are conserved across vertebrate species. Multiple studies have demonstrated that the same basic molecular, cellular, and physiological processes occur during atrophy in both rodents and humans. Thus, models from different vertebrate species for skeletal muscle atrophy have been successfully utilized to understand and predict human atrophy responses including lower vertebrates like fish and frog, and also mammals like rodents, and humans (discussed in Rome, L. R. (2002) Clinical Orthopaedics and Related Research, 403S, S59–S76). For example, atrophy induced by a variety of means in both rodents and humans results in similar changes in muscle anatomy, cross-sectional area, function, fiber type switching, contractile protein expression, and histology. Similarly, Medler compared trends in shortening velocity and force production in skeletal muscles from more than 130 diverse skeletal muscles across vertebrates including insects, crustaceans, mollusks, fish, amphibians, reptiles, birds, and mammals (Medler, S. (2002) Am. J. Physiol. Regulatory Integrative Comp. Physiol. 283, R368–R378). Medler's analysis clearly showed that although differing in size and speed, the skeletal muscle from these diverse species are very similar in their physiological properties like shortening velocity and force production. In addition, several agents have been demonstrated to regulate skeletal muscle atrophy in both rodents and in humans. These agents include anabolic steroids, growth hormone, insulin-like growth factor I, and beta adrenergic agonists. Together, these data demonstrate that skeletal muscle atrophy results from common mechanisms in both rodents and humans.

While some agents have been shown to regulate skeletal muscle atrophy and are approved for use in humans for this indication, these agents have undesirable side effects such as hypertrophy of cardiac muscle, neoplasia, hirsutism, androgenization of females, increased morbidity and mortality, liver damage, hypoglycemia, musculoskeletal pain, increased tissue turgor, tachycardia, and edema. Currently, there are no highly effective and selective treatments for either acute or chronic skeletal muscle atrophy. Thus, there is a need to identify other therapeutic agents which regulate skeletal muscle atrophy.

Muscular Dystrophies

Muscular dystrophies encompass a group of inherited, progressive muscle disorders, distinguished clinically by the selective distribution of skeletal muscle weakness. The two most common forms of muscle dystrophy are Duchenne and Becker dystrophies, each resulting from the inheritance of a mutation in the dystrophin gene, which is located at the Xp21 locus. Other dystrophies include, but are not limited to, limb-girdle muscular dystrophy which results from mutation of multiple genetic loci including the p94 calpain, adhalin, γ-sarcoglycan, and β-sarcoglycan loci; fascioscapulohumeral (Landouzy-Dejerine) muscular dystrophy, myotonic dystrophy, and Emery-Dreifuss muscular dystrophy. The symptoms of Duchenne muscular dystrophy, which occurs almost exclusively in males, include a waddling gait, toe walking, lordosis, frequent falls and difficulty in standing up and climbing stairs. Symptoms start at about 3–7 years of age with most patients confined to a wheelchair by 10–12 years and many die at about 20 years of age due to respiratory complications. Current treatment for Duchenne muscular dystrophy includes administration of prednisone (a corticosteroid drug), which while not curative, slows the decline of muscle strength and delays disability. Corticosteroids, such as prednisone, are believed to act by blocking the immune cell activation and infiltration which are precipitated by muscle fiber damage resulting from the disease. Unfortunately, corticosteroid treatment also results in skeletal muscle atrophy which negates some of the potential benefit of blocking the immune response in these patients. Thus, there is a need to identify therapeutic agents which slow the muscle fiber damage and delay the onset of disability in patients with muscular dystrophies, but cause a lesser degree of skeletal muscle atrophy than current therapies.

One problem associated with identification of compounds for use in the treatment of skeletal muscle atrophy or of muscular dystrophies has been the lack of good screening methods for the identification of such compounds. Applicants have now found that $CRF_2Rs$ are involved in the regulation of skeletal muscle mass or function and that agonists of $CRF_2Rs$ are able to block skeletal muscle atrophy and/or induce hypertrophy of skeletal muscle. The present invention solves the problem of identifying compounds for the treatment of muscle atrophy by providing screening methods using $CRF_2R$ which can be used to identify candidate compounds useful for the treatment of muscle atrophy. The present invention also solves the problem of finding compounds for treatment of muscle dystrophies by providing a screening method to identify candidate compounds which activate both the $CRF_1R$ and $CRF_2R$.

SUMMARY OF THE INVENTION

The present invention relates to the use of CRFRs to identify candidate compounds that are potentially useful in the treatment of skeletal muscle atrophy and or to induce skeletal muscle hypertrophy. In particular, the invention provides in vitro methods for identifying candidate compounds for regulating skeletal muscle mass or function comprising contacting a test compound with a cell expressing $CRF_2R$, or contacting a test compound with isolated $CRF_2R$, and determining whether the test compound either binds to or activates the $CRF_2R$. Another embodiment of the invention relates to a method for identifying candidate therapeutic compounds from a group of one or more candidate compounds which have been determined to bind to or activate $CRF_2R$ comprising administering the candidate compound to a non-human animal and determining whether the candidate compound regulates skeletal muscle mass or muscle function in the treated animal. A further embodiment of the invention relates to a method for identifying candidate compounds for regulating skeletal muscle mass or function comprising, in any order: (i) contacting a test compound with a cell expressing a functional $CRF_2R$, and determining a level of activation of $CRF_2R$ resulting from the test compound; (ii) contacting a test compound with a cell expressing a functional $CRF_1R$, and determining the level of activation of $CRF_1R$ resulting from the test compound; followed by (iiii) comparing the level of $CRF_2R$ activation and the level of $CRF_1R$ activation; and (iv) identifying those test compounds that show similar activity toward $CRF_2R$ and $CRF_1R$ or show selectivity for $CRF_2R$ as candidate compounds for regulating skeletal muscle mass or function.

The invention further provides methods for identifying candidate compounds that prolong or augment the agonist-induced activation of $CRF_2R$ or of a $CRF_2R$ signal transduction pathway. These methods comprise in any order or concurrently: (i) contacting a test compound; with a cell which expresses functional $CRF_2R$ (ii) treating the cell with a $CRF_2R$ agonist for a sufficient time and at a sufficient concentration to cause desensitization of the $CRF_2R$ in control cells; followed by (iii) determining the level of activation of $CRF_2R$ and identifying test compounds that prolong or augment the activation of a CRFR or a CRFR signal transduction pathway as candidate compounds for regulating skeletal muscle mass or function. In a particular embodiment, the present invention relates to a method of identifying candidate therapeutic compounds from a group of one or more candidate compounds determined to prolong or augment the activation of a $CRF_2R$ or of a $CRF_2R$ signal transduction pathway comprising: administering the candidate compound, in conjunction with a $CRF_2R$ agonist, to a non-human animal and determining whether the candidate compound regulates skeletal muscle mass or function in the treated animal.

The invention further provides methods for identifying candidate compounds that increase $CRF_2R$ expression comprising contacting a test compound with a cell or cell lysate containing a reporter gene operatively associated with a $CRF_2R$ gene regulatory element and detecting expression of the reporter gene. Test compounds that increase expression of the reporter gene are identified as candidate compounds for increasing $CRF_2R$ expression. In a particular embodiment, the present invention relates to a method of determining whether those candidate compounds which increase $CRF_2R$ expression can be used to regulate skeletal muscle mass or function in vivo by administering a candidate compound to a non-human animal and determining whether the candidate compound regulates skeletal muscle mass or function in the treated animal.

The invention further provides methods for identifying candidate compounds that increase CRF expression comprising contacting a test compound with a cell or cell lysate containing a reporter gene operatively associated with a CRF gene regulatory element and detecting expression of the reporter gene. Test compounds that increase expression of the reporter gene are identified as candidate compounds for increasing CRF expression. In a particular embodiment, the present invention relates to a method of determining whether those candidate compounds which increase CRF expression can be used to regulate skeletal muscle mass or function in vivo by administering a candidate compound to a non-human animal and determining whether the candidate compound regulates skeletal muscle mass or function in the treated animal.

The present invention also relates to the use of $CRF_2R$ agonists, expression vectors encoding a functional $CRF_2R$, expression vectors encoding a constitutively active $CRF_2R$ or compounds that increase expression of $CRF_2R$, or CRF to treat skeletal muscle atrophy. In particular, the invention provides methods of treating skeletal muscle atrophy, in a subject in need of such treatment, comprising administering to the subject a safe and effective amount of a $CRF_2R$ agonist, an expression vector encoding a functional $CRF_2R$, an expression vector encoding a constitutively active $CRF_2R$, an expression vector encoding a CRF or CRF analog, or a compound that increases expression of $CRF_2R$, or CRF. In a particular embodiment, the present invention relates to a method for treating skeletal muscle atrophy in a subject in need of such treatment comprising administering to the subject a safe and effective amount of a $CRF_2R$ agonist in conjunction with a safe and effective amount of a compound that prolongs or augments the agonist-induced activation of $CRF_2R$, or of a $CRF_2R$ signal transduction pathway.

The present invention also relates to the use of a $CRF_2R$ agonist to increase skeletal muscle mass or function in a subject. In particular, the invention provides methods of increasing skeletal muscle mass or function in a subject in which such an increase is desirable, comprising identifying a subject in which an increase in muscle mass or function is desirable and administering to the subject a safe and effective amount of a CRFR agonist.

The invention further provides for pharmaceutical compositions comprising a safe and effective amount of a $CRF_2R$ agonist and a pharmaceutically-acceptable carrier. In a particular embodiment the pharmaceutical composition comprises a chimeric or human antibody specific for a $CRF_2R$. In another particular embodiment the pharmaceutical composition comprises a CRF or CRF analog, preferably urocortin II.

The present invention also provides for antibodies to $CRF_2R$ and in particular to chimeric or human antibodies that are agonists of $CRF_2R$.

Throughout this application various publications are referenced. The disclosures of these publications in their entireties are hereby incorporated by reference in this application in order to more fully describe the state of the art to which this invention pertains.

SEQUENCE LISTING DESCRIPTION

Each of the CRFR nucleotide and protein sequences or CRF analog protein sequence included in the sequence listing, along with the corresponding Genbank or Derwent accession number(s) and animal species from which it is cloned, is shown in Table I. Also shown are accession numbers for related nucleotide sequences that encode identical, or nearly identical, amino acid sequences as the sequence shown in the sequence listing. These related sequences differ mainly in the amount of 5' or 3' untranslated sequence shown.

TABLE I

| Sequence description | SEQ ID NO: nucleotide, amino acid | Species | Genbank (GB) or Derwent (D) Accession No. for nucleotide sequence | Related Genbank (GB) or Derwent (D) Accession Nos. |
|---|---|---|---|---|
| CRF$_1$R | 1, 2 | Homo sapiens | X72304 (GB) | E11431 (GB) L23332 (GB) I92584 (D) T37068 (D) T28968 (D) Q81952 (D) |
| CRF$_1$R variant | 3, 4 | Homo sapiens | L23333 (GB) | |
| CRF$_1$R variant | 5, 6 | Homo sapiens | NM_004382 (GB) | |
| CRF$_1$R variant | 7, 8 | Homo sapiens | AF180301 (GB) | |
| CRF$_2$R alpha | 9, 10 | Homo sapiens | U34587 (GB) NM_001883 (GB) | E12752 (GB) T12247 (D) T66508 (D) |
| CRF$_2$R beta | 11, 12 | Homo sapiens | AF011406 (GB) | |
| CRF$_2$R gamma | 13, 14 | Homo sapiens | AF019381 (GB) | |
| CRF$_1$R | 15, 16 | Rattus norvegicus | T28970 (D) | L25438 (GB) L24096 (GB) I92586 (D) Q81954 (D) AH006791 (GB) |
| CRF$_2$R alpha | 17, 18 | Rattus norvegicus | U16253 (GB) | NM_022714 (GB) X01009 (D) T12243 (D) |
| CRF$_2$R beta variant | 19, 20 | Rattus norvegicus | T12244 (D) | |
| CRF$_1$R | 21, 22 | Mus musculus | NM_007762 (GB) | X72305 (D) |
| CRF$_2$R | 23, 24 | Mus musculus | T28972 (D) | U17858 (GB) |
| CRF$_2$R | 25, 26 | Mus musculus | NM_009953 (GB) | |
| CRF$_1$R | 27, 28 | Ovis aries | AF054582 (GB) | |
| CRF$_1$R | 29, 30 | Xenopus laevis | Y14036 (GB) | |
| CRF$_2$R | 31, 32 | Xenopus laevis | Y14037 (GB) | |
| CRF$_1$R | 33, 34 | Ameiurus nebulosus | AF229359 (GB) | |
| CRF$_1$R | 35, 36 | Ameiurus nebulosus | AF229361 (GB) | |
| CRF$_2$R | 37, 38 | Ameiurus nebulosus | AF229360 (GB) | |
| CRF$_1$R | 39, 40 | Bos taurus | AB055434 (GB) | |
| CRF$_1$R | 41, 42 | Gallus gallus | L41563 (GB) | |
| Urocortin II | 43 | Mus musculus | AF331517 | |
| Urocortin-related peptide | 44 | Homo sapiens | BC002647 | |

TABLE II

CRF$_2$R (E12752) compared against:

| Organism | | % identity (nt) - BestFit | % identity (aa) - BestFit |
|---|---|---|---|
| CRF$_2$R: | | | |
| U34587 (alpha) AX548810 AR270507 | Homo sapiens | 99% (19–1254) | 99% |
| AF019381 (gamma) | Homo sapiens | 100% (121–1277) | 100% |
| AF011406 (beta) AX658261 | Homo sapiens | 100% (121–1277) | 100% |
| U16253 | Rattus norvegicus | 89% (2–1254) | 93.9% |
| U17858 AR266799 AR255736 AR211444 U21729 AX418266 | Mus musculus | 88% (121–1254) | 92.8% |
| Y14037 | Xenopus laevis | 75.6% (131–1254) | 81.6% |
| E12750 | Homo sapiens | 100% (622–1065) | 100% |
| L41563 | Gallus gallus | 73.7% | 76.1% |
| AF229360 | Ameriurus nebulosus | 76.7% | 80.9% |
| CRF$_1$R: | | | |
| E11431 | Homo sapiens | 75.5% | 74.9% |
| X72305 | Mus musculus | 74.5% | 75.2% |
| AF054582 | Ovis aries | 74.8%% | 73.8% |
| Y14036 | Xenopus laevis | 73.2% | 75.4% |
| AF32293359 | Ameriurus nebulosus | 73.3% | 76.6% |
| AF229361 | Ameriurus nebulosus | 72.1% | 74.7% |
| AF077185 | Sus scrofa (partial) | 76% | 69.6% |

BRIEF DESCRIPTION OF THE FIGURES AND TABLES

FIG. 1 demonstrates the anti-atrophy effect of the $CRF_1R/CRF_2R$ agonist, sauvagine (administered subcutaneously, 2× daily), on the medial gastrocnemius muscle in the mouse sciatic nerve denervation atrophy model.

Figure 2:
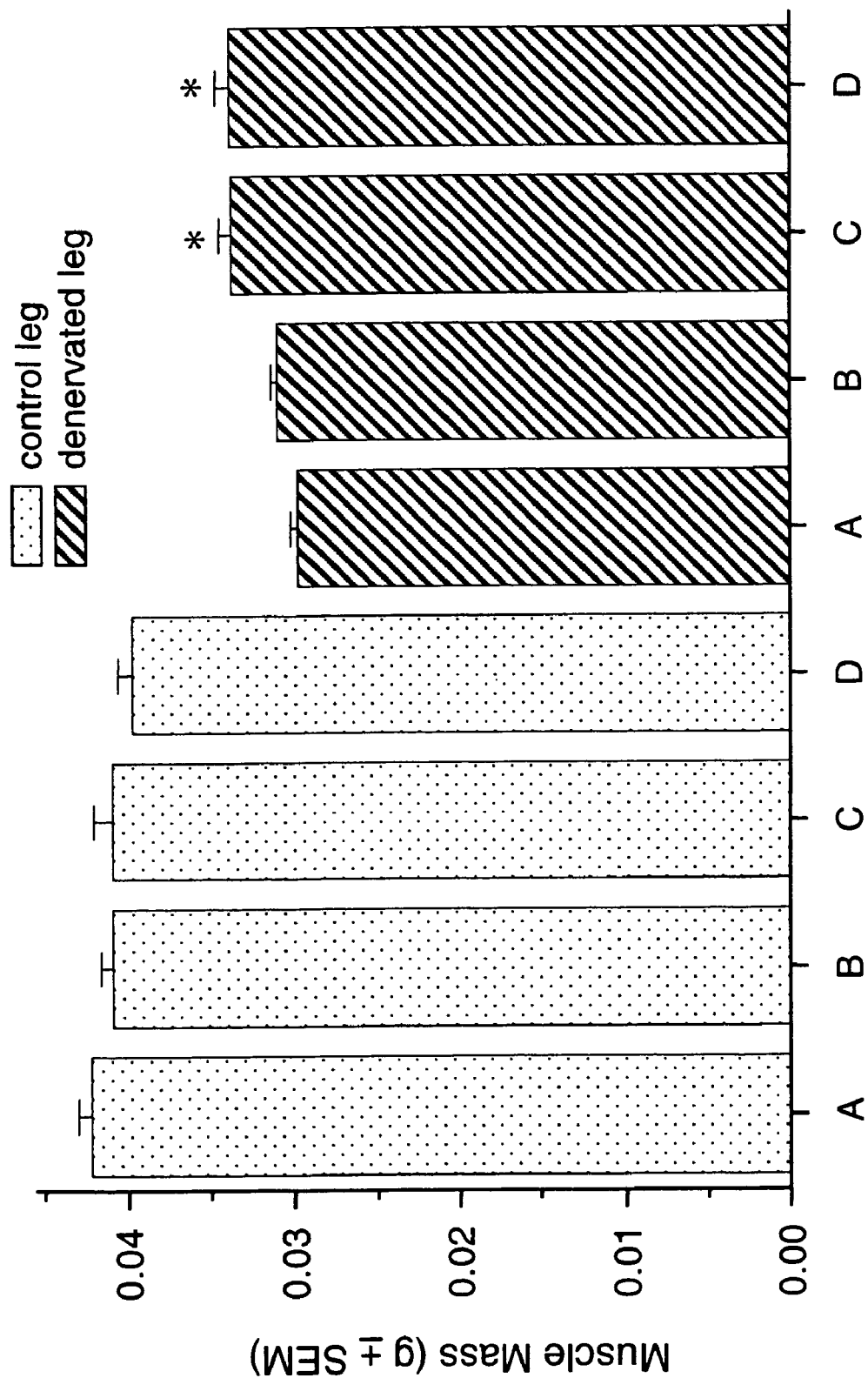

FIG. 2 demonstrates the anti-atrophy effect of sauvagine (administered continuously by osmotic minipump) on the tibialis anterior muscle in the mouse sciatic nerve denervation atrophy model.

Figure 3A:
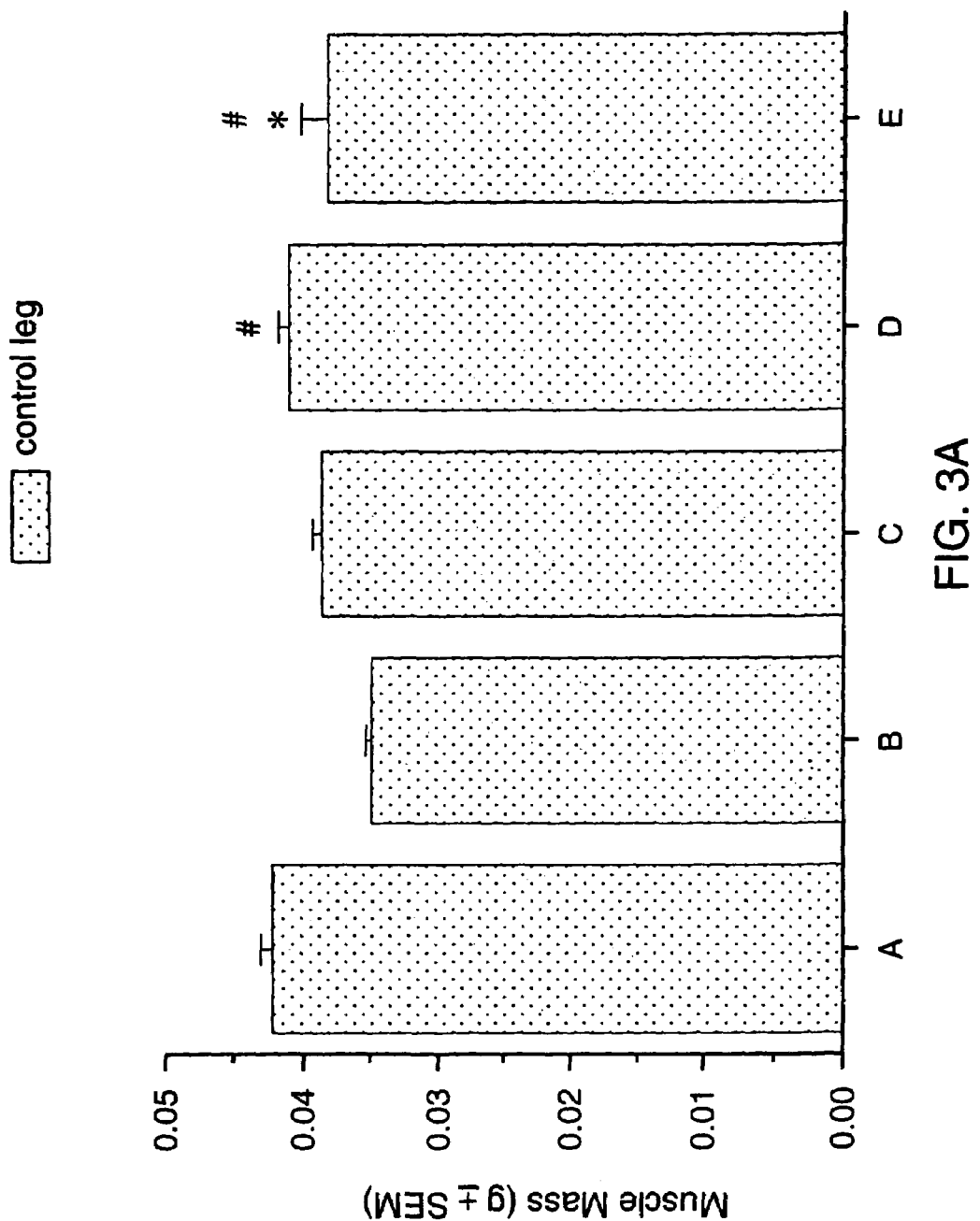
Figure 3B:
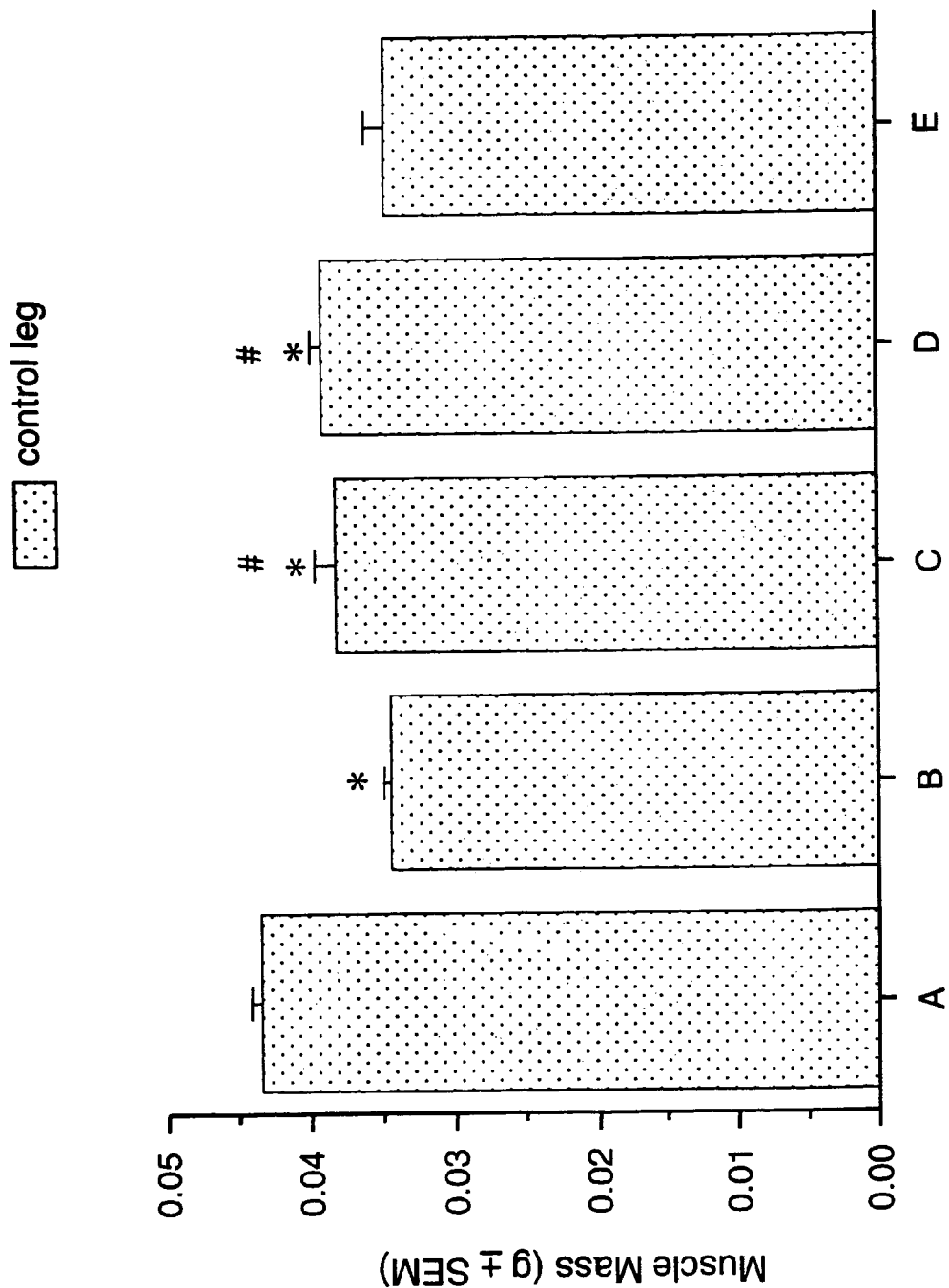

FIGS. 3A and 3B demonstrate the anti-atrophy effect of sauvagine (administered continuously by osmotic minipump) on glucocorticoid-induced atrophy of the tibialis anterior muscle (FIG. 3A) and the medial gastrocnemius muscle (FIG. 3B).

Figure 4A:
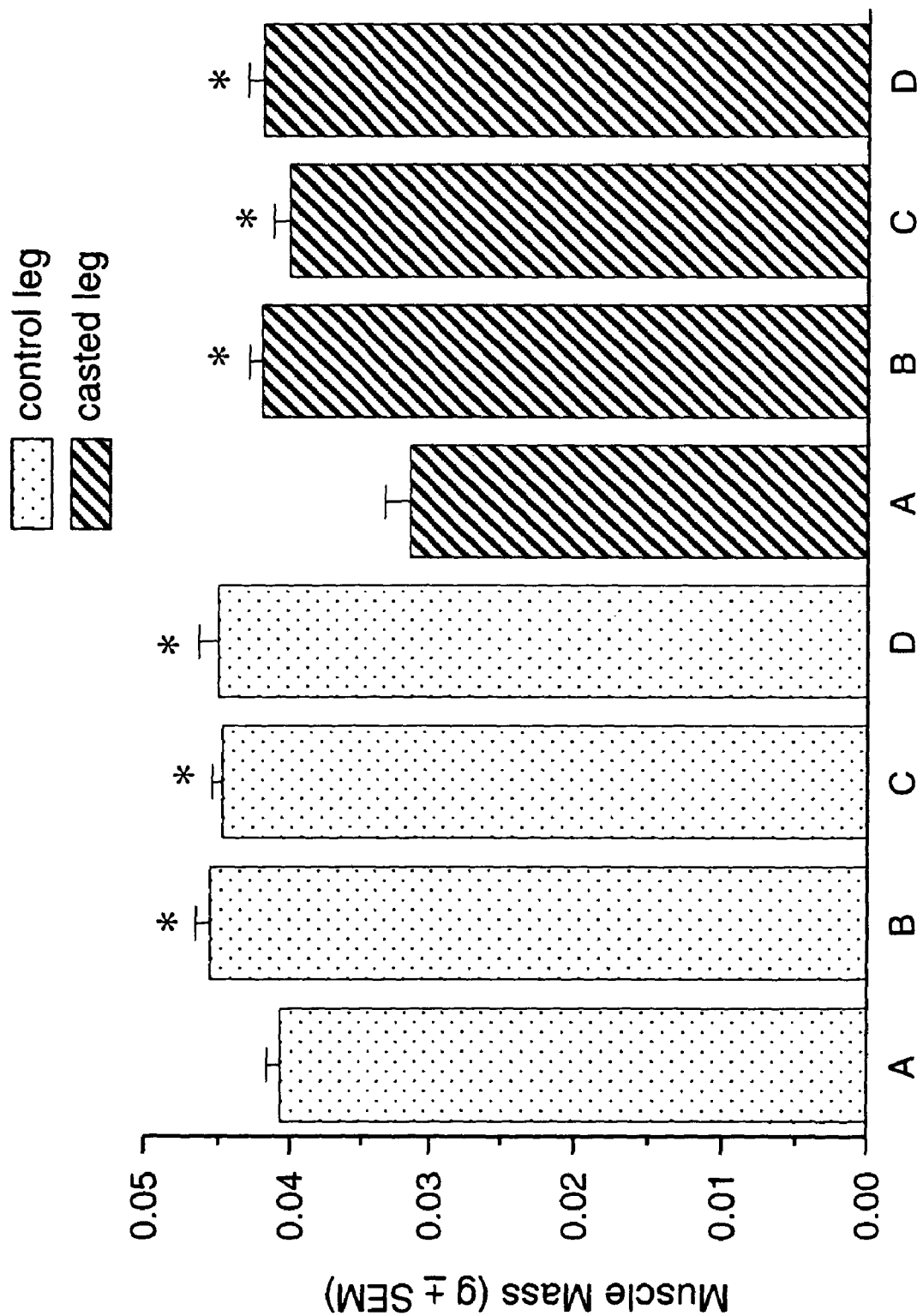
Figure 4B:
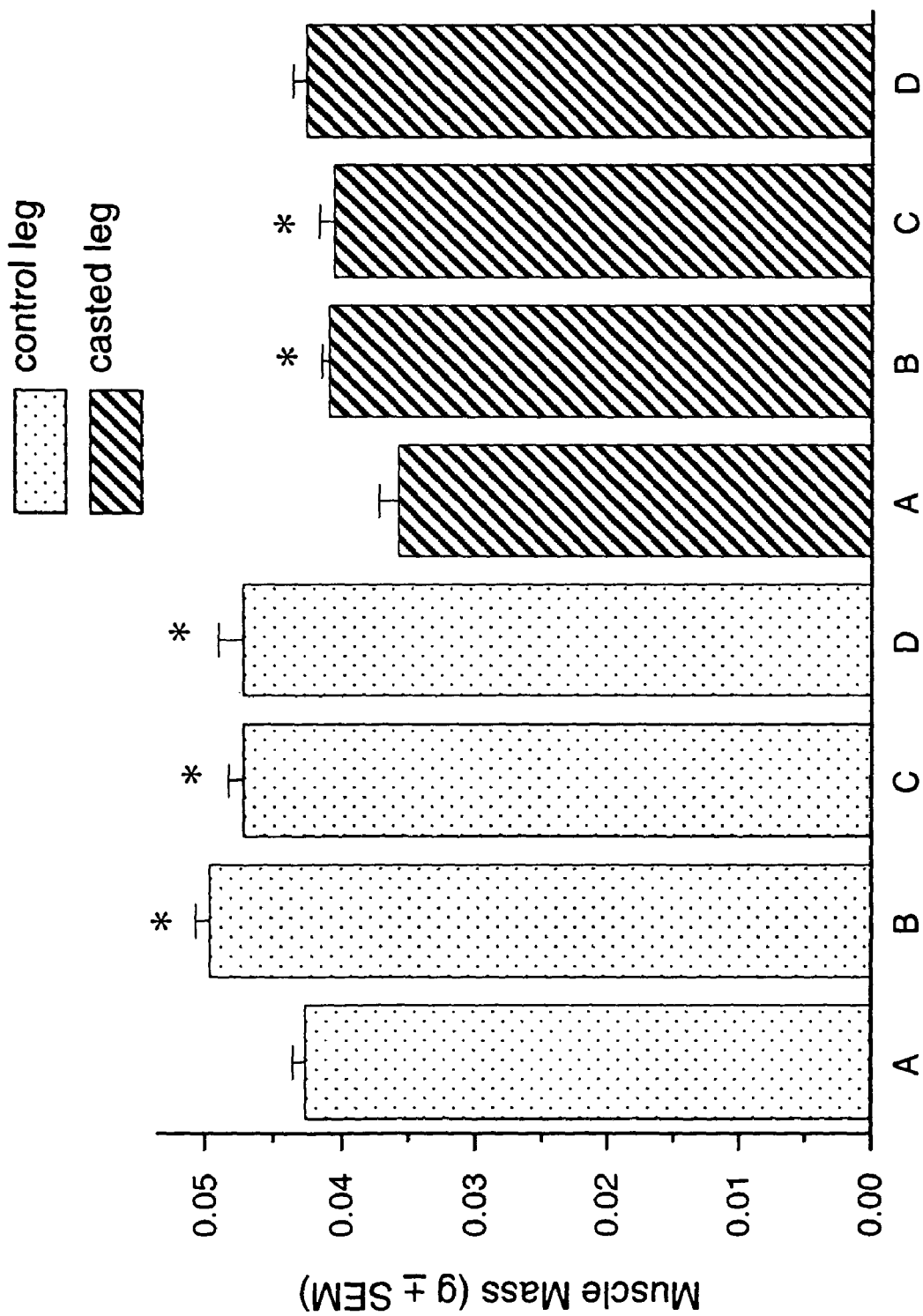

FIG. 4A demonstrates the anti-atrophy effect of sauvagine (administered subcutaneously, 2× daily) on the casting-induced atrophy of the tibialis anterior muscle and hypertrophy-inducing effect on the non-casted (normal) tibialis anterior muscle. FIG. 4B demonstrates the anti-atrophy effect of sauvagine on the casting-induced atrophy of the medial gastrocnemius muscle and the hypertrophy inducing effect of sauvagine on the non-casted (normal) medial gastrocnemius muscle.

Figure 5:
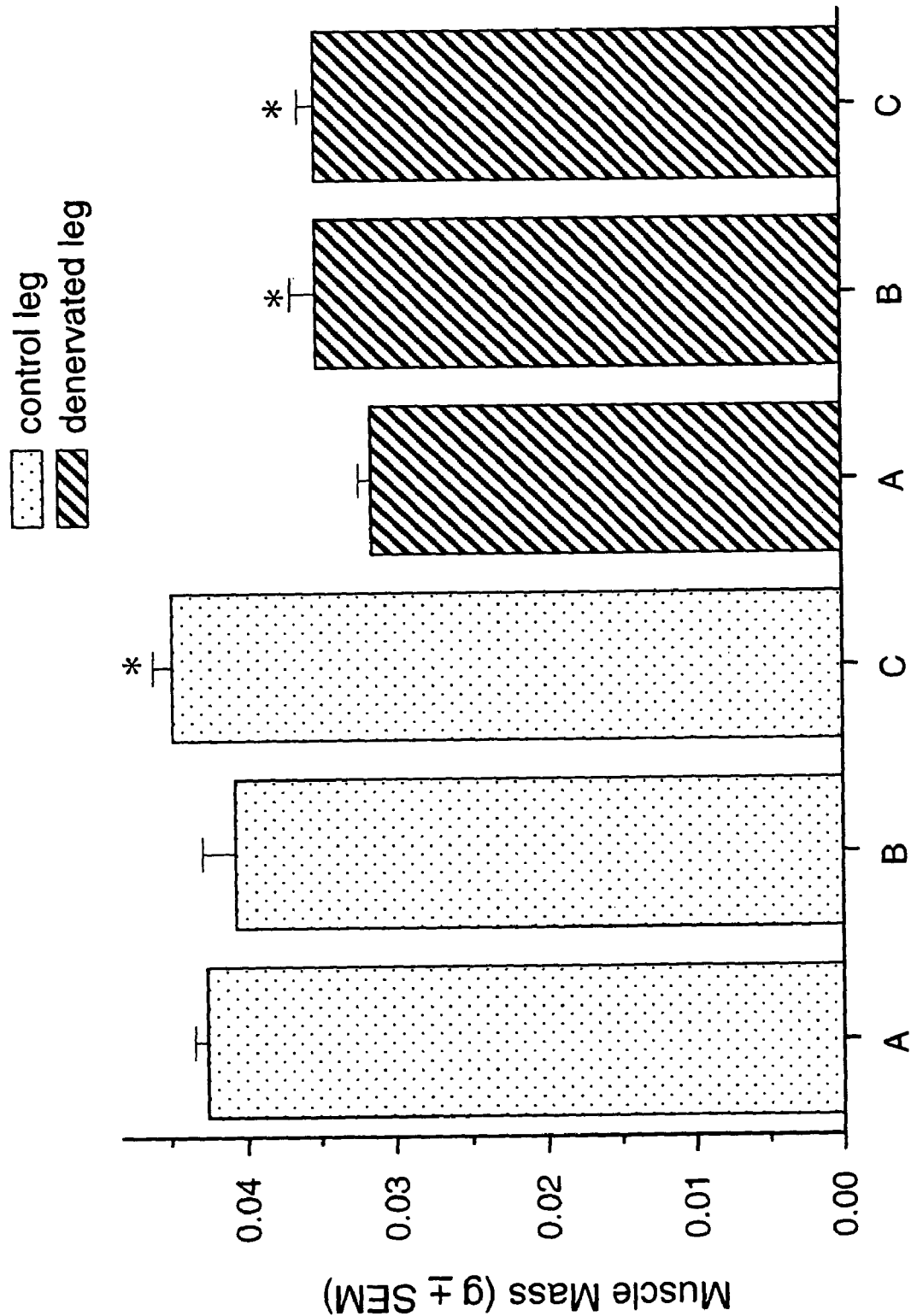

FIG. 5 demonstrates the anti-atrophy and hypertrophy inducing effects of sauvagine and urocortin (administered continuously by osmotic minipump) on the tibialis anterior muscle in the mouse sciatic nerve denervation-induced atrophy model.

Figure 6A:
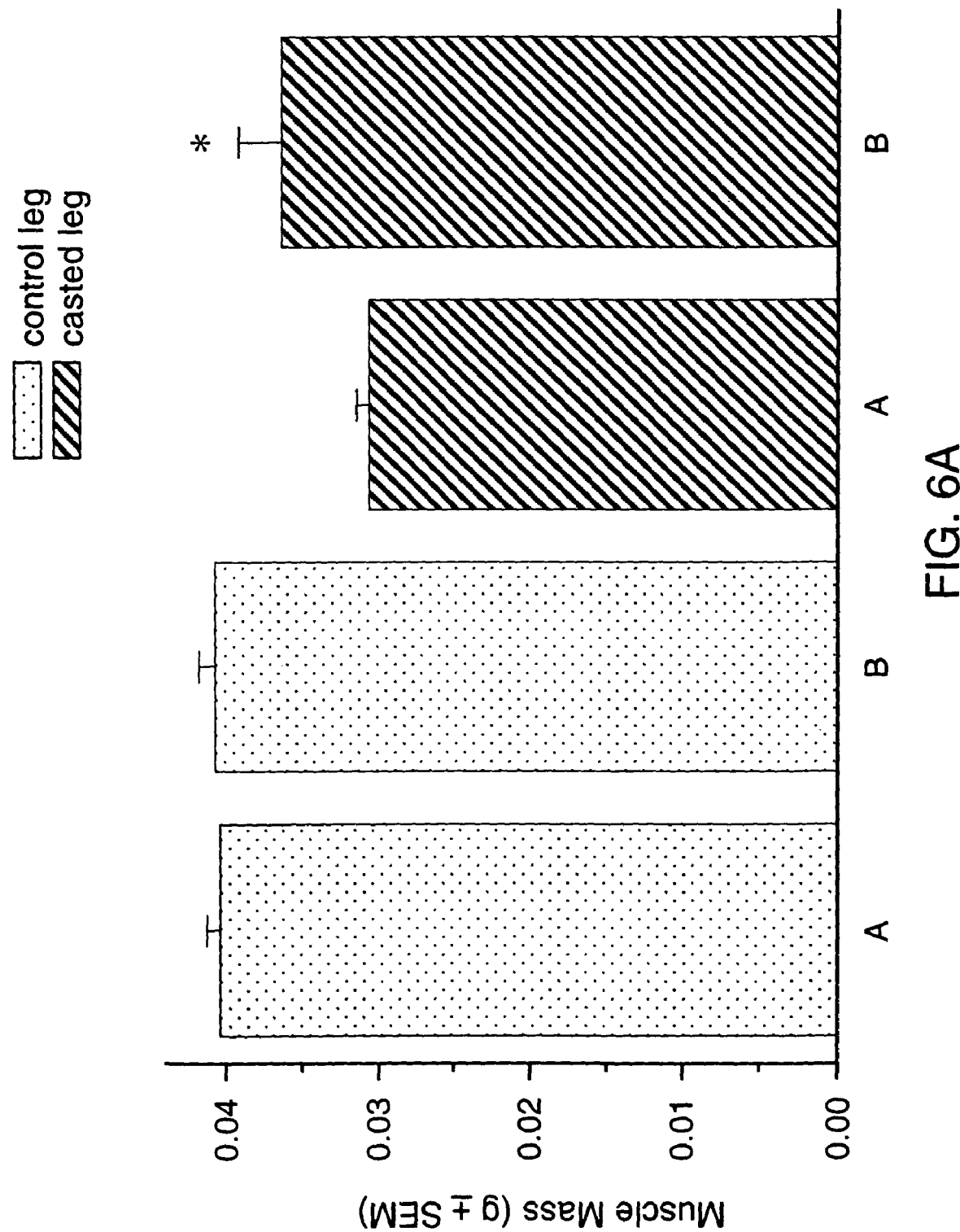
Figure 6B:
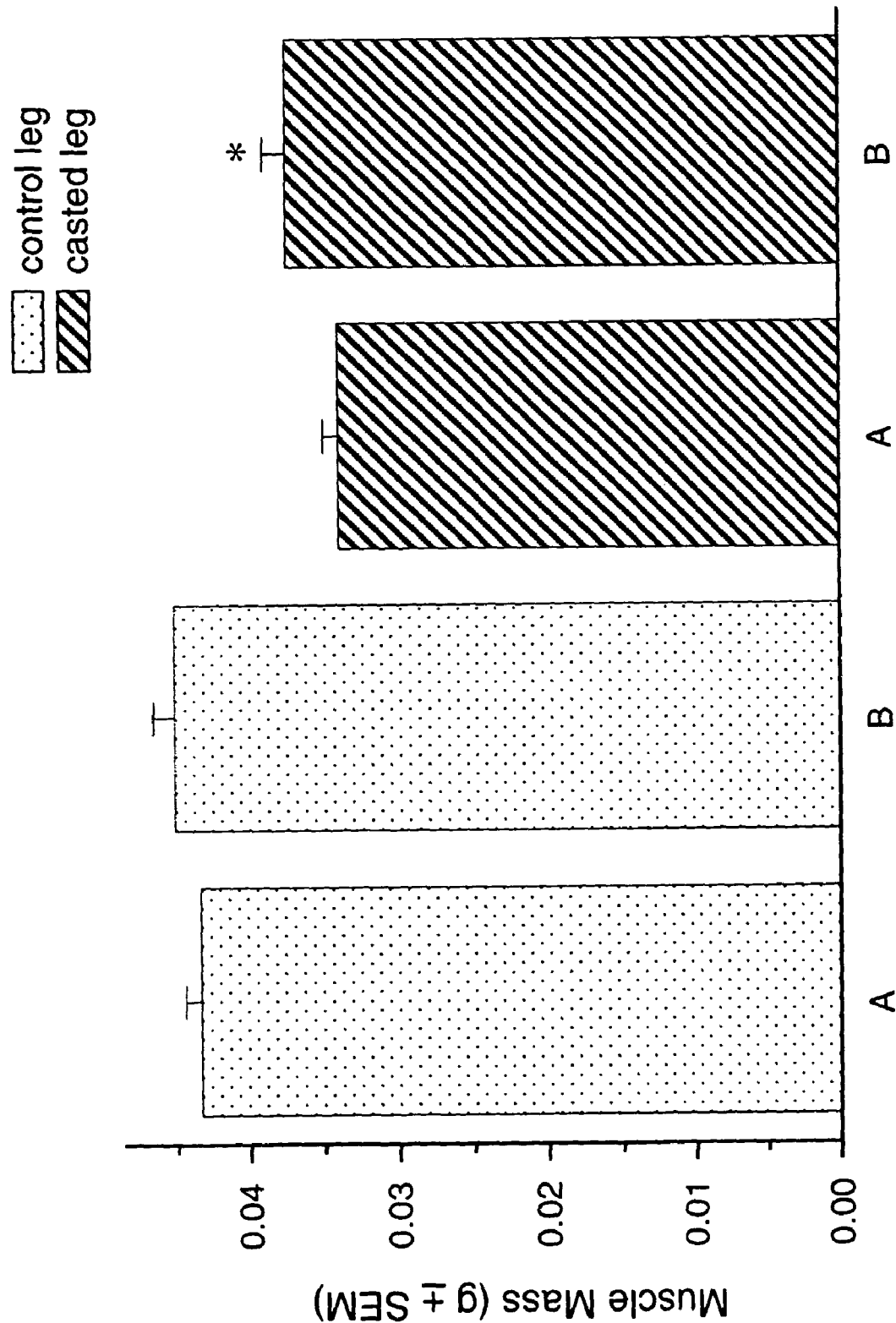
Figure 7A:
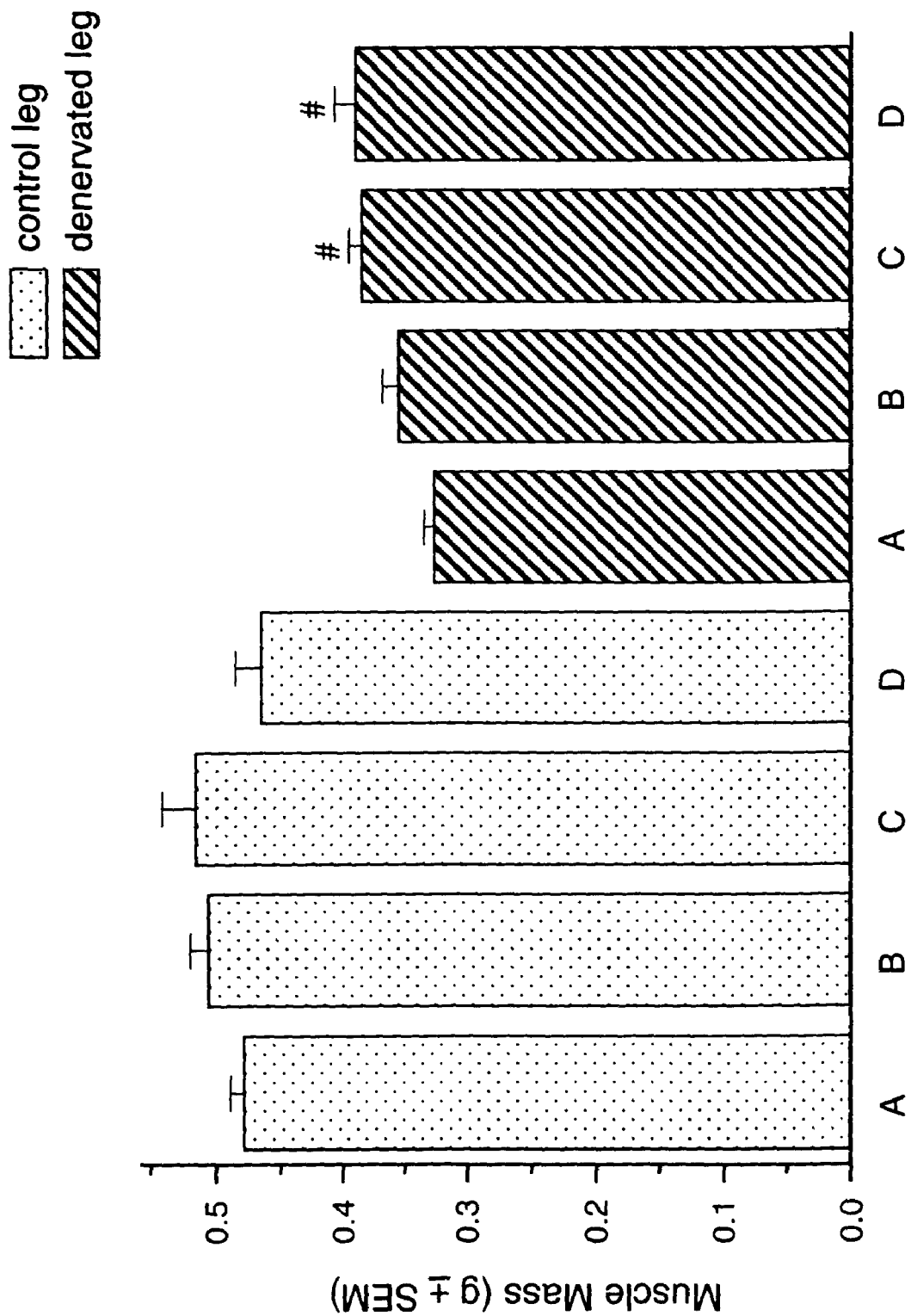
Figure 7B:
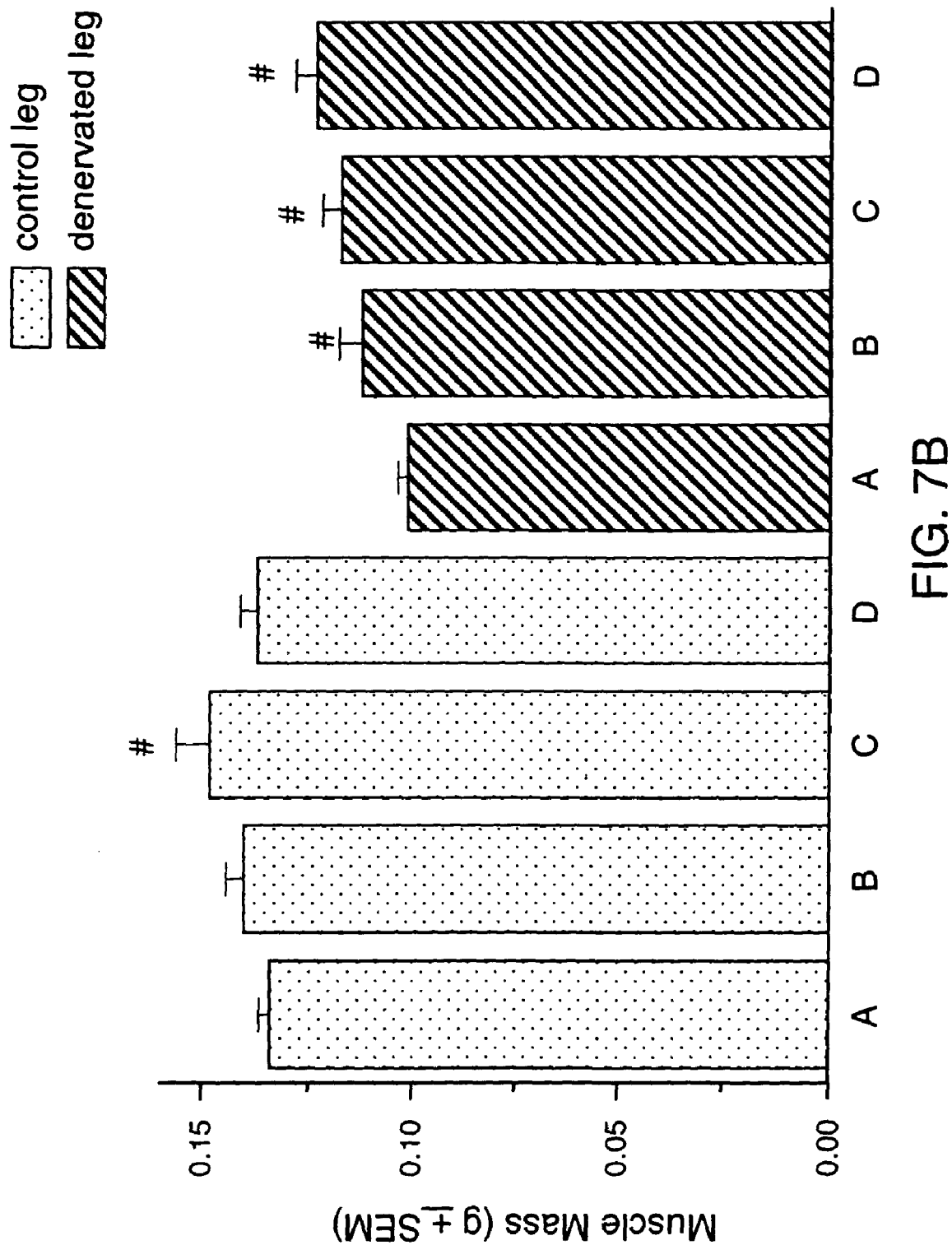
Figure 7C:
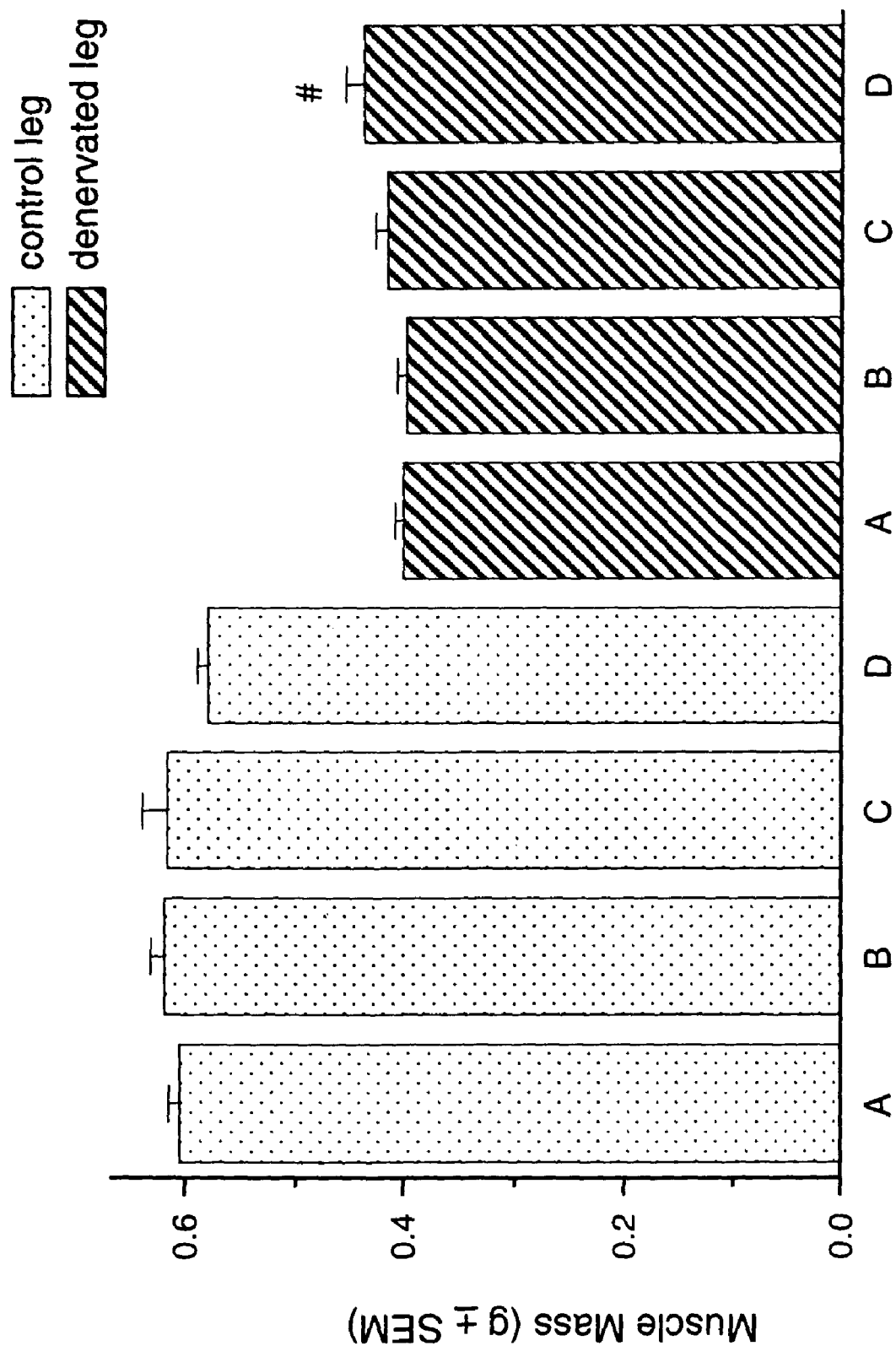
Figure 7D:
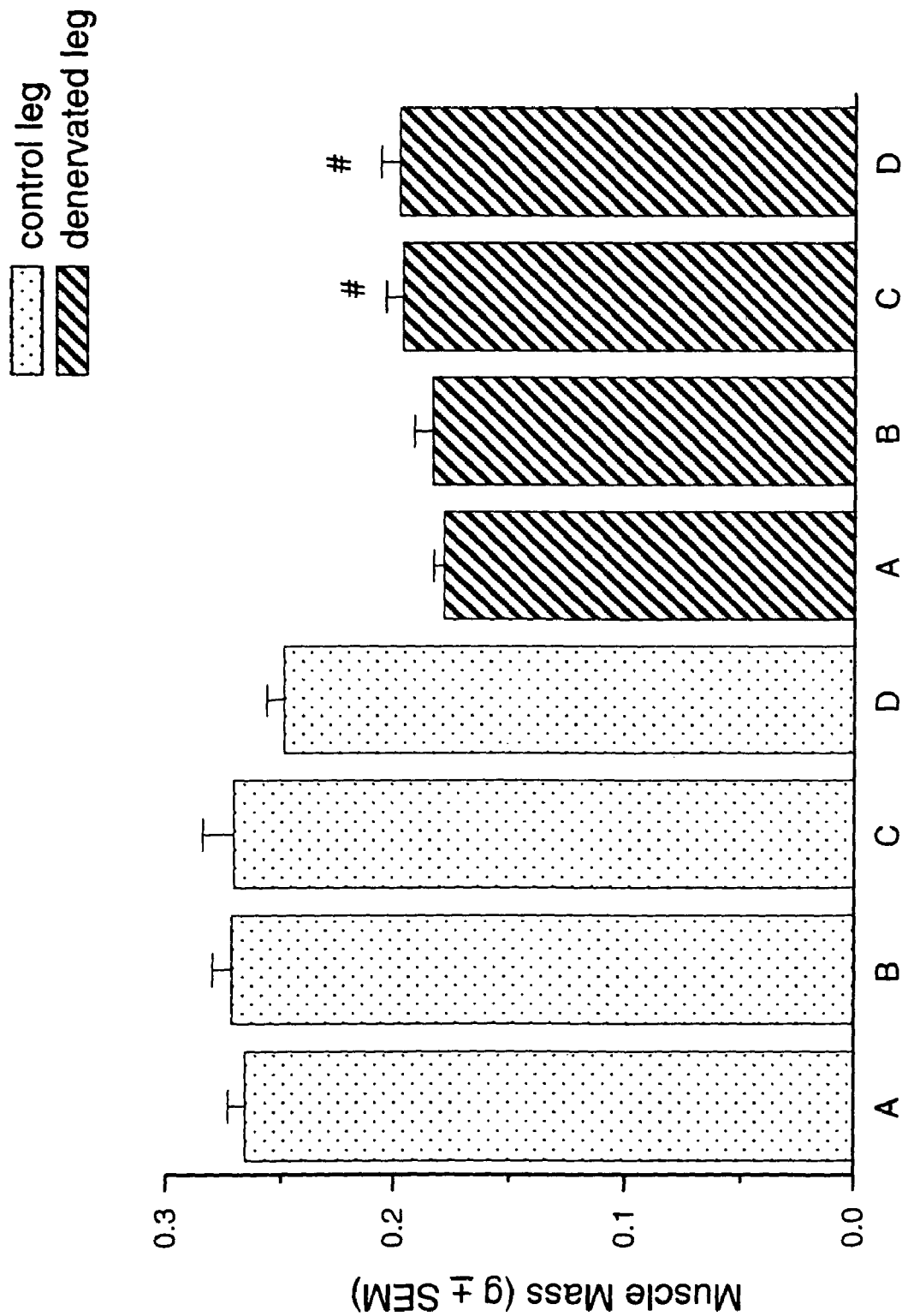

FIGS. 6A and 6B demonstrate the anti-atrophy effects of urocortin (administered subcutaneously, 2× daily) on the disuse-induced atrophy of the tibialis anterior muscle (FIG. 6A) and of the medial gastrocnemius muscle (FIG. 6B).

FIG. 7 demonstrates in the anti-atrophy effect of sauvagine (administered subcutaneously, 2× daily), in the adrenalectomized rat sciatic nerve denervation-induced atrophy model, on the denervation-induced atrophy of the tibialis anterior (FIG. 7A), extensor digitorum longus (EDL) (FIG. 7B), soleus (FIG. 7C), medial gastrocnemius (FIG. 7D), and plantaris (FIG. 7E) muscles. In addition, sauvagine induced hypertrophy of the non-denervated EDL muscle (FIG. 7B).

Figure 8:
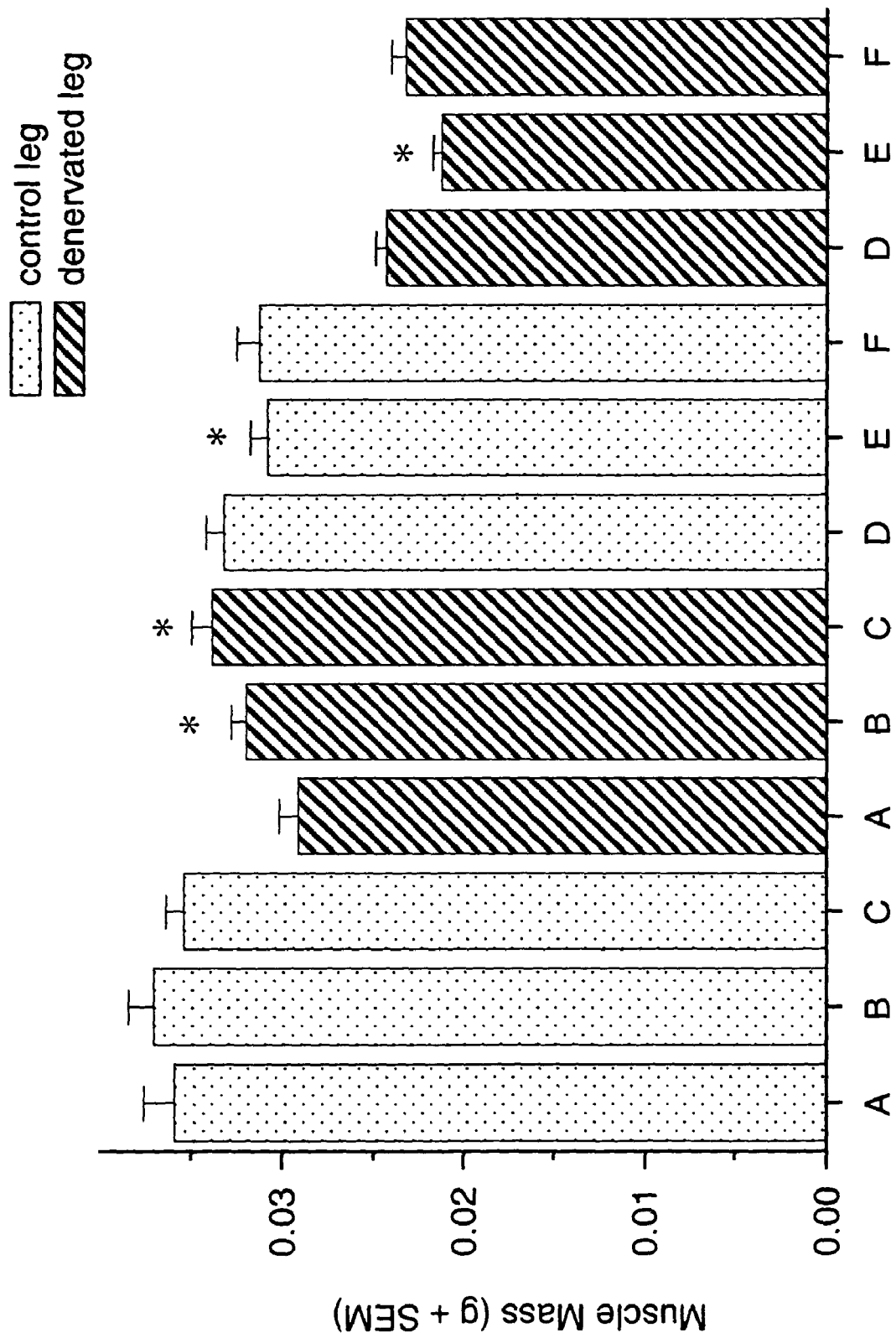

FIG. 8 demonstrates that in the mouse sciatic nerve denervation atrophy model, sauvagine (administered continuously by osmotic minipump) had an anti-atrophy effect on the tibialis anterior muscle in wild-type mice but not in $CRF_2R$ knockout mice.

Figure 9A:
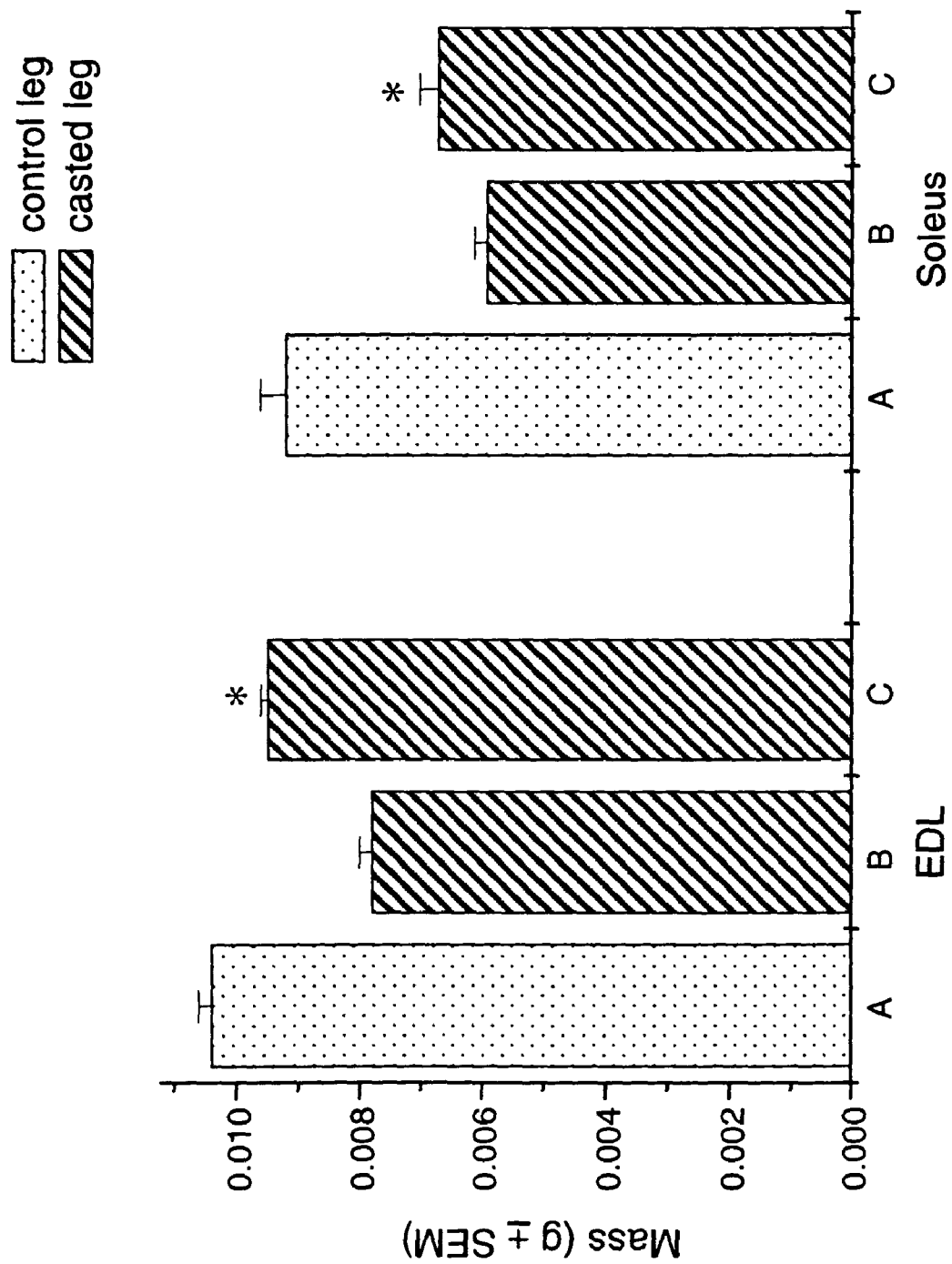
Figure 9B:
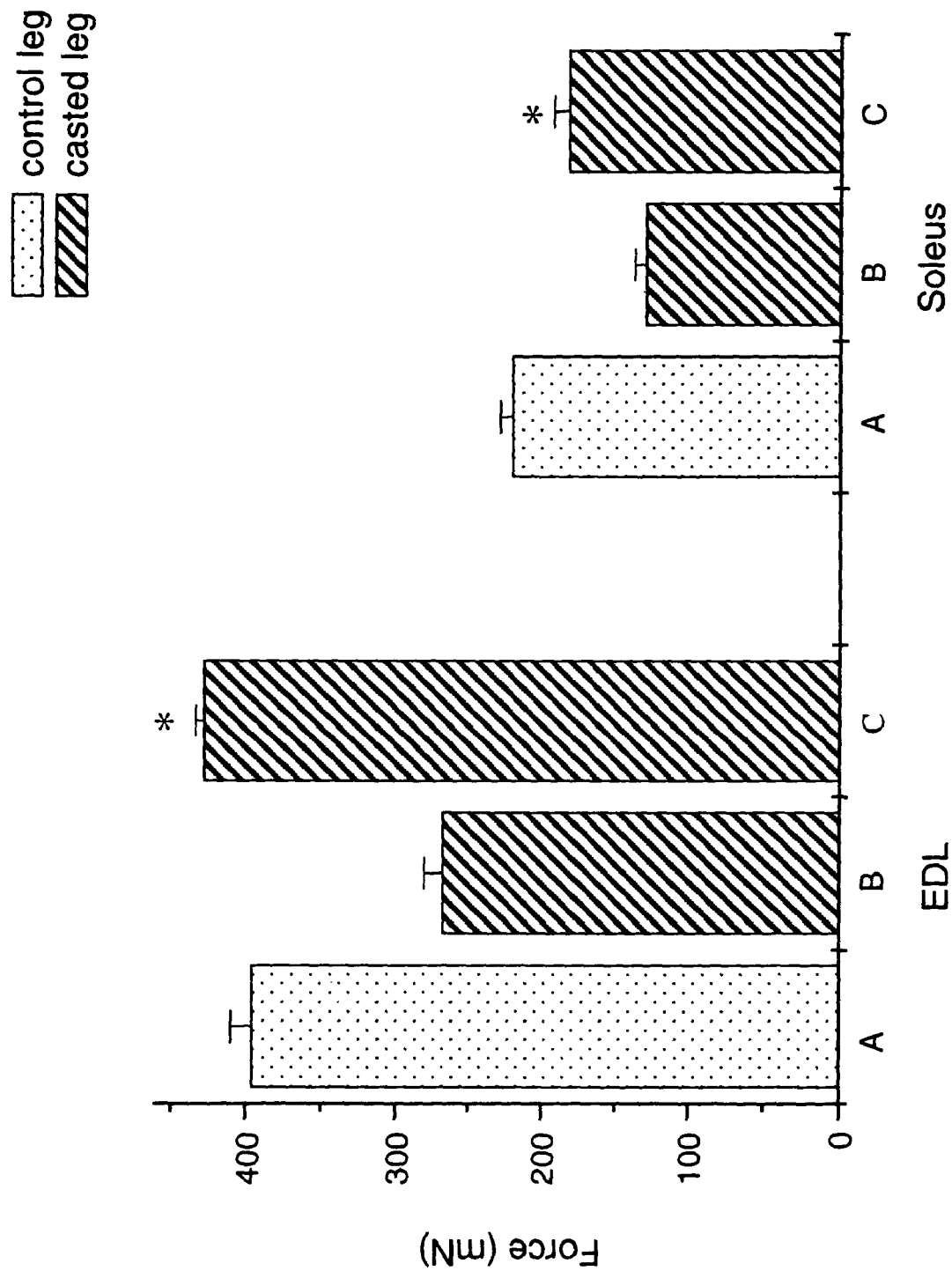

FIGS. 9A and B demonstrate that in a mouse leg casting disuse atrophy model, sauvagine had an anti-atrophy effect on the EDL and soleus muscle as measured by mass (FIG. 9A) or muscle function (FIG. 9B).

Table II shows comparison of human $CRF_2R$ sequences with $CRF_2R$ and $CRF_1R$ sequences from various vertebrate species both at nucleotide and amino acid level.

DETAILED DESCRIPTION OF THE INVENTION

I. Terms and Definitions

The following is a list of definitions for terms used herein.

"Agonist" means any compound, including, but not limited to, antibodies, that activates a receptor. For example, CRFR agonists include, but are not limited to, CRF and CRF analogs.

"Allelic variant" means a variant form of a given gene or gene product. One of skill in the art recognizes that a large number of genes are present in two or more allelic forms in a population and some genes have numerous alleles.

"Antibody", in its various grammatical forms, means immunoglobulin molecules and immunologically active portions of immunoglobulin molecules, i.e., molecules that contain an antigen binding site which specifically binds an antigen. "Purified antibody" means an antibody which has been partially or completely separated from the proteins and naturally-occurring organic molecules with which it is naturally associated. Preferably, the preparation is at least 60% antibody, more preferably at least 75% antibody, more preferably at least 90% antibody, and most preferably at least 99%, by dry weight, antibody.

"Binding affinity" means the propensity for a ligand to interact with a receptor and is inversely related to the dissociation constant for a specific CRF ligand-CRFR interaction. The dissociation constant can be measured directly via standard saturation, competition, or kinetics binding techniques or indirectly via pharmacological techniques involving functional assays and endpoints.

"Chimeric antibody" means an antibody that contains structural elements from two or more different antibody molecules, i.e., from different animal species. Chimeric antibodies include, but are not limited to, antibodies known as "humanized antibodies" which include, but are not limited to, chimeric antibodies generated by the technique known as complementarity determining region grafting.

"CRF" means corticotropin releasing factor which is the same as corticotropin releasing hormone (CRH). Exemplary CRF peptides include r/h CRF and ovine CRF (see U.S. Pat. No. 4,415,558), and the like.

"CRF analog" means substances which act as ligands of CRFRs. Suitable CRF analogs can be obtained from a variety of vertebrate species and include, but are not limited to, substances such as sauvagine (see, e.g., U.S. Pat. No. 4,605,642), urotensin (see, e.g., U.S. Pat. Nos. 4,908,352; and 4,533,654), mouse urocortin II (SEQ ID NO: 43), human urocortin-related peptide (SEQ ID NO: 44) (Reyes, T. M. et al., *Proc. Nat'l Acad Sci* 98:2843–2848 (2001)), urocortin (see, e.g., WO 97/00063) and the CRF analogs described in U.S. Pat. Nos: 4,415,558; 4,489,163; 4,594,329; 4,605,642; 5,109,111; 5,235,036; 5,278,146; 5,439,885; 5,493,006; 5663292; 5,824,771; 5,844,074; and 5,869,450. Each of which is incorporated herein by reference. Preferred CRF analogs are sauvagine, urocortin, urocortin-related peptide, urocortin-II and urotensin.

"CRFR agonist" means a compound or molecule which has the ability to activate $CRF_1R$ or $CRF_2R$, or both. Activation of CRFRs can be measured as described hereinafter.

"CRFR" means $CRF_1R$ or $CRF_2R$.

"$CRF_1R$" means any isoforms of $CRF_1R$ from any animal species. The $CRF_1R$ has previously been referred to as CRF-RA, PC-CRF, CRF, (Perrin, M. H., et al. *Endocrinology* 133:3058–3061 (1993), Chen, R., et al. *Proc. Natl. Acad. Sci. USA* 90:8967–8971 (1993), Chang, C -P. et al., *Neuron* 11:1187–1195 (1993), Kishimoto, T., et al., *Proc. Natl. Acad. Sci.USA,* 92:1108–1112 (1995) and, Vita, N. et al., *FEBS Lett.* 335: 1–5 (1993)) or the CRH receptor.

The definition of $CRF_1R$ includes, but is not limited to, those receptors for which the cDNA or genomic sequence encoding the receptor has been deposited in a sequence database. These sequences include Accession Nos.: X72304, E11431, L23332, I92584, T37068, T28968, Q81952, L23333, NM_004382, AF180301, T28970, L25438, L24096, I92586, Q81954, AH006791, NM-007762, X72305, AF054582, Y14036, AF229359, AF229361, AB055434 and L41563. The nucleotide and protein sequences of these receptors are available from GenBank or Derwent and for convenience representative sequences are given in the sequence listing herein.

"$CRF_2R$" means any isoform of $CRF_2R$ from any animal species. $CRF_2R$ has also been referred to as HM-CRF, CRF-RB, (Kishimoto, T., et al., *Proc. Natl. Acad. Sci. USA*, 92:1108–1112 (1995) and Perrin, M. et al. *Proc. Natl. Acad. Sci. USA* 92:2969–2973 (1995)).

The definition of $CRF_2R$ receptor includes, but is not limited to, those receptors for which the DNA sequence encoding the receptor has been deposited in a sequence database. These sequences include Accession Nos.: U34587, E12752, NM_001883, T12247, T66508, AF011406, AF019381, U16253, T12244, T28972, U17858, NM_009953, Y14037 and AF229360. The nucleotide and protein sequences of these receptors are available from GenBank or Derwent and for convenience, representative sequences are given in the sequence listing herein.

The term "CRFR" also includes truncated and/or mutated proteins wherein regions of the receptor molecule not required for ligand binding or signaling have been deleted or modified. For example one of skill in the art will recognize that a CRFR with one or more conservative changes in the primary amino acid sequence would be useful in the present invention. It is known in the art that substitution of certain amino acids with different amino acids with similar structure or properties (conservative substitutions) can result in a silent change, i.e., a change that does not significantly alter function. Conservative substitutes are well known in the art. For example, it is known that GPCRs can tolerate substitutions of amino acid residues in the transmembrane alpha-helices, which are oriented toward lipid, with other hydrophobic amino acids, and remain functional. $CRF_1Rs$ differing from a naturally occurring sequence by truncations and/or mutations such as conservative amino acid substitutions are also included in the definition of $CRF_1R$. $CRF_2R$ differing from a naturally occurring sequence by truncations and/or mutations such as conservative amino acid substitutions are also included in the definition of $CRFR_2$.

One of skill in the art would also recognize that CRFRs from a species other than those listed above, particularly vertebrate species, would be useful in the present invention. One of skill in the art would further recognize that by using probes from the known CRFR species' sequences, cDNA or genomic sequences homologous to the known sequence could be obtained from the same or alternate species by known cloning methods. Such $CRF_1R$ are also included in the definition of $CRF_1R$ and such $CRF_2R$ are also included in the definition of $CRF_2R$.

In addition, one of skill in the art would recognize that functional allelic variants or functional splice variants of CRFRs might be present in a particular species and that these variants would have utility in the present invention. Splice variants of CRFRs are known, for example U.S. Pat. Nos. 5,888,811; 5,786,203; and 5,728,545, each of which is incorporated herein by reference. Such $CRF_1R$ variants are also included in the definition of $CRF_1R$ and such $CRF_2R$ variants are also included in the definition of $CRF_2R$.

Fusions of a $CRF_1R$ or $CRF_2R$ polypeptide, or a $CRF_1R$ or $CRF_2R$ polypeptide fragment to a non-CRFR polypeptide are referred to as CRFR fusion proteins. Using known methods, one of skill in the art would be able to make fusion proteins of a $CRF_1R$ or a $CRF_2R$ that, while different from native $CRF_1R$ and $CRF_2R$, would remain useful in the present invention. For example the non-CRFR polypeptide may be a signal (or leader) polypeptide sequence which co-translationally or post-translationally directs transfer of the protein from its site of synthesis to another site (e.g., the yeast α-factor leader). Or the non-CRFR polypeptide may be added to facilitate purification or identification of the CRFR (e.g., poly-His, or Flag peptide). $CRF_1R$ fusion proteins are also included within the definition of $CRF_1R$ and $CRF_2R$ fusion proteins are also included within the definition of $CRF_2R$.

"$CRF_2R$ signal transduction pathway" means any signaling pathway (e.g., cAMP, MAP kinase) or combination of signaling pathways that are modulated by the binding of endogenous or exogenous ligands to $CRF_2R$.

"Functional CRFRs" refers to CRFRs, which bind CRF or a CRF analog in vivo or in vitro and are activated as a result of ligand binding.

"Fusion gene" means two or more DNA coding sequences operably associated so as to encode one hybrid protein. A "fusion protein" is the protein product of a fusion gene.

"Inhibit" means to partially or completely block a particular process or activity. For example, a compound inhibits skeletal muscle atrophy if it either completely or partially prevents muscle atrophy.

As used herein, two DNA sequences are said to be "operably associated" if the nature of the linkage between the two DNA sequences does not (1) result in the introduction of a frame-shift mutation, (2) interfere with the ability of a promoter region to direct the transcription of the coding sequences, or (3) interfere with the ability of the corresponding RNA transcript to be translated into a protein. For example, a coding sequence and regulatory sequences are operably associated when they are covalently linked in such a way as to place the transcription of the coding sequence under the influence or control of the regulatory sequences. Thus, a promoter region is operably associated with a coding sequence when the promoter region is capable of effecting transcription of that DNA sequence such that the resulting transcript is capable of being translated into the desired protein or polypeptide.

"Percent identity" means the percentage of nucleotides or amino acids that two sequences have in common, calculated as follows. To calculate the percent identity for a specific sequence (the query), the relevant part of the query sequence is compared to a reference sequence using the BestFit comparison computer program, Wisconsin Package, Version 10.1, available from the Genetics Computer Group, Inc. This program uses the algorithm of Smith and Waterman, *Advances in Applied Mathematics*, Issue 2: 482–489 (1981). Percent identity is calculated with the following default parameters for the BestFit program: the scoring matrix is blosum62.cmp, the gap creation penalty is 8 and the gap extension penalty is 2. When comparing a sequence to the reference sequence, the relevant part of the query sequence is that which is derived from a CRFR sequence. For example, where the query is a CRFR/purification tag fusion protein, only the CRFR polypeptide portion of the sequence is aligned to calculate the percent identity score.

"Polypeptide" means any chain of amino acids, regardless of length or post-translational modification (e.g., phosphorylation or glycosylation).

"Promoter" means a DNA sequence which controls the initiation of transcription and the rate of transcription from a gene or coding region.

"Prophylactic treatment" means preventive treatment of a subject, not currently exhibiting signs of skeletal muscle atrophy, in order to completely or partially block the occurrence of skeletal muscle atrophy. One of skill in the art would recognize that certain individuals are at risk for skeletal muscle atrophy as discussed in the background section herein. Furthermore, one of skill in the art would recognize that if the biochemical changes leading to skeletal muscle atrophy are appropriately regulated, that the occurrence of atrophy would be prevented or reduced in at-risk individuals. For example, muscular dystrophy patients beginning treatment with corticosteroids are at risk for developing skeletal muscle atrophy indicating that prophylactic treatment of such patients would be appropriate.

"Regulate" in all its grammatical forms, means to increase, decrease or maintain, e.g., to regulate skeletal muscle mass or function means to increase, decrease or maintain the level of skeletal muscle mass or function.

"Regulation of skeletal muscle mass or function" includes regulation of skeletal muscle mass, skeletal muscle function or both.

"Regulatory element" means a DNA sequence that is capable of controlling the level of transcription from an operably associated DNA sequence. Included within this definition of regulatory element are promoters and enhancers. E.g., a CRFR gene regulatory element is a DNA sequence capable of controlling the level of transcription from the CRFR gene.

"Reporter gene" means a coding sequence whose product can be detected, preferably quantitatively, wherein the reporter gene is operably associated with a heterologous promoter or enhancer element which is responsive to a signal which is to be measured. The promoter or enhancer element in this context is referred to herein as a "responsive element".

"Selective agonist" means that the agonist has significantly greater activity toward a certain receptor(s) compared with other receptors, not that it is completely inactive with regard to other receptors.

"Skeletal muscle hypertrophy" means an increase in skeletal muscle mass or skeletal muscle function or both.

"Skeletal muscle atrophy" means the same as "muscle wasting" and means a decrease in skeletal muscle mass or skeletal muscle function or both.

"Splice variant" means a mRNA or protein which results from alternative exon usage. One of skill in the art recognizes that, depending on cell type, or even within a single cell type, a mRNA may be expressed in a different form, as a splice variant, and thus the translated protein will be different depending upon the mRNA that is expressed.

A "therapeutically effective amount" of a substance is an amount capable of producing a medically desirable result in a treated patient, e.g., decreases skeletal muscle atrophy, increases skeletal muscle mass or increases skeletal muscle function, with an acceptable benefit: risk ratio; in a human or non-human mammal.

"Therapeutic treatment" means treatment of a subject in which an increase in muscle mass or muscle function is desirable. For example, treatment of a subject currently exhibiting signs of skeletal muscle atrophy in order to partially or completely reverse the skeletal muscle atrophy that has occurred or to completely or partially block the occurrence of further skeletal muscle atrophy would be therapeutic treatment of that subject. The term "therapeutic treatment" also includes, for example, treatment of a subject not exhibiting signs of skeletal muscle atrophy to induce skeletal muscle hypertrophy, e.g., treatment of a livestock animal to increase muscle mass.

The term "treatment" means prophylactic or therapeutic treatment.

Unless otherwise defined, all technical and scientific terms used herein have the same meaning as commonly understood by one of ordinary skill in the arts of protein chemistry, pharmacology, or molecular biology. The methods, materials and examples described herein are not intended to be limiting. Other methods and materials similar or equivalent to those described herein can be used in the practice or testing of the present invention.

II. The Role of CRFRs in Regulation of Skeletal Muscle Mass

One of skill in the art would recognize the utility of the present invention given the information in the prior art and the teachings below. The results described herein demonstrate that administration of a CRF receptor agonist which activates both $CRF_1R$ and $CRF_2R$ (non-selective CRFR agonist) blocks and/or inhibits the skeletal muscle atrophy inducing effect of denervation, disuse or dexamethasone treatment in models of skeletal muscle atrophy. In addition, data show that CRFR agonists do not show this anti-atrophy effect in mice in which $CRF_2R$ has been knocked out. Also, in rats in which the $CRF_1R$ mediated HPA axis has been interrupted by removal of the adrenal glands (surgical adrenalectomy), treatment of these animals with the non-selective CRFR agonists shows an anti-atrophy effect, indicating that the $CRF_2R$ mediates the anti-atrophy effects. Furthermore, results demonstrate that administration of a non-selective CRFR agonist show a hypertrophy inducing effect. Together, these data demonstrate the modulatory role of the $CRF_2R$ in the process of skeletal muscle atrophy. The specific role of CRFRs in vivo was investigated using the pharmacological agents, sauvagine (Bachem Biosciences, Inc. King of Prussia, Pa.) and urocortin (Bachem Biosciences, Inc.), which are selective agonists for CRFRs in various models of skeletal muscle atrophy, described hereinafter. These agents have been well characterized and are described in the scientific literature.

FIGS. 1–7 and 9 show the results of experiments demonstrating that administration of selective agonists of CRFRs results in statistically significant inhibition of skeletal muscle atrophy. FIG. 8 shows that the anti-atrophy effect of the CRFR agonist, sauvagine, is mediated through $CRF_2R$. CRFR agonists administered twice daily in combination with the phosphodiesterase inhibitor, theophylline, resulted in inhibition of skeletal muscle atrophy in animal models of skeletal muscle atrophy. Theophylline was added to potentiate the duration and magnitude of action of the CRFR agonist therefore resulting in increased efficacy of these compounds. Theophylline administered alone in these atrophy models had no effect, demonstrating that the anti-atrophy effect of the CRFR agonist in combination with theophylline was due to the effect of the CRFR agonist. Furthermore, continuous dosing of the CRFR agonist in the absence of theophylline, via osmotic mini-pump, also resulted in inhibition of skeletal muscle atrophy and/or in skeletal muscle hypertrophy. Statistical significance of the results was determined using ANCOVA (Douglas C. Montgomery, Design and Analysis of Experiments, John Wiley and Sons, New York ($2^{nd}$ ed. 1984)). Abbreviations used in FIGS. 1–9: g-gram; SEM-standard error of the mean.

Specifically, FIG. 1 (FIG. 1.) shows that sauvagine inhibits denervation-induced atrophy of the medial gastrocnemius muscle in a mouse sciatic nerve denervation atrophy model. Legend: A—physiological saline (control); B—sauvagine (0.01 mg/kg)+theophylline; C—sauvagine (0.03 mg/kg)+ theophylline; D—sauvagine (0.1 mg/kg)+theophylline; E—sauvagine (1.0 mg/kg)+theophylline;*–$p \leq 0.05$ compared to saline. Following denervation of the right sciatic nerve, male mice were injected subcutaneously in the midscapular region twice daily with sauvagine, at the doses indicated above or vehicle control (physiological saline) for nine days. Sauvagine was co-administered with 30 mg/kg theophylline. On day nine, the medial gastrocnemius muscle was removed and weighed to determine the degree of atrophy.

FIG. 2 (FIG. 2.) shows that sauvagine inhibits denervation-induced atrophy of the tibialis anterior muscle in a mouse sciatic nerve denervation atrophy model. Legend: A—water (control); B—sauvagine (0.1 mg/kg/d); C—sauvagine (0.3 mg/kg/d); D—sauvagine (1.0 mg/kg/d); *–$p \leq 0.05$ compared to water. Following denervation of the right sciatic nerve, male mice were dosed with either sauvagine or vehicle control (physiological saline) by continuous infusion using an Alzet osmotic minipump at 5 μl/hr until the end of the experimental period (without additional theophylline). The daily delivered dose of sauvagine is indicated above. Minipump implantation was performed at the time of sciatic nerve denervation. On day nine the tibialis anterior muscle was removed and weighed to determine the degree of atrophy.

FIG. 3 (FIG. 3.) demonstrates that sauvagine inhibits glucocorticoid-induced muscle atrophy of the tibialis anterior (FIG. 3A) and medial gastrocnemius muscles (FIG. 3B) in the mouse glucocorticoid-induced atrophy model. Legend: A—water only with no dexamethasone included in drinking water (non-atrophied control); B—water+dexamethasone (atrophied control); C—sauvagine (0.1 mg/kg/d)+dexamethasone; D—sauvagine (0.3 mg/kg/d)+dexamethasone; E—sauvagine (1.0 mg/kg/d)+dexamethasone; *–$p \leq 0.05$ compared to water; # –$p \leq 0.05$ compared to water+dexamethasone. Following the addition of the glucocorticoid, dexamethasone, to the drinking water (1.2 mg/kg/d), male mice were dosed with the above indicated agents or vehicle control (physiological saline) by continuous infusion using an Alzet osmotic minipump at 5 μl/hr until the end of the experimental period (without additional theophylline). The daily delivered dose of sauvagine is as indicated above. Minipump implantation was performed at the time of initiation of dexamethasone exposure. Nine days following the initiation of dosing sauvagine, the medial gastrocnemius and tibialis anterior muscles were removed and weighed to determine the degree of atrophy.

FIG. 4 (FIG. 4.) demonstrates that sauvagine inhibits disuse-induced atrophy of the tibialis anterior (FIG. 4A) and medial gastrocnemius (FIG. 4B) muscles. In addition, statistically significant hypertrophy of the medial gastrocnemius and tibialis anterior muscles of the non-casted leg was also observed with sauvagine treatment. Legend: A—physiological saline (control); B—theophylline; C—sauvagine (0.03 mg/kg)+theophylline; D—sauvagine (0.1 mg/kg)+theophylline; E—sauvagine (0.3 mg/kg)+theophylline; *–$p \leq 0.05$ compared to saline. Following casting of the right hind leg, male mice were injected subcutaneously in the midscapular region twice daily, with sauvagine or vehicle control (physiological saline) for ten days at the daily delivered dose indicated. Sauvagine was co-administered with twice daily intra-peritoneal dosing of the phosphodiesterase inhibitor theophylline (30 mg/kg). On day ten, the medial gastrocnemius and tibialis anterior muscles were removed and weighed to determine the degree of atrophy.

FIG. 5 (FIG. 5.) demonstrates that both sauvagine and urocortin inhibit denervation-induced atrophy of the tibialis anterior muscle, in a mouse sciatic nerve denervation atrophy model. In addition, hypertrophy of the non-denervated leg was observed with urocortin treatment. Legend: A—water (control); B—sauvagine (1 mg/kg/d); C—urocortin (1.0 mg/kg/d); *–$p \leq 0.05$ compared to water. Following denervation of the right sciatic nerve, male mice were dosed with the above indicated agents or vehicle control (physiological saline) by continuous infusion using an Alzet osmotic minipump at 5μl/hr until the end of the experimental period (without additional theophylline). The daily delivered dose of the agents is indicated above. Minipump implantation was performed at the same time as the sciatic nerve denervation. On day nine the tibialis anterior muscle was removed and weighed to determine the degree of atrophy.

FIG. 6 (FIG. 6.) demonstrates that urocortin inhibits disuse-induced atrophy of the tibialis anterior (FIG. 6A) and medial gastrocnemius (FIG. 6B) muscles in the mouse leg casting disuse atrophy model. Legend: A—physiological saline (control); B—urocortin (0.3 mg/kg)+theophylline; *–$p \leq 0.05$ compared to saline. Following casting of the right hind leg, male mice were injected subcutaneously in the midscapular region twice daily, with urocortin or vehicle control (physiological saline) for ten days. Urocortin was administered at the doses indicated in the description of FIGS. 6A and 6B. Urocortin was co-administered with twice daily intra-peritoneal dosing of the phosphodiesterase inhibitor theophylline (30 mg/kg). On day ten, the medial gastrocnemius and tibialis anterior muscles were removed and weighed to determine the degree of atrophy.

FIG. 7 (FIG. 7) demonstrates that sauvagine inhibits denervation-induced atrophy of the tibialis anterior (FIG. 7A), EDL (FIG. 7B), soleus (FIG. 7C), medial gastrocnemius (FIG. 7D), and plantaris (FIG. 7E) muscles. In addition, sauvagine caused statistically significant hypertrophy of the non-denervated EDL muscle (FIG. 7B). Legend: A—physiological saline (control); B—sauvagine (0.003 mg/kg)+theophylline; C—sauvagine (0.01 mg/kg)+theophylline; D—sauvagine (0.03 mg/kg)+theophylline; # –$p \leq 0.05$ compared to corresponding controls. Following denervation of the right sciatic nerve, male adrenalectomized rats (adrenalectomized rats were used to remove the skeletal muscle atrophy-inducing effects of activation of the HPA axis via agonisms of the $CRF_1R$) were injected subcutaneously in the midscapular region twice daily, with either sauvagine or vehicle control (physiological saline) for nine days at the doses shown above. Sauvagine was co-administered with 30 mg/kg theophylline. On day nine, the tibialis anterior, extensor digitorum longus (EDL), soleus, medial gastrocnemius, and plantaris muscles were removed and weighed to determine the degree of atrophy.

FIG. 8 (FIG. 8.) demonstrates that sauvagine inhibits the atrophy observed in wild-type but not $CRF_2R$ knockout mice in the mouse sciatic nerve denervation atrophy model. Legend: A–C—wild-type mice; D–F—$CRF_2R$ knockout mice. A and D—water (control); B and E—sauvagine (0.3 mg/kg/d); C and F—sauvagine (1.0 mg/kg/d); *–$p \leq 0.05$ compared to saline. Following denervation of the right sciatic nerve, female wild-type and $CRF_2R$ knockout mice were dosed with sauvagine or vehicle control by continuous infusion using an Alzet osmotic minipump at 5 μl/hr for nine days at the daily delivered dose indicated above. On day nine, the tibialis anterior muscle was removed and weighed to determine the degree of atrophy.

FIG. 9 (FIG. 9) demonstrates that sauvagine inhibits disuse-induced loss of EDL and soleus muscle mass (FIG. 9A) and inhibits loss of muscle function as assessed by measurement of absolute force (FIG. 9B) in the mouse leg casting disuse atrophy model. Legend: A—non casted muscle control; B—casted muscle, saline control; C—casted muscle, sauvagine (0.3 mg/kg)+theophylline (30 mg/kg); *–p≦0.05 compared to saline. Following casting of the right hind leg, male mice were injected subcutaneously in the midscapular region twice daily, with either sauvagine or vehicle control (physiological saline) for ten days at the doses indicated above. Sauvagine was co-admninistered 30 mg/kg theophylline. On day ten, the EDL and soleus muscles were removed and absolute force and mass measurements taken to determine the degree of atrophy.

III. Preparation of CRFRs, CRF or CRF Analogs, or Cell Lines Expressing CRFRs $CRF_1R$, $CRF_2R$, CRF and CRF analogs can be prepared for a variety of uses, including, but not limited to, the generation of antibodies, use as reagents in the screening assays of the present invention, and use as pharmaceutical reagents for the treatment of skeletal muscle atrophy. It will be clear to one of skill in the art that, for certain embodiments of the invention, purified polypeptides will be most useful, while for other embodiments cell lines expressing the polypeptides will be most useful. For example, in situations where it is important to retain the structural and functional characteristics of the CRFR, e.g., in a screening method to identify candidate compounds which activate CRFRs, it is desirable to use cells which express functional CRFRs.

Because CRF and CRF analogs are short polypeptides, the skilled artisan will recognize that these polypeptides will be most conveniently provided by direct synthesis, rather than by recombinant means, using techniques well known in the art. In addition, many of these molecules are commercially available.

Where the source of CRFRs is a cell line expressing the polypeptide, the cells may, for example, endogenously express CRFR, have been stimulated to increase endogenous CRFR expression or have been genetically engineered to express a CRFR. Methods for determining whether a cell line expresses a polypeptide of interest are known in the art, for example, detection of the polypeptide with an appropriate antibody, use of a DNA probe to detect mRNA encoding the protein (e.g., northern blot or PCR techniques), or measuring binding of an agent selective for the polypeptide of interest (e.g., a radiolabeled selective agonist).

The use of recombinant DNA technology in the preparation of $CRF_1R$, $CRF_2R$, or of cell lines expressing these polypeptides is particularly contemplated. Such recombinant methods are well known in the art. To express recombinant $CRF_1R$ or $CRF_2R$, an expression vector that comprises a nucleic acid which encodes the polypeptide of interest under the control of one or more regulatory elements, is prepared. Genomic or cDNA sequences encoding $CRF_1R$ and $CRF_2R$ from several species have been described and are readily available from the GenBank database (available at <http://www.ncbi.nlm.nih.gov/>) or Derwent database (available at <http://www.derwent.co.uk/geneseq/index.html>) as well as in the sequence listing for this application. The accession numbers for $CRF_1R$ and $CRF_2R$ sequences and corresponding SEQ ID NOS. are shown in Table 1. Using this publicly available sequence information, one means of isolating a nucleic acid molecule encoding a $CRF_1R$ or $CRF_2R$ is to screen a genomic DNA or cDNA library with a natural or artificially synthesized DNA probe, using methods well known in the art, e.g., by PCR amplification of the sequence from an appropriate library. Another method is to use oligonucleotide primers specific for the receptor of interest to PCR amplify the cDNA directly from mRNA isolated from a particular tissue (such as skeletal muscle). Such isolated mRNA is commercially available. One of skill in the art would also recognize that by using nucleic acid probes corresponding to portions of the known CRFR receptor sequences the homologous cDNAs or genomic sequences from other species can be obtained using known methods. Particularly useful in the methods of the present invention are CRFR receptors from the species including, but not limited to, human, mouse, rat, pig, monkey, chimpanzee, marmoset, dog, cow, sheep, cat, chicken and turkey. By methods well known in the art, the isolated nucleic acid molecule encoding the CRFR of interest is then ligated into a suitable expression vector. The expression vector, thus prepared, is expressed in a host cell and the host cells expressing the receptor are used directly in a screening assay or the receptor is isolated from the host cells expressing the receptor and the isolated receptor is used in a screening assay.

The host-expression vector systems that may be used for purposes of the invention include, but are not limited to: microorganisms such as bacteria (e.g., E. coli, B. subtilis) transformed with recombinant bacteriophage DNA, plasmid DNA, or cosmid DNA expression vectors containing CRFR nucleotide sequences; yeast (e.g., Saccharomyces, Pichia) transformed with recombinant yeast expression vectors containing CRFR nucleotide sequences; insect cell systems infected with recombinant virus expression vectors (e.g., baculovirus) containing CRFR nucleotide sequences; plant cell systems infected with recombinant virus expression vectors (e.g., cauliflower mosaic virus, tobacco mosaic virus) or transformed with recombinant plasmid expression vectors (e.g., Ti plasmid) containing CRFR nucleotide sequences; or mammalian or vertebrate cell systems (e.g., COS, CHO, HEK293, NIH3T3) harboring recombinant expression constructs containing promoters derived from the genome of mammalian or vertebrate cells (e.g., metallothionein promoter) or from mammalian or vertebrate viruses (e.g., retrovirus LTR) and also containing CRFR nucleotide sequences.

The host cell is used to produce the polypeptide of interest. Because the CRFR is a membrane bound molecule, it is purified from the host cell membranes or the CRFR is utilized while anchored in the cell membrane, i.e., whole cells or membrane fractions of cells are used. Purification or enrichment of the CRFRs from such expression systems is accomplished using appropriate detergents and lipid micelles by methods well known to those skilled in the art.

In bacterial systems, a number of expression vectors may be advantageously selected depending upon the use intended for the gene product being expressed. For example, when a large quantity of such protein is produced for the generation of antibodies to CRFRs, vectors which direct the expression of high levels of protein products are desirable. One skilled in the art is able to generate such vector constructs and purify the proteins by a variety of methodologies including selective purification technologies such as fusion protein selective columns and antibody columns, and non-selective purification technologies.

In an insect protein expression system, the baculovirus A. californica nuclear polyhedrosis virus (AcNPV), is used as a vector to express foreign genes in S. frugiperda cells. In this case, CRFR nucleotide sequences are cloned into non-essential regions of the virus and placed under the control of an AcNPV promoter. The recombinant viruses are then used to infect cells in which the inserted gene is expressed and the protein is purified by one of many techniques known to one skilled in the art.

In vertebrate host cells, a number of viral-based expression systems may be utilized. Utilization of these expression systems often requires the creation of specific initiation signals in the vectors for efficient translation of the inserted nucleotide sequences. This is particularly important if a portion of the CRFR gene is used which does not contain the endogenous initiation signal. The placement of this initiation signal, in frame with the coding region of the inserted nucleotide sequence, as well as the addition of transcription and translation enhancing elements and the purification of the recombinant protein, are achieved by one of many methodologies known to one skilled in the art. Also important in vertebrate host cells is the selection of an appropriate cell type which is capable of the necessary post translational modifications of the recombinant protein. Such modifications, for example, cleavage, phosphorylation, glycosylation, etc., require the selection of the appropriate host cell which contains the modifying enzymes. Such host cells include, but are not limited to, CHO, HEK293, NIH3T3, COS, etc. and are known by those skilled in the art.

For long term, high expression of recombinant proteins, stable expression is preferred. For example, cell lines that stably express CRFRs may be engineered. One of skill in the art, following known methods such as electroporation, calcium phosphate transfection, or liposome-mediated transfection, can generate a cell line that stably expresses CRFRs. This is usually accomplished by transfecting cells using expression vectors which contain appropriate expression control elements (e.g., promoter sequences, enhancer sequences, transcriptional termination sequences, polyadenylation sites, translational start sites, etc.), a selectable marker, and the gene of interest. The selectable marker may either be contained within the same vector, as the gene of interest, or on a separate vector, which is co-transfected with the CRFR sequence containing vector. The selectable marker in the expression vector may confer resistance to the selection and allows cells to stably integrate the vector into their chromosomes and to grow to form foci which in turn can be cloned and expanded into cell lines. Alternatively, the expression vector may allow selection of the cell expressing the selectable marker utilizing a physical attribute of the marker, i.e., expression of Green Fluorescent Protein (GFP) allows for selection of cells expressing the marker using fluorescence activated cell sorting (FACS) analysis.

One of skill in the art is able to select an appropriate cell type for transfection in order to allow for selection of cells into which the gene of interest has been successfully integrated. For example, where the selectable marker is herpes simplex virus thymidine kinase, hypoxanthine-guanine phosphoribosyltransferase or adenine phosphoribosyltransferase, the appropriate cell type would be tk-, hgprt- or aprt- cells, respectively. Or, normal cells can be used where the selectable marker is dhfr, gpt, neo or hygro which confer resistance to methotrexate, mycophenolic acid, G418 or hygromycin, respectively. Such recombinant cell lines are useful for identification of candidate compounds that affect the CRFR activity.

IV. Preparation of CRFR Antibodies

Antibodies that selectively recognize one or more epitopes of a CRFR are also encompassed by the invention. Such antibodies include, e.g., polyclonal antibodies, monoclonal antibodies, chimeric antibodies, human antibodies, single chain antibodies, Fab fragments, F(ab')$_2$ fragments, molecules produced using a Fab expression library, human antibodies (polyclonal or monoclonal) produced in transgenic mice and epitope binding fragments of any of the above. For therapeutic uses, chimeric or human antibodies are preferred; human antibodies are most preferred.

The antibodies can be utilized in conjunction with the compound screening schemes described herein for the evaluation of test compounds, e.g., for immobilization of CRFR polypeptides or such antibodies can be used in conjunction with gene therapy techniques to evaluate, for example, the expression of CRFRs either in cells or directly in patient tissues in which these genes have been introduced. In addition, antibodies of the present invention are useful in the treatment of skeletal muscle atrophy. Antibodies selective for the CRFR can be screened by the methods of the present invention to identify a subset of the antibodies that are CRFR agonists. In addition, anti-idiotype antibodies generated against antibodies specific for CRF or a CRF analog may be useful as CRFR agonists and like anti-CRFR antibodies may be screened for their ability to activate the CRFR by methods of the present invention.

For the production of antibodies, a variety of host animals may be immunized by injection with CRFR, CRF or a CRF analog, anti-CRF antibody, anti-CRF analog antibody, or immunogenic fragments thereof by methods well known in the art. For preparation of an anti-idiotype antibody the immunogen is an anti-CRF antibody or anti-CRF analog antibody. Production of anti-idiotype antibodies is described, for example, in U.S. Pat. No. 4,699,880, incorporated herein by reference. Suitable host animals include, but are not limited to, rabbits, mice, goats, sheep and horses. Immunization techniques are well known in the art. Polyclonal antibodies can be purified from the serum of the immunized animals, or monoclonal antibodies can be generated by methods that are well known in the art. These techniques include, but are not limited to, the well-known hybridoma techniques of Kohler and Milstein, human B-cell hybridoma techniques, and the EBV hybridoma technology. Monoclonal antibodies may be of any immunoglobulin class, including IgG, IgE, IgM, IgA, and IgD containing either kappa or lambda light chains.

Because of the immunogenicity of non-human antibodies in humans, chimeric antibodies are preferred to non-human antibodies when used for therapeutic treatment of human patients. Techniques of producing and using chimeric antibodies are known in the art, and are described in, for example, U.S. Pat. Nos. 5,807,715; 4,816,397; 4,816,567; 5,530,101; 5,585,089; 5,693,761; 5,693,762; 6,180,370; and 5,824,307, all incorporated herein by reference.

Completely human antibodies are particularly desirable for therapeutic treatment of human patients because they are less immunogenic than non-human antibodies or chimeric antibodies. Such antibodies can be produced using transgenic mice which are substantially incapable of expressing endogenous immunoglobulin heavy and light chain genes, but which can express human heavy and light chain genes. The transgenic mice are immunized in the normal fashion with a selected antigen, e.g., all or a portion of CRF$_2$R. Monoclonal antibodies directed against the antigen are obtained using conventional hybridoma technology from these immunized transgenic mice. This technology is described in detail in U.S. Pat. Nos. 5,874,299; 5,877,397; 5,569,825; 5,661,016; 5,770,429; and 6,075,181, all incorporated herein by reference. As an alternative to obtaining human immunoglobulins directly from the culture of the hybridoma cells, the hybridoma cells can be used as a source of rearranged heavy chain and light chain loci for subsequent expression or genetic manipulation. Isolation of genes from such antibody-producing cells is straightforward since high levels of the appropriate mRNAs are available. The recovered rearranged loci can be manipulated as desired. For example, the constant region can be eliminated or exchanged for that of a different isotype or the variable regions can be linked to encode single chain Fv regions. Such techniques are described in WO 96/33735 and WO 96/34096, all incorporated herein by reference.

V. Selection of Test Compounds

Compounds that can be screened in accordance with the assays of the invention include but are not limited to, libraries of known compounds, including natural products, such as plant or animal extracts, synthetic chemicals, biologically active materials including proteins, peptides such as soluble peptides, including but not limited to members of random peptide libraries and combinatorial chemistry derived molecular library made of D- or L- configuration amino acids, phosphopeptides (including, but not limited to, members of random or partially degenerate, directed phosphopeptide libraries), antibodies (including, but not limited to, polyclonal, monoclonal, chimeric, human, anti-idiotypic or single chain antibodies, and Fab, F(ab')$_2$ and Fab expression library fragments, and epitope-binding fragments thereof), organic and inorganic molecules.

In addition to the more traditional sources of test compounds, computer modeling and searching technologies permit the rational selection of test compounds by utilizing structural information from the ligand binding site of CRFR or from already identified agonists of CRFRs. Such rational selection of test compounds can decrease the number of test compounds that must be screened in order to identify a candidate therapeutic compound. CRFRs are GPCRs, and thus knowledge of the CRFR protein sequence allows for the generation of a model of its binding site that can be used to screen for potential ligands. This process can be accomplished in several manners well known in the art. Briefly, the most robust approach involves generating a sequence alignment of the CRFR sequence to a template (derived from the bacterio-rhodopsin or rhodopsin crystal structures or other GPCR model), conversion of the amino acid structures and refining the model by molecular mechanics and visual examination. If a strong sequence alignment cannot be obtained then a model may also be generated by building models of the hydrophobic helices. These are then fitted together by rotating and translating each helix relative to the others starting from the general layout of the known rhodopsin structures. Mutational data that point towards residue-residue contacts may also be used to position the helices relative to each other so that these contacts are achieved. During this process, docking of the known ligands into the binding site cavity within the helices may also be used to help position the helices by developing interactions that would stabilize the binding of the ligand. The model may be completed by refinement using molecular mechanics and loop building of the intracellular and extracellular loops using standard homology modeling techniques. General information regarding GPCR structure and modeling can be found in Schoneberg, T. et. al., *Molecular and Cellular Endocrinology*, 151:181–193 (1999), Flower, D., *Biochimica et Biophysica Acta*, 1422:207–234 (1999), and Sexton, P. M., *Current Opinion in Drug Discovery and Development*, 2(5):440–448 (1999).

Once the model is completed, it can be used in conjunction with one of several existing computer programs to narrow the number of compounds to be screened by the screening methods of the present invention. The most general of these is the DOCK™ program (UCSF Molecular Design Institute, 533 Parnassus Ave, U-64, Box 0446, San Francisco, Calif. 94143-0446). In several of its variants it can screen databases of commercial and/or proprietary compounds for steric fit and rough electrostatic complementarity to the binding site. It has frequently been found that molecules that score well within DOCK™ have a better chance of being ligands. Another program that can be used is FLEXX™ (Tripos Inc., 1699 South Hanley Rd., St. Louis, Mo., 63144-2913 (www.tripos.com)). This program, being significantly slower, is usually restricted to searches through smaller databases of compounds. The scoring scheme within FLEXX™ is more detailed and usually gives a better estimate of binding ability than does DOCK™. FLEXX™ is best used to confirm DOCK™ suggestions, or to examine libraries of compounds that are generated combinatorially from known ligands or templates.

VI. Screening Assays to Identify Candidate Compounds for the Regulation of Skeletal Muscle Mass or Function The finding that $CRF_2R$ plays a role in regulating skeletal muscle atrophy enables various methods of screening one or more test compounds to identify candidate compounds that ultimately may be used for prophylactic or therapeutic treatment of skeletal muscle atrophy. This invention provides methods for screening test compounds for their ability to bind to $CRF_2R$, activate $CRF_2R$, prolong or augment the agonist-induced activation of $CRF_2R$ or of a $CRF_2R$ signal transduction pathway or increase expression of $CRF_2R$ or CRF genes.

Because $CRF_2R$ and $CRF_1R$ are homologous proteins, it is expected that a certain proportion of agonists for $CRF_2R$ will also function as agonists of $CRF_1R$. As discussed above, activation of $CRF_1R$ induces activation of the HPA axis and concomitant production of corticosteroids. In most cases in which an increase in muscle mass or function is desired, it is not desirable to activate the HPA axis. Therefore, in addition to screening test compounds for their ability to activate $CRF_2R$, the invention also provides for the use of $CRF_2R$ and $CRF_1R$ to screen for selective agonists of $CRF_2R$. When selecting candidate compound useful for the treatment of acute or chronic muscle atrophy, which is not related to muscular dystrophy, it is preferable that the candidate compounds be selective for $CRF_2R$. Preferably the candidate compound exhibits 10-fold selectivity for $CRF_2R$ versus $CRF_1R$ (i.e., 10-fold more active against $CRF_2R$ than against $CRF_1R$), more preferably 100-fold selectivity and most preferably 1000-fold or greater selectivity. As published studies have demonstrated a benefit of corticosteroid therapy in the treatment of muscular dystrophies, it may be beneficial that a $CRF_2R$ agonist retain some level of $CRF_1R$ agonism when used to treat muscular dystrophies. Thus, for the treatment of muscular dystrophies, a compound of lower selectivity that activates the $CRF_2R$ as well as the $CRF_1R$, over a similar concentration range, is preferred. Preferably the candidate compound is 100-fold selective for $CRF_2R$ versus $CRF_1R$, more preferably 10-fold selective and most preferably not selective for $CRF_2R$ versus $CRF_1R$ (i.e., the activity of the candidate compound is substantially similar for $CRF_2R$ and $CRF_1R$). Also, in this case, it may be more preferable that the compound is full agonist for $CRF_2R$ while being a partial agonist for $CRF_1R$. Such a candidate compound would therefore have a built-in limit to the maximum degree of cortisol elevation and potential for muscle atrophy, while the anti-atrophy effect mediated through the $CRF_2R$ could be enhanced by increasing the dose. One of skill in the art would be able to readily determine whether a candidate compound is a full or partial agonist of the $CRF_1R$ or $CRF_2R$ using methods known in the art.

For screening for compounds which ultimately will be used to regulate skeletal muscle mass or function through $CRF_2R$ in humans, it is preferred that the initial in vitro screen be carried out using a $CRF_2R$ with an amino acid sequence that is greater than 80% identical to SEQ ID NO: 10 and more preferably greater than 90% identical to SEQ ID NO: 10. More preferably the test compounds will be screened against a human, mouse or rat $CRF_2R$, with the most preferable being human. For screening for compounds which ultimately will be used to regulate skeletal muscle mass or function through $CRF_2R$ in a non-human species it is preferable to use the $CRF_2R$ from the species in which treatment is contemplated.

For screening to determine the level of activity that a test or candidate compound has toward $CRF_1R$ to determine what, if any, selectivity a candidate compound exhibits for $CRF_2R$ versus $CRF_1R$, it is preferred that the initial screen be carried out using a $CRF_1R$ with an amino acid sequence that is greater than 80% identical to SEQ ID NO: 2 and more preferably greater than 90% identical to SEQ ID NO: 2. More preferably the test compounds will be screened against a human, mouse or rat $CRF_1R$, with the most preferable being human. For screening for compounds which ultimately will be used to regulate skeletal muscle mass or function in a non-human species, it is preferable to use the $CRF_1R$ from the species in which treatment is contemplated.

The methods of the present invention are amenable to high throughput applications; however, the use of as few as one test compound in the method is encompassed by the term "screening". Test compounds which bind to $CRF_2R$, activate $CRF_2R$, prolong or augment the agonist-induced activation of $CRF_2R$ or of a $CRF_2R$ signal transduction pathway, or increase expression of $CRF_2R$ or CRF genes, as determined by a method of the present invention, are referred to herein as "candidate compounds." Such candidate compounds can be used to regulate skeletal muscle mass or function. However, more typically, this first level of in vitro screen provides a means by which to select a narrower range of compounds, i.e., the candidate compounds, which merit further investigation in additional levels of screening. The skilled artisan will recognize that a utility of the present invention is to identify, from a group of one or more test compounds, a subset of compounds which merit further investigation. One of skill in the art will also recognize that the assays of the present invention are useful in ranking the probable usefulness of a particular candidate compound relative to other candidate compounds. For instance, a candidate compound which activates $CRF_2R$ at 1000 nM (but not at 10 nM) is of less interest than one which activates $CRF_2R$ at 10 nM. Using such information the skilled artisan may select a subset of the candidate compounds, identified in the first level of screening, for further investigation. By the way of example only, compounds which activate $CRF_2R$ at concentrations of less than 200 nM might be further tested in an animal model of skeletal muscle atrophy, whereas those above that threshold would not be further tested. The skilled artisan will also recognize that, depending on how the group of test compounds is selected, and how the positives are selected, only a certain proportion of test compounds will be identified as candidate compounds, and that this proportion may be very small.

The assay systems described below may be formulated into kits comprising $CRF_2R$ or cells expressing the $CRF_2R$ which can be packaged in a variety of containers, e.g., vials, tubes microtitre well plates, bottles and the like. Other reagents can be included in separate containers and provided with the kit, e.g., positive control samples, negative control samples, buffers and cell culture media.

In one embodiment, the invention provides a method for screening one or more test compounds to identify candidate compounds that bind to $CRF_2R$. Methods of determining binding of a compound to a receptor are well known in the art. Typically, the assays include the steps of incubating a source of the $CRF_2R$ with a labeled compound, known to bind to the receptor, in the presence or absence of a test compound and determining the amount of bound labeled compound. The source of $CRF_2R$ may either be cells expressing $CRF_2R$ or some form of isolated $CRF_2R$, as described herein. The labeled compound can be CRF or any CRF analog labeled such that it can be measured, preferably quantitatively (e.g., $^{125}I$-labeled, europium labeled, fluorescein labeled, GFP labeled, $^{35}S$-methionine labeled). Such methods of labeling are well known in the art. Test compounds that bind to the CRFR cause a reduction in the amount of labeled ligand bound to the receptor, thereby reducing the signal level compared to that from control samples (absence of test compound). Variations of this technique have been described in which receptor binding in the presence and absence of G-protein uncoupling agents can discriminate agonists from antagonists (e.g., binding in the absence and presence of a guanine nucleotide analog i.e., GpppNHp). See Keen, M., *Radioligand Binding Methods for Membrane Preparations and Intact cells* in *Receptor Signal Transduction Protocols*, R. A. J. Challis, (ed), Humana Press Inc., Totoway N.J. (1997).

Because it is desirable to discriminate between compounds which bind specifically to $CRF_2R$, as compared with $CRF_1R$, the assays described above should be conducted using a cell, or membrane from a cell, which expresses only $CRF_2R$ or the assays can be conducted with a recombinant source of $CRF_2R$. Cells expressing both forms of CRFR may be modified using homologous recombination to inactivate or otherwise disable the $CRF_1R$ gene. Alternatively, if the source of CRFR contains more than one CRFR type, the background signal produced by the receptor which is not of interest must be subtracted from the signal obtained in the assay. The background response can be determined by a number of methods, including elimination of the signal from the CRFR which is not of interest by use of antisense, antibodies or selective antagonists. Known antagonists of CRFRs include antalarmin ($CRF_1R$ selective), antisauvagine-30 ($CRF_2R$ selective) and astressin (nonselective for $CRF_1R/CRF_2R$).

In another embodiment, the invention provides methods for screening test compounds to identify candidate compounds which activate $CRF_2R$ and/or $CRF_1R$. Typically, the assays are cell-based; however, cell-free assays are known which are able to differentiate agonist and antagonist binding as described above. Cell-based assays include the steps of contacting cells which express $CRF_1R$ or $CRF_2R$ with a test compound or control and measuring activation of the CRFR by measuring the expression or activity of components of the CRFR signal transduction pathways.

As described in the background section above, CRFRs appear to couple through several different pathways including $G_{\alpha s}$, $G_{\alpha q}$, or $G_{\alpha i}$, depending upon the cell type. It is thought that agonist activation of CRFR allows the receptor to signal via any of these pathways, provided that the necessary pathway components are present in the particular cell type. Thus, to screen for CRFR activation, an assay can use any of the signal transduction pathways as the readout even if the relevant cell type for treatment, in vivo, couples CRFR to skeletal muscle atrophy via a different pathway. One of ordinary skill in the art would recognize that a screening assay would be effective for identifying useful CRFR agonists independent of the pathway by which receptor activation was measured. Assays for measuring activation of these signaling pathways are known in the art.

For example, after contact with the test compound, lysates of the cells can be prepared and assayed for induction of cAMP. cAMP is induced in response to $G_{\alpha s}$ activation. Because $G_{\alpha s}$ is activated by receptors other than CRFR and because a test compound may be exerting its effect through CRFRs or by another mechanism, two control comparisons are relevant for determining whether a text compound increases levels of cAMP via activation of a CRFR. One control compares the cAMP level of cells contacted with a test compound and the cAMP level of cells contacted with a control compound (i.e., the vehicle in which the test compound is dissolved). If the test compound increases cAMP levels relative to the control compound this indicates that the test compound is increasing cAMP by some mechanism. The other control compares the cAMP levels of a CRFR expressing cell line and a cell line that is essentially the same except that it does not express the CRFR, where both of the cell lines have been treated with test compound. If the test compound elevates cAMP levels in the CRFR expressing cell line relative to the cell line that does not express CRFRs, this is an indication that the test compound elevates cAMP via activation of the CRFRs.

In a specific embodiment of the invention, cAMP induction is measured with the use of DNA constructs containing the cAMP responsive element linked to any of a variety of reporter genes can be introduced into cells expressing CRFRs. Such reporter genes include, but are not limited to, chloramphenicol acetyltransferase (CAT), luciferase, glucuronide synthetase, growth hormone, fluorescent proteins (e.g., Green Fluorescent Protein), or alkaline phosphatase. Following exposure of the cells to the test compound, the level of reporter gene expression can be quantitated to determine the test compound's ability to increase cAMP levels and thus determine a test compounds ability to activate the CRFR.

The cells useful in this assay are the same as for the CRFR binding assay described above, except that cells utilized in the activation assays preferably express a functional receptor which gives a statistically significant response to CRF or one or more CRF analog. In addition to using cells expressing full length CRFRs, cells can be engineered which express CRFRs containing the ligand binding domain of the receptor coupled to, or physically modified to contain, reporter elements or to interact with signaling proteins. For example, a wild-type CRFR or CRFR fragment can be fused to a G-protein resulting in activation of the fused G-protein upon agonist binding to the CRFR portion of the fusion protein. (Siefert, R. et al., *Trends Pharmacol. Sci.* 20: 383–389 (1999)). The cells should also preferably possess a number of characteristics, depending on the readout, to maximize the inductive response by CRF or the CRF analog, for example, for detecting a strong induction of a CRE reporter gene; (a) a low natural level of cAMP; (b) G proteins capable of interacting with CRFRs; (c) a high level of adenylyl cyclase; (d) a high level of protein kinase A; (e) a low level of phosphodiesterases; and (f) a high level of cAMP response element binding protein would be advantageous. To increase the response to CRF or a CRF analog, host cells could be engineered to express a greater amount of favorable factors or a lesser amount of unfavorable factors. In addition, alternative pathways for induction of the CRE reporter could be eliminated to reduce basal levels.

In some instances, G protein-coupled receptor responses subside, or become desensitized, after prolonged exposure to an agonist. Another embodiment of the invention provides methods for identifying compounds that prolong or augment the agonist-induced activation of $CRF_2R$, or the $CRF_2R$ signal transduction pathway, in response to a $CRF_2R$ agonist. Such compounds may be used, for example, in conjunction with a $CRF_2R$ agonist for the treatment of skeletal muscle atrophy. Typically the method uses a cell based assay comprising in any order or concurrently (i) contacting the cells with a test compound; (ii) treating cells expressing functional $CRF_2R$ with a $CRF_2R$ agonist at a concentration of agonist and for a period of agonist-receptor exposure sufficient to allow desensitization of the receptor; followed by (iii) determining the level of activation of the $CRF_2R$. One of skill in the art will recognize that several mechanisms contribute to receptor desensitization including, but not limited to, receptor phosphorylation, receptor internalization or degradation and CRFR signal transduction pathway down-modulation. One of skill in the art can determine the appropriate time (i.e., before, during or after agonist treatment) for contacting the cells with the test compounds depending upon which mechanism of desensitization is targeted. For example, contacting the cells with test compounds following agonist treatment, can detect test compounds which block receptor desensitization which occurs as a result of phosphorylation of the receptor.

In another embodiment, the invention provides a method of screening one or more test compound to identify candidate compounds which regulate transcription from the $CRF_2R$ gene or regulate $CRF_2R$ expression. Candidate compounds which regulate transcriptional activity of CRFR genes may be identified using a reporter gene operably associated with a $CRF_2R$ regulatory region (reporter gene construct). Such methods are known in the art. In one such method, the reporter gene construct is contacted with a test compound in the presence of a source of cellular factors and the level of reporter gene expression is determined. A test compound which causes an increase in the level of expression, compared to a control sample, is indicative of a candidate compound which increases transcription of the $CRF_2R$ gene. To provide the cellular factors required for in vitro or in vivo transcription, appropriate cells or cell extracts are prepared from any cell type that normally expresses $CRF_2R$.

Candidate compounds which regulate $CRF_2R$ expression can also be identified in a method wherein a cell is contacted with a test compound and the expression of CRFR is determined. The level of expression of $CRF_2R$ in the presence of the test compound is compared with the level of expression in the absence of the test compound. Test compounds which increase the expression of $CRF_2R$ are identified as candidate compounds for increasing muscle mass or muscle function. Such a method detects candidate compounds which increase the transcription or translation of the $CRF_2R$ or which increase the stability of the mRNA or $CRF_2R$ protein.

In another embodiment, this invention provides methods for screening one or more test compounds to identify candidate compounds which regulate the expression of the CRF or a CRF analog. Such assays are performed essentially as described above for the assays to identify candidate compounds which regulate expression of CRFRs with the following modifications. To identify candidate compound which regulate transcription from the CRF gene or a CRF analog gene, the reporter gene is operably associated with the regulatory region of the CRF gene or CRF analog gene of interest and the source of cellular factors should be from a cell type that expresses the gene of interest.

VII. Screening of Candidate Compounds Using Models of Skeletal Muscle Atrophy

Candidate compounds selected from one or more test compounds by an in vitro assay, as described above, can be further tested for their ability to regulate skeletal muscle mass or function in model systems of skeletal muscle atrophy and/or hypertrophy. Such models of skeletal muscle atrophy or hypertrophy include both in vitro cell culture models and in vivo animal models of skeletal muscle atrophy. Such additional levels of screening are useful to further narrow the range of candidate compounds that merit additional investigation, e.g., clinical trials.

Cell Culture Models of Muscle Atrophy

In vitro models of skeletal muscle atrophy are known in the art. Such models are described, for example, in Vandenburgh, H. H., *In Vitro* 24:609–619 (1988), Vandenburgh, H. H. et al., *J of Biomechanics*, 24 Suppl 1:91–99 (1991), Vandenburgh, H. H et al., *In Vitro Cell. Dev. Biol.*, 24(3): 166–174 (1988), Chromiak, J. A., et al., *In Vitro Cell. Dev. Biol. Anim.*, 34(9):694–703 (1998), Shansky, J., et al., *In Vitro Cell. Dev. Biol. Anim.*, 33(9):659–661 (1997), Perrone, C. E. et al., *J. Biol. Chem.* 270(5):2099–2106 (1995), Chromiac, J. A. and Vandenburgh, H. H., *J. Cell. Physiol.* 159(3):407414 (1994), and Vandenburgh, H. H. and Karlisch, P., *In Vitro Cell. Dev. Biol.* 25(7):607–616 (1989). Such models are useful, but not required, following the in vitro screening described above in order to further narrow the range of candidate compounds that merit testing in an animal model. Cell culture models are treated with candidate compounds and the response of the model to the treatment is measured by assessing changes in muscle markers such as: muscle protein synthesis or degradation, changes in skeletal muscle mass or contractile function. Those compounds which induce significant changes in the muscle markers are typically screened further in an animal model of skeletal muscle atrophy.

Animal Models of Skeletal Muscle Atrophy

The candidate compounds are administered to non-human animals and the response of the animals is monitored, for example, by assessing changes in markers of atrophy or hypertrophy such as: skeletal muscle mass, skeletal muscle function, muscle or myofiber cross-sectional area, contractile protein content, non-contractile protein content or a biochemical or genetic marker that correlates with skeletal muscle mass or function changes. Candidate compounds which induce skeletal muscle hypertrophy or prevent any aspect of skeletal muscle atrophy should be considered as prospective therapeutic candidates for treatment of human skeletal muscle atrophy, and are referred to herein as candidate therapeutic compounds. In addition to assessing the ability of a candidate compound to regulate skeletal muscle atrophy, undesirable side effects such as toxicity may also be detected in such a screen. The absence of unacceptably high levels of side effects may be used as a further criterion for the selection of candidate therapeutic compounds.

A variety of animal models for skeletal muscle atrophy are known in the art, such as those described in the following references: Herbison, G. J., et al. *Arch. Phys. Med. Rehabil.* 60:401–404 (1979), Appell, H-J. *Sports Medicine* 10:42–58 (1990), Hasselgren, P-O. and Fischer, J. E. *World J. Surg.* 22:203–208 (1998), Agbenyega, E. T. and Wareham, A. C. *Comp. Biochem. Physiol.* 102A:141–145 (1992), Thomason, D. B. and Booth, F. W. *J. Appl. Physiol.* 68:1–12 (1990), Fitts, R. H., et al. *J. Appl. Physiol.* 60:1946–1953 (1986), Bramanti, P., et al. *Int. J. Anat. Embryol.* 103:45–64 (1998), Cartee, G. D. *J. Gerontol. A Biol. Sci. Med. Sci.* 50:137–141 (1995), Cork, L. C., et al. *Prog. Clin. Biol. Res.* 229:241–269 (1987), Booth, F. W. and Gollnick, P. D. *Med. Sci. Sports Exerc.* 15:415–420 (1983), Bloomfield, S. A. *Med. Sci. Sports Exerc.* 29:197–206 (1997). Preferred animals for these models are mice and rats. These models include, for example, models of disuse-induced atrophy such as casting or otherwise immobilizing limbs, hind limb suspension, complete animal immobilization, and reduced gravity situations. Models of nerve damage induced atrophy include, for example, nerve crush, removal of sections of nerves which innervate specific muscles, toxin application to nerves and infection of nerves with viral, bacterial or eukaryotic infectious agents. Models of glucocorticoid-induced atrophy include application of atrophy-inducing doses of exogenous glucocorticoid to animals, and stimulation of endogenous corticosteroid production, for example, by application of hormones that activate the hypothalamus-pituitary-adrenal (HPA) axis. Models of sepsis-induced atrophy include, for example, inoculation with sepsis-inducing organisms such as bacteria, treatment of the animal with immune-activating compounds such as bacterial cell wall extract or endotoxin, and puncture of intestinal walls. Models of cachexia-induced atrophy include, for example, inoculation of an animal with tumorigenic cells with cachexia forming potential, infection of an animal with infectious agents (such as viruses which cause AIDS) which result in cachexia and treatment of an animal with hormones or cytokines such as CNTF, TNF, IL-6, IL-1, etc. which induce cachexia. Models of heart failure-induced atrophy include the manipulation of an animal so that heart failure occurs with concomitant skeletal muscle atrophy. Neurodegenerative disease-induced atrophy models include autoimmune animal models such as those resulting from immunization of an animal with neuronal components. Muscular dystrophy-induced models of atrophy include natural or man-made genetically-induced models of muscular dystrophy such as the mutation of the dystrophin gene which occurs in the Mdx mouse.

Animal models of skeletal muscle hypertrophy include, for example, models of increased limb muscle use due to inactivation of the opposing limb, reweighting following a disuse atrophy inducing event, reutilization of a muscle which atrophied because of transient nerve damage, increased use of selective muscles due to inactivation of a synergistic muscle (e.g., compensatory hypertrophy), increased muscle utilization due to increased load placed on the muscle and hypertrophy resulting from removal of the glucocorticoid after glucocorticoid-induced atrophy. Preferred animal atrophy models include the sciatic nerve denervation atrophy model, glucocorticoid-induced atrophy model, and the leg casting disuse atrophy model that are described in further detail below.

The sciatic nerve denervation atrophy model involves anesthetizing the animal followed by the surgical removal of a short segment of either the right or left sciatic nerve, e.g., in mice the sciatic nerve is isolated approximately at the midpoint along the femur and a 3–5 mm segment is removed. This denervates the lower hind limb musculature resulting in atrophy of these muscles. Typically, innervation to the biceps femoris is left intact to provide satisfactory motion of the knee for virtually normal ambulation. Typically, in untreated animals, muscle mass of the denervated muscles is reduced 30–50% ten days following denervation. Following denervation, test compounds are administered e.g., by injection or by continuous infusion, e.g., via implantation of an osmotic minipump (e.g., Alzet, Palo Alto, Calif.), to determine their effect on denervation induced skeletal muscle atrophy. At various times following denervation, the animals are euthanized and lower leg muscles are dissected rapidly from both the denervated and nondenervated legs, the muscles, cleaned of tendons and connective tissue, are weighed. The extent of atrophy in the affected muscles is analyzed, for example, by measuring muscle mass, muscle cross-sectional area, myofiber cross-sectional area or contractile protein content.

The glucocorticoid-induced atrophy model involves the administration of a glucocorticoid to the test animal, e.g., 1.2 mg/kg/day of dexamethasone in the drinking water. Typically, in untreated animals, skeletal muscle mass is reduced 30–50% following ten days of dexamethasone administration. Concomitantly with, or following glucocorticoid administration, test compounds are administered e.g., by injection or by continuous infusion to determine their effect on glucocorticoid-induced skeletal muscle atrophy. At various times following glucocorticoid administration, the extent of atrophy in the affected muscles is analyzed as described above for the denervation model.

The leg casting disuse atrophy model involves casting one hind leg of an animal from the knee down through the foot. Typically, muscle mass is reduced 20–40% after ten days of casting. Following casting, test compounds are administered by injection or by continuous infusion via implantation of an osmotic minipump (e.g., Alzet, Palo Alto, Calif.) to determine their effect on leg casting induced skeletal muscle atrophy. At various times following leg casting, the extent of atrophy in the affected muscles is analyzed as described above for the denervation model.

One of skill in the art would recognize that in screening for compounds for human use, because there are differences between the human $CRF_2R$ and the $CRF_2R$ from other animal species, there may be some false positive or negative results which arise when the screen is carried out using non-human $CRF_2R$. Thus, it is preferable to do the initial in vitro screen using human $CRF_2R$. In certain circumstances, identified candidate compounds may be active toward only the human receptor and not toward a non-human receptor. In such circumstances, it may still be desirable to determine whether these candidate compounds are able to regulate skeletal muscle mass or function in a second level of screening. Because these candidates do not activate non-human $CRF_2R$, a standard in vivo screen with non-human animal is not advised. In such circumstances the second level of screening for these candidates may be performed in transgenic animals that express human CRFRs.

Animals of any species, especially mammals, including, but not limited to, mice, rats, rabbits, guinea pigs, pigs, goats, dogs and non-human primates may be used to generate CRFR transgenic animals. Mice and rats are preferred, mice are most preferred. A variety of techniques are known in the art and may be used to introduce the human CRFR transgenes into animals to produce the founder lines of transgenic animals. Such techniques include, but are not limited to, pronuclear microinjection, retrovirus-mediated gene transfer into germ lines, gene targeting in embryonic stem cells, electroporation of embryos and sperm-mediated gene transfer.

VIII. Gene Therapy Methods for the Treatment of Skeletal Muscle Atrophy

The overall activity of $CRF_2R$ can be increased by overexpressing a gene for $CRF_2R$ (to increase expression of $CRF_2R$) or a constitutively active $CRF_2R$ in the appropriate tissue. CRF levels can be increased, in vivo, by likewise overexpressing a CRF gene. Overexpression of these genes will increase the total cellular $CRF_2R$ activity, thus, regulating skeletal muscle atrophy. The gene or genes of interest are inserted into a vector suitable for expression in the subject. These vectors include, but are not limited to, adenovirus, adenovirus associated virus, retrovirus and herpes virus vectors in addition to other particles that introduced DNA into cells (e.g., liposome, gold particles, etc.) or by direct injection of the DNA expression vector, containing the gene of interest, into human tissue (e.g., muscle).

IX. Pharmaceutical Formulations and Methods for Use

Candidate compounds or candidate therapeutic compounds identified by screening methods described herein, can be administered to individuals to treat skeletal muscle atrophy, or to induce skeletal muscle hypertrophy. To this end, the present invention encompasses methods and compositions for modulating skeletal muscle atrophy, including, but not limited to, skeletal muscle atrophy induced by disuse due to surgery, bed rest, broken bones; denervation/nerve damage due to spinal cord injury; autoimmune disease; infectious disease; glucocorticoid use for unrelated conditions; sepsis due to infection or other causes; nutrient limitation due to illness or starvation; cancer cachexia; chronic inflammation; AIDS cachexia; COPD; congestive heart failure; sarcopenia and genetic disorders; e.g., muscular dystrophies, neurodegenerative diseases. Agonists of $CRF_2R$ can be used to inhibit skeletal muscle atrophy. It is not necessary that effective compounds demonstrate absolute specificity for CRFR. It is contemplated that specific antagonist of other affected receptors can be co-administered with an effective, but nonspecific, agonist. Alternately, this lack of specificity may be addressed by modulation of dose alone, or the dosing regimen.

The candidate compounds or candidate therapeutic compounds identified by the screening methods of the present invention may be administered in conjunction with compounds which prolong or augment the activation of a $CRF_2R$ or of a $CRF_2R$ signal transduction pathway. These may be known compounds, for example, theophylline, or these compounds may be identified by the screening methods of this invention to prolong or augment the activation of a $CRF_2R$ receptor or of a $CRF_2R$ signal transduction pathway.

Dose Determinations

Safety and therapeutic efficacy of compounds which agonize CRFR can be determined by standard procedures using either in vitro or in vivo technologies. Compounds which exhibit large therapeutic indices are preferred, although compounds with lower therapeutic indices are useful if the level of side effects is acceptable. The data obtained from the in vitro and in vivo toxicological and pharmacological techniques can be used to formulate the human range of doses which may be useful. The preferred dose lies in the range in which the circulating concentration of the compound is therapeutically maximal with acceptable safety. The circulating concentration of the compound may vary depending on the dose form, time after dosing, route of administration, etc. Doses outside this range are also useful provided the side effects are acceptable. Such matters as age and weight of the patient, and the like, can be used to determine such matters in the conventional manner. Pharmacogenetic approaches may be useful in optimizing compound selection, doses and dosing regimen in clinical populations.

Formulation and Use

Pharmaceutical compositions for use in the modulation of skeletal muscle atrophy in accordance with the present invention may be formulated using conventional methodologies using pharmaceutically acceptable carriers and excipients. The compositions of this invention are preferably provided in unit dosage form. As used herein, a "unit dosage form" is a composition of this invention containing an amount of a $CRF_2R$ agonist that is suitable for administration to an animal, preferably a mammal, more preferably a human subject, in a single dose, according to good medical practice. Pharmaceutical compositions may be formulated for delivery by, for example, intranasal, transdermal, inhalation, parenteral, cutaneous, oral or rectal administration. For oral administration, the pharmaceutical composition may take the form of tablets or capsules containing the pharmacologically active compound and additives including, but not limited to, binding agents, fillers, lubricants, disintegrants, or wetting agents. The tablets may be coated. Liquid preparations for oral administration include, but are not limited to, syrups, suspensions or dry products which are reconstituted with liquid vehicle before use, containing the pharmacologically active compound and additives including, but not limited to, suspending agents, emulsifying agents, non-aqueous vehicles, preservatives, buffer salts, flavoring, coloring, sweetening agents, etc. Pharmaceutical compositions for oral administration may be formulated for controlled release of the pharmacologically active compounds either in the mouth, stomach or intestinal tract.

For inhalation administration, the compounds for use according to the present invention may be delivered by, but not limited to, the following forms: liquid, powder, gel or in the form of an aerosol spray utilizing either pressurized or non-pressurized propellants in either premeasured or non-premeasured doses. The pharmacologically active compound may be formulated with appropriate fillers, vehicles, preservatives, buffers, etc. For parenteral administration, the pharmacologically active compound may be formulated with acceptable physiological carriers, preservatives, etc. and be prepared as suspensions, solutions, emulsion, powders ready for constitution, etc. for either bolus injection or infusion. Doses of these compounds may be administered by a variety of technologies including hypodermic needles, high pressure devices, etc. For rectal administration, the pharmacologically active compound may be formulated with acceptable physiological carriers, preservatives, etc. for delivery as suppositories, enemas, etc. For cutaneous administration, the pharmacologically active compound may be formulated with acceptable physiological carriers including lotions, emollients, etc. or incorporated into a patch type device. For long term administration, the pharmacologically active compound and appropriate additives such as, but limited to, polymers, hydrophobic materials, resins, etc. may be formulated as a depot preparation for either injection or implantation at multiple sites including but not limited to intramuscular and subcutaneous locations. In addition, the pharmacologically active compound may be administered by a dispensing device.

Monitoring of Effects During Clinical Trials

Monitoring the influence of compounds (e.g., drugs) on the expression or activity of $CRF_2R$ can be employed not only in basic drug screening, but also in clinical trials. For example, the effectiveness of a compound determined by a screening assay to increase $CRF_2R$ receptor activity or $CRF_2R$ receptor expression can be assessed in clinical trials of patients with, or at risk for, skeletal muscle atrophy. At various times following administration of the test compound or placebo, the effect of the compound on the patient can be determined, for example, by observing the change in skeletal muscle mass, skeletal muscle function, biochemical markers of muscle breakdown or quality of life measures. Methods of measuring skeletal muscle mass in human subjects are known in the art and include, for example: measuring the girth of a limb; measuring muscle thickness with for instance, computer tomography, MRI or supersonics; or muscle biopsy to examine morphological and biochemical parameters (e.g., cross-section fiber area, fiber diameter or enzyme activities). Furthermore, because skeletal muscle mass is correlated with skeletal muscle function, muscle function can be used as a surrogate marker of mass and muscle mass changes can be assessed using functional measurements, e.g., strength, the force of a group of synergist muscles, or contraction characteristics found in electromyographic recordings. In addition, muscle protein loss as a result of muscle atrophy can be measured by quantitating levels of amino acids or amino acids derivatives, i.e., 3-methyl histidine, in the urine or blood of a subject. For a review of such methods see Appell, *Sports Med.* 10:42–58 (1990). Quality of life measures include, but are not limited to, the ease of getting out of a chair, number of steps taken before tiring or ability to climb stairs.

EXAMPLES

Example 1

Construction of Vectors for Human $CRF_2R$ Receptor Expression

The human $CRF_2R$ ($hCRF_2R$) DNA sequence, Accession No. E12752, is retrieved and two oligonucleotides including one containing the 5' end of the gene beginning at the initiation codon (5' oligonucleotide) and one containing the 3' end of the gene containing the stop codon (3' oligonucleotide) are synthesized. These oligonucleotides are designed to contain restriction endonuclease sites which are not present in the $hCRF_2R$ gene with one unique site in the 5' oligonucleotide and a different unique restriction endonuclease site in the 3' oligonucleotide In addition, the 3' oligonucleotide contains a polyadenylation addition signal sequence. Double stranded cDNA from human skeletal muscle is purchased from the Universal QUICK-Clone cDNA collection (Clonetech Inc., Palo Alto, Calif., USA). Using the above 5' and 3' oligonucleotides, the $hCRF_2R$ cDNA is amplified by PCR of the human skeletal muscle cDNA using the AdvanTaq PCR kit (Clonetech Inc., Palo Alto, Calif., USA). The $hCRF_2R$ gene PCR product is purified from PCR artifacts by agarose gel electrophoresis and the $hCRF_2R$ gene DNA fragment is purified from the agarose gel using a purification product such as NucleoTrap (Clonetech Inc., Palo Alto, Calif., USA).

Cloning of the $hCRF_2R$ PCR product into the pIRESneo vector (Clonetech Inc., Palo Alto, Calif., USA) is accomplished by first cutting the $hCRF_2R$ PCR product and the pIRESneo vector with the appropriate restriction endonucleases so that the 5' and 3' restriction endonuclease sites are ready for ligation. The pIRESneo vector DNA is ligated to the hCRF$_2$R PCR product DNA using DNA ligase, from the AdvantAge™PCR Cloning Kit (Clonetech Inc., Palo Alto, Calif., USA), according to the manufacturer's recommendations. The ligated vector and insert construct (pIRESneo/hCRF$_2$R)is then used to transform TOP10F' competent *E. coli* cells (Clonetech Inc., Palo Alto, Calif., USA). Transformed cells are plated on LB/X-gal/IPTG plus ampicillin containing agar. White colonies (positive clones) are selected and individually cultured in LB medium. Plasmid DNA is isolated using NucleoBond DNA Purification System (Clonetech Inc., Palo Alto, Calif., USA). The insert from at least one clone is sequenced to ensure that the hCRF$_2$R sequence is correct. HEK293 cells containing a stably integrated Mercury CRE-LUC plasmid (Clonetech Inc., Palo Alto, Calif., USA) are transfected with purified pIRESneo/hCRF$_2$R DNA, having the correct sequence insert, utilizing the CalPhoS™ Mammalian Transfection Kit (Clonetech Inc., Palo Alto, Calif., USA. Cells stably transfected with pIRESneo/hCRF$_2$R DNA are selected by culturing the cells in G418. The stably transfected cells (HEK293/CRE-LUC/pIRESneo/ hCRF$_2$R cells) are propagated in DMEM (Life Technologies, Rockville, Md.) containing 10% fetal bovine serum (Clonetech Inc., Palo Alto, Calif., USA), penicillin/streptomycin solution (Life Technologies, Rockville, Md.), L-glutamine (Life Technologies, Rockville, Md.), and non-essential amino acid (Life Technologies, Rockville, Md.) at 37° C. in a 5% carbon dioxide/95% air atmosphere. The clones are characterized for both CRF binding and CRE-LUC activation following exposure to CRF as described in Example 2 and Example 3. Cells expressing the hCRF$_2$R receptor at an appropriate level and which are appropriately coupled to the CRE-LUC reporter system are then utilized for further analysis.

Example 2

Receptor Binding Assays

Receptor binding analysis of compounds is performed in whole cells by plating the HEK293/CRE-LUC/pIRESneo/hCRF$_2$R cells from Example 1 in a 96 well polylysine coated plate. Cells are seeded in DMEM medium containing 10% fetal bovine serum, penicillin/streptomycin solution, L-glutamine, and non-essential amino acid at 37° C. in a 5% carbon dioxide/95% air atmosphere and incubated overnight. The culture medium is removed and the appropriate amount of CRF covalently labeled with Europium (Eu-CRF) in MEM (Life Technologies, Rockville, Md.)+10% Seablock (Clonetech Inc., Palo Alto, Calif., USA) is added. The cells are incubated with the Eu-CRF for 90 minutes at room temperature then washed 4 times with phosphate buffered saline lacking magnesium and calcium (Life Technologies, Rockville, Md.). Following the final wash, enhancement solution is added (Wallac Inc., Gaithersburg, Md.) and the plate is read on a Wallac plate reader (Wallac Inc., Gaithersburg, Md.) using the BioWorks Europium program. For saturation binding analysis, log doses of Eu-CRF ranging from 10(−12) to 10(−3) M are added to the cells and binding analyzed both in the absence and the presence of a saturating concentration of unlabeled CRF for evaluation of non-specific binding. For competitive binding, a concentration of Eu-CRF is added which is half maximal, in terms of binding, in addition to varying concentrations of the compound of interest.

Example 3

Receptor Activation Assay

Receptor activation analysis is performed by seeding the HEK293/CRE-LUC/pIRESneo/hCRF$_2$R cells of Example 1 into Packard View Plate-96™ (Packard Inc., CA). Cells are seeded in DMEM medium containing 10% fetal bovine serum, penicillin/streptomycin solution, L-glutamine, and non-essential amino acid at 37° C. in a 5% carbon dioxide/95% air atmosphere and incubated overnight. The medium is then removed and replaced with DMEM (Life Technologies, Rockville, Md.) containing 0.01% bovine albumin fraction V (SIGMA, St. Louis, Mo.) containing the compound of interest. The cells are then incubated for four hours at 37° C. in a 5% carbon dioxide/95% air atmosphere after which the medium is removed and the cells are washed twice with Hanks Balanced Salt Solution (Life Technologies, Rockville, Md.). Lysis Reagent (Promega Inc., Madison, Wis.) is then added to the washed cells and the cells are incubated for 20 minutes at 37° C. in a 5% carbon dioxide/95% air atmosphere. The cells are then placed at −80° C. for 20 minutes followed by a 20 minute incubation at 37° C. in a 5% carbon dioxide/95% air atmosphere. After this incubation, LUCIFERASE ASSAY BUFFER®™ LUCIFERASE ASSAY SUBSTRATE®™ (Promega Inc., Madison, Wis.) are added to the cell lysates and luciferase activity quantitated using a luminometer. Relative activity of a compound is evaluated by comparing the increase following exposure to compound to the level of luciferase in HEK cells which contain the CRE-LUC construct without the hCRF$_2$R following exposure to compound. Specificity of response is also checked by evaluating luciferase response of hCRF$_2$R /CRE-LUC HEK cells to compound in the presence and absence of a 10-fold excess of hCRF$_2$R antagonist.

Example 4

Screen to Identify Candidate Compounds that Prolong or Augment the Activation of CRF$_2$R and/or a CRF$_2$R Receptor Signal Transduction Pathway Identification of compounds that prolong or augment the agonist-induced activation of the CRF$_2$R or of a CRF$_2$R signal transduction pathway, involves a variation of the Receptor Activation Assay described in Example 3. Specifically, this assay is performed by seeding the HEK293/CRE-LUC/pIRESneo/hCRF$_2$R receptor cells into Packard View Plate-96 (Packard Inc., Calif.). Cells are seeded in DMEM medium containing 10% fetal bovine serum, penicillin/streptomycin solution, L-glutamine, non-essential amino acid, and saturating amounts of CRF at 37° C. in a 5% carbon dioxide/95% air atmosphere and incubated for 48 hours. The medium is then removed and replaced with DMEM (Life Technologies, Rockville, Md.) containing 0.01% bovine albumin fraction V (SIGMA, St. Louis, Mo.) and CRF in addition to the compound of interest. The cells are then incubated for four hours at 37° C. in a 5% carbon dioxide/95% air atmosphere after which the medium is removed and the cells are washed twice with Hanks Balanced Salt Solution (Life Technologies, Rockville, Md.). Lysis Reagent (Promega Inc., Madison, Wis.) is then added to the washed cells and the cells are incubated for 20 minutes at 37° C. in a 5% carbon dioxide/95% air atmosphere. The cells are then placed at −80° C. for 20 minutes followed by a 20 minute incubation at 37° C. in a 5% carbon dioxide/ 95% air atmosphere. After this incubation, Luciferase Assay Buffer and Luciferase Assay Substrate (Promega Inc., Madison, Wis.) are added to the cell lysates and luciferase activity is quantitated using a luminometer. Test compounds which stimulate fluorescence significantly above the levels of control untreated cells, after correction for variations in cell density, are considered candidate compounds for regulating skeletal muscle mass or function. The compounds of most interest are those that induce relatively higher levels of fluorescence.

Example 5

Screen to Identify Candidate Compounds Specific for $CRF_2R$

Compounds that activate $CRF_2R$ are identified as in Example 3. To select those compounds which show selectivity for $CRF_2R$ over $CRF_1R$, these compounds also are screened against $CRF_1R$. HEK293/CRE-LUC/pIRESneo/ $hCRF_1R$ cells are generated essentially as described in Example 1 except that the human $CRF_1R$ ($hCRF_1R$) DNA sequence, Accession No. X72304, is used for the initial PCR amplification. To determine how active the compounds are against $CRF_1R$, an activation assay is performed essentially as described in Example 3 except that HEK293/CRE-LUC/ pIRESneo/$hCRF_1R$ cells are used to seed the plates. The amount of fluorescence stimulated by the compound in $CRF_2R$ expressing cells is compared with the amount of fluorescence stimulated by the compound in $CRF_1R$ expressing cells. Those compounds which demonstrate a 10-fold better response (on a molar basis) in $CRF_2R$ expressing cells than in $CRF_1R$ expressing cells are then checked further for specificity of response to eliminate differences due to clonal variation. HEK293/CRE-LUC/ pIRESneo/$hCRF_2R$ cells are assayed with the compound in the presence or absence of a 10-fold excess of the $CRF_2R$ antagonist, antisauvagine-30. Those compounds that show greater than 10-fold selectivity for $CRF_2R$ and whose activity is inhibited by antisauvagine-30 are selected as candidate compounds.

Example 6

Screens to Identify Candidate Compounds that Increase $hCRF_2R$ Expression

The sequence containing the promoter region of the $hCRF_2R$ gene, beginning far enough upstream of the transcriptional initiation site to contain all the regulatory elements necessary for physiological expression of the $hCRF_2R$ gene in the appropriate tissue is retrieved from the human genome database. Two oligonucleotides, one containing the 5' end of the promoter region (5' oligonucleotide) and one containing the 3' end of the promoter region including the transcriptional start site (3' oligonucleotide) are synthesized. These oligonucleotides also contain restriction endonuclease sites which are not present in the $hCRF_2R$ gene regulatory region with one unique site in the 5' oligonucleotide and a different unique restriction endonuclease site in the 3' oligonucleotide. The 5' and 3' oligonucleotides are used for PCR amplification of the $hCRF_2R$ gene regulatory region from human DNA (Clonetech Inc., Palo Alto, Calif., USA) using the PCR kit, Advantage®Genomic PCR kit (Clonetech Inc., Palo Alto, Calif., USA). The $hCRF_2R$ gene regulatory region PCR product is purified from PCR artifacts by agarose gel electrophoresis and the $hCRF_2R$ gene regulatory region DNA fragment is purified from the agarose gel using a purification product such as NucleoTrap (Clonetech Inc., Palo Alto, Calif., USA). Cloning of the $hCRF_2R$ gene regulatory region PCR product into the pECFP-1 vector (Clonetech Inc., Palo Alto, Calif., USA) is accomplished by first cutting the $hCRF_2R$ gene regulatory region PCR product and the pECFP-1 vector with the appropriate restriction endonucleases so that the 5' and 3' restriction endonuclease sites are ready for ligation. Ligation of the pECFP-1 vector DNA to the $hCRF_2R$ gene regulatory region PCR product DNA is accomplished using DNA ligase from the AdvantAge™pCR Cloning Kit (Clonetech Inc., Palo Alto, Calif., USA) according to the manufacturer's recommendations. The ligated vector and insert construct is then used to transform TOP10F' competent E. coli cells (Clonetech Inc., Palo Alto, Calif., USA). The cells are plated on LB plus kanamycin containing agar and kanamycin resistant colonies are selected for further analysis. Kanamycin resistant clones are cultured in LB containing kanamycin medium and plasmid DNA is isolated using NucleoBond DNA Purification System (Clonetech Inc., Palo Alto, Calif., USA) and the construct containing the $hVPAC_2$ gene regulatory region is analyzed by DNA sequencing to ensure construct correctness and integrity. Purified construct plasmid DNA containing the $hCRF_2R$ gene regulatory region is then transfected into the HEK293 cells utilizing calcium phosphate-mediated transfection utilizing the CalPhOS™ Mammalian Transfection Kit (Clonetech Inc., Palo Alto, Calif., USA). Transfected cell clones are selected using G418, isolated and propagated in DMEM (Life Technologies, Rockville, Md.) containing 10% fetal bovine serum (Clonetech Inc., Palo Alto, Calif., USA), penicillin/streptomycin solution (Life Technologies, Rockville, Md.), L-glutamine (Life Technologies, Rockville, Md.), non-essential amino acid (Life Technologies, Rockville, Md.) and G418 (Life Technologies, Rockville, Md.) at 37° C. in a 5% carbon dioxide/95% air atmosphere. G418 resistant clones are characterized by Southern blotting to ensure that they contain the $hCRF_2R$ gene promoter sequence; in addition activation of the $hCRF_2R$ gene regulatory region is analyzed using an appropriate stimulating agent. Cells expressing the $hCRF_2R$ gene regulatory region-ECFP at an appropriate level are then used in assays designed to evaluate compounds which can modulate the activity of the $hCRF_2R$ gene regulatory region as follows. The regulatory region activation analysis is performed by seeding the $hCRF_2R$ gene regulatory region-ECFP containing HEK293 cells at an appropriate density into black with clear bottom 96 well microtiter plates and allowed to grow overnight. The following day, the medium is removed and the test compound added in fresh growth medium. The cells are incubated for 16 hours at 37° C. in a 5% carbon dioxide/95% air atmosphere followed by measurement of fluorescence (excitation at 433 (453) nm by detecting emission at 475(501) nm using a fluorometer (biolumin™ 960, Molecular Dynamics/Amersham Pharmacia Biotech, Piscataway, N.J.). Test compounds which stimulate fluorescence significantly above the levels of control untreated cells, after correction for variations in cell density, are considered candidate compounds for regulating skeletal muscle mass or function. The compounds of most interest are those which induce relatively higher levels of fluorescence.

Example 7

Screens to Identify Compounds that Increase Human CRF Expression

The methods for identifying compounds that increase human CRF (hCRF) expression are essentially identical to those for identifying compounds which increase hVPAC$_2$ receptor expression except the regulatory region used is that for the hCRF gene. The sequence containing the regulatory region of the hCRF gene, beginning far enough upstream of the transcriptional initiation site to contain all the regulatory elements necessary for physiological expression of the hCRF gene in the appropriate tissue is retrieved from the human genome database. Two oligonucleotides, one containing the 5' end of the regulatory region (5' oligonucleotide) and one containing the 3' end of the regulatory region including the transcriptional start site (3' oligonucleotide) are synthesized. These oligonucleotides also contain restriction endonuclease sites which are not present in the hCRF gene regulatory region with one unique site in the 5' oligonucleotide and a different unique restriction endonuclease site in the 3' oligonucleotide. The 5' and 3' oligonucleotides are used for PCR amplification of the hCRF gene regulatory region from human DNA (Clonetech Inc., Palo Alto, Calif., USA) using the Advantage®Genomic PCR kit (Clonetech Inc., Palo Alto, Calif., USA). The hCRF gene regulatory region PCR product is purified from PCR artifacts by agarose gel electrophoresis and the hCRF gene regulatory region DNA fragment is purified from the agarose gel using the purification product, NucleoTrap (Clonetech Inc., Palo Alto, Calif., USA). Cloning of the hCRF gene regulatory region PCR product into the pECFP-1 vector (Clonetech Inc., Palo Alto, Calif., USA) is accomplished by first cutting the hCRF gene regulatory region PCR product and the pECFP-1 vector with the appropriate restriction endonucleases so that the 5' and 3' restriction endonuclease sites are ready for ligation. Ligation of the pECFP-1 vector DNA to the hCRF gene regulatory region PCR product DNA is accomplished using DNA ligase from AdvantAge™PCR Cloning Kit (Clonetech Inc., Palo Alto, Calif., USA) according to the manufacturer's recommendations. The ligated vector and insert construct is then used to transform TOP10F' competent *E. coli* cells (Clonetech Inc., Palo Alto, Calif., USA). The cells are plated on LB plus kanamycin containing agar and kanamycin resistant colonies are selected for further analysis. Kanamycin resistant clones are cultured in LB containing kanamycin medium and plasmid DNA is isolated using NucleoBond DNA Purification System (Clonetech Inc., Palo Alto, Calif., USA) and the construct containing the hCRF gene regulatory region is analyzed by DNA sequencing to ensure construct correctness and integrity. Purified construct plasmid DNA containing the hCRF gene regulatory region is then transfected into the HEK293 cells utilizing calcium phosphate-mediated transfection utilizing the CalPhos™ Mammalian Transfection Kit (Clonetech Inc., Palo Alto, Calif., USA). Transfected cell clones are selected using G418, isolated and propagated in DMEM (Life Technologies, Rockville, Md.) containing 10% fetal bovine serum (Clonetech Inc., Palo Alto, Calif., USA), penicillin/streptomycin solution (Life Technologies, Rockville, Md.), L-glutamine (Life Technologies, Rockville, Md.), non-essential amino acid (Life Technologies, Rockville, Md.) and G418 (Life Technologies, Rockville, Md.) at 37° C. in a 5% carbon dioxide/95% air atmosphere. G418 resistant clones are characterized by Southern blotting to ensure that they contain the hCRF gene regulatory region sequence; in addition activation of the hCRF gene regulatory region is analyzed using an appropriate stimulating agent. Cells expressing the hCRF gene regulatory region-ECFP at an appropriate level are then used in assays designed to evaluate compounds which can modulate the activity of the hCRF gene regulatory region as follows. The regulatory region activation analysis is performed as in Example 5 except that clones containing the hCRF gene regulatory region construct are used.

Example 8

Method of Making Human Antibodies which Activate the hCRF$_2$R

Fully human monoclonal antibodies which activate the hCRF$_2$R are produced by first generating recombinant hCRF$_2$R protein as follows. The procedure from Example 1 is followed to obtain the hCRF$_2$R PCR product. This hCRF$_2$R PCR product is then cloned into the pHAT20 vector (Clonetech Inc., Palo Alto, Calif., USA) by first cutting the hCRF$_2$R gene PCR product and the pHAT20 vector with the appropriate restriction endonucleases so that the 5' and 3' restriction endonuclease sites are ready for ligation. Ligation of the pHAT20 vector DNA to the hCRF$_2$R gene PCR product DNA is accomplished using DNA ligase from the AdvantAge™PCR Cloning Kit (Clonetech Inc., Palo Alto, Calif., USA) according to the manufacturer's recommendations. The ligated vector/insert construct is then used to transform TOP10F' competent *E. coli* cells (Clonetech Inc., Palo Alto, Calif., USA). Transformed cells are plated on LB plus ampicillin containing agar and ampicillin resistant colonies are selected for further analysis. Positive clones are cultured in LB medium containing ampicillin and plasmid DNA is isolated using NucleoBond DNA Purification System (Clonetech Inc., Palo Alto, Calif., USA) and the construct containing the hCRF$_2$R gene is analyzed by DNA sequencing the ensure construct correctness and integrity. The hCRF$_2$R -pHAT20 vector DNA is then used for additional PCR cloning by utilizing a 5' oligonucleotide containing the beginning of the HAT sequence and a unique restriction endonuclease site not present in the hCRF$_2$R-pHAT20 construct and the 3' hCRF$_2$R oligonucleotide utilized previously. The oligonucleotide primers are used to PCR amplify the HAT-hCRF$_2$R fusion gene from the hCRF$_2$R-pHAT20 construct and the PCR product is purified as described above. The HAT-hCRF$_2$R fusion gene PCR product is then utilized for cloning into the pBacPAK8 vector using the BacPAK Baculovirus Expression System from Clonetech (Clonetech Inc., Palo Alto, Calif., USA). The ligation of the HAT—hCRF$_2$R fusion gene into the pBacPAK8 vector is essentially as described above. The hCRF$_2$R/HAT-pBacPAK8 construct is then transfected into TOP10'F competent *E. coli* cells, ampicillin resistant cells are selected and plasmid DNA is isolated and checked for construct integrity as described above. This construct is then cotransfected with linearized BacPAK6 DNA into Sf21 insect host cells utilizing the CalPhos™ Mammalian Transfection Kit (Clonetech Inc., Palo Alto, Calif., USA). The insect cells are then incubated for 2–3 days followed by harvest of virus from individual clear plaques. The virus is then amplified in Sf21 cells, the harvested virus titered, and the titered virus used for large scale infection of Sf21 cells utilizing BacPAK Insect Cell Media—all according to the manufacturers recommendations (Clonetech Inc., Palo Alto, Calif., USA). Recombinant HAT-CRF$_2$R fusion protein is then purified using the TALON® CellThru Purification Kit from Clonetech (Clonetech Inc., Palo Alto, Calif., USA) using conditions recommended by the manufacturer. Briefly, infected Sf21 cells are harvested 48 hours after infection and sonicated in extraction/loading buffer. The cell lysate is then put through a TALON® CellThru column. The column is washed twice with extraction/loading buffer and the bound HAT-hCRF$_2$R protein is eluted with elution buffer. The eluted protein is analyzed by SDS-PAGE for integrity and protein concentration is quantitated using the Bio-Rad SDS-PAGE system and protein quantitation systems according to the manufacturer's recommendations (Bio-Rad Laboratories, Hercules, Calif.). Purified HAT-hCRF$_2$R fusion protein is then used for immunizing XenoMouse animals (Abgenix Inc., Fremont, Calif.) for human monoclonal antibody production as follows. 10 μg of purified recombinant HAT-hCRF$_2$R fusion protein in combination with 25 μg of adjuvant monophosphoryl lipid A (Sigma, St. Louis, Mo.) is used to vaccinate 10 XenoMouse animals multiple times over an eight week period. Serum is obtained from vaccinated animals and utilized in an antigen capture ELISA utilizing purified HAT-hCRF$_2$R fusion protein to detect antibodies to the HAT-hCRF$_2$R protein by coating polystyrene ELISA plates (Corning Glass Works, Corning, N.Y.) with HAT-hCRF$_2$R fusion protein, blocked with PBS-1% BSA, washed and incubated at 37° C. for 1 hour with a 1:50 dilution of the serum samples. After washing 5 times with PBS, the plates are incubated at 37° C. for 1 hour with alkaline phosphatase-conjugated goat antibodies to human immunoglobulin G. The plates are then washed 5× with PBS and antibodies detected with p-nitrophenyl phosphate substrate (Sigma, St. Louis, Mo.) in buffer. Optical densities at 405 nm were measured using a plate reader and signal quantitated. Mice with demonstrated high antibody production are used for hybridoma formation. Hybridomas are generated by fusion of splenic cells from the XenoMouse animals with nonsecreting myeloma cell line NSA-bcl 2 using a 4:1 ratio of spleen cells to NSA-bcl2 cells in the presence of 30% polyethylene glycol PEG1450. Fused cells are individually cloned by limiting dilution into 96 well plates and cultured in RPMI-1640 medium containing 10% fetal bovine serum, nonessential amino acids, sodium pyruvate, L-glutamine, 100 u/ml penicillin-streptomycin and hypoxanthine-aminopterin-thymidine (all from Life Technologies, Rockville, Md.). Supernatants from the hypoxanthine-aminopterin-thymidine selected hybridomas were screened for human antibody production by ELISA as described previously. Hybridomas which produce human antibodies to the HAT-hCRF$_2$R fusion protein are selected for large scale antibody production. Monoclonal antibodies are purified by Protein G-Sepharose chromatography. Briefly, the supernatant from cultured hybridoma clones is loaded onto a Protein G-Sepharose column (SIGMA, St. Louis, Mo.) in loading buffer, washed 3 times and the IgG is eluted with elution buffer. These antibodies are then used for screening to evaluate hCRF$_2$R activation (agonism) potential. This is accomplished using the methodology as outlined in Example 3. Those human monoclonal antibodies which demonstrate agonist activity toward the hCRF$_2$R are designated candidate compounds.

Example 9

Determination of Absolute Force Measurement of a Muscle

The extensor digitorum longus (EDL) and soleus muscles are removed, tendon-to-tendon from the casted mouse leg. A silk suture is tied to each tendon of the isolated muscles and the muscles are placed into a plexiglass chamber filled with Ringer solution (137 mM sodium chloride, 24 mM sodium bicarbonate, 11 mM glucose, 5 mM potassium chloride, 1 mM magnesium sulfate, 1 mM sodium phosphate, 0.025 mM tubocurarine, all at pH 7.4 and oxygenated with 95% oxygen/5% carbon dioxide) constantly bubbled with 95% oxygen/5% carbon dioxide maintained at 25° C. Muscles are aligned horizontally between a servomotor lever arm (Model 305B-LR Cambridge Technology Inc., Watertown Mass., USA) and the stainless steel hook of a force transducer (Model BG-50; Kulite Semiconductor Products Inc., Leonia, N.J., USA) and field stimulated by pulses transmitted between two platinum electrodes placed longitudinally on either side of the muscle. Square wave pulses (0.2 ms duration) generated by a personal computer with a Labview board (Model PCI-MIO 16E-4), Labview Inc., Austin, Tex., USA) are amplified (Acurus power amplifier model A25, Dobbs Ferry, N.Y., USA) to increase titanic contraction. Stimulation voltage and muscle length (Lo) are adjusted to obtain maximum isometric twitch force. Maximum titanic force production (Po) is determined from the plateau of the frequency-force relationship.

Example 10

Therapeutic Treatment of Skeletal Muscle Atrophy using a Human Antibody that is an Agonist of the hCRF$_2$R Receptor A human male subject weighing 50 kg and having significant muscular atrophy of the arms and legs due to prolonged bed rest, is treated to reverse the skeletal muscle atrophy. Once each week for a period of 3 months, 15 mls of an aqueous solution of pH 6 comprising an activating antibody of the CRF$_2$R receptor is administered to the subject via intravenous injection. The solution comprises the following:

| Component | Concentration (mg/ml) |
|---|---|
| CRF$_2$R receptor agonist antibody | 20 |
| L-histidine HCl | 0.47 |
| L-histidine | 0.3 |
| α, α-trehalose dihydrate | 20 |
| Polysorbate 20 | 0.1 |
| Bacteriostatic Sterile water | qs to 1 mL |

At the end of the treatment period, the subject exhibits measurable increases of muscle mass, strength and mobility of the arms and legs.

Example 11

Prophylactic Treatment of Skeletal Muscle Atrophy using a Human Antibody that is an Agonist of the hCRF$_2$R Receptor A human female subject weighing 55 kg is scheduled for hip joint replacement surgery in one month. The subject is treated to enhance skeletal muscle mass prior to and following surgery to ultimately reduce the level of skeletal muscle atrophy due to muscle disuse during post-surgery recovery. Specifically, once each week for a period of 1 month prior to surgery and for 2 months post-surgery, 18 ml of an aqueous solution of pH 6.0 comprising an activating antibody of the CRF$_2$R receptor, is administered to the subject via intravenous injection. The solution comprises the following:

| Component | Concentration (mg/ml) |
|---|---|
| CRF$_2$R activating antibody | 20 |
| L-histidine HCl | 0.47 |
| L-histidine | 0.3 |
| α, α-trehalose dihydrate | 20 |
| Polysorbate 20 | 0.1 |
| Bacteriostatic Sterile water | qs to 1 mL |

At the end of the treatment period, the subject exhibits measurable preservation of muscle mass, strength and mobility of the arms and legs as compared to the subject's expected status without antibody therapy.

Example 12

Prophylactic Treatment of Skeletal Muscle Atrophy using a Human Antibody that is an Agonist of the CRF$_2$R Receptor A human female subject weighing 45 kg undergoes a casting procedure to treat a simple fracture of the humerus after a fall. The subject is treated to prevent atrophy of the skeletal muscle of the affected arm and shoulder due to disuse and limited use during fracture healing. Specifically, once each week starting on the day of casting, 13 ml of pH 6.0 comprising the anti-hCRF$_2$R receptor is administered to the subject via intravenous injection. The solution comprises the following:

| Component | Concentration (mg/ml) |
|---|---|
| CRFR activating antibody | 20 |
| L-histidine HCl | 0.47 |
| L-histidine | 0.3 |
| α, α-trehalose dihydrate | 20 |
| Polysorbate 20 | 0.1 |
| Bacteriostatic Sterile water | qs to 1 mL |

At the end of the treatment period, the subject exhibits measurable preservation of muscle mass, strength and mobility of the affected arm and shoulder and a reduced course of physical therapy as compared to the subject's expected status and follow-up treatment without antibody therapy.

Example 13

Prophylactic Treatment of Skeletal Muscle Atrophy using Urocortin-II

A human female subject weighing 60 kg is admitted to the hospital in a comatose state. The subject is treated by this method to prevent atrophy of the skeletal muscle of the entire body due to disuse in the comatose state. Specifically, once each day while in the coma, the subject is administered, via slow intravenous infusion, approximately 500 ml of an aqueous solution that is prepared by addition of 5 ml of the following stock solution to 500 ml of sterile saline:

| Component | Concentration (mg/ml) |
|---|---|
| Urocortin-II | 12 |
| Sodium phosphate buffer, pH 7.4 | 140 |

As a result of treatment, the subject exhibits measurable preservation of skeletal muscle mass and function, and reduced physical therapy needs during the coma and after regaining consciousness, as compared to the subject's status without drug therapy.

Example 14

Therapeutic Treatment of a Patient with Duchenne Muscular Dystrophy using CRF

A male subject weighing 40 kg with an existing diagnosis of Duchenne's Muscular Dystrophy is treated with a compound that exhibits CRF1-R and CRF2-R agonism over a similar dose range. The subject is treated with a sustained-release, depot formulation of the compound in order to improve or retain muscle strength and function over the progression of the disease. Specifically, once each month the subject is administered, via intramuscular injection, 3 ml of an aqueous solution of pH 6.0 comprising the following:

| Component | Concentration (mg/ml) |
|---|---|
| CRH (Corticotropin-Releasing Hormone) | 4 |
| D, L lactic and glycolic acid copolymer | 5 |

As a result of the treatment, the subject experiences either an improvement or an attenuation of the decline of muscle strength or muscle function in timed-function evaluations as compared to that exhibited during the natural progression of the disease.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for identifying candidate compounds for regulating skeletal muscle mass or function, comprising:
   a. contacting a test compound with a vertebrate $CRF_2R$;
   b. determining whether the test compound binds to or activates the $CRF_2R$;
   c. selecting those compounds that bind or activate $CRF_2R$, and further determining whether the test compound regulates muscle mass or function in a skeletal muscle atrophy model system; and
   d. identifying those test compounds that regulate muscle mass or function as candidate compounds for regulating skeletal muscle mass or function.

2. The method for identifying candidate compounds according to claim 1, in which the $CRF_2R$ is expressed on a eukaryotic cell.

3. The method for identifying candidate compounds according to claim 1 wherein the $CRF_2R$ has the amino acid sequence corresponding to the amino acid sequence of SEQ ID NO: 32.

4. The method for identifying candidate compounds according to claim 2, in which determining whether the test compound activates the $CRF_2R$ involves measuring the cellular cAMP level.

5. The method for identifying candidate compounds according to claim 4, in which the cell further comprises a reporter gene operatively associated with a cAMP responsive element and measuring the cellular cAMP level involves measuring expression of the reporter gene.

6. The method for identifying candidate compounds according to claim 5, in which the reporter gene is alkaline phosphatase, chloramphenicol acetyltransferase, luciferase, glucuronide synthetase, growth hormone, placental alkaline phosphatase, or Green Fluorescent Protein.

7. A method for identifying candidate compounds for regulating skeletal muscle mass or function comprising:
   a. contacting a test compound with a cell expressing a functional vertebrate $CRF_2R$, and determining level of activation of $CRF_2R$ resulting from the test compound;
   b. contacting said test compound with a cell expressing a functional vertebrate $CRF_1R$, and determining level of activation of $CRF_1R$ resulting from the test compound;
   c. comparing the level of $CRF_2R$ activation and the level of $CRF_1R$ activation;
   d. selecting those test compounds that selectively activate $CRF_2R$ and further determining whether said test compound regulates muscle mass or function in a skeletal muscle atrophy model system; and
   e. identifying those test compounds that regulate muscle mass or function as candidate compounds for regulating skeletal muscle mass or function.

8. The method according to claim 7 wherein the candidate compound exhibits a 100-fold or greater selectivity for $CRF_2R$.

9. The method according to claim 7 wherein the candidate compound exhibits a 1000-fold or greater selectivity for $CRF_2R$.

10. The method according to claim 7 wherein the candidate compound exhibits between 1-fold and 100-fold selectivity for $CRF_2R$.

* * * * *